US008168774B2

(12) United States Patent
Graham et al.

(10) Patent No.: US 8,168,774 B2
(45) Date of Patent: *May 1, 2012

(54) CONTROL OF GENE EXPRESSION

(75) Inventors: Michael Wayne Graham, Chapel Hill (AU); Robert Norman Rice, Sinnamon Park (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 435 days.

This patent is subject to a terminal disclaimer.

(21) Appl. No.: 11/218,999

(22) Filed: Sep. 2, 2005

(65) Prior Publication Data

US 2006/0014715 A1    Jan. 19, 2006

Related U.S. Application Data

(60) Division of application No. 10/821,710, filed on Apr. 8, 2004, now abandoned, which is a continuation of application No. 10/646,070, filed on Aug. 22, 2003, now Pat. No. 7,754,697, which is a continuation of application No. 09/646,807, filed as application No. PCT/AU99/00195 on Mar. 19, 1999, now abandoned, which is a continuation-in-part of application No. 09/100,812, filed on Jun. 19, 1998, now Pat. No. 6,573,099, and a continuation-in-part of application No. 09/100,813, filed on Jun. 19, 1998, now abandoned.

(30) Foreign Application Priority Data

Mar. 20, 1998 (AU) .......................... PP2492
Mar. 20, 1998 (AU) .......................... PP2499

(51) Int. Cl.
    *C07H 21/04*    (2006.01)
(52) U.S. Cl. ....................................... 536/24.5
(58) Field of Classification Search .................. 536/24.5
    See application file for complete search history.

(56) References Cited

U.S. PATENT DOCUMENTS

| 3,931,397 A | 1/1976 | Harnden |
| 4,130,641 A | 12/1978 | Ts'o et al. |
| 4,283,393 A | 8/1981 | Field et al. |
| 4,469,863 A | 9/1984 | Ts'o et al. |
| 4,605,394 A | 8/1986 | Skurkovich |
| 4,629,320 A | 12/1986 | Lersmacher et al. |
| 4,689,320 A | 8/1987 | Kaji et al. |
| 4,766,072 A | 8/1988 | Jendrisak et al. |
| 5,017,488 A | 5/1991 | McAllister et al. |
| 5,024,938 A | 6/1991 | Nozaki et al. |
| 5,034,323 A | 7/1991 | Jorgensen |
| 5,107,065 A | 4/1992 | Shewmaker et al. |
| 5,173,410 A | 12/1992 | Ahlquist |
| 5,190,931 A | 3/1993 | Inouye |
| 5,198,346 A | 3/1993 | Ladner |
| 5,208,149 A | 5/1993 | Inouye |
| 5,231,020 A | 7/1993 | Jorgensen |
| 5,270,163 A | 12/1993 | Gold et al. |
| 5,272,065 A | 12/1993 | Inouye et al. |
| 5,283,184 A | 2/1994 | Jorgensen |
| 5,349,126 A | 9/1994 | Chappell et al. |
| 5,365,015 A | 11/1994 | Grierson et al. |
| 5,405,775 A | 4/1995 | Inouye et al. |
| 5,413,906 A * | 5/1995 | Eberle et al. ................... 435/5 |
| 5,434,070 A | 7/1995 | Inouye et al. |
| 5,453,566 A | 9/1995 | Shewmaker et al. |
| 5,457,189 A * | 10/1995 | Crooke et al. ............. 536/24.5 |
| 5,474,935 A | 12/1995 | Chatterjee et al. |
| 5,496,698 A | 3/1996 | Draper |
| 5,514,546 A | 5/1996 | Kool |
| 5,530,192 A | 6/1996 | Murase et al. |
| 5,578,716 A | 11/1996 | Szyf et al. |
| 5,580,703 A | 12/1996 | Kotin et al. |
| 5,580,767 A | 12/1996 | Cowsert et al. |
| 5,583,021 A | 12/1996 | Dougherty |
| 5,597,718 A | 1/1997 | John et al. |
| 5,602,242 A * | 2/1997 | Ahlquist et al. ........... 536/23.72 |
| 5,624,803 A | 4/1997 | Noonberg et al. |
| 5,631,148 A | 5/1997 | Urdea |
| 5,643,762 A | 7/1997 | Ohshima et al. |
| 5,683,985 A | 11/1997 | Chu et al. |
| 5,686,649 A | 11/1997 | Chua et al. |
| 5,691,140 A | 11/1997 | Noren et al. |
| 5,693,773 A | 12/1997 | Kandimalla et al. |
| 5,707,835 A | 1/1998 | Haseloff et al. |
| 5,714,323 A | 2/1998 | Ohshima et al. |
| 5,719,054 A | 2/1998 | Boursnell et al. |
| 5,739,309 A | 4/1998 | Dattagupta et al. |
| 5,747,308 A | 5/1998 | Bebbington et al. |
| 5,747,338 A | 5/1998 | Giese et al. |
| 5,780,269 A | 7/1998 | Inouye et al. |

(Continued)

FOREIGN PATENT DOCUMENTS

AU    34025/93    8/1995

(Continued)

OTHER PUBLICATIONS

Appeal Brief filed on Mar. 6, 2009 in U.S. Appl. No. 10/805,804.*

(Continued)

*Primary Examiner* — Brian Whiteman
(74) *Attorney, Agent, or Firm* — John P. White; Gary J. Gershik; Cooper & Dunham LLP

(57) ABSTRACT

The present invention relates generally to a method of modifying gene expression and to synthetic genes for modifying endo gene expression in a cell, tissue or organ of a transgenic organism, in particular a transgenic animal or plant. More particularly, the invention utilizes recombinant DNA technology to post-transcriptionally modify or modulate the expression of a target gene in tissue, organ or whole organism, thereby producing novel phenotypes. Novel synthetic genes and genetic constructs which are cap repressing delaying or otherwise reducing the expression of an endogenous gene or a target gene in an organism when introduced are also provided.

76 Claims, 68 Drawing Sheets

U.S. PATENT DOCUMENTS

| | | | |
|---|---|---|---|
| 5,795,715 A | 8/1998 | Livache et al. |
| 5,798,265 A | 8/1998 | Springer et al. |
| 5,801,154 A | 9/1998 | Baracchini et al. |
| 5,808,036 A | 9/1998 | Kool |
| 5,814,500 A | 9/1998 | Dietz |
| 5,850,026 A | 12/1998 | DeBonte et al. |
| 5,858,981 A | 1/1999 | Schreiber et al. |
| 5,859,347 A | 1/1999 | Brown et al. |
| 5,874,555 A | 2/1999 | Dervan et al. |
| 5,891,855 A | 4/1999 | Florkiewicz |
| 5,908,779 A | 6/1999 | Carmichael et al. |
| 5,939,600 A | 8/1999 | Goldbach et al. |
| 5,952,546 A | 9/1999 | Bedbrook et al. |
| 5,972,704 A | 10/1999 | Draper et al. |
| 5,998,383 A | 12/1999 | Wright et al. |
| 6,010,908 A | 1/2000 | Gruenert et al. |
| 6,022,863 A | 2/2000 | Peyman |
| 6,054,299 A | 4/2000 | Conrad |
| 6,069,298 A | 5/2000 | Gengenbach et al. |
| 6,133,024 A | 10/2000 | Helene et al. |
| 6,146,886 A | 11/2000 | Thompson |
| 6,150,585 A | 11/2000 | Goldbach et al. |
| 6,225,290 B1 | 5/2001 | German et al. |
| 6,291,504 B1 | 9/2001 | Nugiel et al. |
| 6,344,316 B1 | 2/2002 | Lockhart et al. |
| 6,350,575 B1 | 2/2002 | Lusky et al. |
| 6,369,038 B1 | 4/2002 | Blumenfeld et al. |
| 6,372,965 B1 | 4/2002 | Lightner et al. |
| 6,423,885 B1 | 7/2002 | Waterhouse et al. |
| 6,451,603 B1 | 9/2002 | Atkins et al. |
| 6,506,559 B1 | 1/2003 | Fire et al. |
| 6,531,647 B1 | 3/2003 | Baulcombe et al. |
| 6,573,099 B2 | 6/2003 | Graham |
| 6,610,321 B2 | 8/2003 | Huang et al. |
| 6,635,805 B1 | 10/2003 | Baulcombe et al. |
| 6,849,448 B1 | 2/2005 | D'Apice |
| 6,919,466 B2 | 7/2005 | Lightner et al. |
| 6,995,258 B1 | 2/2006 | Rossietal. |
| 7,064,185 B2 | 6/2006 | Lau |
| 7,754,697 B2 | 7/2010 | Graham et al. |
| 8,048,670 B2 | 11/2011 | Graham et al. |
| 8,053,419 B2 | 11/2011 | Graham et al. |
| 8,067,383 B2 | 11/2011 | Graham et al. |
| 2002/0086356 A1 | 7/2002 | Tuschl et al. |
| 2002/0114784 A1 | 8/2002 | Li et al. |
| 2002/0150968 A1 | 10/2002 | Wang et al. |
| 2002/0150986 A1 | 10/2002 | Lau |
| 2002/0166144 A1 | 11/2002 | Green et al. |
| 2002/0168707 A1 | 11/2002 | Graham |
| 2003/0018993 A1 | 1/2003 | Gutterson et al. |
| 2003/0027783 A1 | 2/2003 | Zernicka-Goetz et al. |
| 2003/0036197 A1 | 2/2003 | Glassman et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0061626 A1 | 3/2003 | Plaetinck et al. |
| 2003/0074684 A1 | 4/2003 | Graham et al. |
| 2003/0148519 A1 | 8/2003 | Engelke et al. |
| 2003/0165894 A1 | 9/2003 | Waterhouse et al. |
| 2004/0022748 A1 | 2/2004 | Ananthapadmanabhan et al. |
| 2004/0106566 A1 | 6/2004 | Lin et al. |
| 2004/0138168 A1 | 7/2004 | Satishchandran et al. |
| 2004/0234504 A1 | 11/2004 | Verma et al. |
| 2004/0266005 A1 | 12/2004 | Graham et al. |
| 2008/0050342 A1 | 2/2008 | Fire et al. |
| 2008/0081373 A1 | 4/2008 | Fire et al. |
| 2008/0248576 A1 | 10/2008 | Fire et al. |
| 2011/0076681 A1 | 3/2011 | Waterhouse et al. |

FOREIGN PATENT DOCUMENTS

| | | |
|---|---|---|
| AU | 20891/91 | 10/1997 |
| AU | 20891/97 | 10/1997 |
| AU | 729454 | 5/1998 |
| AU | 729454 | 2/2001 |
| AU | 2001195225 A1 | 1/2002 |
| CA | 2012312 | 9/1990 |
| CA | 2370628 A1 | 10/2000 |
| EP | 0213921 A2 | 3/1987 |
| EP | 0213931 A2 | 3/1987 |
| EP | 0223399 | 5/1987 |
| EP | 0240208 | 10/1987 |
| EP | 0281380 A2 | 9/1988 |
| EP | 0286224 A2 | 10/1988 |
| EP | 0300680 A2 | 1/1989 |
| EP | 0303516 A2 | 2/1989 |
| EP | 0306347 A2 | 3/1989 |
| EP | 0308066 A2 | 3/1989 |
| EP | 0318281 A2 | 5/1989 |
| EP | 0325018 A2 | 7/1989 |
| EP | 0347501 A1 | 12/1989 |
| EP | 0350151 A2 | 1/1990 |
| EP | 0387775 | 9/1990 |
| EP | 0467349 | 1/1992 |
| EP | 0522880 | 1/1993 |
| EP | 560156 | 9/1993 |
| EP | 0647715 | 4/1995 |
| EP | 465572 | 6/1995 |
| EP | 077936 | 6/1997 |
| EP | 0779365 A2 | 6/1997 |
| EP | 0784094 A1 | 7/1997 |
| EP | 242016 | 10/1997 |
| EP | 0532380 | 1/1999 |
| EP | 921195 | 6/1999 |
| EP | 0983370 B1 | 3/2000 |
| EP | 0426195 B1 | 10/2001 |
| EP | 0458367 B1 | 10/2001 |
| EP | 1229134 | 9/2002 |
| GB | 2353282 A | 2/2001 |
| GB | 2377221 A | 9/2001 |
| JP | H09-110894 A | 4/1997 |
| JP | H09-227413 A | 9/2007 |
| WO | WO 89/05852 | 6/1989 |
| WO | WO 89/10396 | 11/1989 |
| WO | 90/11682 | 10/1990 |
| WO | WO 90/12094 A1 | 10/1990 |
| WO | WO 90/12488 A2 | 11/1990 |
| WO | WO 90/14090 A1 | 11/1990 |
| WO | WO 91/02069 | 2/1991 |
| WO | WO 91/16426 | 10/1991 |
| WO | WO 91/16440 | 10/1991 |
| WO | WO 92/04456 | 3/1992 |
| WO | WO 92/11375 | 7/1992 |
| WO | WO 92/11376 | 7/1992 |
| WO | WO 92/13070 | 8/1992 |
| WO | WO 92/17596 | 10/1992 |
| WO | WO 92/18522 A1 | 10/1992 |
| WO | 92/19732 | 11/1992 |
| WO | WO 92/21757 | 12/1992 |
| WO | WO 93/05159 | 3/1993 |
| WO | WO 93/10251 | 5/1993 |
| WO | 93/17098 | 9/1993 |
| WO | 93/23551 | 11/1993 |
| WO | 94/01550 | 1/1994 |
| WO | WO 94/01550 | 1/1994 |
| WO | WO 94/03607 | 2/1994 |
| WO | WO 94/07367 | 4/1994 |
| WO | WO 94/09143 | 4/1994 |
| WO | 94/17194 | 8/1994 |
| WO | WO 94/17194 | 8/1994 |
| WO | WO 94/18337 | 8/1994 |
| WO | WO 94/29465 | 12/1994 |
| WO | WO 95/03406 A2 | 2/1995 |
| WO | WO 95/07993 | 3/1995 |
| WO | WO 95/08350 | 3/1995 |
| WO | 95/10607 | 4/1995 |
| WO | WO 95/09920 | 4/1995 |
| WO | 95/15378 | 6/1995 |
| WO | WO 95/15394 | 6/1995 |
| WO | WO 95/18223 A1 | 7/1995 |
| WO | WO 95/18854 A1 | 7/1995 |
| WO | 65/23225 | 8/1995 |
| WO | WO 95/34668 | 12/1995 |
| WO | 96/08558 | 3/1996 |
| WO | WO 95/35706 A1 | 11/1996 |
| WO | 97/01952 | 1/1997 |
| WO | WO 97/10360 A1 | 3/1997 |

| | | |
|---|---|---|
| WO | WO 97/11170 | 3/1997 |
| WO | WO 97/11170 A1 | 3/1997 |
| WO | WO 97/13865 | 4/1997 |
| WO | WO 97/16559 | 5/1997 |
| WO | WO 92/18625 | 10/1997 |
| WO | 97/44450 | 11/1997 |
| WO | WO 97/44460 | 11/1997 |
| WO | WO 97/49814 | 12/1997 |
| WO | WO 98/05770 A2 | 2/1998 |
| WO | 98/18811 | 5/1998 |
| WO | 98/37213 | 8/1998 |
| WO | 98/36083 | 9/1998 |
| WO | 98/44138 | 10/1998 |
| WO | 98/53083 | 11/1998 |
| WO | WO 98/50408 A1 | 11/1998 |
| WO | WO 99/09045 | 2/1999 |
| WO | 99/15682 | 4/1999 |
| WO | 99/25853 | 5/1999 |
| WO | WO 99/29879 | 6/1999 |
| WO | 99/32619 | 7/1999 |
| WO | 99/49029 | 9/1999 |
| WO | 99/53050 | 10/1999 |
| WO | 99/61631 | 12/1999 |
| WO | WO 99/61632 | 12/1999 |
| WO | 00/01846 | 1/2000 |
| WO | 00/11895 | 8/2000 |
| WO | 00/44914 | 8/2000 |
| WO | 00/63364 | 10/2000 |
| WO | WO 00/63397 | 10/2000 |
| WO | 01/04313 | 1/2001 |
| WO | WO 01/12824 A1 | 2/2001 |
| WO | 01/29058 | 4/2001 |
| WO | 01/36646 | 5/2001 |
| WO | 01/48183 | 7/2001 |
| WO | 01/70949 | 9/2001 |
| WO | 01/88114 | 11/2001 |
| WO | 02/044321 | 6/2002 |
| WO | 03/006477 | 1/2003 |
| WO | 03/022052 | 3/2003 |
| WO | 03/027298 | 4/2003 |
| WO | 03/056012 | 7/2003 |
| WO | WO 2003/076619 A1 | 9/2003 |
| WO | WO 03/095647 A2 | 11/2003 |

OTHER PUBLICATIONS

Declaration of David M. Stalker filed in opposition to Australian Patent Application No. 778474 (Nov. 4, 2008).*
Reply brief to Examiner's Answer filed on Aug. 26, 2009, U.S. Appl. No. 10/805,804.*
Whatron et al. Journal of General Virology 1994, 75:945-948.*
Que Q. et al., (1998) "Distinct Patterns Of Pigment Suppression Are Produced By Allelic Sense and Antisense Chalcone Synthase Transgenes In Petunia Flowers" *The Plant Journal* 13:401-409.
Partial European Search Report issued Nov. 2, 2007 in connection with European Patent Application No. 07008204.5.
Mar. 7, 2008 Communication To The Examiner, including Mar. 7, 2008 Declaration of Michael Graham, Ph.D. in connection with Merged Reexamination Nos. 90/007,247 and 90/008,096, filed Oct. 4, 2004 and May 18, 2006, respectively.
Agrawal, S. et al. (1995) "Self-Stabilized Oligonucleotides as Novel Antisense Agents", pp. 105-120.
Agrawal et al. (2000.) "Antisense therapeutics: is it as simple as complementary base recognition?" Molecular Medicine Today 6:72-81.
Agrawal, N. et al. (2003) "RNA Interference: Biology, Mechanism, and Applications", Microb. Mol. Biol. Rev. 67:657-685.
Anderson WF, Nature 392:25-30, 1998.
Angell, S.M. et al. (1997), Consistent Gene Silencing in Transgenic Plants Expressing a Replicating Potato Virus X RNA:, The EMBO Journal 16(12): 3675-3684.
Assaad, F.F., et al. (1993), Epigenetic Repeat-Induced Gene Silencing (RIGS) in Arabidopsis. Plant Molecular Biology 22(6): 1067-1085.
Bahramian, M. B. et al., (1999) "Transcriptional and Post-transcriptional Silencing of Rodent α1 (I) Collagen by a Homologous Transcriptionally Self-Silenced Transgene" Molecular and Cellular Biology, vol. 19, No. 1:274-283.

Balandin, T., et al. (1997) "Silencing of a .beta.-1-3-glucanase Transgene is Overcome During Seed Formation", Plant Molecular Biology 34(1) 125-137.
Baulcomb, D.C. (1996) RNA as a Target and an Initiator of Post-Transcriptional Gene Silencing in Transgenic Plants, Plant Molecular Biology 32(1-2): 79-88.
Bevec et al. (1994) "Constitutive expression of chimeric Neo-Rev response element transcripts suppresses HIV-1 replication in human CD4+ T Lymphocytes." Human Gene Therapy 5: 193-201.
Bhan, P. et al. (1997) "2',5'-Linked Oligo-3'-deoxyribonucleoside Phosphorothiate Chimeras: Thermal Stability and Antisense Inhibition of Gene Expression" Nucleic Acids Research, vol. 1, No. 16:3310-3317.
Billy, E. et al. (2001) "Specific interference with gene expression induced by long, double-stranded RNA in mouse embryonal teratocarcinoma cell lines." Proceedings of the National Academy of Sciences of the United States of America 98(25):14428-33.
Bingham, P.M. (1997) "Cosuppression Comes to the Animals". Cell 90(3): 385-387.
Birchler, J. A. (2000) "Making noise about silence: repression of repeated genes in animals" Current Opinion in Genetics & Development 10:211-216.
Boldin, M.P. et al. (1996) "Inovolvement of MACH, a Novel MORT1/FADD-Interacting Protease, in Fas/APO-1-and TNF Receptor-Induced Cell Death" Cell 85:803-815.
Borecky, L. et al. (1981-1982) "Therapeutic Use of Double-Stranded RNAs in Man" Tex Rep Biol Med 14:575-581.
Braich, R. (1997) Regiospecific Solid-Phase Synthesis of Branched Oligonucleotides. Effect of 2', 5'(or 2',3'-) and 3', 5'-Phosphodiester Linkages on the Formation of Hairpin DNA.
Brigneti, Gianinna et al., "Viral pathogenicity determinants are suppressors of transgene silencing in Nicotiana benthamiana", The EMBO Journal, 17(22): 6739-6746 (1998).
Brummelkamp, R. et al. "A System for Stable Expression of Short Interfering RNAs in Mammalian Cells"Science vol. 296:550-553.
Cameron, F.H. and Jennings, P.A. (1991) "Inhibition of Gene Expression by a Short Sense Fragment". Nucleic Acids Research 19(3): 469-475.
Cameron et al. (1994) "Multiple Domains in a Ribozyme Construct Confer Increased Suppressive Activity in Monkey Cells" Antisense Research and Development 4:87-94.
Caplen, Natasha J. et al., "dsRNA-mediated gene silencing in cultured Drosophila cells: a tissue culture model for the analysis of RNA interference", Gene, 252: 95-105 (2000).
Carthew, R. W. (2001) "Gene Silencing by Double-Stranded RNA" Curr. Op. Cell. Biol. 13:244-248.
Chuah et al. (1994) "Inhibition of human immunodeficiencyvirus Type-1 by retroviral vectors expressing antisense-TAR". Human Gene Therapy 5: 1467-1475.
Cogoni, C., et al. (1994), "Suppression of Gene Expression by Homologous Transgenes", Antonie Van Leeuwenhoek 65(3): 205-209.
Cogoni, Carlo et al., "Gene silencing in Neurospora crassa requires a protein homologous to RNA-dependent RNA polymerase", Nature, vol. 399: 166-169 (1999).
Cogoni, Carlo et al., "Posttranscriptional Gene Silencing in Neurospora by a RecQ DNA Helicase", Science, 286: 2342-2344 (1999).
Cogoni, C., et al. (1996), "Transgene Silencing of the al-1 Gene in Vegetative Cells of Neurospora is Mediated by a Cytoplasmic Effector, and Does not Depend on DNA-DNA Interactions or DNA Methylation", The EMBO Journal 15(12): 3153-3163.
Cogoni, C., et al. (1997), "Isolations of Quelling-Defective (qde) Mutants Impaired in Posttranscriptional Transgene-Induced Gene Silencing in Neurospora Crassa". Proceeding of the National Academy of Sciences of the United States of America 94(19): 10233-10238.
Cogoni, C., et al. (2000) "Post-transcriptional gene silencing across kingdoms" Current Opinion in Genetics & Development 10:638-643.
Cohli et al. (1994) "Inhibition of HIV-1 multiplication in a human CD4+ lymphocytic cell line expressing antisense and sense RNA molecules containing HIV-1 packaging signal and Rev response element(s)" Antisense Research and Development 4:19-26.

Courtney-Gutterson, et al. (1994), "Modification of Flower Color in Florist's Chrysanthemum: Production of White-flowering Variety Through Molecular Genetics", Biotechnology 12(3): 268-271.

Couzin, Jennifer (2002) "Small RNAs Make Big Splash" Science 298:2296-2297.

Czauderna, F. et al. (2003) "Structural Variations and Stabilising Modifications of Synthetic siRNAs in Mammalian Cells" Nucleic Acids Research vol. 31, No. 11:1-12.

Dalmay, Tamas et al., "An RNA-Dependent RNA Polymerase Gene in Arabidopsis Is Required for Posttranscriptional Gene Silencing Mediated by a Transgene but Not by a Virus", Cell, 101: 543-553 (2000).

de Carvalho Niebel, F. et al. "Post-transscriptional Cosuppression of .beta.-1,3-glucanase Genes Does Not Effect Accumulation of Transgene Nuclear mRNA", The Plant Cell 7(3): 347-358.

de Carvalho F., et al. (1992), "Suppression of .beta.-1,3-glucanase Transgene Expression in Homozygous Plants", The EMBO Journal 11(7): 2595-2602.

De Lange, P., et al., (1995), "Suppression of Flavonoid Flower Pigmentation Genes in Petunia Hybrida by the Introduction of Antisense and Sense Genes", Current Topics in Microbiology and Immunology 197: 57-75.

Depicker, A., et al. (1997), "Post-transcriptional Gene Silencing in Plants", Current Opinion in Cell Biology 9(3): 373-382.

Ding, Shou Wei, "RNA silencing", Current Opinion in Biotechnology, 11: 152-156 (2000).

Doench, J. G. et al. (2003) "siRNA Can Function as miRNAs" Genes and Development 17:438-442.

Domeier, Mary Ellen et al., "A Link Between RNA Interference and Nonsense-Mediated Decay in Caenorhabditis elegans", Science, 289: 1928-1930 (2000).

Dorer et al. (1994) "Expansion of transgene repeats cause heterochromatin formation and gene silencing in Drosophilia". Cell 77: 993-1002.

Dorer, D.R. and Henikoff, S. (1997) Transgene Repear Arrays Interact with Distant Heterochromatin and Cause Silencing in cis and trans. Genetics 147(3):1181-1190.

Dykxhoorn, D. et al. (2003) "Killing the Messenger: Short RNAs that Silence Gene Expression." Nature Reviews Molecular Cell Biology vol. 4:457-467.

Elbashir, S. M. et al. (2001) "Duplexes of 21-nucleotide RNAs mediate RNA interference in cultured mammalian cells." Nature 411(6836):494-8.

Elbashir, S. M. et al. (2001) "Functional Anatomy of siRNAs for mediating Efficient RNAi in Drosophila Melanogaster Embryo Lysate" The EMBO Journal, vol. 20, No. 23:6877-6888.

Elbashir, S. M. et al. (2002) "Analysis of Gene Function in Somatic Mammalian Cells Using Small Interfering RNAs" Methods 26:199-213.

Engdahl, H.M., et al. (1997) "A Two Unit Antisense RNA Cassette Test System for Silencing of Target Genes", Nucleic Acids Research 25(16): 3218-3227.

English, J.J., et al. (1996) "Suppression of Virus Accumulation in Transgenic Plants Exhibiting Silencing of Nuclear Genes", The Plant Cell 8(2): 179-188.

Fire, A., Xu, S.Q., Montgomery, M.K. Kostas, S.A. Driver, S.E. and Mello, C.C. (1998), "Potent and Specific Genetic Interference by Double-Standard RNA in Caenorhabditis elegans", Nature, 391 (6668): 806-811.

Fire, et al. (1991) "Production of Antisense RNA Leads to Effective and Specific Inhibition of Gene Expression in C. Elegans Muscle" Development, 113(2): 503-514.

Fire, A. (1999) "RNA-triggered gene silencing" Trends Genet. 15(9):358-363.

Flavell, R.B. (1994) "Inactivation of Gene Expression in Plants as a Consequence of Specific Sequence Duplication" Proc. Natl. Acad. Sci. 99:3490-3496.

Fraser et al. (1996) "Effects of c-myc first exons and 5' synthetic hairpins on RNA translation in oocytes and early embryos of Xenopus laevis" Oncogene 12(6):1223-30.

Garrick, D., Fiering, S., Martin, D.I. and Whitelaw, E. (1998), "Repeat-Induced Gene Silencing in Mammals", Nature Genetics 18(1): 56-59.

Gervaix et al. (1997) "Multigene antiviral vectors inhibit diverse human immunodeficiency virus type 1 clades". Journal of Virology 71(4): 3048-3053.

Giordano, E. et al. (2000) "RNAi Triggered by Symmetrically Transcribed Transgenes in Drosophilia Melanogaster" Genetics, 160:637-648.

"Analysis of Hoxd-13 and Hoxd-11 Misexpression in Chick Limb Buds Reveals That Hox Genes Affedt Bith Bone Condensation, and Growth" Development 124:627-636.

Good et al., (1997) "Expression of small, therapeutic RNAs in human cell nuclei" Gene Ther. 4(1):45-54.

Grant, Sarah R. (1999) "Dissecting the Mechanisms of Post-transcriptional Gene Silencing: Divide and Conquer" Cell 96:303-306.

Grasby, J. et al. "Purine Functional Groups in Essential Residues of the Hairpin Ribozyme Required for Catalytic Cleavage of RNA", Biochemistry 34:4068-4076.

Griffey, R. H. et al., (1996) "2'O-Aminopropyl Ribonucleotides: A Zwitterrionic Modification That Enhances The Exonuclease Resistance and Biological Activity of Antisense Oligonucleotides" J. Med. Chem. 39:5100-5109

Gryaznov, S.M. et al. (1993) "Template Controlled Coupling and Recombination of Oligonucleotide Blocks Containing Thiophosphoryl Groups" Nucleic Acids Research, vol. 21, No. 6:1403-1408.

Gura, Trisha, "A silence that speaks volumes", Nature, 404: 804-808 (2000).

Ha, Iiho et al., (1996) "A Bulged 1in-14 RNA Duplex is Sufficient For Caenorhabditis Elegans 1in-14 Temporal Gradient Formation" Gene and Development 10:3041-3050.

Hamilton, A.J., et al. (1998) "A Transgene with Repeated DNA Causes High Frequency, Post-Transcriptional Suppression of ACC-Oxidase Gene Expression in Tomato", The Plant Journal 15(6): 737-746.

Hamilton, Andrew J. et al., "A Species of Small Antisense RNA in Posttranscriptional Gene Silencing in Plants", Science, 286: 950-952 (1999).

Hammond, Scott M. et al., "An RNA-directed nuclease mediates post-transcriptional gene silencing in Drosophila cells", Nature, 414: 293-296 (2000).

Hannon, G.J. (2002) "RNA Interference" Nature, vol. 418:244-251.

Harborth et al. (2003) "Sequence, Chemical, and Structural Variation of Small Interfering RNAs and Short Hairpin RNAs and the Effect on Mammalian Gene Silencing" Antisense and Nucleic Acid Drug Development 13:83-105.

Hoke, Glenn et al., (1991) "Effects of Phosporothioate Capping on Antisense Oligonucleotide Stability, Hybridization and Antiviral Efficacy Versus Herpes Simplex Virus Infection", vol. 19, No. 20:5743-5748.

Holen et al. (2002) "Positional effects of short interfering RNAs targeting the human coagulation trigger Tissue Factor" Nucleic Acids Research 30(8):1757-1766.

Hungarian Patent Office Search Report mailed Jul. 13, 2004, for Hungary patent application No. P0101225, 1 page.

Jen et al. (2000) "Suppression of Gene Expression by Targeted Disruption of Messenger RNA:Available Options and Current Strategies" Stem Cells 18:307-319.

Jorgensen, R. (1990), "Altered Gene Expression in Plants Due to Trans Interactions Between Homologous Genes", Trends in Biotechnology 8(12): 340-344.

Jergensen, R.A. et al. (1996), "Chalcone Synthase Cosuppression Phenotypes in Petunia Flowers: Comparison of Sense vs. Antisense Constructs and Single-Copy vs. Complex T-DNA Sequences", Plant Molecular Biology 31(5): 957-973.

Jorgensen, R.A. et al. (1999) "Do Unintended Antisense Transcripts Contribute To Sense Cosuppression in Plants" TIG 15:11-12.

Kappel et al. Current Opinion in Biotechnology 3:548-553 1992.

Katsuki, Motoya et al., "Conversion of Normal Behavior to Shiverer by Myelin Basic Protein Antisense cDNA in Transgenic Mice", Science, 241: 593-595 (1988).

Kennerdell, Jason (1998) "Use of dsRNA-Mediated Genetic Interference to Demonstrate that Frizzled and Frizzled 2 Act in the Wingless Pathway" Cell, vol. 95:1017-1026.

Kennerdell, Jason (2000) "Heritable Gene Silencing in Drosophila Using Double-Stranded RNA" Nature Biotechnology, 18:896-898.

Kibler et al. (1997) "Double Stranded RNA is a Trigger for Apoptosis in Vaccinia Virus Infected Cells" Journal of Virology, 71(3):1992-2003.

Kitabwalla, M. (2002) "RNA Interference—A New Weapon Against HIV and Beyond" N Engl J. Med, vol. 347, No. 17:1364-1367.

Klink, V.P. et al. (2000) "The Efficacy of RNAi in the Study of the Plant Cytoskeleton" J. Plant Growth Reg. 19:371-384.

Knoester, M. et al. (1997), "Modulation of Stress-Inducible Ethylene Biosynthesis by Sense and Antisense Gene Expression in Tobacco", Plant Science 126(2): 173-183.

Kook, Yoon Hoh et al., "The effect of antisense inhibition of urokinase receptor in human squamous cell carcinoma on malignancy", The EMBO Journal, 13(17): 3983-3991 (1994).

Kowolik, C.M. (2001) "Locus Control Region of the Human CD2 Gene in a Lentivirus Vector Confers Position-Independent Transgene Expression" Journal of Virology, vol. 75, No. 10:4641-4648.

Kowolik, C.M. (2002) "Preferential Transduction of Human Hepatocytes with Lentiviral Vectors Pseudotyped by Sendai Virus F Protein" Molecular Therapy, vol. 5, No. 6:762-769.

Kozak (1989) "Circumstances and mechanisms of inhibition of translation by secondary structure in eucaryotic mRNAs" Mol. Cell. Biol. 9:5134-5142.

Kreutzer, R. et al. "Specific Inhibition of Viral Gene Expression by Double-Stranded RNA in Vitro", Fall Meeting S169.

Kumar Madhur, (1998) "Antisense RNA: Function and Fate of Duplex RNA in Cells of Higher Eukaryotes" Microbiology and Molecular Biology Reviews, vol. 62, No. 4:1415-1434.

Kunz, C., et al (1996) "Developmentally Regulated Silencing and Reactivaation of Tabacco Chitinase Transgene Expression", The Plant Journal 10(3): 437-450.

Lee, K.Y., et al., (1997), "Post-transcriptional Gene Silencing of ACC Synthase in Tomato Results from Cytoplasmic RNA Degradation", The Plant Journal 12(5): 1127-1137.

Lee, R.C., et al. (1993), The C. elegans Heterochronic Gene lin-4 Encodes Small RNAs with Antisense Complementarity to lin-14. Cell 75: 843-854.

Lee et al. (1994) "Inhibition of human immunodeficiency virus type 1 human T cells by a potent Rev response element decoy consisting of 13-nucleotide minimal Rev-binding domain". Journal of Virology 68 (12): 8254-8264.

Li, Y.X. et al. (1999) "Double-Stranded RNA Injections Produces Null Phenotype in Zebrafish" Development Biology vol. 210:238 at 346.

Liebhaber et al. (1992) "Translation inhibition by an mRNA coding region secondary structure is determined by its proximity to the AUG initiation condon" J. Mol. Biol. 226:609-621.

Lin, R. (1999) "Policing Rougue Genes", Nature Vol. 402:128-129.

Lindbo, John et al., "Induction of a Highly Specific Antiviral State in Transgenic Plants: Implications for Regulation of Gene Expression and Virus Resistance", The Plant Cell, 5(12): 1749-1759 (1993).

Lingelbach et al. (1988) "An extended RNA/RNA duplex structure within the coding region of mRNA does not block translational elongaton" Nuc. Acids Res. 16:3405-3414.

Lipinski, C. et al. (1997) "Experimental and Computational Approaches to Estimate solubility and Permeability in Drug Discovery and Development Settings" Advanced Drug Delivery Reviews 23:3-25.

Lisziewicz et al. (1993) "Inhibition of human immunodeficiency virus type 1 replication by regulated expression of a polymeric Tat activation response RNA decoy as a strategy for gene therapy in AIDS." Proceedings of the National Academy of Sciences of the United States of America 90:8000-8004.

Lisziewicz, J. et al. (1991) "Tat-Regulated Production of Multimerized TAR RNA Inhibits HIV-1 Gene Expression" New Biologist 3:82-89.

Loomis et al. (1991) "Antisense RNA inhibition of expression of a pair of tandemly repeated genes results in a delay in cell-cell adhesion in Dictyostelium" Antisense Res. Dev. 1:255-260.

Ma, Michael Y.X. et al. (1993) "Design and Synthesis of RNA Miniduplexes via a Synthetic Linker Approach" Biochemistry 32:1751-1758.

Majumdar, A. et al. (1998) "Targeted Gene Knockout Mediated by Triple Helix Forming Oligonucleotides", Nature Genetics vol. 20:212-214.

Marathe, R. et al. (2000) "RNA virues as inducers, suppressors and targets of post-transcriptional gene silencing" Plant Molecular Biology 43:295-306.

Marx, Jean, "Interfering With Gene Expression", Science, 288: 1370-1372 (2000).

Matzke, M.A., et al. (1998), "Epigenetic Silencing of Plant Transgenes as a Consequence of Diverse Cellular Defence Responses", Cellular and Molecular Life Sciences 54(1): 94-103.

Matzke, M.A. et al. (1995) "How and Why Do Plants Inactivate Homologous (Trans)genes" Plant Physiol. 107:679-685.

Matzke, M.A. et al. (2003) "RNAi Extends Its Reach" Science:1060-1061.

McKenzie, et al., (1999) Transplantation, Science Inc.: 827-874.

McManus, M. T. (2002) "Gene Silencing in Mammals by Small Interfering RNAs" Reviews, vol. 3:737-747.

McManus, et al. (2002) "Gene Silencing using micro-RNA designed hairpins" RNA 8:842-860.

McManus, et al. (2002) "Small Interfering RNA-Mediated Gene Silencing in T Lymphocytes" Journal of Immunology 169:5754-5760.

Metzlaff, M. et al. (1997) "RNA-Mediated RNA Degradation and Chalcone Synthase A Silencing in Petunia" Cell 88:845-854.

Meyer, P. (1996), "Repeat-induced Gene Silencing—Common Mechanisms in Plants and Fungi", Biological Chemistry Hoppe-Seyler 377(2): 87-95.

Mikoshiba et al. (1991) "Molecular biology of myelin basic protein: gene rearrangement and expression of anti-sense RNA in myelin-deficient mutants" Comp. Biochem. Physiol. 98-51-61.

Milhaud, P.G. et al. (1991) "Free and Liposome-Encapsulated Double-Stranded RNAs as Inducers of Interferon, Interleukin-6, and Cellular Toxicity" Journal of Interferon Research 11:261-265.

Montgomery, M.K. (1998) "Double-Stranded RNA as a Mediator in Sequence-Specific Genetic Silencing and Co-Suppression" TIG, vol. 14, No. 7:255-258.

Montgomery, M.K. (1998) "RNA as a Target of Double-Stranded RNA-Mediated Genetic Interference in Caenorhabditis Elegans" Proc. Natl. Acad. Sci. vol. 95:15502-15507.

Moroni, Maria Cristina et al., "EGF-R Antisense RNA Blocks Expression of the Epidermal Growth Factor Receptor and Suppresses the Transforming Phenotype of a Human Carcinoma Cell Line", The Journal of Biological Chemistry, 267(5): 2714-2722 (1992).

Moss, E.G. et al. (1997) "The Cold Shock Domain Protein LIN-28 Controls Development Timing in C. Elegans and is Regulated by the lin-4 RNA", Cell, Vol. 88:637-646.

Mueller, E., et al. (1995) "Homology-dependent Resistance—Transgenic Virus Resistance in Plants Related to Homology-Dependent Gene Silencing", The Plant Journal 7(6): 1001-1013.

Napoli, C., et al. (1990), Introduction of a Chimeric Chalcone Synthase Gene into Petunia Results in Reversible So-Suppression of Homologous Genes in trans, The Plant Cell 2(4): 279-289.

Nellen, W. and Lichtenstein C. (1993), "What Makes a Messenger RNA Anti-Sensitive?" Trends in Biochemical Sciences 18(11): 419-423.

Ngo, Huan et al. (1998) "Double-Stranded RNA Induces mRNA Degradation in Trypanosoma Brucei" Proc. Natl. Acad. Sci. vol. 95:14687-14692.

Nielsen, P. et al. (1997) "A Novel Class of Conformationally Restricted Oligonucleotide Analogues: Synthesis of 2', 3'-Bridged Monomers and RNA-Selective Hybridisaion" Chem. Commun. pp. 825-826.

Nikiforov, T.T. et al. (1992) "Oligodeoxynucleotides Containing 4-thiothymidine and 6-thiodeoxyguanosine as affinity labels for the Eco RV Restriction Endonuclease and Modification Methylase" Nucleic Acids Research, vol. 20, No. 6:1209-1214.

Oates, A.C. et al. (2000) "Too Much Interference: Injection of Double-Stranded RNA Has Nonspecific Effects in the Zebrafish Embryo" Development Biology 224:20-28.

Okano et al. (1991) "Myelin basic protein gene and the function of antisense RNA in its repression in myelin-deficient mutant mouse" J. Neurochem. 56:560-567.

Opalinska et al. (2002) "Nucleic-Acid Therapeutics: Basic Principles and Recent Applications" Nature Reviews 1:503-514.

Paddison, P. J. et al. (2002) Short Hairpin RNAs (shRNAs) Induce Sequence-Specific Silencing in Mammalian Cells' Genes and Development 16:948-958.

Palauqui, J.C. et al. (1997), Systemic Acquired Silencing: Transgene-specific Post-transscriptional Silencing is Transmitted by Grafting from Silenced Stocks to Non-silenced scions, The EMBO Journal 16: 4738-4745.

Palauqui, Jean-Christophe et al., "Transgenes are dispensable for the RNA degradation step of cosuppression" Plant Biology, 95: 9675-9680 (1998).

Pal-Bhadra, M. Bhadra U. and Birchler, J.A. (1997) "Cosuppression in Drosophila: Gene Silencing of Alcohol Dehydrogenase by White-Adh Tarnsgenes is Polycomb Dependent" Cell 90(3): 385-387.

Pang, S.Z., et al. (1997) "Nontarget DNA Sequences Reduce the Transgene Length Necessary for RNA-mediated Tospovirus Resistance in Transgenic Plants", Proceedings of the National Academy of Sciences of the United States of America 94(15): 8261-8266.

Park, Y.D. et al. (1996) "Gene Silencing Mediated by Promotor Homology Occurs at the Level of Transcription and Results in Meiotically Heritable Alterations in Methylation and Gene Activity", The Plant Journal 9(2): 183-194.

Pegram, M.D. et al. (1998) "Phase II study of Receptor-Enhanced Chemosensitivity Using Recombinant Humanized Anti-p185$^{HER2/nue}$ Monoclonal Antibody Plus Cisplain in Patients With HER2/Neu—Overexpressing Metastatic Breast Cancer Refratory to Chemotherapy Treatment" Journal of Clinical Oncology, vol. 16, No. 8:2659-2671.

Pelletier et al. (1985) "Insertion mutagenesis to increase secondary structure within the 5' noncoding region of a eukaryotic mRNA reduces translational efficiency" Cell, 40:515-526.

Peng, J. et al. (2001) "Development of an MFG-Based Retroviral Vector System for Secretion of High Levels of Functionally Active Human BMP4" Molecular Therapy, vol. 4, No. 2:95-104.

Piccin et al. (2001) "Efficient and Heritable Runctional Knock-out of an Adult Phenotype in Drosophila using a GAL4-Driven Hairpin RNA Incorporating a Heterologous Spacer" Nucleic Acids Research, 23(12) E55:1-5.

Plasterk, R. et al. (2000) "The Silence of the Genes" Curr. Op. Gen. Div. 10:562-567.

Putlitz, J. (1999) "Specific Inhibition of Hepatitis B Virus Replication by Sense RNA" Antisense & Nucleic Acid Drug Development 9:241-252.

Que, Q., et al. (1997), "The Frequency and Degree of Cosuppression by Sense Chalcone Synthase Transgenes Are Dependent on Transgene Promoter Strength and Are Reduced by Premature Nonsense Codons in the Transgene Coding Sequence" Plant Cell 9:1357-1368.

Que, Q., et al. (1998), "Homology-based Control of Gene Expression Patterns in Transgenic Petunia Flowers" Developmental Genetics 22(1): 100-109.

Randall et al. (2003) "Clearance of replicating hepatitis C virus replicon RNAs in cell culture by small interfering RNAs" PNAS 100(1):235-240.

Regalado, A. (Aug. 2002) "Turing Off Genes Sheds New Light on How They Work" The Wall Street Journal, 4 pages.

Romano, N., et al. (1992), "Quelling: Transient Inactivation of Gene Expression in Neurospora Crassa by Transformation with Homologous Sequences", Molecular Microbiology 6(22): 3343-3353.

Sadiq, M., et al. (1994), "Developmental Regulation of Antisense-mediated Gene Silencing in Dictyostelium" Antisense Research & Development 4(4): 263-267.

Sarver, N. et al., (1990) "Ribozymes as Potential Anti-HIV-1 Therapeutics Agents" Science 247:1222-1225.

Schaller, H. (2003) "The Role of Sterols in Plant Growth and Development" Prog. Lipid Res. 42:163-175.

Schwarz, D.S. et al. (2002) "Evidence that siRNAs Function as Guides, Not Primers in the Drosophila and Human RNAi Pathways" Molecular Cell, vol. 10:537-548.

Schmidt, F.R. "RNA Interference Detected 20 years ago" Nat. Biotechnol. 22:267-268.

Schmidt, F.R. et al. (1983) "Cycloheximide Induciton of a flatoxin Synthesis in a Nontoxigenic Strain of Aspergillus Flavus" Bio/Technology 1:794-795.

Schmidt, F.R. (1986) "Viral Influences on a flatoxin Formation by Aspergillus Flavus" Appl Microbiol. Biotechnol. 23:238-252.

Schramke, V. (2003) "Hairpin RNAs and Retrotransposon LTRs Effect RNAi and Chromatin-Based Gene Silencing" Science 301:1069-1074.

Selker (1999) "Gene Silencing: repeats that count" Cell 97(2):157-160.

Sharp, Phillip (1999) "RANi and Double-Stranded RNA" Genes and Development 13(2):139-141.

Shi, Y. (1998) "A CBP/p300 Homolog Specific Multiple Differentiation Pathways in Caenorhabditis Elegans" Genes and Development (12)7:943.

Sijen, T., et al. (1996) "RNA-mediated Virus Resistance—Role of Repeated Transgenes and Delineation of Targeted Regions", The Plant Cell 8(12): 2277-2294.

Singer, M.J. et al. (1995) "Genetic and Epigenetic Inactivation of Repetitive Sequences in Neurospora Crassa: RIP, DNA Methylation, and Quelling", Current Topics in Microbiology and Immunology 197: 165-177.

Sinha, N.D. (1997) "Large-Scale Synthesis: Approaches to Large-Scale Synthesis of Oligodeoxynecleotides and their Analogs" Antisense From Technology to Therapy Lab Manual and Textbook, vol. 6:30-58.

Skripkin, E. et al. (1996) "Psoralen Crosslinking Between Human Immunodeficiency Virus Type 1 RNA and Primer tRNA$_3^{Lys}$" Nucleic Acids Research, vol. 24, No. 3:509-514.

Smardon, Anne et al., "EGO-1 is related to RNA-directed RNA polymerase an fuctions in germ-line development and RNA interference in C. elegans" Current Biology, 10(4): 169-178 (2000).

Smith, Neil et al., "Total Silencing by introspliced hairpin RNAs", Nature, 407: 319-320 (2000).

Smyth, D.R. (1997) "Gene Silencing: Cosuppression at a Distance", Current Biology 7(12): R793-795.

Stam, M., et al. (1997) "The Silence of Genes in Transgenic Plants", Annals of Botany 79(1): 3-12.

Steinecke, P. et al. (1992) "Expression of a Chimeric Ribozyme Gene Results in Endocucleolytic Cleavage of a Target mRNA and a Concomitant Reduction of Gene Expression in vivo" Nucleic Acids Res. 23:2259-2268.

Strauss, Evelyn (199) "Candidate Gene Silencers' Found" Science vol. 286, pp. 886.

Sullenger et al. (1990) "Overexpression of TAR sequences rendered cells resistant to human immundeficiency virus replication". Cell 63: 8254-8264.

Sullenger et al. (1990) "Expression of Chimeric tRNA-Driven Antisense Transcripts Renders NIH 3T3 Cells Highly Resistant to Moloney Murine Leukemia Virus Replication" Mol. Cell. Biol. 10:6512-6523.

Sullenger et al. (1991) "Analysis of trans-acting response decoy RNA-mediated inhibition of human immunodeficiency virus type 1 transactivation". Journal of Virology 65(12): 6811-6816.

Sullenger et al. (1993) "Tethering Ribozymes to a Retroviral Packaging Signal for Destruction of Viral RNA" Science 262:1566-1569.

Sun et al. (1993) "Resistance to human immunodeficiency virus type 1 infection conferred by trnasduction of human peripheral blood lymphocytes with ribozyme, antisense, or polymeric transactivation response element constructs". Proceedings of the National Academy of Sciences of the United States of America 92: 7272-7276.

Svoboda, P. et al. (2000) "Selective reduction of dormant maternal mRNAs in mouse oocytes by RNA interference." Development 127 (19):4147-4156.

Svoboda, P. et al. (2001) "RNAi in Mouse Oocytes and Preimplantation Embryos: Effectiveness of Hairpin dsRNA" Biochem. Biophys Res Commun., 287(5):1099-1104.

Tabara, Hiroaki et al., "The rde-1 Gene, RNA Interference, and Transposon Silencing in C. elegans", Cell, 99: 123-132 (1999).

Tanzer, M.M., et al. (1997), "Characterization of Post-Transcriptionally Suppressed Transgene Expression that Confers Resistance to Tobacco Etch Virus Infection in Tobacco", The Plant Cell 9(8): 1411-1423.

Tavernarakis, N. et al., (2000) "Heritable and inducible genetic interference by double-stranded RNA encoded by transgenes" Nature Genetics 24:180-183.

Tijsterman, M. et al. (2002) "The Genetics of RNA Silencing" Ann. Rev. Genet. 36:489-519.

Timmons, L. (1998) "Specific Interference by Ingested dsRNA" Nature, vol. 395:854.

Touchette, "Gene Therapy—Not Ready for Prime Time (News)" Nat. Med. 2(1) 7-8, 1996.

Tuschl, Thomas et al., "Targeted mRNA degradation by double-stranded RNA in vitro ", Genes & Development, 13: 3191-3197 (1999).

Uhlmann, E. (1990) "Antisense Oligonucleotides: A New Therapeutic Principle" Chemical Reviews, vol. 9, No. 4:544-584.

Ui-Tei, K. et al. (2000) "Sensitive assay of RNA interference in Drosophila and Chinese hamster cultured cells using firefly luciferase gene as target" Federation of European Biochemical Societies Letters 479:79-82.

Vacheret, H. Nussaume, et al. (1997) "A Transciptionally Active State is Required for Post-Transcriptional Silencing (Cosuppresion) of Nitrate Reductase Host Genes and Transgenes", The Plant Cell 9(8): 1495-1504.

Van der Krol, et al. "Flavonoid Genes in Petunia: Addition of a Limited Number Of Gene Copies May Lead to a Suppression of Gene Expression", The Plant Cell 2(4): 291-299.

Van der Krol, et al. (1990), "Inhibition of Flower Pigmentation by Antisense CHS Genes: Promoter and Minimal Sequence Requirements for the Antisense Effect", Plant Molecular Biology 14(4): 457-466.

Verma et al. "Gene Therapy—Promises, Problems and Prospects", Nature 389:239-242, 1997.

Viville, in Transgenic Animals, Houdebine (eds), Harwood academic publishers, France. pp307-321, 1997.

Voinnet, Olivier et al. , "Systemic Spread of Sequence-Specific Transgene RNA Degradation in Plants Is Initiated by Localized Introduction of Ectopic Promoterless DNA", Cell, 95: 177-187 (1998).

Wall RJ, "Transgenic Livestock: Progress and Prospects for the Future", Therigenology 45:57-68, 1996.

Wang et al "A factor IX-deficient mouse model for hemophilia B gene therapy", PNAS 94:11563-11566, 1997.

Wargelius, A. et al. (1999) "Double-Stranded RNA Induces Specific Development Defects in Zebrafish Embryos" Biochemical and Biophysical Research Communications 263:156-161.

Wassenegger, Michael et al., "Signalling in gene silencing", Elsevier Science, 4(6): 207-209 (1999).

Waterhouse, Peter et al., "Virus resistance and gene silencing in plants can be induced by simultaneous expression of sense and antisense RNA", Plant Biology, 95: 13959-13964 (1998).

Watson (1988) "A new revision of the sequence of plasmid pBR322" Gene 70:399-403.

Weaver et al. (1981) "Introduction by molecular cloning of artifactual inverted sequences at the 5' terminus of the sense strand of bovine parathyroid hormone cDAN" PNAS 78:4073-4077.

Wess, L. (2003) "Early Days for RNAi" BioCentury, vol. 11, No. 12:A1-23.

Wianny, Florence et al., "Specific interference with gene function by double-stranded RNA in early mouse development", Nature Cell Biology, 2: 70-75 (2000).

Yam, P.Y. et al. (2002) "Design of HIV Vectors for Efficient Gene Delivery into Human Hematopoietic Cells" Molecular Therapy, vol. 5, No. 4:479-484.

Yamamoto, R. et al. (1997) "Inhibition of Transcription by the TAR RNA of HIV-1 in a Nuclear Extract of HeLa Cells" Nucleic Acids Research, vol. 25, No. 17:3445-3450.

Yang, S. et al., (2001) "Specific double-stranded RNA interference in undifferentiated mouse embryonic stem cells" Molecular and Cellular Biology 21(22):7807-16.

Yee, Jiing-Kuan, (2001) "Prospects for Gene Therapy Using HIV-Based Vectors" Somatic Cell and Molecular Genetics, vol. 26, Nos. 1/6:159-173.

Zamore, Phillip D. et al., "RNAi: Double-Stranded RNA Directs the ATP-Dependent Cleavage of mRNA at 21 to 23 Nucleotide Intervals", Cell, 101: 25-33 (2000).

Zhao, J.J. et al. (1993) "Generating Loss-of-Function Phenotype of the Fushi Tarazu Gene with a Targeted Ribozyme in Drosophila" Nature 365:448-451.

International Search Report mailed on Nov. 14, 2002, for PCT patent application No. PCT/AU02/01326 filed Sep. 27, 2002, 4 pages.

International Search Report mailed on May 10, 2001, for PCT patent application No. PCT/AU01/00297 filed Mar. 16, 2001, 2 pages.

International Search Report mailed on May 10, 1999, for PCT patent application No. PCT/AU99/00195 filed Mar. 19, 1999, 3 pages.

Written Opinion mailed on Apr. 17, 2004, for PCT application No. PCT/AU03/01177 filed Sep. 9, 2003, 7 pages.

de Feyter R et al. (1996) "A ribozyme gene and an antisense gene are equally effective in conferring resistance to tobacco mosaic virus on transgenic tobacco" Mol Gen Genet. 250: 329-338.

Suggestion of Interference Pursuant to 37 C.F.R. § 41.202, submitted Apr. 15, 2009, in connection with U.S. Appl. No. 11/364,183, filed Mar. 1, 2006, including attachments thereto.

U.S. Patent Publication No. 2005/0095199 A1, published May 5, 2005 (U.S. Appl. No. 10/482,888, filed Jun. 14, 2004; Steven Whyard et al.), including complete file history.

Advisory Action issued Mar. 25, 2009 in connection with Merged Reexamination Nos. 90/007,247 and 90/008,096, filed Oct. 4, 2004 and May 18, 2006, respectively.

Petition Under 37 C.F.R. § 1.181 submitted Apr. 3, 2009 in connection with Merged Reexamination Nos. 90/007,247 and 90/008,096, filed Oct. 4, 2004 and May 18, 2006, respectively.

Petition Under 37 C.F.R. § 1.182 submitted Apr. 3, 2009 in connection with Merged Reexamination Nos. 90/007,247 and 90/008,096, filed Oct. 4, 2004 and May 18, 2006, respectively.

Petition For Extension of Time submitted Apr. 22, 2009 in connection with Merged Reexamination Nos. 90/007,247 and 90/008,096, filed Oct. 4, 2004 and May 18, 2006, respectively.

Advisory Action issued Apr. 24, 2009 in connection with Merged Reexamination Nos. 90/007,247 and 90/008,096, filed Oct. 4, 2004 and May 18, 2006, respectively.

Decision on Petition Under 37 C.F.R. § 1.181 issued Apr. 25, 2009 in connection with Merged Reexamination Nos. 90/007,247 and 90/008,096, filed Oct. 4, 2004 and May 18, 2006, respectively.

Decision on Petition For Extension of Time issued Apr. 27, 2009 in connection with Merged Reexamination Nos. 90/007,247 and 90/008,096, filed Oct. 4, 2004 and May 18, 2006, respectively.

Amendment submitted Apr. 15, 2009, in connection with U.S. Appl. No. 11/364,183, filed Mar. 1, 2006.

Declaration of Geoffrey Ellacott submitted Apr. 15, 2009, in connection with U.S. Appl. No. 11/364,183, filed Mar. 1, 2006.

Declaration of Neil Smith submitted Apr. 15, 2009, in connection with U.S. Appl. No. 11/364,183, filed Mar. 1, 2006.

Declaration of Peter Michael Waterhouse submitted Apr. 15, 2009, in connection with U.S. Appl. No. 11/364,183, filed Mar. 1, 2006.

Declaration of Dr. Michael Metzlaff Under 37 C.F.R. § 1.132 submitted Apr. 15, 2009, in connection with U.S. Appl. No. 11/364,183, filed Mar. 1, 2006.

Clemens MJ. (1997) "PKR—a protein kinase regulated by double-stranded RNA," Int J Biochem Cell Biol. 29(7):945-9.

Jacobs BL, Langland JO. "When two strands are better than one: the mediators and modulators of the cellular responses to double-stranded RNA," Virology (1996) 219(2):339-49.

Paul CP, Good PD, Winer I, Engelke DR. (2002) "Effective expression of small interfering RNA in human cells," Nat Biotechnol. 20(5):505-8.

Amendment submitted May 4, 2009 in connection with U.S. Appl. No. 10/821,726, filed Apr. 8, 2004.

Giering J.C., et al. (2008) "Expression of shRNA from a tissue-specific pol II promoter is an effective and safe RNAi therapeutic," Mol Ther. 16(9):1630-6.

Song J., et al. (2004) "Poly(U) and polyadenylation termination signals are interchangeable for terminating the expression of shRNA from a pol II promoter," Biochem Biophys Res Commun. 323(2):573-8.

Ruiz F, Vayssi3 L, Klotz C, Sperling L, Madeddu L. (1998) "Homology-dependent gene silencing in Paramecium," Mol Biol Cell. 9(4):931-43.

Sánchez Alvarado A, Newmark PA. (1999) "Double-stranded RNA specifically disrupts gene expression during planarian regeneration," Proc Natl Acad Sci U S A. 96(9):5049-54.

Amendment submitted May 11, 2009 in connection with U.S. Appl. No. 11/179,504, filed Jul. 13, 2005.

Amendment submitted May 11, 2009 in connection with U.S. Appl. No. 10/646,070, filed Jul. 13, 2005.

Office Action issued May 11, 2009 in connection with U.S. Appl. No. 09/287,632, filed Apr. 7, 1999.

Office Action issued May 12, 2009 in connection with U.S. Appl. No. 11/607,062, filed Dec. 1, 2006.

Restriction Requirement issued May 4, 2009 in connection with U.S. Appl. No. 11/841,737, filed Aug. 20, 2007.

Office Action, issued Jun. 9, 2009 in connection with U.S. Appl. No. 10/646,070, filed Jul. 13, 2005.

Amendment submitted Jul. 15, 2009 in connection with U.S. Appl. No. 10/646,070, filed Jul. 13, 2005.

Amendment submitted Jul. 15, 2009 in connection with U.S. Appl. No. 10/571,384, filed Jun. 1, 2006.

Appeal Brief submitted Jul. 27, 2009 in connection with Merged Reexamination Nos. 90/007,247 and 90/008,096, filed Oct. 4, 2004 and May 18, 2006, respectively.

Final Office Action issued May 15, 2009 in connection with U.S. Appl. No. 10/346,853, filed Jan. 17, 2003.

Final Office Action issued Aug. 13, 2009 in connection with U.S. Appl. No. 11/179,504, filed Jul. 13, 2005.

Notice to the applicant regarding a non-compliant or non-responsive amendment issued Sep. 4, 2009 in connection with U.S. Appl. No. 10/821,726, filed Apr. 8, 2004.

Examiner Interview Summary Record (PTOL-413) issued Aug. 12, 2009 in connection with U.S. Appl. No. 11/364,183, filed Mar. 1, 2006.

Supplemental Response or Supplemental Amendment submitted Aug. 10, 2009 in connection with U.S. Appl. No. 11/364,183, filed Mar. 1, 2006.

Notice to the applicant regarding a non-compliant or non-responsive amendment issued Jul. 9, 2009 in connection with U.S. Appl. No. 11/364,183, filed Mar. 1, 2006.

Non-Final Rejection issued Aug. 12, 2009 in connection with U.S. Appl. No. 11/841,737, filed Aug. 20, 2007.

Amendment submitted Jul. 6, 2009 in connection with U.S. Appl. No. 11/841,737, filed Aug. 20, 2007.

Amendment submitted Sep. 24, 2009 in connection with U.S. Appl. No. 10/759,841, filed Jan. 15, 2004.

Communication in response to a non-compliant or non-responsive amendment submitted Oct. 5, 2009 in connection with U.S. Appl. No. 10/821,726, filed Apr. 8, 2004.

Office Action issued Oct. 1, 2009 in connection with U.S. Appl. No. 10/571,384, filed Jun. 1, 2006.

Supplemental Amendment To May 4, 2009 Amendment Filed In Response To Nov. 3, 2008 Office Action And Supplemental Information Disclosure Statement subnitted Oct. 7, 2009 in connection with U.S. Appl. No. 10/821,726, filed Apr. 8, 2004.

Notification of Non-compliant Appeal Brief in Ex Parte Reexamination issued Oct. 22, 2009 in connection with Merged Reexamination Nos. 90/007,247 and 90/008,096, filed Oct. 4, 2004 and May 18, 2006, respectively.

Communication in Response to Notification of Non-compliant Appeal 'Brief submitted Nov. 2, 2009 in connection with Merged Reexamination Nos. 90/007,247 and 90/008,096, filed Oct. 4, 2004 and May 18, 2006, respectively.

Amendment submitted Nov. 5, 2009 in connection with U.S. Appl. No. 09/287,632, filed Apr. 7, 1999.

Office Action issued Nov. 4, 2009 in connection with U.S. Appl. No. 11/364,183, filed Mar. 1, 2006.

Examiner's Answer issued Jan. 7, 2010 in response to applicant's Appeal Brief filed Jun. 27, 2009 in connection with Merged Reexamination Nos. 90/007,247 and 90/008,096, filed Oct. 4, 2004 and May 18, 2006, respectively.

Supplemental Amendment To Oct. 15, 2009 Amendment Filed In Response To May 15, 2009 Final Office Action, Summary of Examiner Interviews, And Supplemental Information Disclosure Statement submitted Dec. 21, 2009 in connection with U.S. Appl. No. 10/346,853, filed Jan. 17, 2003.

Amendment in Response to May 15, 2009 Final Office Action as a Submission to Accompanying Request for Continued Examination submitted Oct. 15, 2009 in connection with U.S. Appl. No. 10/346,853, filed Jan. 17, 2003.

Supplemental Amendment to Sep. 24, 2009 Amendment, Summary of Dec. 17, 2009 Examiner Interview, and Supplemental Information Disclosure Statement submitted Dec. 21, 2009 in connection with U.S. Appl. No. 10/759,841, filed Jan. 15, 2004.

Terminal Disclaimer submitted Nov. 11, 2009 in connection with U.S. Appl. No. 10/646,070, filed Jul. 13, 2005.

Terminal Disclaimer submitted Dec. 14, 2009 in connection with U.S. Appl. No. 10/646,070, filed Jul. 13, 2005.

Office Action issued Dec. 8, 2009 in connection with U.S. Appl. No. 09/287,632, filed Apr. 7, 1999.

Revised Amendment and Reply submitted Aug. 10, 2009 in connection with U.S. Appl. No. 11/364,183, filed Mar. 1, 2006.

Wolff et al. (1995) "Mutational analysis of human U6 RNA: stabilizing the intramolecular helix blocks the spliceosomal assembly pathway," Biochim. Biophys. Acta 1263: 39-44.

Image of U6 snoRNA secondary structure retrieved from http://gene.fudan.sh.cn/snoRNASecStruct/Box%20C&D/Homo%20sapiens/U16_ss_p0001.jpg on Sep. 17, 09.

Response submitted Feb. 3, 2010 in connection with U.S. Appl. No. 11/179,504, filed Jul. 13, 2005.

Advisory Action issued Feb. 16, 2010 in connection with U.S. Appl. No. 11/179,504, filed Jul. 13, 2005.

Notice of Allowability issued Jan. 27, 2010 in connection with U.S. Appl. No. 10/646,070, filed Aug. 22, 2003.

Allen et al. (2007) "Development of strategies for conditional RNA interference," J. Gene Med. 9: 287-298.

Reply Brief to Examiner's Answer filed on Mar. 8, 2010, in connection with merged Reexamination Control Nos. 90/007,247 and 90/008,096, filed Oct. 4, 2004 and May 18, 2006, respectively.

Request for Oral Hearing submitted Mar. 8, 2010, in connection with merged Reexamination Control Nos. 90/007,247 and 90/008,096, filed Oct. 4, 2004 and May 18, 2006, respectively.

Office Action issued Aug. 28, 2009 in connection with Canadian Patent Application No. 2455490, issued by the Canadian Intellectual Property Office.

Third party observations under article 115 EPC against European Patent Application EP 98964202.0 in the name of Carnegie Institution of Washington, submitted to and received by the EPO on Mar. 24, 2009.

Jan. 23, 2003 Statutory Declaration of Neil Andrew Smith, including Exhibits NAS1-NAS25, submitted in re Opposition to Australian Patent Application No. 743316.

May 1, 2008 Declaration Under 37 C.F.R. § 1.131 of Peter Michael Waterhouse, Michael Wayne Graham, Ming-Bo Wang and Neil A. Smith, including Exhibits 1 to 5, submitted May 1, 2008 in connection with U.S. Appl. No. 09/287,632, filed Apr. 7, 1999.

May 8, 2008 Declaration Under 37 C.F.R. § 1.131 of Peter Michael Waterhouse, Michael Wayne Graham, and Ming-Bo Wang, including Exhibits 1 to 3, submitted Jul. 2, 2008 in connection with U.S. Appl. No. 11/364,183, filed Mar. 1, 2006.

Currently pending claims of U.S. Appl. No. 09/287,632, filed Apr. 7, 1999, particularly claims 63, 64, and 103.

Currently pending claims of U.S. Appl. No. 11/364,183, filed Mar. 1, 2006, particularly claim 39.

Nov. 2, 2010 Communication from the UK Intellectual Property Office in connection with GB 2353282, including a Request for Revocation Under s72 UK Patent Act, 1977 filed Sep. 29, 2010 and amended Request for Revocation Under s72 UK Patent Act 1977 filed Oct. 28, 2010.

Ecker, J.R., Devis, R.W., (1986) "Inhibition of gene expression in plant cells by expression of antisense RNA," PNAS 83(15): 5372-5376.

Pal-Bhadra, M., Bhadra U. and Birchlor, J.A. (1997) "Cosuppression in Drosophila: Gene Silencing of Alcohol Dehydrogenase by White-Adh Tarnsgenes is Polycomb Dependent" Cell 90 (3):479-90.

Office Action issued Mar. 9, 2010 in connection with U.S. Appl. No. 10/759,841, filed Jan. 15, 2004.

Office Action isaued Mar. 9, 2010 in connection with U.S. Appl. No. 10/821,726, filed Apr. 8, 2004.

Office Action issued Apr. 15, 2010 in connection with U.S. Appl. No. 10/346,853, filed Jan. 7, 2003.

Amendment as a Submission to Accompanying Request for Continued Examination submitted Apr. 19, 2010 in connection with U.S. Appl. No. 11/179,504, filed Jul. 13, 2005.

Examiner Interview Summary Record (PTOL-413) issued Apr. 15, 2010 in connection with U.S. Appl. No. 10/759,841, filed Jan. 15, 2004.

Wharton et al. (1994) Journal of General Virology, 75:945-948.

Supplemental Information Disclosure Statement submitted Apr. 27, 2010 in connection with U.S. Appl. No. 10/646,070, filed Aug. 22, 2003.

Appeal Brief submitted Apr. 8, 2010 in connection with U.S. Appl. No. 09/287,632, filed Apr. 7, 1999.

Amendment submitted Feb. 12, 2010 in connection with U.S. Appl. No. 11/841,737, filed Aug. 20, 2007.

Final Rejection issued Apr. 23, 2010 in connection with U.S. Appl. No. 11/841,737, filed Aug. 20, 2007.

Supplementary European Search Report issued Feb. 12, 2010 in connection with European Patent Application No. 04761272.

Beck, J., et al. (1995), "Efficient hammerhead ribozyme-mediated cleavage of the structured hepatitis B virus encapsidation signal in vitro and in cell extracts, but not in intact cells," Nucleic Acids Research, vol. 23, No. 24: 4954-4962.

De Angelis, F.G., et al. (2002), "Chimeric snRNA molecules carrying antisense sequences against the splice junctions of exon 51 of the dystrophin pre-mRNA induce exon skipping and restoration of a dystrophin synthesis in delta 48-50 DMD cells," PNAS, vol. 99, No. 14: 9456-9461.

Suter, D., et al. (1999), "Double-target antisense U7 snRNAs promote efficient skipping of an aberrant exon in three human beta-thalassemic mutation," Human Molecular Genetics, vol. 8: 2415-2423.

Baulcomb (1996), "Mechanisms of Pathogen-Derived Resistance to Viruses in Transgenic Plants," Plant Cell, vol. 8:1833-1844.

Genbank Accession No. L26296, Jun. 28, 1994.

Genbank Accession No. AF 124360, Jul. 21, 2000.

Genbank Accession No. A65102, Nov. 14, 2006.

Genbank Accession No. AF043841, Jun. 5, 1999.

Request for Ex Parte Reexamination of U.S. Patent No. 7,138,565, including Exhibits A-K, submitted Apr. 9, 2010.

Notice of Reexamination Request Filing Date, issued Apr. 20, 2010 in connection with Reexamination Control No. 90/009,722, filed Apr. 12, 2010.

Notice of Assignment of Reexamination Request, issued Apr. 20, 2010 in connection with Reexamination Control No. 90/009,722, filed Apr. 12, 2010.

Order Granting Request for Ex Parte Reexamination, issued May 13, 2010 in connection with Reexamination Control No. 90/009,722, filed Apr. 12, 2010.

Reply to the Nov. 4, 2009 Office Action submitted May 4, 2010 in connection with U.S. Appl. No. 11/364,183, filed Mar. 1, 2006.

Amendment submitted Mar. 12, 2009 in connection with U.S. Appl. No. 11/593,056, filed Nov. 6, 2006.

Office Action issued Jun. 24, 2009 in connection with U.S. Appl. No. 11/593,056, filed Nov. 6, 2006.

Amendment submitted Dec. 23, 2009 in connection with U.S. Appl. No. 11/593,056, filed Nov. 6, 2006.

Final Office Action issued Mar. 24, 2010 in connection with U.S. Appl. No. 11/593,056, filed Nov. 6, 2006.

Doelling et al. (1995), PNAS vol. 8:683-692.

Examination Report issued May 10, 2010 in connection with European Patent Application No. 02748428.6.

Office Communication issued Jun. 8, 2010 in connection with U.S. Appl. No. 11/364,183, filed Mar. 1, 2006.

Issue Notification issued Jun. 23, 2010 in connection with U.S. Appl. No. 10/646,070, filed Aug. 22, 2003.

Office Communication issued Jun. 11, 2010 in connection with U.S. Appl. No. 11/364,183, filed Mar. 1, 2006.

Jun. 17, 2010 Declaration of Interference issued in connection with U.S. Appl. No. 11/364,183, filed Mar. 1, 2006.

Jun. 15, 2010 Amendment in Response to Mar. 9, 2010 Office Action, Summary of April 8, 2010 Examiner Interview, and Supplemental Information Disclosure Statement submitted in connection with U.S. Appl. No. 10/759,841, file Jan. 15, 2004.

Communication in Response to Dec. 30, 2009 Office Action, Petition for Three-Month Extension of Time and Supplemental Information Disclosure Statement submitted Jun. 30, 2010 in connection with U.S. Appl. No. 10/482,888, filed Jun. 14, 2004.

Jun. 15, 2010 Supplemental Information Disclosure Statement submitted in connection with U.S. Appl. No. 10/759,841, filed Jan. 15, 2004.

Sep. 29, 2010 Decision of the BPAI in connection with merged Reexamination Control Nos. 90/007,247 and 90/008,096, filed Oct. 4, 2004 and May 18, 2006, respectively.

Sep. 1, 2010 Notice of Allowance issued in connection with U.S. Appl. No. 10/759,841, filed Jan. 15, 2004.

Sep. 22, 2010 Final Office Action issued in connection with U.S. Appl. No. 10/482,888, filed Jun. 14, 2004.

Examiner's Answer issued Jul. 7, 2010 in connection with U.S. Appl. No. 09/287,632, filed Apr. 7, 1999.

Reply Brief submitted Sep. 7, 2010 in connection with U.S. Appl. No. 09/287,632, filed Apr. 7, 1999.

Redeciaration of Interference issued Jul. 6, 2010 in connection with U.S. Appl. No. 11/364,183, filed Mar. 1, 2006.

Redeclaration of Interference issued Sep. 10, 2010 in connection with U.S. Appl. No. 11/364,183, filed Mar. 1, 2006.

Office Action issued. Sep. 30, 2010 in connection with Reexamination Control No. 90/009,722, filed Apr. 12, 2010.

Waibel et al. (1990) "RNA polymerase specificity at transcription of Arabidopsis U snRNA genes determined by promoter element spacing," Letters to Nature, vol. 346, pp. 199-202).

Waibel et al., (1990) "U6 snRNA genes of Arabidopsis are transcribed by RNA polymerase III but contain the same two upstream promoter elements as RNA polymerase II transcribed U-snRNA genes," Nucleic Acids Research, vol. 18, No. 12, pp. 3451-3458.

Marshallsay et al. (1992) "Characterization of the U3 and U6 snRNA genes from wheat: U3 snRNA genes in monocot plants are transcribed by RNA polymerase III," Plant Molecular Biology, vol. 19, pp. 973-983.

Redeclaration of Interference issued Nov. 17, 2010 in connection with U.S. Appl. No. 11/364,183, filed Mar. 1, 2006.

Dec. 9, 2010 Petition to Withdraw from Issue Pursuant to 37 C.F.R. 1.313(c), including a Request for Continued Examination, Amendment, and Supplemental Information Disclosure Statement submitted in connection with U.S. Appl. No. 10/759,841, filed Jan. 15, 2004.

Nov. 30, 2010 Amendment submitted in connection with Reexamination Control No. 90/009,722, filed Apr. 12, 2010.

Counter-Statement of Commonwealth Scientific and Industrial Research Organisation submitted in connection with Application Under s72 UK Patent Act 1977 to Revoke Patent No. GB 2353282, filed Sep. 29, 2010 and amended Oct. 28, 2010.

Office Action issued Dec. 16, 2010 in connection with U.S. Appl. No. 11/179,504, filed Jul. 13, 2005.

Jan. 26, 2011 Office Action issued in connection with U.S. Appl. No. 10/346,853, filed Jan. 17, 2003.

Nov. 5, 2010 Notice of Intent to Issue Reexamination Certificate in connection with merged Reexamination Control Nos. 90/007,247 and 90/008,096, filed Oct. 4, 2004 and May 18, 2006, respectively.

Ex patre Reexamination Certificate issued March 8, 2011 in connection with merged Reexamination Control Nos. 90/007,247 and 90/008,096, filed Oct. 4, 2004 and May 18, 2006, respectively.

Amendment in Response to Jan. 26, 2011 Office Action submitted Feb. 16, 2011 in connection with U.S. Appl. No. 10/346,853, filed Jan. 17, 2003.

Mar. 30, 2011 Office Action issued in connection with U.S. Appl. No. 10/759,841, filed Jan. 15, 2004.
Amendment and Supplemental Information Disclosure Statement as a Submission Accompanying a Request for Continued Examination filed Dec. 15, 2010 in connection with U.S. Appl. No. 10/821,726, filed Apr. 8, 2004.
Office Action issued Mar. 22, 2011 in connection with U.S. Appl. No. 10/821,726, filed Apr. 8, 2004.
Amendment and Supplemental Information Disclosure Statement as a Submission Accompanying a Request for Continued Examination filed Dec. 15, 2010 in connection with U.S. Appl. No. 11/218,999, filed Sep. 2, 2005.
Office Communication Issued Mar. 11, 2011 in connection with Reexamination Control No. 90/009,722, filed Apr. 12, 2010.
Office Action issued Apr. 19, 2011 in connection with U.S. Appl. No. 10/346,853, filed Jan. 7, 2003.
Supplemental Amendment and Statement of the Substance of Interview submitted Apr. 8, 2011 in connection with Reexamination Control No. 90/009,722, filed Apr. 12, 2010.
Examination Report issued Mar. 4, 2011 in connection with European Application No. 04015041.9.
Examination Report issued Mar. 4, 2011 in connection with European Application No. 05013010.3.
May 13, 2011 Response to Apr. 19, 2011 Office Action submitted in connection with U.S. Appl. No. 10/346,853, filed Jan. 7, 2003.
Amendment in Response to Dec. 16, 2010 Office Action submitted May 16, 2011 in connection with U.S. Appl. No. 11/179,504, filed Jul. 13, 2005.
Amendment and Supplemental Information Disclosure Statement filed Jun. 22, 2011 in connection with U.S. Appl. No. 10/821,726, filed Apr. 8, 2004.
Supplemental Information Disclosure Statement filed Jun. 22, 2011 in connection with U.S. Appl. No. 10/821,726, filed Apr. 8, 2004.
Jun. 22, 2011 Office Action issued in connection with Reexamination Control No. 90/009722, filed Apr. 12, 2010.
Amendment in Response to Mar. 30, 2011 Office Action and Supplemental Information Disclosure Statement submitted Jun. 28, 2011 in connection with U.S. Appl. No. 10/759,841, filed Jan. 15, 2004.
May 16, 2011 Request for Revocation Under s72 UK Patent Act 1977 of GB2353282.
Tatsuo, et al. (1997) "Comparison of three non-viral transfection methods for foreign gene expression in early chicken embryos in ovo" Biochemical and Biophysical Research Communications 230, 376-380.
Izant and Wentraub (1984) "Inhibition of Thymidine Kinase Gene Expression by Anti-Sense RNA: A molecular Approach to Genetic Analysis," Cell vol. 36, 1007-1015.
Davenloo, D. Et al. (1984) "Cloning and expression of the gene for bacteriophage T7 RNA polymerase," PNAS vol. 81, pp. 2035-2039.
Rosenberg, A. et al. (1987) "Vectors for selective expression of cloned DNAs by T7 RNA polymerase," Gene. 1987;56(1):125-35.
Jul. 25, 2011 Notice of Allowance issued in connection with U.S. Appl. No. 10/821,726, filed Apr. 8, 2004.
Aug. 4, 2011 Notice of Allowance issued in connection with U.S. Appl. No. 10/346,853, filed Jan. 7, 2003.
U.S. Appl. No. 09/056,767, filed Apr. 8, 1998 (Peter Michael Waterhouse et al.)
U.S. Appl. No. 09/127,735, filed Aug. 3, 1998 (Peter Michael Waterhouse et al.)
U.S. Appl. No. 09/287,632, filed Apr. 7, 1999 (Peter Michael Waterhouse et al.)
U.S. Appl. No. 60/068,562, filed Dec. 23, 1997 (Fire et al.)
U.S. Appl. No. 60/068,562, filed Dec. 23, 1997 (Fire et al.) (redacted version).
Feb. 22, 2011 Amendment submitted in connection with U.S. Appl. No. 10/482,888, filed Jun. 14, 2004.
Apr. 18, 2011 Office Action issued in connection with U.S. Appl. No. 10/482,888, filed Jun. 14, 2004.
Sep. 19, 2011 Response to Apr. 18, 2011 Office Action submitted in connection with U.S. Appl. No. 10/482,888, filed Jun. 14, 2004.
Oct. 27, 2011 Notice of Allowance issued in connection with U.S. Appl. No. 10/482,888, filed Jun. 14, 2004.

Aug. 22, 2011 Reply to Jun. 22, 2011 Office Action submitted in connection with Reexamination Control No. 90/009,722, filed Apr. 12, 2010.
Sep. 14, 2011 Examiner Interview Summary Record issued in connection with Reexamination Control No. 90/009,722, filed Apr. 12, 2010.
Oct. 12, 2011 Statement of the Substance of an Interview and Supplemental Amendment submitted in connection with Reexamination Control No. 90/009,722, filed Apr. 12, 2010.
Oct. 12, 2011 Amended Claims (As Allowed) submitted in connection with Reexamination Control No. 90/009,722, filed Apr. 12, 2010.
Dec. 6, 2011 Notice of Intent to Issue Ex Parte Reexamination Certificate issued in connection with Reexamination Control No. 90/009,722, filed Apr. 12, 2010.
Jul. 12, 2011 Final Office Action issued in connection with U.S. Appl. No. 11/179,504, filed Jul. 13, 2005.
Aug. 24, 2011 Response to Jul. 12, 2011 Final Office Action submitted in connection with U.S. Appl. No. 11/179,504, filed Jul. 13, 2005.
Sep. 2, 2011 Advisory Action issued in connection with U.S. Appl. No. 11/179,504, filed Jul. 13, 2005.
Sep. 9, 2011 Examiner Interview Summary Record issued in connection with U.S. Appl. No. 11/179,504, filed Jul. 13, 2005.
Sep. 19, 2011 Examiner Interview Summary Record issued in connection with U.S. Appl. No. 11/179,504, filed Jul. 13, 2005.
Nov. 11, 2011 Amendment in Response to Jul. 12, 2011 Final Office Action and Sep. 2, 2011 Advisory Action and Petition for a One-Month Extension of Time issued in connection with U.S. Appl. No. 11/179,504, filed Jul. 13, 2005.
Nov. 25, 2011 Advisory Action issued in connection with U.S. Appl. No. 11/179,504, filed Jul. 13, 2005.
Aug. 9, 2011 Final Office Action issued in connection with U.S. Appl. No. 10/759,841, filed Jan. 15, 2004.
Aug. 10, 2011 Response to Aug. 9, 2011 Final Office Action submitted in connection with U.S. Appl. No. 10/759,841, filed Jan. 15, 2004.
Aug. 25, 2011 Notice of Allowance issued in issued in connection with U.S. Appl. No. 10/759,841, filed Jan. 15, 2004.
Kreutzer et al., "Specific inhibition of viral gene expression by double-stranded RNA in vitro," Annual Fall Meeting of the GBH, Abstract for Poster No. 328, p. S169 (1999).
US 5,578,716, 11/1996, Szyf et al. (redacted version).
US 5,631,148, 05/1997, Urdea (redacted version).
US 6,506,559, 01/2003, Fire et al. (redacted version).
U.S. Appl. No. 60/068,562, filed Dec. 23, 1997, Fire et al.
U.S. Appl. No. 60/068,562, filed Dec. 23, 1997, Fire et al. (redacted version).
U.S. Appl. No. 11/905,368, filed Sep. 28, 2007, Andrew Fire et al.
U.S. Appl. No. 09/056,767, filed Apr. 8, 1998, Peter Michael Waterhouse et al.
U.S. Appl. No. 09/127,735, filed Aug. 3, 1998, Peter Michael Waterhouse et al.
U.S. Appl. No. 09/287,632, filed Apr. 7, 1999, Peter Michael Waterhouse et al.
Complete file history for U.S. Patent No. 6,423,885 B1, issued Jul. 23, (U.S. Appl. No. 09/373,720, filed Aug. 13, 1999; Peter Michael Waterhouse and Ming-Bo Wang).
U.S. Patent No. 7,138,565 B2, issued Nov. 21, 2006 (U.S. Appl. No. 10/152,808, filed May 23, 2002; Peter Michael Waterhouse and Ming-Bo Wang), including complete file history.
Amendment submitted Apr. 7, 2006 in connection with U.S. Appl. No. 10/152,808, filed May 23, 2002.
Amendment submitted Jul. 13, 2005, including Terminal Disclaimer in with U.S. Appl. No. 10/152,808, filed May 23, 2002.
Amendment submitted Oct. 22, 2004 in connection with U.S. Appl. No. 10/152,808, filed May 23, 2002.
Notice of Allowability, including Examiner's Statement of Reasons for Allowance issued Jul. 11, 2006 in connection with U.S. Appl. No. 10/152,808, filed May 23, 2002.
Office Action issued Jan. 13, 2005 in connection with U.S. Serial 10/152,808, filed May 23, 2002.
Office Action issued Oct. 7, 2005 in connection with U.S. Appl. No. 10/152,808, filed May 23, 2002.

Office Action issued Sep. 22, 2004 in connection with U.S. Serial No. 10/152,808, filed May 23, 2002.
Preliminary Amendment submitted May 23, 2002 in connection with U.S. Appl. No. 10/152,808, filed May 23, 2002.
U.S. Patent Publication No. 2007-0056057 A1, published Mar. 8, 2007 (U.S. Appl. No. 11/593,056, filed Nov. 6, 2006; Peter Michael Waterhouse and Ming-Bo Wang), including complete file history.
Amendment submitted Jun. 12, 2008 in connection with U.S. Appl. No. 11/593,056, filed Nov. 6, 2006.
Communication submitted Sep. 21, 2007 in connection with U.S. Appl. No. 11/593,056, filed Nov. 6, 2006.
Office Action issued Dec. 12, 2007 in connection with U.S. Appl. No. 11/593,056, filed Nov. 6, 2006.
Office Action issued Jul. 24, 2007 in connection with U.S. Appl. No. 11/593,056, filed Nov. 6, 2006.
Office Action issued Sep. 12, 2008 in connection with U.S. Appl. No. 11/593,056, filed Nov. 6, 2006.
Preliminary Amendment submitted Nov. 6, 2006 in connection with U.S. Appl. No. 11/593,056, filed Nov. 6, 2006.
U.S. Published Application No. 2005/0251877A1, published Nov. 10, 2005 (U.S. Appl. No. 11/179,504, filed Jul. 13, 2005; Peter Michael Waterhouse and Ming-Bo Wang), including complete file history.
Advisory Action issued Jun. 6, 2008 in connection with U.S. Appl. No. 11/179,504, filed Jul. 13, 2005.
Amendment submitted Feb. 15, 2008 in connection with U.S. Appl. No. 11/179,504, filed Jul. 13, 2005, including Exhibit A.
Amendment submitted Feb. 28, 2007 in connection with U.S. Appl. No. 11/179,504, filed Jul. 13, 2005.
Amendment submitted Oct. 18, 2007 in connection with U.S. Appl. No. 11/179,504, filed Jul. 13, 2005.
Amendment submitted Sep. 2, 2008 in connection with U.S. Appl. No. 11/179,504, filed Jul. 13, 2005.
Amendment, including Exhibits A and B submitted May 21, 2008 in connection with U.S. Appl. No. 11/179,504, filed Jul. 13, 2005.
Communication submitted Sep. 2, 2008 in connection with U.S. Appl. No. 11/179,504, filed Jul. 13, 2005.
Interview Summary for Feb. 1, 2008 Interview in connection with U.S. Appl. No. 11/179,504, filed Jul. 13, 2005.
Office Action issued Apr. 18, 2007 in connection with U.S. Appl. No. 11/179,504, filed Jul. 13, 2005.
Office Action issued Dec. 20, 2007 in connection with U.S. Appl. No. 11/179,504, filed Jul. 13, 2005.
Office Action issued Jan. 30, 2007 in connection with U.S. Appl. No. 11/179,504, filed Jul. 13, 2005.
Office Action issued Jul. 30, 2008 in connection with U.S. Appl. No. 11/179,504, filed Jul. 13, 2005.
Office Action issued Mar. 21, 2008 in connection with U.S. Appl. No. 11/179,504, filed Jul. 13, 2005.
Office Action issued Nov. 10, 2008 in connection with U.S. Appl. No. 11/179,504, filed Jul. 13, 2005.
Preliminary Amendment submitted Jul. 13, 2005 in connection with U.S. Appl. No. 11/179,504, filed Jul. 13, 2005.
U.S. Published Application No. 2003/074684 A1, published Apr. 17, 2003 (U.S. Appl. No. 09/997,905, filed Nov. 30, 2001; Michael Wayne Graham and Robert Norman Rice), including complete file history.
Complete file history of U.S. Patent No. 6,573,099, Jun. 3, 2003 (U.S. Appl. No. 09/100,812, filed Jun. 19, 1998; Michael Wayne Graham and Robert Norman Rice).
Advisory Action issued Feb. 15, 2002 in connection with U.S. Appl. No. 09/100,812, filed Jun. 19, 1998.
Amendment submitted Apr. 29, 2002 in connection with U.S. Appl. No. 09/100,812, filed Jun. 19, 1998.
Amendment submitted Nov. 10, 2000 in connection with U.S. Appl. No. 09/100,812, filed Jun. 19, 1998.
Amendment submitted Nov. 12, 2001 in connection with U.S. Appl. No. 09/100,812, filed Jun. 19, 1998.
Amendment submitted Oct. 17, 2002 in connection with U.S. Appl. No. 09/100,812, filed Jun. 19, 1998.
Amendment submitted Sep. 26, 2002 in connection with U.S. Appl. No. 09/100,812, filed Jun. 19, 1998.

Communication submitted Apr. 3, 2000 in connection with U.S. Appl. No. 09/100,812, filed Jun. 19, 1998.
Declaration of Kenneth Clifford Reed submitted Sep. 26, 2002 in connection with U.S. Appl. No. 09/100,812, filed Jun. 19, 1998.
Declaration of Michael Wayne Graham submitted Apr. 29, 2002 in connection with U.S. Appl. No. 09/100,812, filed Jun. 19, 1998.
Declaration of Michael Wayne Graham submitted Sep. 26, 2002 in connection with U.S. Appl. No. 09/100,812, filed Jun. 19, 1998.
Interview Summary issued Jan. 11, 2001 in connection with U.S. Appl. No. 09/100,812, filed Jun. 19, 1998.
Interview Summary issued Sep. 18, 2002 in connection with U.S. Appl. No. 09/100,812, filed Jun. 19, 1998.
Notice of Allowability, including Examiner's Amendment and Examiner's Statement of Reasons for Allowance issued Nov. 20, 2002 in connection with U.S. Appl. No. 09/100,812, filed Jun. 19, 1998.
Office Action issued Dec. 2, 1999 in connection with U.S. Serial No. 09/100,812, filed Jun. 19, 1998.
Office Action issued Feb. 12, 2001 in connection with U.S. Serial No. 09/100,812, filed Jun. 19, 1998.
Office Action issued May 10, 2000 in connection with U.S. Appl. No. 09/100,812, filed Jun. 19, 1998.
U.S. Published Application No. 2003/0159161 A1, published Aug. 21, 2003 (U.S. Appl. No. 10/346,853, filed Jan. 17, 2003; Michael Wayne Graham and Robert Norman Rice), including complete file history.
Amendment and Request for Continued Examination submitted Jan. 7, 2009 in connection with U.S. Appl. No. 10/346,853, filed Jan. 17, 2003.
Amendment submitted Apr. 16, 2008 in connection with U.S. Appl. No. 10/346,853, filed Jan. 17, 2003.
Amendment submitted Dec. 27, 2006 in connection with U.S. Appl. No. 10/346,853, filed Jan. 17, 2003.
Amendment submitted Feb. 22, 2007, in connection with U.S. Appl. No. 10/346,853, filed Jan. 17, 2003.
Amendment submitted Jan. 17, 2003 in connection with U.S. Appl. No. 10/346,853, filed Jan. 17, 2003.
Amendment submitted Mar. 25, 2003 in connection with U.S. Appl. No. 10/346,853, filed Jan. 17, 2003.
Amendment submitted Oct. 17, 2007 in connection with U.S. Appl. No. 10/346,853, filed Jan. 17, 2003.
Communication submitted Aug. 2, 2005 in connection with U.S. Appl. No. 10/346,853, filed Jan. 17, 2003.
Decision on Petition to Make Special Under 37 CFR 1.102(d) submitted Jul. 27, 2004 in connection with U.S. Appl. No. 10/346,853, filed Jan. 17, 2003.
Interview Summary issued Dec. 11, 2007 in connection with U.S. Appl. No. 10/346,853, filed Jan. 17, 2003.
Notice of Improper Request for Continued Examination issued Oct. 29, 2008 in connection with U.S. Appl. No. 10/346,853, filed Jan. 17, 2003.
Office Action issued Apr. 17, 2007 in connection with U.S. Appl. No. 10/346,853, filed Jan. 17, 2003.
Office Action issued Jan. 16, 2008 in connection with U.S. Appl. No. 10/346,853, filed Jan. 17, 2003.
Office Action issued Jul. 22, 2005 in connection with U.S. Appl. No. 10/346,853, filed Jan. 17, 2003.
Office Action issued Jul. 7, 2008 in connection with U.S. Appl. No. 10/346,853, filed Jan. 17, 2003.
Office Action issued Jun. 27, 2006 in connection with U.S. Appl. No. 10/346,853, filed Jan. 17, 2003.
Petition for Unintentionally Delayed Claim of Priority under 37 CFR §1.78(a) (3) submitted Dec. 27, 2006 in connection with U.S. Appl. No. 10/346,853, filed Jan. 17, 2003.
Petition to Make Special Under 37 CFR 1.102(d) submitted Jul. 27, 2004 in connection with U.S. Appl. No. 10/346,853, filed Jan. 17, 2003.
Request for Continued Examination submitted Oct. 7, 2008 in connection with U.S. Appl. No. 10/346,853, filed Jan. 17, 2003.
U.S. Published Application No. 2004/0180439 A1, pub. Sep. 16, 2004 (U.S. Appl. No. 10/759,841, filed Jan. 15, 2004; Michael Wayne Graham and Robert Norman Rice), including complete file history.

Amendment submitted Apr. 15, 2008 in connection with U.S. Appl. No. 10/759,841, filed Jan. 15, 2004.
Amendment submitted Dec. 29, 2006 in connection with U.S. Appl. No. 10/759,841, filed Jan. 15, 2004.
Amendment submitted Feb. 21, 2007, in connection with U.S. Appl. No. 10/759,841, filed Jan. 15, 2004.
Amendment submitted Oct. 25, 2007 in connection with U.S. Appl. No. 10/759,841, filed Jan. 15, 2004.
Amendment submitted Oct. 31, 2006 in connection with U.S. Appl. No. 10/759,841, filed Jan. 15, 2004.
Amendment submitted Oct. 9, 2008 in connection with U.S. Appl. No. 10/759,841, filed Jan. 15, 2004.
Interview Summary for Dec. 22, 2008 in connection with U.S. Appl. No. 10/759,841, filed Jan. 15, 2004.
Interview Summary for Feb. 12, 2009 Interview in connection with U.S. Appl. No. 10/759,841, filed Jan. 15, 2004.
Interview Summary issued Dec. 11, 2007 in connection with U.S. Appl. No. 10/759,841, filed Jan. 15, 2004.
Office Action issued Apr. 25, 2007 in connection with U.S. Appl. No. 10/759,841, filed Jan. 15, 2004.
Office Action issued Jan. 22, 2009 in connection with U.S. Appl. No. 10/759,841, filed Jan. 15, 2004.
Office Action issued Jan. 6, 2009 in connection with U.S. Appl. No. 10/759,841, filed Jan. 15, 2004.
Office Action issued Jan. 8, 2008 in connection with U.S. Appl. No. 10/759,841, filed Jan. 15, 2004.
Office Action issued Jul. 31, 2006 in connection with U.S. Appl. No. 10/759,841, filed Jan. 15, 2004.
Office Action issued Jul. 9, 2008 in connection with U.S. Appl. No. 10/759,841, filed Jan. 15, 2004.
Office Action issued Nov. 29, 2006 in connection with U.S. Appl. No. 10/759,841, filed Jan. 15, 2004.
Preliminary Amendment submitted Jan. 15, 2004 in connection with U.S. Appl. No. 10/759,841, filed Jan. 15, 2004.
Complete file history for U.S. Published Application No. 2004/0266005 A1, published Dec. 30, 2004 (U.S. Appl. No. 10/821,726, filed Apr. 8, 2004; Michael Wayne Graham et al.)
Amendment and Request for Continued Examination Submitted Sep. 5, 2008 in connection with U.S. Appl. No. 10/821,726, filed Apr. 8, 2004.
Amendment submitted Aug. 2, 2007 in connection with U.S. Appl. No. 10/821,726, filed Apr. 8, 2004.
Amendment submitted Dec. 14, 2006 in connection with U.S. Appl. No. 10/821,726, filed Apr. 8, 2004.
Amendment submitted Nov. 14, 2005 in connection with U.S. Appl. No. 10/821,726, filed Apr. 8, 2004.
Amendment submitted Nov. 30, 2006 in connection with U.S. Appl. No. 10/821,726, filed Apr. 8, 2004.
Amendment submitted Oct. 31, 2007 in connection with U.S. Appl. No. 10/821,726, filed Apr. 8, 2004.
Amendment, including Exhibits A to C submitted Sep. 5, 2008 in connection with U.S. Appl. No. 10/821,726, filed Apr. 8, 2004.
Communication issued Apr. 2, 2007 in connection with U.S. Appl. No. 10/821,726, filed Apr. 8, 2004.
Decision on Petition to Make Special Under 37 CFR 1.102(d) issued Jul. 28, 2004 in connection with U.S. Appl. No. 10/821,726, filed Apr. 8, 2004.
Office Action issued May 30, 2006 in connection with U.S. Appl. No. 10/821,726, filed Apr. 8, 2004.
Office Action issued Nov. 3, 2008 in connection with U.S. Appl. No. 10/821,726, filed Apr. 8, 2004.
Office Action issued Nov. 6, 2007 in connection with U.S. Appl. No. 10/821,726, filed Apr. 8, 2004.
Office Action issued Oct. 14, 2005 in connection with U.S. Appl. No. 10/821,726, filed Apr. 8, 2004.
Office Action issued Sep. 2, 2008 in connection with U.S. Appl. No. 10/821,726, filed Apr. 8, 2004.
Petition to Make Special Under 37 CFR 1.102(d) submitted Jul. 28, 2004 in connection with U.S. Appl. No. 10/821,726, filed Apr. 8, 2004.
Preliminary Amendment submitted Apr. 8, 2004 in connection with U.S. Appl. No. 10/821,726, filed Apr. 8, 2004.
Request to Correct Inventorship Under 37 C.F.R. §1.48(a) submitted Dec. 12, 2007 in connection with U.S. Appl. No. 10/821,726, filed Apr. 8, 2004.
U.S. Published Application No. 2005/0250208 A1, pub. Nov. 10, 2005 (U.S. Appl. No. 11/180,928, filed Jul. 13, 2005; Michael Wayne Graham et al.), including complete file history.
Amendment submitted Dec. 22, 2006, in connection with U.S. Appl. No. 11/180,928, filed Jul. 13, 2005.
Amendment submitted Jun. 6, 2008 in connection with U.S. Appl. No. 11/180,928, filed Jul. 13, 2005.
Amendment submitted Oct. 17, 2007 in connection with U.S. Appl. No. 11/180,928, filed Jul. 13, 2005.
Communication submitted Mar. 6, 2007 in connection with U.S. Appl. No. 11/180,928, filed Jul. 13, 2005.
Interview Summary issued Dec. 11, 2007 in connection with U.S. Appl. No. 11/180,928, filed Jul. 13, 2005.
Office Action issued Apr. 17, 2007 in connection with U.S. Appl. No. 11/180,928, filed Jul. 13, 2005.
Office Action issued Feb. 6, 2007 in connection with U.S. Appl. No. 11/180,928, filed Jul. 13, 2005.
Office Action issued Jan. 8, 2008 in connection with U.S. Appl. No. 11/180,928, filed Jul. 13, 2005.
Office Action issued Oct. 31, 2006 in connection with U.S. Appl. No. 11/180,928, filed Jul. 13, 2005.
Preliminary Amendment submitted Jul. 13, 2005 in connection with U.S. Appl. No. 11/180,928, filed Jul. 13, 2005.
Request to Correct Inventorship Under 37 C.F.R. §1.48(a) filed Oct. 17, 2007 in connection with U.S. Appl. No. 11/180,928, filed Jul. 13, 2005.
U.S. Published Application No. 2004/0237145 A1, published Nov. 25, 2004 (U.S. Appl. No. 10/821,710, filed Apr. 8, 2004; Michael Wayne Graham et al.), including complete file history.
Advisory Action issued Jul. 20, 2007 in connection with U.S. Appl. No. 10/821,710, filed Apr. 8, 2004.
Advisory Action issued Sep. 14, 2005 in connection with U.S. Appl. No. 10/821,710, filed Apr. 8, 2004.
Amendment submitted Apr. 29, 2005 in connection with U.S. Appl. No. 10/821,710, filed Apr. 8, 2004.
Amendment submitted Aug. 29, 2005 in connection with U.S. Appl. No. 10/821,710, filed Apr. 8, 2004.
Amendment submitted Dec. 15, 2004 in connection with U.S. Appl. No. 10/821,710, filed Apr. 8, 2004.
Amendment submitted Feb. 7, 2008 in connection with U.S. Appl. No. 10/821,710, filed Apr. 8, 2004.
Amendment submitted Jul. 12, 2007 in connection with U.S. Appl. No. 10/821,710, filed Apr. 8, 2004.
Amendment submitted Jul. 25, 2007 in connection with U.S. Appl. No. 10/821,710, filed Apr. 8, 2004.
Amendment submitted Nov. 20, 2006 in connection with U.S. Appl. No. 10/821,710, filed Apr. 8, 2004.
Amendment submitted Oct. 31, 2007 in connection with U.S. Appl. No. 10/821,710, filed Apr. 8, 2004.
Decision on Petition to Make Special Under 37 CFR 1.102(d) submitted Jul. 23, 2004 in connection with U.S. Appl. No. 10/821,710, filed Apr. 8, 2004.
Interview Summary issued Nov. 6, 2006 in connection with U.S. Appl. No. 10/821,710, filed Apr. 8, 2004.
Notice of Abandonment issued Dec. 15, 2008 in connection with U.S. Appl. No. 10/821,710, filed Apr. 8, 2004.
Office Action issued Apr. 17, 2008 in connection with U.S. Appl. No. 10/821,710, filed Apr. 8, 2004.
Office Action issued Aug. 7, 2007 in connection with U.S. Appl. No. 10/821,710, filed Apr. 8, 2004.
Office Action issued Feb. 11, 2005 in connection with U.S. Appl. No. 10/821,710, filed Apr. 8, 2004.
Office Action issued Feb. 8, 2005 in connection with U.S. Appl. No. 10/821,710, filed Apr. 8, 2004.
Office Action issued Jan. 12, 2007 in connection with U.S. Appl. No. 10/821,710, filed Apr. 8, 2004.
Office Action issued Jun. 19, 2006 in connection with U.S. Appl. No. 10/821,710, filed Apr. 8, 2004.
Office Action issued Jun. 29, 2005 in connection with U.S. Appl. No. 10/821,710, filed Apr. 8, 2004.

Office Action issued Oct. 15, 2004 in connection with U.S. Appl. No. 10/821,710, filed Apr. 8, 2004.
Petition to Make Special Under 37 CFR 1.102(d) submitted Jul. 23, 2004 in connection with U.S. Appl. No. 10/821,710, filed Apr. 8, 2004.
Preliminary Amendment submitted Dec. 21, 2005 in connection with U.S. Appl. No. 10/821,710, filed Apr. 8, 2004.
Request to Correct Inventorship Under 37 C.F.R. §1.48(a) submitted Dec. 12, 2007 in connection with U.S. Appl. No. 10/821,710, filed Apr. 8, 2004.
U.S. Published Application No. 2006/0014715, published Jan. 19, 2006 (U.S. Appl. No. 11/218,999, filed Sep. 2, 2005; Michael Wayne Graham et al.), including complete file history.
Amendment submitted Feb. 19, 2008 in connection with U.S. Appl. No. 11/218,999, filed Sep. 2, 2005.
Amendment submitted Jun. 17, 2008 in connection with U.S. Appl. No. 11/218,999, filed Sep. 2, 2005.
Amendment submitted Oct. 31, 2007 in connection with U.S. Appl. No. 11/218,999, filed Sep. 2, 2005.
Office Action issued May 21, 2008 in connection with U.S. Appl. No. 11/218,999, filed Sep. 2, 2005.
Office Action issued Sep. 17, 2007 in connection with U.S. Appl. No. 11/218,999, filed Sep. 2, 2005.
Office Action issued Sep. 30, 2008 in connection with U.S. Appl. No. 11/218,999, filed Sep. 2, 2005.
Preliminary Amendment To The Accompanying Divisional Application Filed Under 37 C.F.R. §1.53, Submission of Sequence Listing and Information Disclosure Statement submitted Sep. 2, 2005 in connection with U.S. Serial No. 11/278,999, filed Sep. 2, 2005.
Request to Correct Inventorship Under 37 C.F.R. §1.48(a) submitted Oct. 31, 2007 in connection with U.S. Appl. No. 11/218,999, filed Sep. 2, 2005.
U.S. Published Application No. 2004/0064842 A1, Apr. 1, 2004 (U.S. U.S. Appl. No. 10/646,070, filed Aug. 22, 2003; Michael Wayne Graham and Robert Norman Rice), including complete file history.
Amendment issued Jan. 24, 2008 in connection with U.S. Appl. No. 10/646,070, filed Aug. 22, 2003.
Amendment submitted Apr. 7, 2005 in connection with U.S. Appl. No. 10/646,070, filed Aug. 22, 2003.
Amendment submitted Aug. 11, 2006 in connection with U.S. Appl. No. 10/646,070, filed Aug. 22, 2003.
Amendment submitted Dec. 15, 2004 in connection with U.S. Appl. No. 10/646,070, filed Aug. 22, 2003.
Amendment submitted Dec. 27, 2005 in connection with U.S. Appl. No. 10/646,070, filed Aug. 22, 2003.
Amendment submitted Feb. 28, 2007 in connection with U.S. Appl. No. 10/646,070, filed Aug. 22, 2003.
Amendment submitted Jul. 24, 2006 in connection with U.S. Appl. No. 10/646,070, filed Aug. 22, 2003.
Amendment submitted Jul. 24, 2008 in connection with U.S. Appl. No. 10/646,070, filed Aug. 22, 2003.
Amendment submitted Jun. 22, 2006 in connection with U.S. Appl. No. 10/646,070, filed Aug. 22, 2003.
Amendment submitted Oct. 10, 2008 in connection with U.S. Appl. No. 10/646,070, filed Aug. 22, 2003.
Amendment submitted Oct. 29, 2007 in connection with U.S. Appl. No. 10/646,070, filed Aug. 22, 2003.
Amendment, including Exhibits A to I submitted Jul. 24, 2008 in connection with U.S. Appl. No. 10/646,070, filed Aug. 22, 2003.
Decision on Petition to Make Special Under 37 CFRr 1.102(d) submitted Jul. 27, 2004 in connection with U.S. Appl. No. 10/646,070, filed Aug. 22, 2003.
Interview Summary issued Dec. 11, 2007 in connection with U.S. Appl. No. 10/646,070, filed Aug. 22, 2003.
Notice to Comply with Requirements for Patent Applications Containing Nucleotide Sequence and/or Amino Acid Protein Sequence Disclosures issued Oct. 27, 2005 in connection with U.S. Appl. No. 10/646,070, filed Aug. 22, 2003.
Office Action issued Apr. 27, 2007 in connection with U.S. Appl. No. 10/646,070, filed Aug. 22, 2003.
Office Action issued Aug. 11, 2006 in connection with U.S. Appl. No. 10/646,070, filed Aug. 22, 2003.
Office Action issued Aug. 28, 2006 in connection with U.S. Appl. No. 10/646,070, filed Aug. 22, 2003.
Office Action issued Jul. 24, 2006 in connection with U.S. Appl. No. 10/646,070, filed Aug. 22, 2003.
Office Action issued Nov. 4, 2008 in connection with U.S. Appl. No. 10/646,070, filed Aug. 22, 2003.
Office Action issued Oct. 15, 2004 in connection with U.S. Appl. No. 10/646,070, filed Aug. 22, 2003.
Petition to Make Special Under 37 Cfr 1.102(d) submitted Jul. 27, 2004 in connection with U.S. Appl. No. 10/646,070, filed Aug. 22, 2003.
Preliminary Amendment submitted Aug. 22, 2003 in connection with U.S. Appl. No. 10/646,070, filed Aug. 22, 2003.
U.S. Appl. No. 09/100,813, filed Jun. 19, 1998 (Michael Wayne Graham), including complete file history.
U.S. Appl. No. 09/646,807, filed Dec. 5, 2000 (Michael Wayne Graham et al.), including complete file history.
Amendment submitted Dec. 18, 2002 in connection with U.S. Appl. No. 09/646,807, filed Dec. 5, 2000.
Amendment submitted Dec. 27, 2005 in connection with U.S. Appl. No. 09/646,807, filed Dec. 5, 2000.
Amendment submitted Dec. 28, 2006 in connection with U.S. Appl. No. 09/646,807, filed Dec. 5, 2000.
Amendment submitted Dec. 7, 2004 in connection with U.S. Appl. No. 09/646,807, filed Dec. 5, 2000.
Amendment submitted Mar. 10, 2005 in connection with U.S. Appl. No. 09/646,807, filed Dec. 5, 2000.
Amendment submitted Sep. 8, 2003 in connection with U.S. Appl. No. 09/646,807, filed Dec. 5, 2000.
Communication issued Feb. 17, 2005 in connection with U.S. Appl. No. 09/646,807, filed Dec. 5, 2000.
Communication issued Oct. 27, 2005 in connection with U.S. Appl. No. 09/646,807, filed Dec. 5, 2000.
Office Action issued Dec. 17, 2003 in connection with U.S. Appl. No. 09/646,807, filed Dec. 5, 2000.
Office Action issued Jul. 8, 2008 in connection with U.S. Appl. No. 09/646,807, filed Dec. 5, 2000.
Office Action issued Jun. 28, 2006 in connection with U.S. Appl. No. 09/646,807, filed Dec. 5, 2000.
Office Action issued Mar. 7, 2003 in connection with U.S. Appl. No. 09/646,807, filed Dec. 5, 2000.
Office Action issued Nov. 18, 2002 in connection with U.S. Appl. No. 09/646,807, filed Dec. 5, 2000.
Petition for Unintentionally Delayed Claim of Priority under 37 CFR § 1.78(a) submitted Dec. 28, 2006 in connection with U.S. Appl. No. 09/646,807, filed Dec. 5, 2000.
Preliminary Amendment submitted Jul. 30, 2001 in connection with U.S. Appl. No. 09/646,807, filed Dec. 5, 2000.
Preliminary Amendment subinitted May 14, 2001 in connection with U.S. Appl. No. 09/646,807, filed Dec. 5, 2000.
Preliminary Amendment submitted Sep. 20, 2000 in connection with U.S. Appl. No. 09/646,807, filed Dec. 5, 2000.
Request to Correct Inventorship Under 37 C.F.R. §1.48(a) submitted Dec. 12, 2007 in connection with U.S. Appl. No. 09/646,807, filed Dec. 5, 2000.
File of Re-examination Control No. 90/007,247, filed Oct. 4, 2004 including all references cited and disclosed, rejections and arguments therein (reexamination of U.S. Patent No. 6,573,099, issued Jun. 3, 2003 from U.S. Appl. No. 09/100,812).
Amendment submitted Jun. 12, 2006 in connection with U.S. Reexamination No. 90/007,247, filed Oct. 4, 2004.
Amendment submitted Nov. 28, 2005 in connection with U.S. Reexamination No. 90/007,247, filed Oct. 4, 2004.
Declaration [of Michael Graham, Ph.D.] Under 37 C.F.R. § 1.131 included With the Amendment submitted Jun. 12, 2006 in connection with U.S. Reexamination No. 90/007,247, filed Oct. 4, 2004.
Declaration of Michael Graham Under 37 C.F.R. § 1.132 included with the Amendment submitted Nov. 28, 2005 in connection with U.S. Reexamination No. 90/007,247, filed Oct. 4, 2004.
Ex Parte Reexamination Interview Summary issued Oct. 25, 2005 in connection with U.S. Reexamination No. 90/007,247, filed Oct. 4, 2004.

Letter to Examiner submitted Mar. 1, 2006, including a copy of a communication from the Australian Patent Office in connection with U.S. Reexamination No. 90/007,247, filed Oct. 4, 2004.
Office Action issued Apr. 12, 2006 in connection with U.S. Reexamination No. 90/007,247, filed Oct. 4, 2004.
Office Action issued Aug. 31, 2005 in connection with U.S. Reexamination No. 90/007,247, filed Oct. 4, 2004.
Order Granting/Denying Request for Ex Parte Rexamination issued. Dec. 7, 2004 in connection with U.S. Reexamination No. 90/007,247, filed Oct. 4, 2004.
Request for Reexamination Pursuant to 35 U.S.C. §§ 302-307 and 37 C.F.R. § 1.510, submitted Oct. 4, 2004 in connection with U.S. Reexamination No. 90/007,247, filed Oct. 4, 2004.
Statement of the Content of the Interview Under 37 C.F.R. § 1.560(b) in connection with U.S. Reexamination No. 90/007,247, filed Oct. 4, 2004.
Amendment submitted Apr. 24, 2007 in connection with Merged Reexamination Nos. 90/007,247 and 90/008,096, filed Oct. 4, 2004 and May 18, 2006, respectively.
Amendment submitted Aug. 3, 2007 in connection with Merged Reexamination Nos. 90/007,247 and 90/008,096, filed Oct. 4, 2004 and May 18, 2006, respectively.
Declaration [of Kenneth Reed, Ph.D.] Under 37 C.F.R. § 1.131 submitted Apr. 24, 2007 in connection with Merged Reexamination Nos. 90/007,247 and 90/008,096, filed Oct. 4, 2004 and May 18, 2006, respectively.
Declaration [of Michael Graham, Ph.D.] Under 37 C.F.R. § 1.131 submitted Apr. 24, 2007 in connection with Merged Reexamination Nos. 90/007,247 and 90/008,096, filed Oct. 4, 2004 and May 18, 2006, respectively.
Interview Summary issued Jul. 6, 2007 in connection with Merged Reexamination Nos. 90/007,247 and 90/008,096, filed Oct. 4, 2004 and May 18, 2006, respectively.
Interview Summary issued Mar. 2, 2007 in connection with Merged Reexamination Nos. 90/007,247 and 90/008,096, filed Oct. 4, 2004 and May 18, 2006, respectively.
Office Action issued Apr. 11, 2008 in connection with Merged Reexamination Nos. 90/007,247 and 90/008,096, filed Oct. 4, 2004 and May 18, 2006, respectively.
Office Action issued Jan. 24, 2007 in connection with Merged Reexamination Nos. 90/007,247 and 90/008,096, filed Oct. 4, 2004 and May 18, 2006, respectively.
Statement of the Content of the Interview Under 37 C.F.R. § 1.560(b) in connection with Merged Reexamination Nos. 90/007,247 and 90/008,096, filed Oct. 4, 2004 and May 18, 2006, respectively.
Summary of the Interview and Comments on Examiner's Notes submitted Mar. 16, 2007 in connection with Merged Reexamination Nos. 90/007,247 and 90/008,096, filed Oct. 4, 2004 and May 18, 2006, respectively.
Declaration of Dr. Arthur Riggs Under Under 37 C.F.R. §1.132, including Exhibits A to I submitted Feb. 26, 2009 in connection with Merged Reexamination Nos. 90/007,247 and 90/008,096, filed Oct. 4, 2004 and May 18, 2006, respectively.
Amendment after Final submitted Feb. 26, 2009 in connection with Merged Reexamination Nos. 90/007,247 and 90/008,096, filed Oct. 4, 2004 and May 18, 2006, respectively.
Amendment submitted Jul. 11, 2008 in connection with Merged Reexamination Nos. 90/007,247 and 90/008,096, filed Oct. 4, 2004 and May 18, 2006, respectively.
Interview Summary issued Feb. 12, 2009 in connection with Merged Reexamination Nos. 90/007,247 and 90/008,096, filed Oct. 4, 2004 and May 18, 2006, respectively.
Interview Summary issued Jun. 12, 2008 in connection with Merged Reexamination Nos. 90/007,247 and 90/008,096, filed Oct. 4, 2004 and May 18, 2006, respectively.
Amendment submitted Nov. 28, 2007 in connection with Merged Reexamination Nos. 90/007,247 and 90/008,096, filed Oct. 4, 2004 and May 18, 2006, respectively.
Office Action issued Nov. 26, 2008 in connection with Merged Reexamination Nos. 90/007,247 and 90/008,096, filed Oct. 4, 2004 and May 18, 2006, respectively.

Office Action issued Nov. 19, 2008 in connection with Merged Reexamination Nos. 90/007,247 and 90/008,096, filed Oct. 4, 2004 and May 18, 2006, respectively.
File of Re-examination Control No. 90/008,096, filed May 18, 2006 including all references cited and disclosed, rejections and arguments therein (reexamination of U.S. Patent No. 6,573,099, issued Jun. 3, 2003 from U.S. Appl. No. 09/100,812).
Housekeeping Amendment submitted Nov. 27, 2006 in connection with U.S. Reexamination No. 90/008,096, filed May 18, 2006.
Notice of Failure to Comply with Ex Parte Reexamination Request Filing Requirements [37 CFR 1.510(c)] issued May 23, 2006 in connection with U.S. Reexamination No. 90/008,096, filed May 18, 2006.
Order Granting/Denying Request for Ex Parte Rexamination issued Jul. 20, 2006 in connection with U.S. Reexamination No. 90/008,096, filed May 18, 2006.
Reply to Notice of Failure to Comply with Ex Parte Reexamination Request Filing Requirements submitted Jun. 14, 2006 in connection with U.S. Reexamination No. 90/008,096, filed May 18, 2006.
Request for Reexamination Pursuant to 35 U.S.C. §§ 302-307 and 37 C.F.R. §§1.502 and 1.510, submitted May 18, 2006 in connection with U.S. Reexamination No. 90/008,096, filed May 18, 2006.
U.S. Patent Publication No. 2008/0044906 A1, published Feb. 21, 2008 (U.S. Appl. No. 10/571,384, filed Jun. 1, 2006; Peter Michael Waterhouse et al.) including complete file history.
Amendment submitted Dec. 19, 2008 in connection with U.S. Appl. No. 10/571,384, filed Jun. 1, 2006.
Amendment submitted Feb. 8, 2007 in connection with U.S. Appl. No. 10/571,384, filed as a §371 national stage of PCT International Application No. PCT/AU2004/01237.
Office Action issued Jan. 15, 2009 in connection with U.S. Appl. No. 10/571,384, filed Jun. 1, 2006.
Office Action issued Jun. 19, 2008 in connection with U.S. Appl. No. 10/571,384, filed Jun. 1, 2006.
Preliminary Amendment submitted Mar. 10, 2006 in connection with U.S. Appl. No. 10/571,384, filed as a §371 national stage of PCT International Application No. PCT/AU2004/01237.
Abstract in English for European Patent Publication No. 0560156, published Sep. 15, 1993, retrieved from esp@acenet on Apr. 22, 2008.
Pending claims for U.S. Appl. No. 10/282,996, filed Oct. 30, 2002.
Pending claims for U.S. Appl. No. 10/283,190, filed Oct. 30, 2002.
Pending claims for U.S. Appl. No. 10/283,267, filed Oct. 30, 2002.
Pending claims for U.S. Appl. No. 11/826,385, filed Jul. 13, 2007.
Pending claims for U.S. Appl. No. 11/905,368, filed Sep. 28, 2007.
Pending claims for U.S. Appl. No. 11/905,449, filed Oct. 1, 2007.
Advisory Action issued Apr. 11, 2002 in connection with U.S. Appl. No. 09/287,632, filed Apr. 7, 1999.
Amendment submitted Apr. 2, 2002 in connection with U.S. Appl. No. 09/287,632, filed Apr. 7, 1999.
Amendment submitted Aug. 21, 2000 in connection with U.S. Appl. No. 09/287,632, filed Apr. 7, 1999.
Amendment submitted Aug. 24, 2001 in connection with U.S. Appl. No. 09/287,632, filed Apr. 7, 1999.
Amendment submitted Aug. 8, 2007, in connection with U.S. Appl. No. 09/287,632, filed Apr. 7, 1999.
Amendment submitted Jan. 16, 2003 in connection with U.S. Appl. No. 09/287,632, filed Apr. 7, 1999.
Amendment submitted Jul. 7, 2003 in connection with U.S. Appl. No. 09/287,632, filed Apr. 7, 1999.
Amendment submitted Jun. 11, 2001 in connection with U.S. Appl. No. 09/287,632, filed Apr. 7, 1999.
Amendment submitted Mar. 5, 2001 in connection with U.S. Appl. No. 09/287,632, filed Apr. 7, 1999.
Amendment submitted May 1, 2008 in connection with U.S. Appl. No. 09/287,632, filed Apr. 7, 1999.
Amendment submitted May 10, 2006, in connection with U.S. Appl. No. 09/287,632, filed Apr. 7, 1999.
Amendment submitted Nov. 22, 2006 in connection with U.S. Appl. No. 09/287,632, filed Apr. 7, 1999.
Amendment submitted Sep. 12, 2005, in connection with U.S Appl. No. 09/287,632, filed Apr. 7, 1999.

Communication issued Aug. 21, 2001 in connection with U.S. Appl. No. 09/287,632, filed Apr. 7, 1999.
Communication issued Dec. 3, 2004, in connection with U.S. Appl. No. 09/287,632, filed Apr. 7, 1999.
Communication issued Jul. 21, 2000 in connection with U.S. Appl. No. 09/287,632, filed Apr. 7, 1999.
Communication issued Jun. 2, 1999 in connection with U.S. Appl. No. 09/287,632, filed Apr. 7, 1999.
Communication issued Mar. 25, 2004 in connection with U.S. Appl. No. 09/287,632, filed Apr. 7, 1999.
Communication submitted May 18, 2001 in connection with U.S. Appl. No. 09/287,632, filed Apr. 7, 1999.
Declaration of Dr. Elizabeth Salisbury Dennis Under 37 C.F.R. §1.132, including Exhibits 1 to 14 submitted Aug. 8, 2007 in connection with U.S. Appl. No. 09/287,632, filed Apr. 7, 1999.
Declaration of Dr. Marc De Block Under 37 C.F.R. §1.132, including Annexes 1 and 2 submitted Aug. 8, 2007, in connection with U.S. Appl. No. 09/287,632, filed Apr. 7, 1999.
Interview Summary issued Jul. 29, 2004 in connection with U.S. Appl. No. 09/287,632, filed Apr. 7, 1999.
Interview Summary issued Jun. 2, 2006, in connection with U.S. Appl. No. 09/287,632, filed Apr. 7, 1999.
Interview Summary issued Nov. 30, 2007 in connection with U.S. Appl. No. 09/287,632, filed Apr. 7, 1999.
Interview Summary of Sep. 5, 2002 Interview in connection with U.S. Appl. No. 09/287,632, filed Apr. 7, 1999.
May 1, 2008 Declaration Under 37 C.F.R. § 1.131, including Exhibits 1 to 5 of Peter Michael Waterhouse, Michael Wayne Graham, Ming-Bo Wang and Neil A. Smith in connection with U.S. Appl. No. 09/287,632, filed Apr. 7, 1999.
May 7, 2008 Declaration Under 37 C.F.R. 1.132 of Peter Robert Schofield Resubmission in connection with U.S. Appl. No. 09/287,632, filed Apr. 7, 1999.
Nov. 1, 2007 Declaration Under 37 C.F.R. § 1.131, including Exhibits 1 to 5 of Dr. Elizabeth Salisbury Dennis in connection with U.S. Appl. No. 09/287,632, filed Apr. 7, 1999.
Office Action issued Apr. 9, 2003 in connection with U.S. Appl. No. 09/287,632, filed Apr. 7, 1999.
Office Action issued Feb. 8, 2007, in connection with U.S. Appl. No. 09/287,632, filed Apr. 7, 1999.
Office Action issued Jul. 16, 2002 in connection with U.S. Appl. No. 09/287,632, filed Apr. 7, 1999.
Office Action issued Jun. 22, 2006 in connection with U.S. Appl. No. 09/287,632, filed Apr. 7, 1999.
Office Action issued Mar. 11, 2005 in connection with U.S. Appl. No. 09/287,632, filed Apr. 7, 1999.
Office Action issued Nov. 1, 2007, in connection with U.S. Serial No. 09/287,632, filed Apr. 7, 1999.
Office Action issued Nov. 10, 2005 in connection with U.S. Appl. No. 09/287,632, filed Apr. 7, 1999.
Office Action issued Nov. 2, 2001 in connection with U.S. Appl. No. 09/287,632, filed Apr. 7, 1999.
Office Action issued Nov. 3, 2004 in connection with U.S. Appl. No. 09/287,632, filed Apr. 7, 1999.
Office Action issued Oct. 3, 2000 in connection with U.S. Appl. No. 09/287,632, filed Apr. 7, 1999.
Office Action issued Sep. 19, 2008 in connection with U.S. Appl. No. 09/287,632, filed Apr. 7, 1999.
Petition To Correct Inventorship Pursuant to 37 C.F.R. 1.48(a) submitted Sep. 13, 2006 in connection with U.S. Appl. No. 09/287,632, filed Apr. 7, 1999.
Preliminary Amendment submitted Jun. 28, 1999 in connection with U.S. Appl. No. 09/287,632, filed Apr. 7, 1999.
Summary of Interview submitted Aug. 6, 2004 in connection with U.S. Appl. No. 09/287,632, filed Apr. 7, 1999.
Amendment submitted Mar. 19, 2009 in connection with U.S. Appl. No. 09/287,632, filed Apr. 7, 1999.
March 18, 2009 Declaration Under 37 C.F.R. 1.131 including Annexes I to III, of Dr. Michael Metzlaff in connection with U.S. Appl. No. 09/287,632, filed Apr. 7, 1999.
U.S. Patent Publication No. 2004-0214330, published Oct. 28, 2004 (U.S. Appl. No. 10/755,328, filed Jan. 13, 2004; Peter Michael Waterhouse et al.), including complete file history.
Office Action issued Sep. 1, 2005 in connection with U.S. Appl. No. 10/755,328, filed Jan. 13, 2004.
Preliminary Amendment submitted Jan. 13, 2004 in connection with U.S. Appl. No. 10/755,328, filed Jan. 13, 2004.
U.S. Patent Publication No. 2006-0178335, published Aug. 10, 2006 (U.S. Appl. No. 11/364,183, filed Mar. 1, 2006; Peter Michael Waterhouse et al.), including complete file history.
Amendment submitted Jan. 10, 2008 in connection with U.S. Appl. No. 11/364,183, filed Mar. 1, 2006.
Amendment submitted Jul. 2, 2008 in connection with U.S. Appl. No. 11/364,183, filed Mar. 1, 2006.
Interview Summary for Feb. 1, 2008 Interview in connection with U.S. Appl. No. 11/364,183, filed Mar. 1, 2006.
Interview Summary from Feb. 11, 2009 Interview in connection with U.S. Appl. No. 11/364,183, filed Mar. 1, 2006.
Jul. 3, 2008 Declaration Under 37 C.F.R. § 1.131, including Exhibits 1 to 3 of Peter Michael Waterhouse, Michael Wayne Graham, and Ming-Bo Wang in connection with U.S. Appl. No. 11/364,183, filed Mar. 1, 2006.
Office Action issued Apr. 17, 2008 in connection with U.S. Appl. No. 11/364,183, filed Mar. 1, 2006.
Office Action issued Jul. 10, 2007 in connection with U.S. Appl. No. 11/364,183, filed Mar. 1, 2006.
Preliminary Amendment submitted Mar. 1, 2006 in connection with U.S. Appl. No. 11/364,183, filed Mar. 1, 2006.
U.S. Patent Publication No. 2007-0078105, published Apr. 4, 2007 (U.S. Appl. No. 11/607,062, filed Dec. 1, 2006; Peter Michael Waterhouse et al.), including complete file history.
Amendment submitted Jan. 30, 2009 in connection with U.S. Appl. No. 11/607,062, filed Dec. 1, 2006.
Office Action issued Jul. 31, 2008 in connection with U.S. Appl. No. 11/607,062, filed Dec. 1, 2006.
Preliminary Amendment submitted Dec. 1, 2006 in connection with U.S. Appl. No. 11/607,062, filed Dec. 1, 2006.
U.S. Patent Publication No. 2008-0104732 A1, published May 1, 2008 (U.S. Appl. No. 11/841,737, filed Aug. 20, 2007; Peter Michael Waterhouse et al.), including complete file history.
Amendment submitted Jan. 16, 2008 in connection with U.S. Appl. No. 11/841,737, filed Aug. 20, 2007.
Notice of Publication issued May 1, 2008 in connection with U.S. Appl. No. 11/841,737, filed Aug. 20, 2007.
Amendment submitted Nov. 4, 2005 in connection with U.S. Appl. No. 10/282,996, filed Oct. 30, 2002.
Office Action issued Jan. 25, 2006 in connection with U.S. Appl. No. 10/282,996, filed Oct. 30, 2002.
Decision to refuse a European patent application dated Jul. 11, 2005, filed in EP 99 910 039.9.
"Table of animal viruses inactivated by RNAi, footnotes for individual viruses are provided" as Annex B of Statement setting out the Grounds of Appeal dated Nov. 11, 2005, filed in EP 99 910 039.9.
"References" as Annex C of Statement setting out the Grounds of Appeal dated Nov. 11, 2005, filed in EP 99 910 039.9.
"Summary of the Construction of pAM320" as Annex D of Statement setting out the Grounds of Appeal dated Nov. 11, 2005, filed in EP 99 910 039.9.
Appeal submitted Nov. 11, 2005 against decision to refuse a European patent application issued Jul. 11, 2005, filed in EP 99 910 039.9.
Appeal No. T 1491/05-3308, issued Apr. 24, 2007, Technical Board of Appeal of the European Patent Office.
European Search Report mailed Jun. 3, 2005, for C04015041, filed Mar. 19, 1999, 4 pages.
European Search Report issued for EP05016726, completed on Mar. 8, 2006.
EPO Form 2001 dated Jul. 16, 2007 in connection with European Patent Application No. 05013010.3.
EPO Form 2906 dated Jul. 16, 2007 in connection with European Patent Application No. 05013010.3.
In re Opposition to Australian Patent Application No. 743316, Declaration of Dr. Peter Waterhouse.
In re Opposition to Australian Patent Application No. 743316, Declaration of Dr. Robert de Feyter.
In re Opposition to Australian Patent Application No. 743316, Statement of Grounds and Particulars of Opposition.

In re Opposition to Australian Patent Application No. 743316, Statutory Declaration of Dr. Michael Wayne Graham.
In re Opposition to Australian Patent Application No. 743316, Statutory Declaration of Dr. Robert Norman Rice.
In re Opposition to Australian Patent Application No. 743316, Statutory Declaration of Geoffrey Alan Ellacott.
In re Opposition to Australian Patent Application No. 743316, Statutory Declaration of Kenneth Clifford Reed.
In re Opposition to Australian Patent Application No. 743316, Statutory Declaration of Ming-Bo Wang.
In re Opposition to Australian Patent Application No. 743316, Statutory Declaration of Neil Andrew Smith.
In re Opposition to Australian Patent Application No. 743316, Statutory Declaration of William John Pickering.
International Preliminary Report on Patentability issued by the International Bureau of WIPO on Mar. 13, 2006 in connection with International Application No. PCT/AU2004/001237.
International Search Report mailed on Oct. 16, 2000, for PCT application No. PCT/IB00/01133 filed Aug. 14, 2000.
International Search Report issued by the International Searching Authority (ISA/AU) on Oct. 20, 2004 in connection with International Application No. PCT/AU2004/001237.
Minutes of Oral Proceeding dated Jul. 12, 2005, filed in EP 99 910 039.9.
Reply to Summons to attend Oral Proceeding filed May 13, 2005 in European Patent Application No. 99 910 039.9-2401.
Request for correction of minutes filed Aug. 2, 2005 in EP 99 910 039.9.
Statement setting out the Grounds of Appeal dated Nov. 11, 2005, filed in EP 99 910 039.9.
"Table describing sequences used to inhibit viral replication" as Annex A of Statement setting out the Grounds of Appeal dated Nov. 11, 2005, filed in EP 99 910 039.9.
Written Opinion mailed on Mar. 19, 2001, for PCT application No. PCT/IB00/01133 filed Aug. 14, 2000.
Written Opinion of the International Searching Authority issued by the International Preliminary Examining Authority (IPEA/AU) on Oct. 20, 2004 in connection with International Application No. PCT/AU2004/001237.
Abdurashitov, M.A., et al. (1997) "BstAPI, an ApaBi Isochizomer, Cleaves DNA at 5'-GCANNNNTGC-3'," Nucleic Acids Res., vol. 25, No. 12, pp. 2301-2302.
Agami et al. (2002) "RNAi and Related Mechanisms And Their Potential Use For Therapy" Current Opinion in Chemical Biology 6:829-834.
Agrawal, S. (1996) "Antisense oligonucleotides: towards clinical trials," Trends Biotechnol. 14(10):376-87.
Akgün, E., et al. (1997) "Palindrome resolution and recombination in the mammalian germ line," Mol. Cell. Biol. 17(9):5559-70.
Akhtar, S., and Rossi, J.J. (1996) "Anti-HIV therapy with antisense oligonucleotides and ribozymes: realistic approaches or expensive myths?" J. Antimicrob. Chemother. 38(2):159-65.
Alberts, B., et al. (1989) "Molecular Biology of the Cell" 2nd ed., pp. 102, 486487 and 532-535 (Garland Publishing, Inc., New York, NY, pubs.)
Bahner, I. et al. (1996) "Transduction of human CD34+ hematopoietic progenitor cells by a retroviral vector expressing an RRE decoy inhibits human immunodeficiency virus type 1 replication in myelomonocytic cells produced in long-term culture," J. Virol. 70(7):4352-60.
Barabino, S.M., et al. (1997) "Inactivation of the zebrafish homologue of Chx10 by antisense oligonucleotides causes eye malformations similar to the ocular retardation phenotype," Mech. Dev. 63:133-143.
Barbeau, B., et al. (1996) "Characterization of the human and mouse Fli-1 promoter regions," Biochim. Biophys. Acta 1307(2):220-32.
Barry et al. (1993) "Methylation induced premeiotically in ascobolus: coextension with DNA repeat legths and effect on transcript elongation" Proc. Natl. Acad. Sci. 90:4557-4561.
Bass, Brenda L. (2001) "RNA Interference: The Short Answer," Nature, 411: 428-429.

Baum, E.Z., and Ernst, V.G. (1983) "Inhibition of protein synthesis in reticulocyte lysates by a double-stranded RNA component in HeLa mRNA," Biochem. Biophys. Res. Commun. 114(1):41-9.
Becker, W.M., and Deamer, D.W. (1991) "The World of the Cell," pp. 474 to 477 (The Benjamin/Cummings Publishing Company, Inc., Redwood City, California, pub.)
Berns, K., et al. (2004) "A large-scale RNAi screen in human cells identifies new components of the p53 pathway," Nature 428:431-437.
Bhargava A., et al. (2002) "Glucocorticoids prolong Ca(2+) transients in hippocampal-derived H19-7 neurons by repressing the plasma membrane Ca (2+)-ATPase-1" Mol Endocrinol. 16 (7):1629-37.
Bhargava A., et al. (2004) "Long double-stranded RNA-mediated RNA interference as a tool to achieve site-specific silencing of hypothalamic neuropeptides" Brain Res Brain Res Protoc. (2):115-25.
Bigler, J., and Eisenman, R.N. (1995) "Novel location and function of a thyroid hormone response element," EMBO J. 14(22):5710-23.
Bisat, F., et al. (1988) "Differential and cell type specific expression of murine alpha-interferon genes is regulated on the transcriptional level," Nucl. Acids Res. 16(13):6067-83.
Bissler, J.J. (1998) "DNA inverted repeats and human disease," Front Biosci. 3:408-418.
Blomberg et al. (1990) "Control of Replication of Plasmid R1: the Duplex Between the Antisense RNA, CopA and its Target, CopT, is Processed Specifically in vivo and in vitro by Rnase III" The EMBO Journal 9:2331-2340.
Bramlage et al. (1998) "Designing Ribozymes for the Inhibition of Gene Expression," TIBTECH, 16:434-438.
Branch, A.D. (1998) "A good antisense molecule is hard to find," Trends Biochem. Sci. 23(2):45-50.
Brantl et al. (1991) "Copy Number Control of the Streptococcal Plasmid p1P501 Occurs at Three Levels" Nucleic Acids Research 20:395-400.
Braun and Hemenway (1992) "Expression of Amino-Terminal Portions or Full-Length Viral Replicase Genes in Transgenic Plants Confers Resistance to Potato Virus X Infection" Plant Cell 4:735-744.
Brederode et al. (1995) "Replicase-Mediated Resistance to Alfalfa Mosaic Virus" Virology 207:467-474.
Brown, D.T., and Sittman, D.B. (1993) "Identification through overexpression and tagging of the variant type of the mouse H1e and H1c genes," J. Biol. Chem. 268(1):713-8.
Brummel, D. et al. (2003) "Inverted repeat of a heterologous 3'-untranslated region for high-efficiency, high-throughput gene silencing" The Plant Journal 33:793-800.
Brussian, J.A. et al., (1993) "An Arabidopsis Mutant with a Reduced Level of cab140 RNA is a Result of Cosuppression" The Plant Cell, American Society of Plant Physiologists, Rockville, MD, USA, 5:667-677.
Buchan, K.W., et al. (1994) "Characterization of three non-peptide endothelin receptor ligands using human cloned ETA and ETB receptors," Br. J. Pharmacol. 112(4):1251-7.
Buchman, A.R., and Berg, P. (1998) "Comparison of intron-dependent and intron-independent gene expression," Mol. Cell. Biol. 8(10):4395-405.
Bussey, H., et al. (2006) "From worm genetic networks to complex human diseases" Nat. Genet. 38(8):862-863.
Byzova et al. (2004) "Transforming Petals Into Sepaloid Organs in Araidopsis and Oilseed Rape: Implementation of the Hairpin RNA Mediated Gene Silencing Technology in an Organ-Specific Manner" Planta 218:379-87.
Cameron et al. (1989) "Specific Gene Supression by Engineered Ribozymes in Monkey Cells" Proc. Natl. Acad. Sci. USA 86:9139-9143.
Caplen et al. (2002) "A New Approach to the Inhibition of Gene Expression" Trends in Biotechnology 20:49-51.
Carr et al. (1992) "Resistance to Tobacco Mosaic Virus Induced by the 54-k Da Gene Sequence Requires Expression of the 54-k Da Protein" Mol. Plant Microbe Interact. 5:397-404.
Chen et al. (2003) "Temporal and Spatial Control of Gene Silencing in Transgenic Plants by Inducible Expression of Double Stranded RNA" The Plant Journal 36:731-40.

Chernajovsky, Y., et al. (1996) "Human kinesin light (beta) chain gene: DNA sequence and functional characterization of its promoter and first exon," DNA Cell Biol. 15(11):965-74.

Chou, S.H., et al. (2003) "Unusual DNA duplex and hairpin motifs," Nucleic Acids Res. 31(10):2461-74.

Christy, R.J., and Huang, R.C. (1988) "Functional analysis of the long terminal repeats of intracisternal A-particle genes: sequences within the U3 region determine both the efficiency and direction of promoter activity," Mol. Cell. Biol. 8(3):1093-102.

Citron et al. (1990) "The c4 Repressors of Bacteriophages P1 and P7 Are Antisense RNAs" Cell 62:591-598.

Clusel, C., et al. (1993) "Ex vivo regulation of specific gene expression by nanomolar concentration of double-stranded dumbbell oligonucleotides," Nucleic Acids Res. 21(15):3405-11.

Clusel, C., et al. (1995) "Inhibition of HSV-1 proliferation by decoy phosphodiester oligonucleotides containing ICP4 recognition sequences," Gene Expr. 4(6):301-9.

Coleman, J., et al. (1984) "The use of RNAs complementary to specific mRNAs to regulate the expression of individual bacterial genes" Cell 37:429-436.

Covey et al. (1997) "Plants Combat Infection by Gene Silencing," Nature 385:781-782.

Dale et al. (1990) "Intra-and Intermolecular Site-Specific Recombination in Plant Cells Mediated by Bacteriophage P1 Recombinase" Gene 91:79-85.

Dale et al. (2000) "A test of the model to predict unusually stable RNA hairpin loop stability" RNA 6 608-615.

Davis, BM et al. (1997) "Expansion of a CUG trinucleotide repeat in the 3' untranslated region of myotonic dystrophy protein kinase transcripts results in nuclear retention of transcripts," Proc. Natl. Acad. Sci. USA 94:7388-7393.

A.G., et al. (1991) "Expression of an antisense viral gene in transgenic tobacco confers resistance to the DNA virus tomato golden mosaic virus ," Proc. Natl. Acad. Sci. U. S.A. 88:6721-6725.

de Feyter R et al. (1996) "A ribozyme gene and an antisense gene are equally effective in conferring resistance to tobacco mosaic virus on transgenic tobacco" Mol Gen Genet. 250: 329D338.

Dec. 17, 2004 edition (2004) Biotechnol. News 24(30):1-12 (Yanicek, C., ed., CTB International Publishing, Inc., Maplewood, N.J., pub.)

DeCoy, D.L., et al. (1995) "Anti sense DNA down-regulates proteins kinase C-epsilon and enhances vasopressin-stimulated Na+ absorption in rabbit cortical collecting duct" J. Clin. Invest. 95(6):2749-56.

Definition of "copy" (1995) Webster's New World Dictionary, p. 135, Neufeldt, V., and Sparks, A.N., eds., Simon & Schuster Inc., New York, NY.

Definition of "palindrome" (1999) Glossary of biotechnology and genetic engineering, p. 172, Zaid, A., et al., eds., Food and Agriculture Organization of the United Nations, Rome, Italy.

Denoya et al. (1986) "Translational Autoregulation of ermC 23S rRNA Methyltransferase Expression in *Bacillus subtilis*" Journal of Bacteriology 113-1141.

Dhalla, A.K., et al. (1998) "chk-YB-1b, a Y-box binding protein activates transcription from rat alpha1(I) procollagen gene promoter," , Biochem. J. 336(2):373-379.

Diallo M., et al. (2003) "Long endogenous dsRNAs can induce complete gene silencing in mammalian cells and primary cultures" Oligonucleotides. 13(5) :381-92.

Dobrikova, E.Y., et al. (1996) "T7 DNA-dependent RNA polymerase can transcribe RNA from tick-borne encephalitis virus (TBEVv) cDNA with SP6 promoter," FEBS Lett. 382(3):327-9.

Doelling JH and Pikaard CS (1995) "The minimal ribosomal RNA gene promoter of *Arabidopsis thaliana* includes a critical element at the transcription initiation site" Plant J. Nov;8(5):683-92.

Dolnick, B.J. (1997) "Naturally occurring antisense RNA,." Pharmacol. Ther. 75(3):179-84.

Donahue C.P. et al. (1997) "Kinetics of Hairpin Ribozyme Cleavage in Yeast" RBA 3:961-973.

Dougherty, W.G., et al. (1997) "Transgene and Gene Suppression: telling us something new?" Current Opinion in Cell Biology, Current Biology, UK, 7:399-405.

Dronkert, M.L. (2000) "Mouse RAD54 affects DNA double-strand break repair and sister chromatid exchange," Mol. Cell. Biol. 20(9):3147-56.

Eckner et al. (1991) "Mature mRNA 3' End Formation Stimulates RNA Export From the Nucleus," EMBO J. 10:3513-3522.

Egli and Braus (1994) "Uncoupling of mRNA 3' Cleavage and Polyadenylation by Expression of a Hammerhead Ribozyme in Yeast," J. Biol. Chem. 269:27378-27383.

Elroy-Stein, O., and Moss, B. (1990) "Cytoplasmic expression system based on constitutive synthesis of bacteriophage T7 RNA polymerase in mammalian cells," Proc. Natl. Acad. Sci. U.S.A. 87(17):6743-7.

Erratum to Yu, M., et al. (1993) "A hairpin ribozyme inhibits expression of diverse strains of human immunodeficiency virus type 1," Proc. Natl. Acad. Sci. Usa 90(17):8303.

Escudé, C., et al. (1996) "Stable triple helices formed by oligonucleotide N3'→P5' phosphoramidates inhibit transcription elongation," Proc. Natl. Acad. Sci. U.S.A. 93(9):4365-9.

Exhibit A from *Benitec Australia Ltd. v. Nucleonics, Inc.*, Civil Litigation Action No. 04-174 (D. Del.) (JJF), filed Mar. 22, 2004; Exhibit A, 380 pages, submitted Jan. 28, 2005.

Exhibit B from *Benitec Australia Ltd. v. Nucleonics, Inc.*, Civil Litigation Action No. 04-174 (D. Del.) (JJF), filed Mar. 22, 2004; Exhibit B, 20 pates, submitted Jan. 28, 2005.

Faruqi, T.R., and DiCorleto, P.E. (1997) "IFN-gamma inhibits double-stranded RNA-induced E-selectin expression in human endothelial cells," J. Immunol. 159(8):3989-94.

Faske, M. et al. (1997) "Transgenic Tobacco Plants Expressing Pea Chloroplast *Nmdh* cDNA in Sense and AntiSense Orientation," Plant Physiol., Am. Soc. Of Plant Physiologists, Lancaster, Pa, 115:705-715.

Fedoriw A.M., et al. (2004) "Transgenic RNAi reveals essential function for CTCF in H19 gene imprinting" Science. 303(5655):238-40.

Fiaschi, T., et al. (1997) "The 5'-untranslated region of the human muscle acylphosphatase mRNA has an inhibitory effect on protein expression," FEBS Lett. 417(1):130-4.

Finkler, A., et al. (1992) "Immunity and resistance to the KP6 toxin of *Ustilago maydis*," Mol. Gen. Genet. 233(3):395-403.

Fire et al. (1998) "Potent and Specific Genetic Interference by Double-Stranded RNA in *Caenorhabditis elegans*" Nature 391:806-822.

Fuerst, T.R., et al. (1986) "Eukaryotic transient-expression system based on recombinant vaccinia virus that synthesizes bacteriophage T7 RNA polymerase," Proc. Natl. Acad. Sci. U.S.A. 83(21):8122-6.

Gan L., et al. (2002) "Specific interference with gene expression and gene function mediated by long dsRNA in neural cells" J Neurosci Methods. 121(2):151-7.

Gao, L., et al. (1997) "Human genes encoding U3 snRNA associate with coiled bodies in interphase cells and are clustered on chromosome 17p11.2 in a complex inverted repeat structure," Nucleic Acids Res. 25(23):4740-7.

Garcia et al. (2004) "A Classical Arabinogalactan Protein in Essential for the Initiation of Female Gametogenesis in Arabidopsis" The Plant Cell 16:2614-28.

586Gessani, S., et al. (1989) "Activators of protein kinase C enhance accumulation of interferon-beta mRNA in murine cell lines," J. Interferon Res. 9(5):543-50.

Gilbert, S.F. (1997) "Development Biology" 5th ed., Sinauer Associates Inc., Sunderland, MA, pubs.

Gimmi, E.R., et al. (1989) "Alterations in the pre-mRNA topology of the bovine growth hormone polyadenylation region decrease poly(A) site efficiency," Nucleic Acids Res. 17(17):6983-98.

Giovannangeli, C., et al. (1997) "Accessibility of nuclear DNA to triplex-forming oligonucleotides: the integrated HIV-1 provirus as a target," Proc. Natl. Acad. Sci. U.S.A. 94(1):79-84.

Gitlin, L., et al. (2005) "Poliovirus escape from RNA interference: short interfering RNA-target recognition and implications for therapeutic approaches," J. Virol. 79:1027-1035.

Goodwin et al. (1996) "Genetic and Biochemical Dissection of Transgenic RNA-Mediated Virus Resistance" Plant Cell 8:95-105.

Graham, G. (1990) "RNA transcripts of the human immunodeficiency virus transactivation response element can inhibit action of the viral transactivator" Proc. Nat'l Acad. Sci. Usa 87:5817-5821.

Graham, G.J., and Maio, J.J. (1992) "A rapid and reliable method to create tandem arrays of short DNA sequences," Biotechniques 13(5):780-9.

Graham, M.W. et al. (1996) "Co-suppression, Anti-Sense and Synthetic Viral Resistance: a Common Mechanism!" Symposium 4-3, Abstract for talk given by Michael Graham at the Lorne Genome Conference, Victoria, Australia, Feb. 1996.

Groger, R.K., et al. (1989) "Directional antisense and sense cDNA cloning using Epstein-Barr virus episomal expression vectors," Gene 81(2):285-94.

Gross, H.J., et al. (1982) "Nucleotide Sequence and Secondary Structure of Citrus Exocortis and Chrysanthemum Stunt Viroid," Eur. J. Biochem. 121(2):249-57.

Gunsalus, K.C., and Piano, F. (2005) "RNAi as a tool to study cell biology: building the genome-phenome bridge" Curr. Opin. Cell. Biol.17 (1):3-8.

Guo et al. (2003) "A Chemical Regulated Inducible RNAi System in Plants" The Plant Journal 34:383-92.

Hacker, A., et al. (1995) "Expression of Sry, the mouse sex determining gene," Development 121(6):1603-14.

Haines, D.S., et al. (1991) "Cellular response to double-stranded RNA," J. Cell. Biochem. 46(1):9-20.

Hama et al. (1990) "Organization of the Replication Control Region of Plasmid Collb-P9" Journal of Bacteriology 1983-1991.

Hamilton et al. (1990) "Antisense Gene That Inhibits Synthesis of the Hormone Ethylene in Transgenic Plants" Nature 346:284-287.

Harbinder, S., et al. (1997) "Genetically targeted cell disruption in *Caenorhabditis elegans*," Proc. Natl. Acad. Sci. U.S.A. 94(24):13128-33.

Harborth et al. (2001) "Identification of Essential Genes in Cultured Mammalian Cells Using Small Interfering RNAs," J. Cell Sci., 114: 4557-4565.

Harcourt, B.H., et al. (1998) "Ebola virus inhibits induction of genes by double-stranded RNA in endothelial cells," Virology 252(1):179-88.

Harfe, B.D., et al. (1998) "Analysis of a *Caenorhabditis elegans* Twist homolog identifies conserved and divergent aspects of mesodermal patterning," Genes Dev. 12(16):2623-35.

Haselbeck, R.C., and Greer, C.L. (1993) "Minimum intron requirements for tRNA splicing and nuclear transport in Xenopus oocytes," Biochemistry 32(33):8575-81.

Haseloff et al. (1988) "Simple RNA Enzymes With New and Highly Specific Endonuclease Activities," Nature 334:585-591.

Heard, D.J., et al. (1995) "An upstream U-snRNA gene-like promoter is required for transcription of the *Arabidopsis thaliana* 7SL RNA gene," Nucleic Acids Res. 23(11):1970-6.

Henderson, S.T., and Petes, T.D. (1993) "Instability of a plasmid-borne inverted repeat in *Saccharomyces cerevisiae*," Genetics 134(1):57-62.

Hergersberg, M. (1998) Inaugural Dissertation, Universität Koln.

Hirashima, A., et al. (1986) "Engineering of the mRNA-interfering complementary RNA immune system against viral infection," Proc. Natl. Acad. Sci. U.S.A. 83(20):7726-30.

Hirashima, A., et al. (1989) "Artificial immune system against viral infection involving antisense RNA targeted to the 5'-terminal noncoding region of coliphage SP RNA," J. Biochem. 106(1):163-6.

Hobbs et al. (1990) "The Effect of T-DNA Copy Number, Position and Methylation on Reporter Gene Expression in Tobacco Transformants" Plant Mol. Biol. 15:851-864.

Homann, M., et al. (1996) "Dissociation of long-chain duplex RNA can occur via strand displacement in vitro: biological implications" Nucleic Acids Res. 24(22):4395-4400.

Huang Y and Carmichael G (1996) "Role of polyadenylation in nucleocytoplasmic transport of mRNA" Mol. Cell. Biol. 16: 1534-1542.

Imazeki, F., et al. (1988) "Integrated structures of duck hepatitis B virus DNA in hepatocellular carcinoma," J. Virol. 62(3):861-5.

Ingelbrecht et al. (1994) "Postranscriptional Silencing of Reporter Transgenes in Tobacco Corrects with DNA Methylation" 91:10502-10506.

Itaya A et al., (2001) "Potato spindle tuber viroid as Inducer of RNA Silencing in Infected Tomato," Mol. Plant Microbe In. 14(11):1332-1334.

James, W. (1991) "Towards gene-inhibition therapy: a review of progress and prospects in the field of antiviral antisense nucleic acids and ribozymes," Antivir. Chem. Chemother. 2(4):191-214.

Jin, Z., et al. (1991) "Expression of firefly luciferase gene in *Xenopus laevis* oocyte," Chin. J. Biotechnol. 7(4):279-84.

Jorgensen et al. (1987) "T-DNA is Organized Predominantly In Inverted Repeat Structures in Plants Transformed with Agrobacterium Tumefaciens C58 Derivatives" Mol. Gen. Genet. 207:471-477.

July 20, 2007 decision of United States Court of Appeals for the Federal Circuit, 06-1122, in *Benitec Australia Ltd. v. Nucleonics, Inc., Cert. Denied*, Apr. 21, 2008.

Kawcheck et al. (1991) "Sense and Antisense RNA-Mediated Resistance to Potato Leafroll Virus in Russet Burbank Potato Plants" 4:247-253.

Kelton, C.A., et al. (1992) "The cloning of the human follicle stimulating hormone receptor and its expression in COS-7, CHO, and Y-1 cells," Mol. Cell. Endocrinol. 89 (1-2):141-51.

Kim S & Wold BJ (1985) "Stable Reduction of Thymidine Kinase Activity in Cells Expressing High Levels of Anti-Sense RNA" Cell vol. 42, 129-138.

Klaff, P., et al. (1996) "RNA structure and the regulation of gene expression," Plant Mol. Biol. 32(1-2):89-106.

Krystal, G.W., et al. (1990) "N-myc mRNA forms an RNA-RNA duplex with endogenous antisense transcripts," Mol. Cell. Biol. 10(8):4180-91.

Kubo et al. (1989) "mRNA Secondary Structure in an Open Reading Frame Reduces Translation Efficiency in *Bacillus subtilis*" Journal of Bacteriology 171:4080-4082.

Kuipers et al. (1995) "Factors Affecting the Inhibition by Antisense RNA of Granule-Bound Starch Synthase Gene Expression in Potato" Mol. Gen. Genet. 246:745-755.

Kumagai et al. (1995) "Cytoplasmic Inhibition of Carotenoid Biosynthesis With Virus-Derived RNA" Genetics 92:1679-1683.

Kumar M and Carmichael G (1998) "Antisense RNA: Function and Fate of Duplex RNA in Cells of Higher Eukaryotes" Microbiol. Mol. Biol. Rev. 62(4): 1415-1434.

Lazar, S. et al. (2004) "Selective degradation of cyclin B1 mRNA in rat oocytes by RNA interference (RNAi)" J Mol Endocrinol. 33(1):73-85.

Lee et al. (2003) "Making a Better RNAi Vector for Drosophila: Use of Intron Spacers" Methods 30:322-9.

Lee, S.W., et al. (1996) "The hemagglutinin genes hagB and hagC of Porphyromonas gingivalis are transcribed in vivo as shown by use of a new expression vector," Infect. Immun. 64(11):4802-10.

Leech et al. (1993) "Expression of myb-related Genes in the Moss, Physcomitrella patens" The Plant Journal 3:51-61.

Levin, J.Z., et al. (2000) "Methods of double-stranded RNA-mediated gene inactivation in *Arabidopsis* and their use to define an essential gene in methionine biosynthesis" Plant Mol. Biol. 44(6):759-775.

Li et al. (2005) "The Cotton ACTIN1 Gene is Functionally Expressed in Fibers and Participates in Fiber Elongation" The Plant Cell 17:859-75.

Lindbo & Dougherty (1992) "Pathogen-Derived Resistance to a Potyvirus: Immune and Resistant Phenotypes in Transgenic Tobacco Expressing Altered Forms of a Potyvirus Coat Protein Nucleotide Sequence" Mol. Plant Micr. Int. 5:144-153.

Lindbo & Dougherty (1992) "Untranslatable Transcripts of the Tobacco Etch Virus Coat Protein Gene Sequence Can Interfere With Tobacco Etch Virus Replication in Transgenic Plants and Protoplasts" Virology 189:725-733.

Lindbo, John et al. (2001) "Virus-Mediated Reprogramming of Gene Expression in Plants" Current Opinion in Plant Biology, 4:181-185.

Liu, Z. et al. (1994) "An Efficient New Method to Inhibit Gene Expression" Molecular Biotechnology 2:107, 109-118.

Liu, Z. et al. (1994) "Nuclear Antisense RNA: An Efficient New method to Inhibit Gene Expression," Molecular Biotechnology 2: 107-118.

Z. et al. (1994) "Targeted Nuclear Antisense RNA Mimics Natural Antisense-Induced Degradation of Polyoma Virus Early RNA" PNAS 91:4258-4262.

Liziewicz et al. (1991) "Tat-Regulated Production of Multimerized TAR RNA Inhibits HIV-I Gene Expression" The New Biologist 3:82-89.

Lo et al. (1992) "Inhibition of Replication of HIB-1by Retroviral Vectors Expressing tat-Antisense an Anti-tat Ribozyme RNA" Virology 190:176-183.

Lodish et al. (c1999) "Molecular Cell Biology" Chapter 11, Section 11.2. (New York: W. H. Freeman & Co.)

Longstaff et al. (1993) "Extreme Resistance to Potato Virus X Infection in Plants Expressing a Modified Component of the Putative Viral Replicase" EMBO J. 12:379-386.

Lovett et al. (1990) "Translational Attenuation as the Regulator of Inducible cat Genes" Journal of Bacteriology 172:1-6.

Macé, K., and Gazzolo, L. (1991) "Interferon-regulated viral replication in chronically HIV1-infected promonocytic U937 cells" Res Virol. 42(2-3):213-20.

Manche, Lisa et al. (1992) "Interactions Between Double-Stranded RNA Regulators and the Protein Kinase DAI," Mol. Cell. Biol., 12(11): 5238-5248.

Marathe, R.P (1997) "*CIS*-Repeat Induced Gene Silencing in Tobacco," Ph.D. Thesis, University of South Carolina.

Marathe, R.P. et al. (1997) "*Cis* Repeat Induced Gene Silencing in Tobacco," Abstract P10141.

Matthieu, J.M., et al. (1992) "Myelin-deficient mutant mice. An in vivo model for inhibition of gene expression by natural antisense RNA" Ann. N. Y. Acad. Sci. 660:188-92.

Mayne, L.V., et al. (1988) "SV 40—transformed normal and DNA-repair-deficient human fibroblasts can be transfected with high frequency but retain only limited amounts of integrated DNA" Gene 66(1):65-76.

McCormack, S.J., et al. (1992) "Mechanism of interferon action: identification of a RNA binding domain within the N-terminal region of the human RNA-dependent P1/eIF-2 alpha protein kinase," Virol. 188(1):47-56.

McGarry, T.J., and Lindquist, S. (1986) "Inhibition of heat shock protein synthesis by heat-inducible antisense RNA," Proc. Natl. Acad. Sci. U.S.A 83:399-403.

McNair, A.N., et al. (1994) "Hepatitis delta virus replication in vitro is not affected by interferon-alpha or -gamma despite intact cellular responses to interferon and dsRNA," J. Gen. Virol. 75(Pt. 6):1371-8.

Memelink et al. (1992) "Structure and Regulatin of Tobacco Extension" The Plant Journal 4:1011-1012.

Mercola, D., and Cohen, J.S. (1995) "Antisense approaches to cancer gene therapy," Cancer Gene Ther. 2(1):47-59.

Mette, et al. (1999) "Production of Aberrant Promoter Transcripts Contributes to Methylation and Silencing of Unlinked Homologous Promoters in trans," The EMBO Journal 18:241-248.

Mette, M.F., et al. (2000) "Transcriptional silencing and promoter methylation triggered by double-stranded RNA," EMBO J. 19(19):5194-201.

Meyer, P. (1995) "Understanding and Controlling Transgene Expression" TIBTECH 13:332-337.

Meyer, P. (1996) "Homology-Dependent Gene Silencing in Plants" Ann. Rev. Plant Physiol. Plant Mol. Biol. 47:23-48.

Mikoshiba, K., et al. (1990) "Chimeric and molecular genetic analysis of myelin-deficient (shiverer and mld) mutant mice," Ann. N.Y. Acad. Sci. 605:166-82.

Miller et al. (1991) "A Satellite RNA of Barley Yellow Dwarf Virus Contains a Novel Hammerhead Structure in the Self-Cleavage Domain" Virology 183:711-720.

Minks MA et al. (1979) "Structural requirements of double-stranded RNA for the activation of 2',5'-oligo(A) polymerase and protein kinase of interferon-treated HeLa cells" J. Biol. Chem. vol. 254, No. 20: 10180-10183.

Morishita, R., et al. (1996) "Role of transcriptional cis-elements, angiotensinogen gene-activating elements, of angiotensinogen gene in blood pressure regulation," Hypertension 27 (3 Pt. 2):502-7.

Morris, K.V., et al. (2004) "Small interfering RNA-induced transcriptional gene silencing in human cells," Science 305 (5688):1289-92.

Nagy, E., Rigby, W.F. (1995) "Glyceraldehyde-3-phosphate dehydrogenase selectively binds AU-rich RNA in the NAD(+)-binding region (Rossmann fold)," J. Biol. Chem. 270 (6):2755-63.

Ngo, V.N., et al. (2006) "A loss-of-function RNA interference screen for molecular targets in cancer," Nature 441:106-110.

Noguchi, M., et al. (1994) "Characterization of an antisense Inr element in the eIF-2 alpha gene," J. Biol. Chem. 269(46):29161-7.

Noonberg SB et al. (1994) "In vivo generation of highly abundant sequence-specific oligonucleotides for antisense and triplex gene regulation " Nucleic Acids Research vol. 22 No. 14:2830-2836.

O'Brien et al. (2002) "Molecular Analysis of the Stylar-Expressed Solanum Chacoense Small Asparagine-rich Protein Family Related to the HT Modifier of Gametophytic Self-Incompatibility in Nicotiana" The Plant Journal 22:985-96.

Paddison, P.J. et al. (2002) "RNA Interference: The New Somatic Cell Genetics?" Cancer Cell, 2:17-23.

Paddison, P.J., et al. (2002) "Stable suppression of gene expression by RNAi in mammalian cells," Proc. Natl. Acad. Sci. U.S.A. 99:1443-1448.

Paddison, P.J., et al. (2004) "A resource for large-scale RNA interference-based screens in mammals" Nature 428:427-431.

Palmiter, R.D., et al. (1984) "Transmission distortion and mosaicism in an unusual transgenic mouse pedigree," Cell 36(4):869-77.

Pang et al. (1996) "Post-transctriptional Transgene Silencing and Consequent Tospovirus Resistance in Trangenic Lettuce are Affected by Transgene Dosage and Plant Development" Plant J. 9:899-909.

Papefthimiou et al. (2001) "Replicating potato spindle tuber viroid RNA is accomplished by short RNA fragments that are characteristic of posttranscriptional gene silencing," Nucleic Acids Res. 29(11):2395-2400.

Park, W.S., et al. (2001) "Specific inhibition of HIV-1 gene expression by double-stranded RNA," Nucleic Acids Research Suppl. 1:219-220.

Park, W.S., et al. (2002) "Prevention of HIV-1 infection in human peripheral blood mononuclear cells by specific RNA interference," Nucleic Acids Res. 30:4830-4835.

Parrish, S. et al. (2000) "Functional Anatomy of a dsRNA Trigger: Differential Requirement for the Two Trigger Strands in RNA Interference" Mol. Cell 6:1077-1087.

Pe'ery, T., and Mathews, M.B. (1997) "Synthesis and purification of single-stranded RNA for use in experiments with PKR and in cell-free translation systems," Methods 11(4):371-81.

Perkel, J.M. (2006) "Off-Target Effects Plague Drosophila RNAi" The Scientist, pp. 1-5.

Peyman (1997) Basic Science of Vascular Disease (Chapter 17, p. 17).

Plasmid map for pCR2.1.

Polyadenylation, Wikipedia, 3 pages, http://en.wikipedia.org/wiki/Polyadenylation (Feb. 20, 2007).

Polyadenylation, Wikipedia, 3 pages, http://en.wikipedia.org/wiki/Polyadenylation (Feb. 20, 2007) (redacted).

690Powell et al. (1990) "Protection Against Tobacco Mosaic Virus Infection in Transgenic Plants Requires Accumulation of Coat Protein Rather than Coat Protein RNA Sequences" Virology 175:124-130.

Powell-Abel et al. (1986) "Delay of Disease Development in Trangenic Plants that Express the Tobacco Mosaic Virus Coat Protein Gene" Science 232:738-743.

Powell-Coffman, J.A., et al. (1996) "Onset of C. elegans gastrulation is blocked by inhibition of embryonic transcription with an RNA polymerase antisense RNA," Dev. Biol. 178:472-83.

Prasad, B.V., et al. (1996) "Visualization of ordered genomic RNA and localization of transcriptional complexes in rotavirus" Nature 382(6590):471-473.

Pratt, G., et al. (1988) "Regulation of in vitro translation by double-stranded RNA in mammalian cell mRNA preparations," Nucleic Acids Res. 16(8):3497-510.

Proud et al. (1995) "PKR: a New Name and New Roles" TIBS 241-246.

Ramezani et al (1997) "Inhibition of HIV-1 replication by retroviral vectors expressing monomeric and multimeric hammerhead ribozymes" Gene Therapy 4 861-867.

Raponi, M., and Arndt, G.M. (2003) "Double-stranded RNA-mediated gene silencing in fission yeast," Nucleic Acids Res. 31(15):4481-9.

Ratcliff, F., et al. (1997) "A Similarity Between Viral Defense and Gene Silencing in Plants," Science 276(5318):1558-1560.

Redenbaugh et al. (1992) "Safety Assessment of Genetically Engineered Fruits and Vegetables—A Case Study of the FlavrSavr™ Tomato," CRC Press, Boca Raton, FL.

Resnekov, O., et al. (1989) "RNA secondary structure is an integral part of the in vitro mechanism of attenuation in simian virus 40," J. Biol. Chem. 264(17):9953-9.

Reuben, M., et al. (1994) "Cloning and expression of the rabbit gastric CCK-A receptor," Biochim. Biophys. Acta 1219(2):321-7.

Robbins, M.A., and Rossi, J.J. (2005) "Sensing the danger in RNA," Nature Med. 11:250-251.

Robertson, G., et al. (1996) "Age-dependent silencing of globin transgenes in the mouse," Nucleic Acids Res. 24(8):1465-71.

Rocheleau, C.E., et al. (1997) "Wnt signaling and an APC-related gene specify endoderm in early C. elegans embryos," Cell 90(4):707-16.

Rodriguez, D., et al. (1990) "Regulated expression of nuclear genes by T3 RNA polymerase and lac repressor, using recombinant vaccinia virus vectors," J. Virol. 64(10):4851-7.

Roy, P., et al. (1990) "Effect of mRNA secondary structure on the efficiency of translational initiation by eukaryotic ribosomes," Eur. J. Biochem. 191(3):647-52.

Rubio et al., (1999) "Broad Spectrum Protection Against Tombusviruses Elicited by Defective Interfering RNAs in Transgenic Plants" J. Virology 73:5070-5078.

Ruskin, B., and Fink, G.R. (1993) "Mutations in PoL1 increase the mitotic instability of tandem inverted repeats in Saccharomyces cerevisiae," Genetics 134(1):43-56.

Sabl, J.F., and Henikoff, S. (1996) "Copy number and orientation determine the susceptibility of a gene to silencing by nearby heterochromatin in Drosophila," Genetics 142(2):447-58.

Sachs A. and Wahle E. (1993) "Poly(A) tail metabolism and function in eucaryotes" J. Biol. Chem. 268:22955-22958.

Sambrook, J., et al. "Molecular Cloning. A Laboratory Model," 2nd ed., pp. 16.1 to 16.81 (Cold Spring Harbor Laboratory Press, Cold Spring Harbor, New York, pub.) 1989.

Samuel et al. (2002) "Double-Jeopardy: Both Overexpression and Suppression of a Redox-Activated Plant Mitogen-Activated Protein Kinase Render Tobacco Plants Ozone Sensitive" The Plant Cell 14:2059-69.

Sanford, J.C., et al. (1985) "The Concept of Parasite-Derived Resistance-Deriving Resistance Genes from the Parasite's own Genome," J. Theor. Biol. 13:395-405.

Savin, K.W., et al. (1995) "Antisense ACC Oxidase RNA Delays Carnation Petal Senescence," Hortscience 30(5):970-972.

Scherr et al. (2003) "Gene Silencing Mediated by Small Interfering RNA's in Mammalian Cells" Current Medicinal Chemistry 10:245-256.

Schiebel, W. et al. (1993a) "RNA-directed RNA Polymerase from Tomato Leaves" The Journal of Biological Chemistry 268(16):11858-11867.

Schiebel, W. et al. (1993b) "RNA-directed RNA Polymerase from Tomato Leaves" The Journal of Biological Chemistry 268(16):11858-11867.

Schiedner, G., et al. (1998) "Genomic DNA transfer with a high-capacity adenovirus vector results in improved in vivo gene expression and decreased toxicity," Nat. Genet. 18(2):180-3.

Schmitt, H.P., et al. (1986) "Characterization of cloned sequences complementary to F9 cell double-stranded RNA and their expression during differentiation," Differentiation 30(3):205-10.

Seife et al. (2003) "Breakthrough of the Year" Science 302:2038-2045.

Sheehy, R.E. et al. (1998), "Reduction of Polygalacturonase Activity in Tomato Fruit by Antisense RNA" Proc. Natl. Acad. Sci, USA 85:8805-8809.

Shi, Y. (2000) "Mammalian RNAi for the masses" Trends Genet. 19(1):9-12.

Sijen et al., Post-transcriptional gene-silencingRNAs on the attack or on the defense?, 2000, BioEssays, vol. 22, pages.

Silva, J.M., et al. (2005) "Second-generation shRNA libraries covering the mouse and human genomes" Nat Genet. 37:1281-1288.

Silverman, T.A., et al. (1992) "Role of sequences within the first intron in the regulation of expression of eukaryotic initiation factor 2 alpha," J. Biol. Chem. 267(14):9738-42.

Simons, R.W. (1988) "Naturally occurring antisense RNA control—a brief review," Gene 2(1-2):35-44.

Smith, Neil et al. (1994) "Transgenic Plant Virus Resistance Mediated by Untranslatable Sense RNAs: Expression, Regulation, and Fate of Nonessential RNAs" Plant Cell 6:1441-1453.

Smolinski, P.A. (1995) "Double-stranded RNA induces sickle erythrocyte adherence to endothelium: a potential role for viral infection in vaso-occlusive pain episodes in sickle cell anemia," Blood 85(10):2945-50.

Smythe, J.A., and Symonds, G. (1995) "Gene therapeutic agents: the use of ribozymes, antisense, and RNA decoys for HIV-1 infection," Inflamm. Res. 44(1):11-5.

Sonoda, K., et al. (1996) "Asymmetric deletion of the junction between the short unique region and the inverted repeat does not affect viral growth in culture and vaccine-induced immunity against Marek's disease," Vaccine 14(4):277-84.

Stam et al. (1997) "Post-Transcriptional Silencing of Chalcone Synthase in Petunia by Inverted Transgene Repeats," The Plant Journal vol. 12, No. 1, pp. 63-82.

Stein P., et al. (2003) "Transgenic RNAi in mouse oocytes: a simple and fast approach to study gene function" Dev Biol. 256(1):187-93.

Sun et al., (1995) "Target Sequence-Specific Inhibition of HIV-1 Replication by Ribozymes Directed to tat RNA" Nucleic Acides Research 23:2909-2913.

Sun, L.Q., et al. (1994) "Ribozyme-mediated suppression of Moloney murine leukemia virus and human immunodeficiency virus type I replication in permissive cell lines," Proc. Natl. Acad. Sci. U.S.A. 91(21):9715-9.

Svoboda P., et al. (2004) "Lack of homologous sequence-specific DNA methylation in response to stable dsRNA expression in mouse oocytes" Nucleic Acids Res. 32(12):3601-6.

Svoboda P., et al. (2004) "RNAi and expression of retrotransposons MuERV-L and IAP in preimplantation mouse embryos" Dev Biol. 269(1):276-85.

Swamynathan, S.K., et al. (1997) "Chicken YB-2, a Y-box protein, is a potent activator of Rous sarcoma virus long terminal repeat-driven transcription in avian fibroblasts," J. Virol. 71:2873-2880.

Swaney, S. et al. (1995) "RNA-Mediated Resistance with Nonstructural Genes from the Tobacco Etch Virus Genome," MPMI 8(6):1005-1011.

Sweetser, D.A., et al. (1988) "Transgenic mice containing intestinal fatty acid-binding protein-human growth hormone fusion genes exhibit correct regional and cell-specific expression of the reporter gene in their small intestine," Proc. Natl. Acad. Sci. U.S.A. 85(24):9611-5.

Symington, L.S. (2002) "Role of RAD52 epistasis group genes in homologous recombination and double-strand break repair," Microbiol. Mol. Biol. Rev. 66(4):630-70.

Szyf et al. (1992) "Induction of Myogenic Differentiation by an Expression Vector Encoding the DNA Methyltransferase cDNA Sequence in the Antisense Orientation" J. Biol. Chem., 267:12831-12836.

Tabara, H., et al. (1998) "RNAi in C. elegans: Soaking in the Genome Sequence," Science 282(5388):430-431.

Takahashi et al. (1997) "Development of Necrosis and Activation of Disease Resistance in Transgenic Plants with Severely Reduced Catalase Levels" The Plant Journal 11:993-1005.

Tanaka, H., et al. (1994) "Sequence-specific interaction of alpha-beta-anomeric double-stranded DNA with the p50 subunit of NF kappa B: application to the decoy approach," Nucleic Acids Res. 22(15):3069-74.

Tang, J.Y., et al: (1993) "Self-stabilized antisense phosphorothioates: properties and anti-HIV activity" Nucleic Acids Res. 21(11):2729-2735.

Thomas, C.L., et al. (2001) "Size constraints for targeting post-transcriptional gene silencing and for Rna-directed methylation in Nicotiana benthamiana using a potato virus X vector," Plant J. 25(4):417-25.

Thompson et al. (1995) "Improved Accumulation and Activity of Ribozyme Expressed From a tRNA-based Rna Polymerase III Promoter" Nucleic Acids Research 23:2259-2268.

Tosic, M., et al. (1990) "Post-transcriptional events are responsible for low expression of myelin basic protein in myelin deficient mice: role of natural antisense RNA," EMBO J. 9(2):401-6.

Trojan, J., et al. (1992) "Loss of tumorigenicity of rat glioblastoma by episome-based antisense cDNA transcription of insulin-like growth factor I," Proc. Natl. Acad. Sci. USA 89:4874-4878.

Trojan, J., et al. (1992) "Loss of tumorigenicity of rat glioblastoma by episome-based antisense cDNA transcription of insulin-like growth factor I," Proc. Natl. Acad. Sci. USA 89:4874-4878 (redacted).

Tuschl T. (2002) "Expanding small RNA interference" Nat Biotechnol. May;20 (5):446-8.

Usdin, T.B., et al. (1993) "SP6 RNA polymerase containing vaccinia virus for rapid expression of cloned genes in tissue culture," Biotechniques 14(2):222-4.

Vaish et al. (1998) "Recent Developments in the Hammerhead Ribozyme Field" Nucleic Acids Res. 26:5237-5242.

Van Blokland et al. (1996) "Post-Transcriptional Suppression of Synthase Chalcone Genes in Petunia Hybrida and the Accumulation of Unspliced pre-mRNAA, Mechanisms and Applications of Gene Silencing".

Van Blokland, R. et al. (1994) "Transgene-mediated Suppression of Chalcone Synthase Expression in *Petunia hybrida* Results from an increase in RNA Turnover" Rhe Plant Journal 6(6)861-877.

van Eldik et al. (1998) "Silencing of β-1,3-glucanase Genes in Tobacco Correlates With an Increased Abundance of RNA Degradation Intermediates," Nucleic Acids Res 26:5176-5181.

van Houdt et al. (1997) "Post-Transcriptional Silencing of a Neomycin Phosphotransferase II Transgene Correlates With the Accumulation of Unproductive RNAs and With Increased Cytosine Methylation of 3' Flanking Regions," Plant Journal 12:379-392.

Van Steeg, H., et al. (1991) "The translation in vitro of rat ornithine decarboxylase mRNA is blocked by its 5' untranslated region in a polyamine-independent way," Biochem J. 274 (Pt. 2):521-6.

Vaucheret et al. (1992) "Inhibition of Tobacco Nitrite Reductase Activity by Expression of Antisense RNA" The Plant Journal 2:559-569.

Vickers, T.A., et al. (2003) "Efficient Reduction of Target RNAs by Small Interfering RNA and RNase H-dependent Antisense Agents. A comparative analysis" J. Biol. Chem. 278(9):7108-7118.

Volloch, V.Z., et al. (1994) "Evolutionarily conserved elements in the 5' untranslated region of beta globin mRNA mediate site-specific priming of a unique hairpin structure during cDNA synthesis," Nucleic Acids Res. 22(24):5302-9.

Wagner et al. (1998) "Double-stranded RNA poses puzzle" Nature 391:744-745.

Wallace RB et al. (1979) "Hybridization of synthetic oligodeoxyribonucleotides to phi chi 174 DNA: the effect of single base pair mismatch." Nucleic Acids Res. 6(11):3543-57.

Wang, S., and Dolnick, B.J. (1993) "Quantitative evaluation of intracellular sense: antisense RNA hybrid duplexes." Nucleic Acids Res. 21(18):4383-4391.

Wang, Z.Q., et al. (1994) "An unusual nucleoporin-related messenger ribonucleic acid is present in the germ cells of rat testis," Biol. Reprod. 51(5):1022-30.

Wassenegger and Pelissier (1998) "A Model for RNA-Mediated Gene Silencing in Higher Plants," Plant Mol. Biol. 37:349-362.

Weerasinghe et al. (1991) "Resistance to Human Immunodeficiency Virus Type 1 (HIV-1) Infection in Human CD4 Lymphocyte-Derived Cell Lines Conferred by Using Retroviral Vectors Expressing an HIV-1 RNA-Specific Ribozyme" Journal of Virology 65:5531-5534.

Welch P.J. et al. (1998) "Expression of Ribozymes in Gene Transfer Systems to Modulate Target RNA Levels" Current Opinion in Biotechnology 9:486-496.

Wesley SV et al. (2001) "Construct design for efficient, effective and high-throughput gene silencing in plants," Plant J. 27(6):581-590.

Williams, T., and Fried, M. (1986) "A mouse locus at which transcription from both DNA strands produces mRNAs complementary at their 3' ends," Nature 322(6076):275-9.

Wolffe, A.P. (1997) "Transcription control: repressed repeats express themselves," Curr Biol. 7(12):R796-8.

Wu H et al. (1998) "Identification and Partial Purification of Human Strand RNase Activity" J Biol Chem, vol. 273, Issue 5, 2532-2542.

Wu, C., et al. (1994) "Interferon-stimulated response element and NF kappa B sites cooperate to regulate double-stranded RNA-induced transcription of the IP-10 gene," J. Interferon Res. 14(6):357-63.

Wu, S., and Kaufman, R.J. (1996) "Double-stranded (ds) RNA binding and not dimerization correlates with the activation of the dsRNA-dependent protein kinase (PKR)," J. Biol. Chem. 271(3):1756-63.

Xiong, Y., et al. (1995) "Signaling properties of mouse and human corticotropin-releasing factor (CRF) receptors: decreased coupling efficiency of human type II CRF receptor," Endocrinology 136(5):1828-34.

Xu, M., et al. (1989) "Immunoglobulin kappa gene expression after stable integration. II. Role of the intronic MAR and enhancer in transgenic mice," J Biol Chem.264(35):21190-5.

Yamamoto, T., et al. (2002) "Double-stranded nef RNA interferes with human immunodeficiency virus type 1 replication," Microbio. Immunol. 46:809-817.

Yang, D., et al. (2000) "Evidence that processed small dsRNAs may mediate sequence-specific mRNA degradation during RNAi in Drosophila embryos," Curr. Biol. 10(19) :1191-1200.

Yarney, T.A., et al. (1993) "Molecular cloning and expression of the ovine testicular follicle stimulating hormone receptor," Mol. Cell. Endocrinol. 93(2):219-26.

Yi C.E., et al. (2003) "Specific and potent RNA interference in terminally differentiated myotubes" J Biol Chem. 278(2):934-9.

Yu et al. (1995) "In Vitro and in Vivo Characterization of a Second Functional Hairpin Ribozyme Against HIV-1" Virology 26:381-386.

Yu J., et al. (2004) "Transgenic RNAi-mediated reduction of MSY2 in mouse oocytes results in reduced fertility" Dev Biol. 268(1):195-206.

Yu, J.Y., et al. (2002) "RNA interference by expression of short-interfering RNAs and hairpin RNAs in mammalian cells," Proc. Natl. Acad. Sci. USA 99(9):6047-52.

Yu, M., et al. (1993) "A hairpin ribozyme inhibits expression of diverse strains of human immunodeficiency virus type 1," Proc. Natl. Acad. Sci. USA 90:6340-6344.

Yu, M., et al. (1993) "A hairpin ribozyme inhibits expression of diverse strains of human immunodeficiency virus type 1," Proc. Natl. Acad. Sci. Usa 90:6340-6344 (redacted).

Yu, M., et al. (1994) "Progress towards gene therapy for HIV infection," Gene Ther. 1(1):13-26.

Zakharian, R.A., et al. (1986) "[Stimulation by double-stranded RNA of the transformation of pro- and eukaryotic cells]," Dokl. Akad. Nauk. SSSR 288(5):1251-3.

Zhang et al. (2004) "Single Processing Center Models for Human Dicer and Bacterial RNase III," Cell (118): 57-68.

Zhao, Y. et al. (2001) "Use of a vector based on Potato Virus X in a whole plant assay to demonstrate nuclear targeting of Potato spindle tuber viroid," J. Gen. Virol. 82:1491-1497.

Zhou et al. (1994) "Inhibition of HIV-1 in Human T-Lymphocytes by Transduced anti-tat and rev Hammerhead Ribozymes" Gene 149:33-39.

Zrenner et al. (1995) "Evidence of the Crucial Role of Sucrose Synthase for Sink Strength Using Transgenic Potato Plants" The Plant Journal 7:97-107.

Australian Written Opinion for SG200205122-5 dated Oct. 24, 2005.

Advisory Action issued Mar. 25, 2009 in connection with Merged Reexamination No. 90/007,247 and 90/008,096, filed Oct. 4, 2004 and May 18, 2006, respectively.

Jan. 26, 2012 Notice Of Opposition filed in connection with European Patent No. 1068311 by Potter Clarkson on behalf of "Strawman Limited", pp. 1-30.

Jan. 27, 2012 Notice Of Opposition filed in connection with European Patent No. 1068311 by Carnegie Institution of Washington and University of Massachusetts, pp. 1-22.

Jan. 23, 2012 Notice Of Opposition filed in connection with European Patent No. 1068311 by BASF SE, pp. 1-43.

Jan. 26, 2012 Notice Of Opposition filed in connection with European Patent No. 1068311 by Syngenta International AG, pp. 1-30.

Feb. 3, 2012 Third Party Observations under Article 115 EPC filed on behalf of Commonwealth Scientific and Industrial Research Organisation and Bayer CropScience N.V. against European Patent Application No. 98964202.0, pp. 1-10.

Jan. 26, 2012 Non-Final Notice of Reasons for Rejection mailed on Jan. 31, 2012 in connection with Japanese Patent Application No. 2000-543598, including English language translation, pp. 1-8.

English language copy of the claims which are presently pending in Japanese Patent Application No. 2000-543598, pp. 1-11.

* cited by examiner

FIGURE 25

ClapBC.PVY

FIGURE 46 pBC.PVY.LNYV.PYV

FIGURE 52

Restriction sites from left to right: XhoI, SalI, AccI, EcoRV, EcoRI, EcoRV, EcoRI, HindIII, ClaI, EcoRV, EcoRI, NotI, XbaI, BamHI Segments: PVY (→), LNYV (→), YVPd (←)

pBC.PVY.LNYV.YVP Δ

```
SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Primer Bgl-GFP for Green Fluorescent Protein in
      jellyfish.

<400> SEQUENCE: 1
agatctgtaa acggccacaa gttcag                                            26

<210> SEQ ID NO 2
<211> LENGTH: 26
<212> TYPE: DNA
<213> ORGANISM: Artificial Sequence
<220> FEATURE:
<223> OTHER INFORMATION: Primer GFP-Bam for Green Fluorescent Protein in
      jellyfish.

<400> SEQUENCE: 2
ggatccttgt acagctcgtc catgcc                                            26

<210> SEQ ID NO 3
<211> LENGTH: 74
<212> TYPE: DNA
<213> ORGANISM: Artificial Sequence
<220> FEATURE:
<223> OTHER INFORMATION: Primer SV40-1 for SV40 late promoter.

<400> SEQUENCE: 3
gtcgacaata aaatatcttt attttcatta catctgtgtg ttggttttt gtgtgatttt        60 tgcaaaagcc tagg                                                         74

<210> SEQ ID NO 4
<211> LENGTH: 31
<212> TYPE: DNA
<213> ORGANISM: Artificial Sequence
<220> FEATURE:
<223> OTHER INFORMATION: Primer SV40-2 for SV40 late promoter.

<400> SEQUENCE: 4
gtcgacgttt agagcagaag taacacttcc g                                      31

<210> SEQ ID NO 5
```

```
<211> LENGTH: 38
<212> TYPE: DNA
<213> ORGANISM: Artificial Sequence
<220> FEATURE:
<223> OTHER INFORMATION: Primer BEV-1 for the BEV RNA-dependant RNA
      polymerase from virus.

<400> SEQUENCE: 5
cggcagatct aacaatggca ggacaaatcg agtacatc                              38

<210> SEQ ID NO 6
<211> LENGTH: 31
<212> TYPE: DNA
<213> ORGANISM: Artificial Sequence
<220> FEATURE:
<223> OTHER INFORMATION: Primer BEV-2 for the BEV RNA-dependant RNA
      polymerase from virus.

<400> SEQUENCE: 6
cccgggatcc tcgaaagaat cgtaccactt c                                     31

<210> SEQ ID NO 7
<211> LENGTH: 29
<212> TYPE: DNA
<213> ORGANISM: Artificial Sequence
<220> FEATURE:
<223> OTHER INFORMATION: Primer BEV-3 for the BEV RNA-dependant RNA
      polymerase from virus.

<400> SEQUENCE: 7
gggcggatcc ttagaaagaa tcgtaccac                                        29

<210> SEQ ID NO 8
<211> LENGTH: 28
<212> TYPE: DNA
<213> ORGANISM: Artificial Sequence
<220> FEATURE:
<223> OTHER INFORMATION: Primer BEV-4 for the BEV RNA-dependant RNA
      polymerase from virus.

<400> SEQUENCE: 8
cggcagatct ggacaaatcg agtacatc                                         28

<210> SEQ ID NO 9
<211> LENGTH: 37
<212> TYPE: DNA
<213> ORGANISM: Artificial Sequence
<220> FEATURE:
<223> OTHER INFORMATION: Primer NOS 5' for the NOS terminator sequence
      from agrobacterium.

<400> SEQUENCE: 9
ggattcccgg gacgtcgcga atttcccccg atcgttc                               37

<210> SEQ ID NO 10
<211> LENGTH: 33
<212> TYPE: DNA
<213> ORGANISM: Artificial Sequence
<220> FEATURE:
<223> OTHER INFORMATION: Primer NOS 3' for the NOS terminator sequence
      from agrobacterium.

<400> SEQUENCE: 10
ccatggccat ataggcccga tctagtaaca tag                                   33

<210> SEQ ID NO 11
<211> LENGTH: 33
<212> TYPE: DNA
```

```
<213> ORGANISM: Artificial Sequence
<220> FEATURE:
<223> OTHER INFORMATION: Primer SCBV 5' for the SCBV promoter sequence
      from virus.

<400> SEQUENCE: 11
ccatggccta tatggccatt ccccacattc aag                                     33

<210> SEQ ID NO 12
<211> LENGTH: 27
<212> TYPE: DNA
<213> ORGANISM: Artificial Sequence
<220> FEATURE:
<223> OTHER INFORMATION: Primer SCBV 3' for the SCBV promoter sequence
      from virus.

<400> SEQUENCE: 12
aacgttaact tctacccagt tccagag                                            27

<210> SEQ ID NO 13
<211> LENGTH: 28
<212> TYPE: DNA
<213> ORGANISM: Artificial Sequence
<220> FEATURE:
<223> OTHER INFORMATION: Primer LNYV 1 for the LNYV 4 KB gene from
      virus.

<400> SEQUENCE: 13
atgggatccg ttatgccaag aagaagga                                           28

<210> SEQ ID NO 14
<211> LENGTH: 24
<212> TYPE: DNA
<213> ORGANISM: Artificial Sequence
<220> FEATURE:
<223> OTHER INFORMATION: Primer LNYV 2 for the LNYV 4 KB gene from
      virus.

<400> SEQUENCE: 14
tgtggatccc taacggaccc gatg                                               24

<210> SEQ ID NO 15
<211> LENGTH: 72
<212> TYPE: DNA
<213> ORGANISM: Artificial Sequence
<220> FEATURE:
<223> OTHER INFORMATION: Primer PVY1 for the PVY Nia region from virus.

<400> SEQUENCE: 15
taatgaggat gatgtcccta cctttaattg gcagaaattt ctgtggaaag acagggaaat        60
ctttcggcat tt                                                            72

<210> SEQ ID NO 16
<211> LENGTH: 72
<212> TYPE: DNA
<213> ORGANISM: Artificial Sequence
<220> FEATURE:
<223> OTHER INFORMATION: Primer PVY2 for the PVY Nia region from virus.

<400> SEQUENCE: 16
ttctgccaat taaggtagg gacatcatcc tcattaaaat gccgaaagat ttccctgtct         60
ttccacagaa at                                                            72
```

CONTROL OF GENE EXPRESSION

This application is a divisional of U.S. Ser. No. 10/821,710, filed Apr. 8, 2004, now abandoned, which is a continuation of U.S. Ser. No. 10/646,070, filed Aug. 22, 2003 now U.S. Pat. No. 7,754,697, which is a continuation of U.S. Ser. No. 09/646,807, filed Dec. 5, 2000, now abandoned, which is a §371 National Stage of PCT International Application No. PCT/AU99/00195, filed Mar. 19, 1999, which is a continuation-in-part of U.S. Ser. No. 09/100,812, filed Jun. 19, 1998, now U.S. Pat. No. 6,573,099, issued Jun. 3, 2003, and of U.S. Ser. No. 09/100,813, filed Jun. 19, 1998, now abandoned, which claims benefit of Australian Provisional Patent Application No. PP2492, filed Mar. 20, 1998 and Australian Provisional Patent Application No. PP2499, filed Mar. 20, 1998. The contents of all of the referenced applications are hereby incorporated by reference into this application.

FIELD OF THE INVENTION

The present invention relates generally to a method of modifying gene expression and to synthetic genes for modifying endogenous gene expression in a cell, tissue or organ of a transgenic organism, in particular a transgenic animal or plant. More particularly, the present invention utilises recombinant DNA technology to post-transcriptionally modify or modulate the expression of a target gene in a cell, tissue, organ or whole organism, thereby producing novel phenotypes. Novel synthetic genes and genetic constructs which are capable of repressing delaying or otherwise reducing the expression of an endogenous gene or a target gene in an organism when introduced thereto are also provided.

GENERAL

Bibliographic details of the publications referred to in this specification are collected at the end of the description.

As used herein the term "derived from" shall be taken to indicate that a specified integer may be obtained from a particular specified source or species, albeit not necessarily directly from that specified source or species.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only. Functionally-equivalent products, compositions and methods are clearly within the scope of the invention, as described herein.

Sequence identity numbers (SEQ ID NOS.) containing nucleotide and amino acid sequence information included in this specification are collected after the Abstract and have been prepared using the programme PatentIn Version 2.0. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (eg. <400>1, <400>2, etc).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine; V represents a nucleotide other than Thymine, D represents a nucleotide other than Cytosine and N represents any nucleotide residue.

The designation of amino acid residues referred to herein, as recommended by the IUPAC-IUB Biochemical Nomenclature Commission, are listed in Table 1.

TABLE 1

| Amino Acid | Three-letter code | One-letter code |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Aspartate/Asparagine | Baa | B |
| Glutamate/Glutamine | Zaa | Z |
| Any amino acid | Xaa | X |

BACKGROUND TO THE INVENTION

Controlling metabolic pathways in eukaryotic organisms is desirable for the purposes of producing novel traits therein or introducing novel traits into a particular cell, tissue or organ of said organism. Whilst recombinant DNA technology has provided significant progress in an understanding of the mechanisms regulating eukaryotic gene expression, much less progress has been made in the actual manipulation of gene expression to produce novel traits. Moreover, there are only limited means by which human intervention may lead to a modulation of the level of eukaryotic gene expression.

One approach to repressing, delaying or otherwise reducing gene expression utilise a mRNA molecule which is transcribed from the complementary strand of a nuclear gene to that which is normally transcribed and capable of being translated into a polypeptide. Although the precise mechanism involved in this approach is not established, it has been postulated that a double-stranded mRNA may form by base pairing between the complementary nucleotide sequences, to produce a complex which is translated at low efficiency and/or degraded by intracellular ribonuclease enzymes prior to being translated.

Alternatively, the expression of an endogenous gene in a cell, tissue or organ may be suppressed when one or more copies of said gene, or one or more copies of a substantially similar gene are introduced into the cell. Whilst the mechanism involved in this phenomenon has not been established and appears to be involve mechanistically heterogeneous processes. For example, this approach has been postulated to involve transcriptional repression, in which case somatically-heritable repressed states of chromatin are formed or alternatively, a post-transcriptional silencing wherein transcription initiation occurs normally but the RNA products of the co-suppressed genes are subsequently eliminated.

The efficiency of both of these approaches in targeting the expression of specific genes is very low and highly variable results are usually obtained. Inconsistent results are obtained using different regions of genes, for example 5'-untranslated regions, 3'-untranslated regions, coding regions or intron sequences to target gene expression. Accordingly, there currently exists no consensus as to the nature of genetic sequences which provide the most efficient means for repressing, delaying or otherwise reducing gene expression using existing technologies. Moreover, such a high degree of variation exists between generations such that it is not possible to predict the level of repression of a specific gene in the progeny of an organism in which gene expression was markedly modified.

Recently, Dorer and Henikoff (1994) demonstrated the silencing of tandemly repeated gene copies in the *Drosophila* genome and the transcriptional repression of dispersed *Drosophila* Adh genes by Polycomb genes (i.e. the Pc-G system; Pal-Bhadra et al, 1997). However, such silencing of tandemly repeated gene copies is of little utility in an attempt to manipulate gene expression in an animal cell by recombinant means, wherein the sequences capable of targeting the expression of a particular gene are introduced at dispersed locations in the genome, absent the combination of this approach with gene-targeting technology. Whilst theoretically possible, such combinations would be expected to work at only low-efficiency, based upon the low efficiency of gene-targeting approaches used in isolation and further, would require complicated vector systems. Additionally, the utilisation of transcriptional repression, such as the *Drosophila* Pc-G system, would appear to require some knowledge of the regulatory mechanisms capable of modulating the expression of any specific target gene and, as a consequence, would be difficult to implement in practice as a general technology for repressing, delaying or reducing gene expression in animal cells.

The poor understanding of the mechanisms involved in these phenomena has meant that there have been few improvements in technologies for modulating the level of gene expression, in particular technologies for delaying, repressing or otherwise reducing the expression of specific genes using recombinant DNA technology.

Furthermore, as a consequence of the unpredictability of these approaches, there is currently no commercially-viable means for modulating the level of expression of a specific gene in a eukaryotic or prokaryotic organism.

Thus, there exists a need for improved methods of modulating gene expression, in particular repressing, delaying or otherwise reducing gene expression in animal cells for the purpose of introducing novel phenotypic traits thereto. In particular, these methods should provide general means for phenotypic modification, without the necessity for performing concomitant gene-targeting approaches.

SUMMARY OF THE INVENTION

The invention is based in part on the surprising discovery by the inventors that cells which exhibit one or more desired traits can be produced and selected from transformed cells comprising a nucleic acid molecule operably linked to a promoter, wherein the transcription product of the nucleic acid molecule comprises a nucleotide sequence which is substantially identical to the nucleotide sequence of a transcript of an endogenous or non-endogenous target gene, the expression of which is intended to be modulated. The transformed cells are regenerated into whole tissues, organs or organisms capable of exhibiting novel traits, in particular virus resistance and modified expression of endogenous genes.

Accordingly, one aspect of the present invention provides a method of modulating the expression of a target gene in an animal cell, tissue or organ, said method at least comprising the step of introducing to said cell, tissue or organ one or more dispersed nucleic acid molecules or foreign nucleic acid molecules comprising multiple copies of a nucleotide sequence which is substantially identical to the nucleotide sequence of said target gene or a region thereof or complementary thereto for a time and under conditions sufficient for translation of the mRNA product of said target gene to be modified, subject to the proviso that the transcription of said mRNA product is not exclusively repressed or reduced.

In a particularly preferred embodiment, the dispersed nucleic acid molecules or foreign nucleic acid molecules comprises a nucleotide sequence which encodes multiple copies of an mRNA molecule which is substantially identical to the nucleotide sequence of the mRNA product of the target gene. More preferably, the multiple copies of the target molecule are tandem direct repeat sequences.

In a more particularly preferred embodiment, the dispersed nucleic acid molecule or foreign nucleic acid molecule is in an expressible form such that it is at least capable of being transcribed to produce mRNA.

The target gene may be a gene which is endogenous to the animal cell or alternatively, a foreign gene such as a viral or foreign genetic sequence, amongst others. Preferably, the target gene is a viral genetic sequence.

The invention is particularly useful in the modulation of eukaryotic gene expression, in particular the modulation of human or animal gene expression and even more particularly in the modulation of expression of genes derived from vertebrate and invertebrate animals, such as insects, aquatic animals (eg. fish, shellfish, molluscs, crustaceans such as crabs, lobsters and prawns, avian animals and mammals, amongst others).

A variety of traits are selectable with appropriate procedures and sufficient numbers of transformed cells. Such traits include, but are not limited to, visible traits, disease-resistance traits, and pathogen-resistance traits. The modulatory effect is applicable to a variety of genes expressed in plants and animals including, for example, endogenous genes responsible for cellular metabolism or cellular transformation, including oncogenes, transcription factors and other genes which encode polypeptides involved in cellular metabolism.

For example, an alteration in the pigment production in mice can be engineered by targeting the expression of the tyrosinase gene therein. This provides a novel phenotype of albinism in black mice. By targeting genes required for virus replication in a plant cell or an animal cell, a genetic construct which comprises multiple copies of nucleotide sequence encoding a viral replicase, polymerase, coat protein or uncoating gene, or protease protein, may be introduced into a cell where it is expressed, to confer immunity against the virus upon the cell.

In performance of the present invention, the dispersed nucleic acid molecule or foreign nucleic acid molecule will generally comprise a nucleotide sequence having greater than about 85% identity to the target gene sequence, however, a higher homology might produce a more effective modulation of expression of the target gene sequence. Substantially greater homology, or more than about 90% is preferred, and even more preferably about 95% to absolute identity is desirable.

The introduced dispersed nucleic acid molecule or foreign nucleic acid molecule sequence, needing less than absolute homology, also need not be full length, relative to either the primary transcription product or fully processed mRNA of the target gene. A higher homology in a shorter than full length sequence compensates for a longer less homologous sequence. Furthermore, the introduced sequence need not have the same intron or exon pattern, and homology of non coding segments will be equally effective. Normally, a sequence of greater than 20-100 nucleotides should be used, though a sequence of greater than about 200-300 nucleotides would be preferred, and a sequence of greater than 500-1000 nucleotides would be especially preferred depending on the size of the target gene.

A second aspect of the present invention provides a synthetic gene which is capable of modifying target gene expression in a cell, tissue or organ of a prokaryotic or eukaryotic organism which is transfected or transformed therewith, wherein said synthetic gene at least comprises a dispersed nucleic acid molecular foreign nucleic acid molecule comprising multiple copies of a nucleotide sequence which is substantially identical to the nucleotide sequence of said target gene or a derivative thereof or a complementary sequence thereto placed operably under the control of a promoter sequence which is operable in said cell, tissue or organ.

A third aspect of the invention provides a synthetic gene which is capable of modifying the expression of a target gene in a cell, tissue or organ of a prokaryotic or eukaryotic organism which is transfected or transformed therewith, wherein said synthetic gene at least comprises multiple structural gene sequences, wherein each of said structural gene sequences comprises a nucleotide sequence which is substantially identical to the nucleotide sequence of said target gene or a derivative thereof or a complementary sequence thereto and wherein said multiple structural gene sequences are placed operably under the control of a single promoter sequence which is operable in said cell, tissue or organ.

A fourth aspect of the present invention provides a synthetic gene which is capable of modifying the expression of a target gene in a cell, tissue or organ of a prokaryote or eukaryote which is transfected or transformed therewith wherein said synthetic gene at least comprises multiple structural gene sequences wherein each of said structural gene sequences is placed operably under the control of a promoter sequence which is operable in said cell, tissue or organ and wherein each of said structural gene sequences comprises a nucleotide sequence which is substantially identical to the nucleotide sequence of said target gene or a derivative thereof or a complementary sequence thereto.

A fifth aspect of the present invention provides a genetic construct which is capable of modifying the expression of an endogenous gene or target gene in a transformed or transfected cell, tissue or organ wherein said genetic construct at least comprises the synthetic gene of the invention and one or more origins of replication and/or selectable marker gene sequences.

In order to observe many novel traits in multicellular organisms such as plants and animals, in particular those which are tissue-specific or organ-specific or developmentally-regulated, regeneration of a transformed cell carrying the synthetic genes and genetic constructs described herein into a whole organism will be required. Those skilled in the art will be aware that this means growing a whole organism from a transformed plant cell or animal cell, a group of such cells, a tissue or organ. Standard methods for the regeneration of certain plants and animals from isolated cells and tissues are known to those skilled in the art.

Accordingly, a sixth aspect of the invention provides a cell, tissue, organ or organism comprising the synthetic genes and genetic constructs described herein.

BRIEF DESCRIPTION OF THE DRAWINGS

Figure 25:
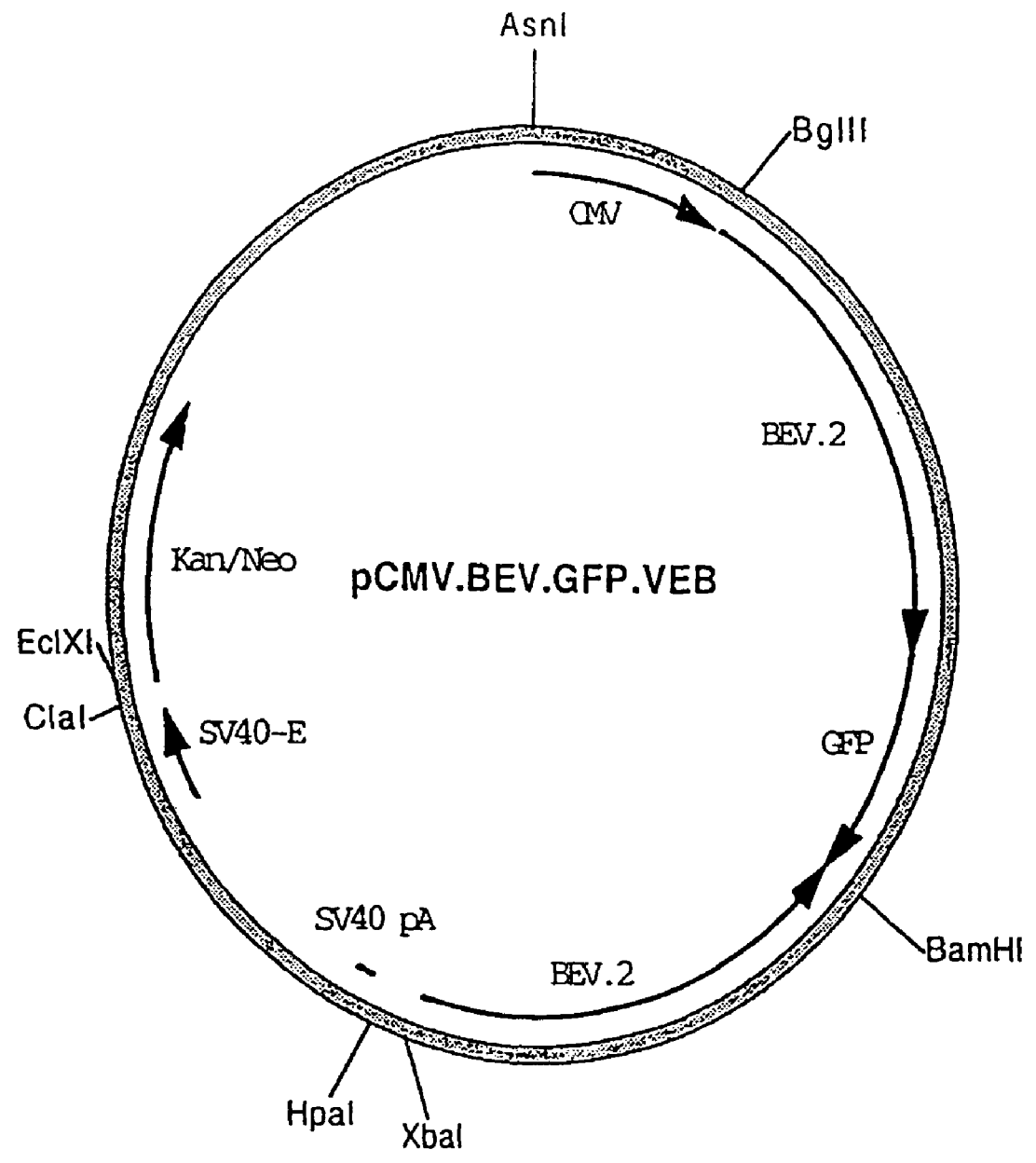

FIG. 25 is a diagrammatic representation of the plasmid pCMV.BEV.GFP.VEB.

FIG. 46 is a diagrammatic representation of the plasmid pClapBC.PVY.

FIG. 52 is a diagrammatic representation of the plasmid pBC.PVY.LNYV.PVY.

FIG. 53 is a diagrammatic representation of the plasmid pBC.PVY.LNYV.YVPΔ.

Figure 63:
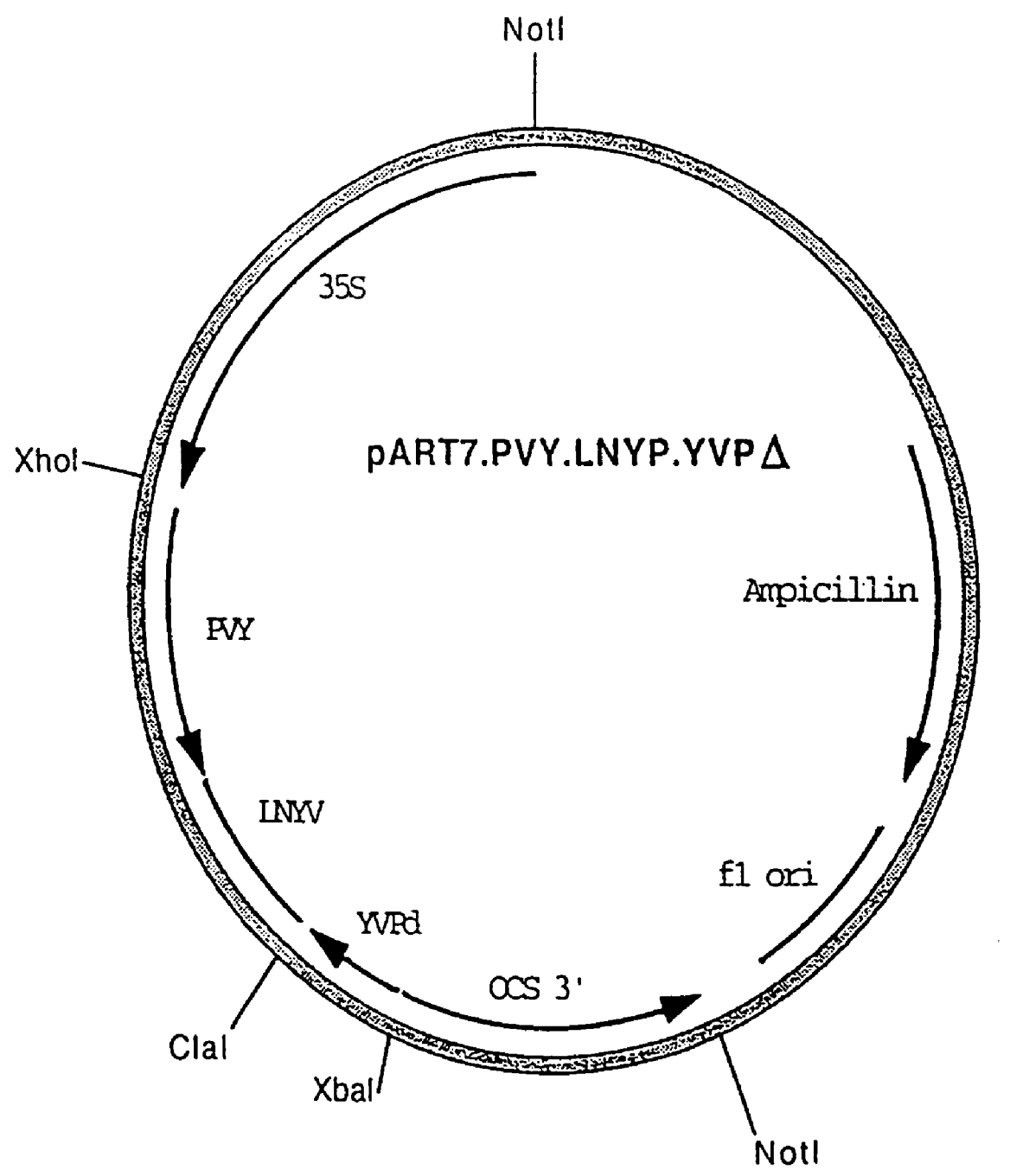

FIG. 63 is a diagrammatic representation of the plasmid pART7.PVY.LNYV.YVPΔ.

Figure 64:
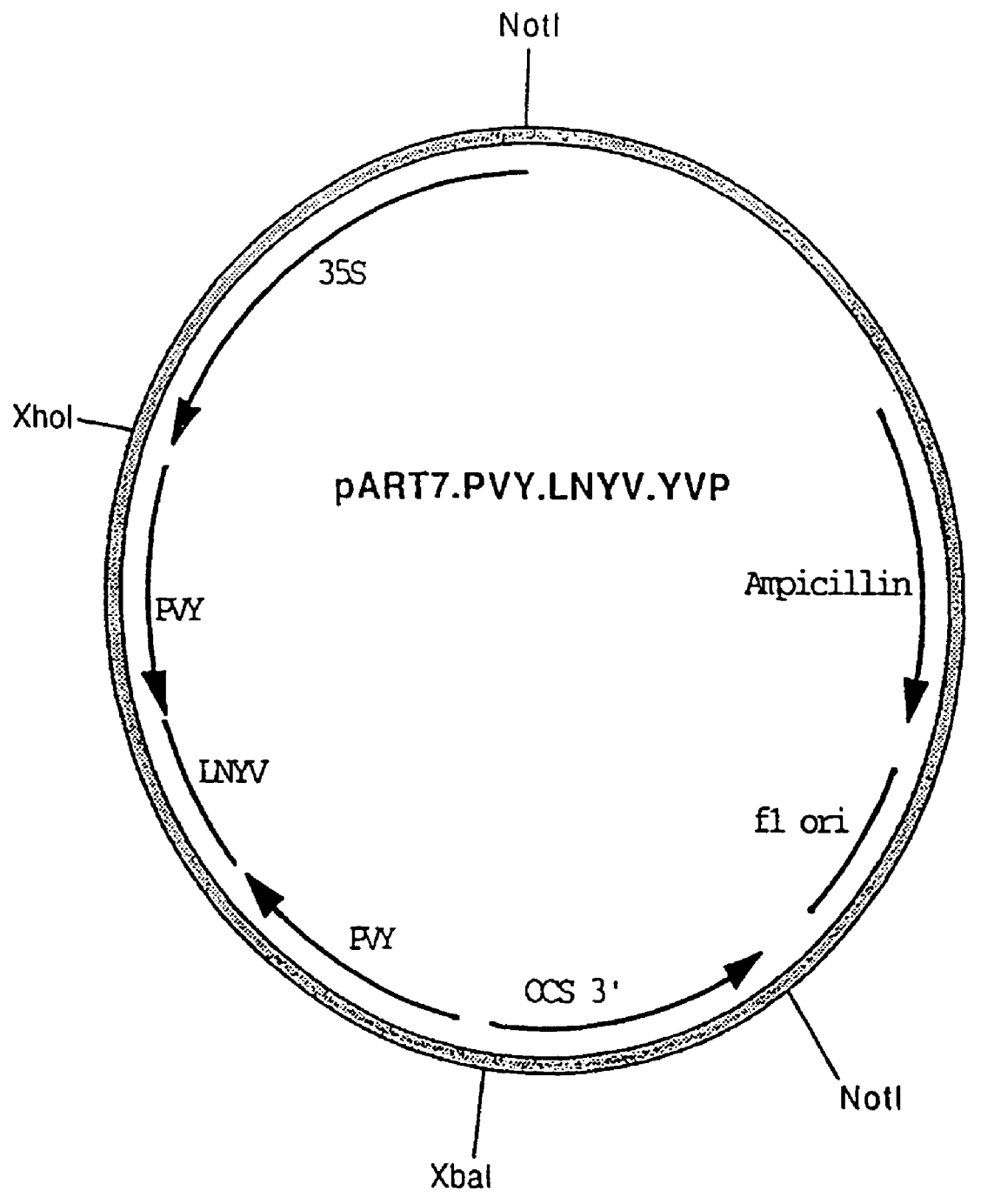

FIG. 64 is a diagrammatic representation of the plasmid pART7.PVY.LNYV.YVP.

FIG. 65 is a diagrammatic representation of pART7.35S.PVY.SCBV.YVP.

FIG. 66 is a diagrammatic representation of pART7.35S.PVYx3.SCBV.YVPx3.

FIG. 67 is a diagrammatic representation of pART7.PVYx3.LNYV.YVPx3.

DETAILED DESCRIPTION OF THE INVENTION

Figure 1:
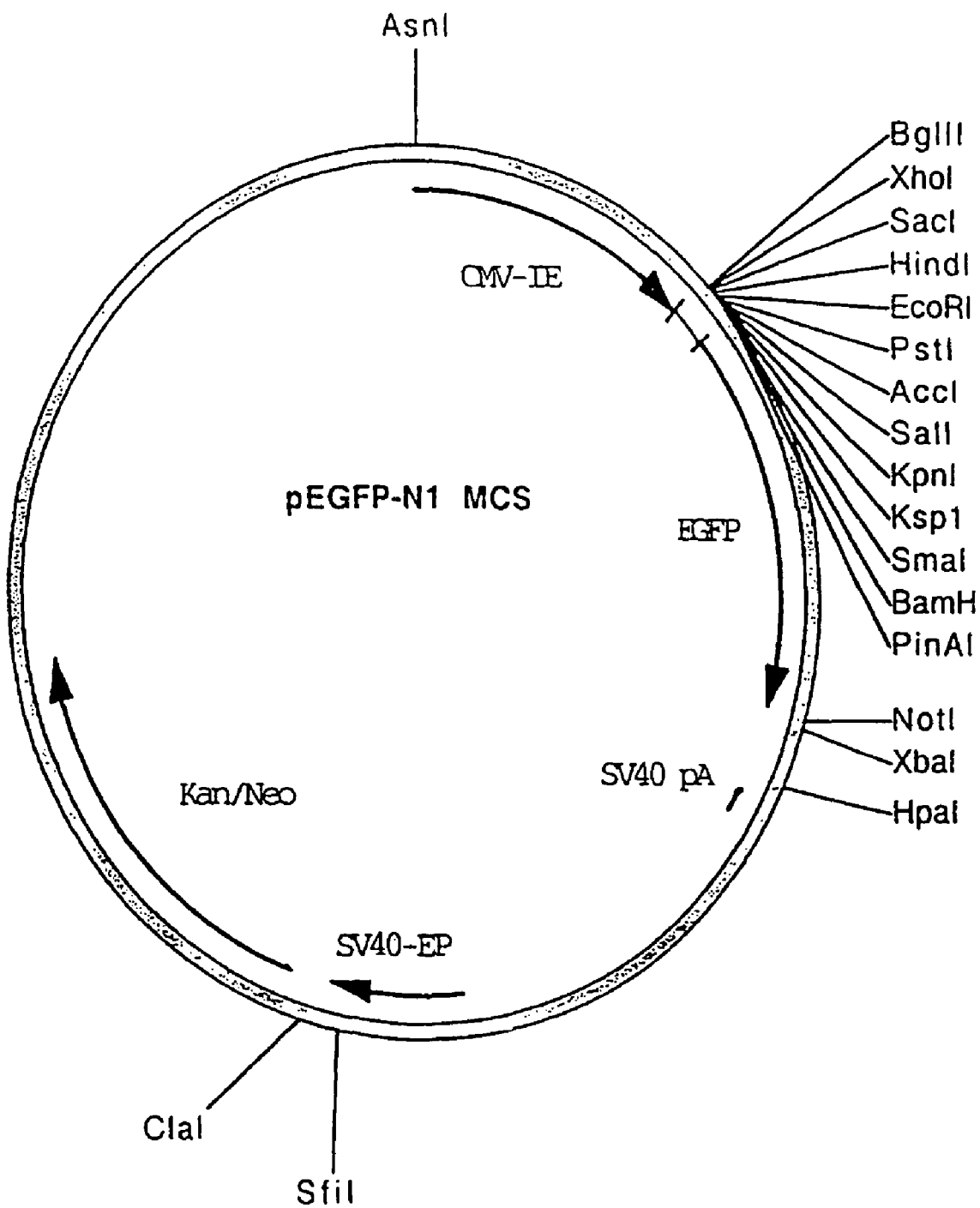
FIG. 1 is a diagrammatic representation of the plasmid pEGFP-N1 MCS.

The present invention provides a method of modulating the expression of a target gene in a cell, tissue or organ, said method at least comprising the step of introducing to said cell, tissue or organ one or more dispersed nucleic acid molecules or foreign nucleic acid molecules comprising multiple copies of a nucleotide sequence which is substantially identical to the nucleotide sequence of said target gene or a region thereof or complementary thereto for a time and under conditions sufficient for translation of the mRNA product of said target gene to be modified, subject to the proviso that the transcription of said mRNA product is not exclusively repressed or reduced.

By "multiple copies" is meant that two or more copies of the target gene are presented in close physical connection or juxtaposed, in the same or different orientation, on the same nucleic acid molecule, optionally separated by a stuffer fragment or intergenic region to facilitate secondary structure formation between each repeat where this is required. The stuffer fragment may comprise any combination of nucleotide or amino acid residues, carbohydrate molecules or oligosaccharide molecules or carbon atoms or a homologue, analogue or derivative thereof which is capable of being linked covalently to a nucleic acid molecule.

Preferably, embodiment, the stuffer fragment comprises a sequence of nucleotides or a homologue, analogue or derivative thereof.

More preferably, the stuffer fragment comprises a sequence of nucleotides of at least about 10-50 nucleotides in length, even more preferably at least about 50-100 nucleotides in length and still more preferably at least about 100-500 nucleotides in length.

Wherein the dispersed or foreign nucleic acid molecule comprises intron/exon splice junction sequences, the stuffer fragment may serve as an intron sequence placed between the 3'-splice site of the structural gene nearer the 5'-end of the gene and the 5'-splice site of the next downstream unit thereof. Alternatively, wherein it is desirable for more than two adjacent nucleotide sequence units of the dispersed foreign nucleic acid molecule to be translated, the stuffer fragment placed there between should not include an in-frame translation stop codon, absent intron/exon splice junction sequences at both ends of the stuffer fragment or the addition of a translation start codon at the 5' end of each unit, as will be obvious to those skilled in the art.

Preferred stuffer fragments are those which encode detectable marker proteins or biologically-active analogues and derivatives thereof, for example luciferase, β-galacturonase, β-galactosidase, chloramphenicol acetyltransferase or green fluorescent protein, amongst others. Additional stuffer fragments are not excluded.

According to this embodiment, the detectable marker or an analogue or derivative thereof serves to indicate the expression of the synthetic gene of the invention in a cell, tissue or organ by virtue of its ability to confer a specific detectable phenotype thereon, preferably a visually-detectable phenotype.

As used herein, the term "modulating" shall be taken to mean that expression of the target gene is reduced in amplitude and/or the timing of gene expression is delayed and/or the developmental or tissue-specific or cell-specific pattern of target gene expression is altered, compared to the expression of said gene in the absence of the inventive method described herein.

Whilst not limiting the scope of the invention described herein, the present invention is directed to a modulation of gene expression which comprises the repression, delay or reduction in amplitude of target gene expression in a specified cell, tissue or organ of a eukaryotic organism, in particular a plant such as a monocotyledonous or dicotyledonous plant, or a human or other animal and even more particularly a vertebrate and invertebrate animal, such as an insect, aquatic animal (eg. fish, shellfish, mollusc, crustacean such as a crab, lobster or prawn, an avian animal or a mammal, amongst others).

More preferably, target gene expression is completely inactivated by the dispersed nucleic acid molecules or foreign nucleic acid molecules which has been introduced to the cell, tissue or organ.

Whilst not being bound by any theory or mode of action, the reduced or eliminated expression of the target gene which results from the performance of the invention may be attributed to reduced or delayed translation of the mRNA transcription product of the target gene or alternatively, the prevention of translation of said mRNA, as a consequence of sequence-specific degradation of the mRNA transcript of the target gene by an endogenous host cell system.

It is particularly preferred that, for optimum results, sequence-specific degradation of the mRNA transcript of the target gene occurs either prior to the time or stage when the mRNA transcript of the target gene would normally be translated or alternatively, at the same time as the mRNA transcript of the target gene would normally be translated. Accordingly, the selection of an appropriate promoter sequence to regulate expression of the introduced dispersed nucleic acid molecule or foreign nucleic acid molecule is an important consideration to optimum performance of the invention. For this reason, strong constitutive promoters or inducible promoter systems are especially preferred for use in regulating expression of the introduced dispersed nucleic acid molecules or foreign nucleic acid molecules.

The present invention clearly encompasses reduced expression wherein reduced expression of the target gene is effected by lowered transcription, subject to the proviso that a reduction in transcription is not the sole mechanism by which this occurs and said reduction in transcription is at least accompanied by reduced translation of the steady-state mRNA pool.

The target gene may be a genetic sequence which is endogenous to the animal cell or alternatively, a non-endogenous genetic sequence, such as a genetic sequence which is derived from a virus or other foreign pathogenic organism and is capable of entering a cell and using the cell's machinery following infection.

Wherein the target gene is a non-endogenous genetic sequence to the animal cell, it is desirable that the target gene encodes a function which is essential for replication or reproduction of the viral or other pathogen. In such embodiments, the present invention is particularly useful in the prophylactic and therapeutic treatment of viral infection of an animal cell or for conferring or stimulating resistance against said pathogen.

Preferably, the target gene comprises one or more nucleotide sequences of a viral pathogen of a plant or an animal cell, tissue or organ.

For example, in the case of animals and humans, the viral pathogen may be a retrovirus, for example a lentivirus such as the immunodeficiency viruses, a single-stranded (+) RNA virus such as bovine enterovirus (BEV) or Sinbis alphavirus. Alternatively, the target gene can comprise one or more nucleotide sequences of a viral pathogen of an animal cell, tissue or organ, such as but not limited to a double-stranded DNA virus such as bovine herpes virus or herpes simplex virus I (HSV I), amongst others.

In the case of plants, the virus pathogen is preferably a potyvirus, caulimovirus, badnavirus, geminivirus, reovirus, rhabdovirus, bunyavirus, tospovirus, tenuivirus, tombusvirus, luteovirus, sobemovirus, bromovirus, cucomovirus, ilavirus, alfamovirus, tobamovirus, tobravirus, potexvirus and clostrovirus, such as but not limited to CaMV, SCSV, PVX, PVY, PLRV, and TMV, amongst others.

With particular regard to viral pathogens, those skilled in the art are aware that virus-encoded functions may be complemented in trans by polypeptides encoded by the host cell. For example, the replication of the bovine herpes virus genome in the host cell may be facilitated by host cell DNA polymerases which are capable of complementing an inactivated viral DNA polymerase gene.

Accordingly, wherein the target gene is a non-endogenous genetic sequence to the animal cell, a further alternative embodiment of the invention provides for the target gene to encode a viral or foreign polypeptide which is not capable of being complemented by a host cell function, such as a virus-specific genetic sequence. Exemplary target genes according to this embodiment of the invention include, but are not limited to genes which encode virus coat proteins, uncoating proteins and RNA-dependent DNA polymerases and RNA-dependent RNA polymerases, amongst others.

In a particularly preferred embodiment of the present invention, the target gene is the BEV RNA-dependent RNA polymerase gene or a homologue, analogue or derivative thereof or PVY Nia protease-encoding sequences.

The cell in which expression of the target gene is modified may be any cell which is derived from a multicellular plant or animal, including cell and tissue cultures thereof. Preferably, the animal cell is derived from an insect, reptile, amphibian, bird, human or other mammal. Exemplary animal cells include embryonic stem cells, cultured skin fibroblasts, neuronal cells, somatic cells, haematopoietic stem cells, T-cells and immortalised cell lines such as COS, VERO, HeLa, mouse C127, Chinese hamster ovary (CHO), WI-38, baby hamster kidney (BHK) or MDBK cell lines, amongst others Such cells and cell lines are readily available to those skilled in the art. Accordingly, the tissue or organ in which expression of the target gene is modified may be any tissue or organ comprising such animal cells.

Preferably the plant cell is derived from a monocotyledonous or dicotyledonous plant species or a cell line derived therefrom.

As used herein, the term "dispersed nucleic acid molecule" shall be taken to refer to a nucleic acid molecule which comprises one or more multiple copies, preferably tandem direct repeats, of a nucleotide sequence which is substantially identical or complementary to the nucleotide sequence of a gene which originates from the cell, tissue or organ into which said nucleic acid molecule is introduced, wherein said nucleic acid molecule is non-endogenous in the sense that it is introduced to the cell, tissue or organ of an animal via recombinant means and will generally be present as extrachromosomal nucleic acid or alternatively, as integrated chromosomal nucleic acid which is genetically-unlinked to said gene. More particularly, the "dispersed nucleic acid molecule" will comprise chromosomal or extrachromosomal nucleic acid which is unlinked to the target gene against which it is directed in a physical map, by virtue of their not being tandemly-linked or alternatively, occupying a different chromosomal position on the same chromosome or being localised on a different chromosome or present in the cell as an episome, plasmid, cosmid or virus particle.

By "foreign nucleic acid molecule" is meant an isolated nucleic acid molecule which has one or more multiple copies, preferably tandem direct repeats, of a nucleotide sequence which originates from the genetic sequence of an organism which is different from the organism to which the foreign nucleic acid molecule is introduced. This definition encompasses a nucleic acid molecule which originates from a different individual of the same lowest taxonomic grouping (i.e. the same population) as the taxonomic grouping to which said nucleic acid molecule is introduced, as well as a nucleic acid molecule which originates from a different individual of a different taxonomic grouping as the taxonomic grouping to which said nucleic acid molecule is introduced, such as a gene derived from a viral pathogen.

Accordingly, a target gene against which a foreign nucleic acid molecule acts in the performance of the invention may be a nucleic acid molecule which has been introduced from one organism to another organism using transformation or introgression technologies. Exemplary target genes according to this embodiment of the invention include the green fluorescent protein-encoding gene derived from the jellyfish *Aequoria victoria* (Prasher et al., 1992; International Patent Publication No. WO 95/07463), tyrosinase genes and in particular the murine tyrosinase gene (Kwon et al., 1988), the *Escherchia coli* lacI gene which is capable of encoding a polypeptide repressor of the lacZ gene, the porcine α-1,3-galactosyltransferase gene (NCBI Accession No. L36535) exemplified herein, and the PVY and BEV structural genes exemplified herein or a homologue, analogue or derivative of said genes or a complementary nucleotide sequence thereto.

The present invention is further useful for simultaneously targeting the expression of several target genes which are co-expressed in a particular cell, for example by using a dispersed nucleic acid molecule or foreign nucleic acid molecule which comprises nucleotide sequences which are substantially identical to each of said co-expressed target genes.

By "substantially identical" is meant that the introduced dispersed or foreign nucleic acid molecule of the invention and the target gene sequence are sufficiently identical at the nucleotide sequence level to permit base-pairing there between under standard intracellular conditions.

Preferably, the nucleotide sequence of each repeat in the dispersed or foreign nucleic acid molecule of the invention and the nucleotide sequence of a part of the target gene sequence are at least about 80-85% identical at the nucleotide sequence level, more preferably at least about 85-90% identical, even more preferably at least about 90-95% identical and still even more preferably at least about 95-99% or 100% identical at the nucleotide sequence level.

Notwithstanding that the present invention is not limited by the precise number of repeated sequences in the dispersed nucleic acid molecule or the foreign nucleic acid molecule of the invention, it is to be understood that the present invention requires at least two copies of the target gene sequence to be expressed in the cell.

Preferably, the multiple copies of the target gene sequence are presented in the dispersed nucleic acid molecule or the foreign nucleic acid molecule as tandem inverted repeat sequences and/or tandem direct repeat sequences. Such configurations are exemplified by the "test plasmids" described herein that comprise Galt, BEV or PVY gene regions.

Preferably, the dispersed or foreign nucleic acid molecule which is introduced to the cell, tissue or organ comprises RNA or DNA.

Preferably, the dispersed or foreign nucleic acid molecule further comprises a nucleotide sequence or is complementary to a nucleotide sequence which is capable of encoding an amino acid sequence encoded by the target gene. Even more preferably, the nucleic acid molecule includes one or more ATG or AUG translational start codons.

Standard methods may be used to introduce the dispersed nucleic acid molecule or foreign nucleic acid molecule into the cell, tissue or organ for the purposes of modulating the expression of the target gene. For example, the nucleic acid molecule may be introduced as naked DNA or RNA, optionally encapsulated in a liposome, in a virus particle as attenuated virus or associated with a virus coat or a transport protein or inert carrier such as gold or as a recombinant viral vector or bacterial vector or as a genetic construct, amongst others.

Administration means include injection and oral ingestion (e.g. in medicated food material), amongst others.

The subject nucleic acid molecules may also be delivered by a live delivery system such as using a bacterial expression system optimised for their expression in bacteria which can be incorporated into gut flora. Alternatively, a viral expression system can be employed. In this regard, one form of viral expression is the administration of a live vector generally by spray, feed or water where an infecting effective amount of the live vector (e.g. virus or bacterium) is provided to the animal. Another form of viral expression system is a non-replicating virus vector which is capable of infecting a cell but not replicating therein. The non-replicating viral vector provides a means of introducing to the human or animal subject genetic material for transient expression therein. The mode of administering such a vector is the same as a live viral vector.

The carriers, excipients and/or diluents utilised in delivering the subject nucleic acid molecules to a host cell should be acceptable for human or veterinary applications. Such carriers, excipients and/or diluents are well-known to those skilled in the art. Carriers and/or diluents suitable for veterinary use include any and all solvents, dispersion media, aqueous solutions, coatings, antibacterial and antifungal agents, isotonic and absorption delaying agents, and the like. Except insofar as any conventional media or agent is incompatible with the active ingredient, use thereof in the composition is contemplated. Supplementary active ingredients can also be incorporated into the compositions.

In an alternative embodiment, the invention provides a method of modulating the expression of a target gene in a cell, tissue or organ, said method at least comprising the steps of:
(i) selecting one or more dispersed nucleic acid molecules or foreign nucleic acid molecules which comprise multiple copies of a nucleotide sequence which is substantially identical to the nucleotide sequence of said target gene or a region thereof or which is complementary thereto; and
(ii) introducing said dispersed nucleic acid molecules or foreign nucleic acid molecules to said cell, tissue or organ for a time and under conditions sufficient for translation of the mRNA product of said target gene to be modified, subject to the proviso that the transcription of said mRNA product is not exclusively repressed or reduced.

To select appropriate nucleotide sequences for targeting expression of the target gene, several approaches may be employed. In one embodiment, multiple copies of specific regions of characterised genes may be cloned in operable connection with a suitable promoter and assayed for efficacy in reducing target gene expression. Alternatively, shotgun libraries comprising multiple copies of genetic sequences may be produced and assayed for their efficacy in reducing target gene expression. The advantage associated with the latter approach is that it is not necessary to have any prior knowledge of the significance of any particular target gene in specifying an undesirable phenotype in the cell. For example, shotgun libraries comprising virus sub-genomic fragments may be employed and tested directly for their ability to confer virus immunity on the animal host cell, without prior knowledge of the role which any virus genes play in pathogenesis of the host cell.

As used herein, the term "shotgun library" is a set of diverse nucleotide sequences wherein each member of said set is preferably contained within a suitable plasmid, cosmid, bacteriophage or virus vector molecule which is suitable for maintenance and/or replication in a cellular host. The term "shotgun library" includes a representative library, in which the extent of diversity between the nucleotide sequences is numerous such that all sequences in the genome of the organism from which said nucleotide sequences is derived are present in the "set" or alternatively, a limited library in which there is a lesser degree of diversity between said sequences. The term "shotgun library" further encompasses random nucleotide sequences, wherein the nucleotide sequence comprises viral or cellular genome fragments, amongst others obtained for example by shearing or partial digestion of genomic DNA using restriction endonucleases, amongst other approaches. A "shotgun library" further includes cells, virus particles and bacteriophage particles comprising the individual nucleotide sequences of the diverse set.

Preferred shotgun libraries according to this embodiment of the invention are "representative libraries", comprising a set of tandem repeated nucleotide sequences derived from a viral pathogen of a plant or an animal.

In a particularly preferred embodiment of the invention, the shotgun library comprises cells, virus particles or bacteriophage particles comprising a diverse set of tandem-repeated nucleotide sequences which encode a diverse set of amino acid sequences, wherein the member of said diverse set of nucleotide sequences are placed operably under the control of a promoter sequence which is capable of directing the expression of said tandem-repeated nucleotide sequence in the cell.

Accordingly, the nucleotide sequence of each unit in the tandem-repeated sequence may comprise at least about 1 to 200 nucleotides in length. The use of larger fragments, particularly employing randomly sheared nucleic acid derived from viral, plant or animal genomes, is not excluded.

The introduced nucleic acid molecule is preferably in an expressible form.

By "expressible form" is meant that the subject nucleic acid molecule is presented in an arrangement such that it may be expressed in the cell, tissue, organ or whole organism, at least at the transcriptional level (i.e. it is expressed in the animal cell to yield at least an mRNA product which is optionally translatable or translated to produce a recombinant peptide, oligopeptide or polypeptide molecule).

By way of exemplification, in order to obtain expression of the dispersed nucleic acid molecule or foreign nucleic acid molecule in the cell, tissue or organ of interest, a synthetic gene or a genetic construct comprising said synthetic gene is produced, wherein said synthetic gene comprises a nucleotide sequence as described supra in operable connection with a promoter sequence which is capable of regulating expression therein. Thus, the subject nucleic acid molecule will be operably connected to one or more regulatory elements sufficient for eukaryotic transcription to occur.

Accordingly, a further alternative embodiment of the invention provides a method of modulating the expression of a target gene in an animal cell, tissue or organ, said method at least comprising the steps of:
(i) selecting one or more dispersed nucleic acid molecules or foreign nucleic acid molecules which comprise multiple copies, preferably tandem repeats, of a nucleotide sequence which is substantially identical to the nucleotide sequence of said target gene or a region thereof or which is complementary thereto;
(ii) producing a synthetic gene comprising said dispersed nucleic acid molecules or foreign nucleic acid molecules;
(iii) introducing said synthetic gene to said cell, tissue or organ; and
(iv) expressing said synthetic gene in said cell, tissue or organ for a time and under conditions sufficient for translation of the mRNA product of said target gene to be modified, subject to the proviso that the transcription of said mRNA product is not exclusively repressed or reduced.

Reference herein to a "gene" or "genes" is to be taken in its broadest context and includes:
(i) a classical genomic gene consisting of transcriptional and/or translational regulatory sequences and/or a coding region and/or non-translated sequences (i.e. introns, 5'- and 3'-untranslated sequences); and/or
(ii) mRNA or cDNA corresponding to the coding regions (i.e. exons) and 5'- and 3'-untranslated sequences of the gene; and/or
(iii) a structural region corresponding to the coding regions (i.e. exons) optionally further comprising untranslated sequences and/or a heterologous promoter sequence which consists of transcriptional and/or translational regulatory regions capable of conferring expression characteristics on said structural region.

The term "gene" is also used to describe-synthetic or fusion molecules encoding all or part of a functional product, in particular a sense or antisense mRNA product or a peptide, oligopeptide or polypeptide or a biologically-active protein.

The term "synthetic gene" refers to a non-naturally occurring gene as hereinbefore defined which preferably comprises at least one or more transcriptional and/or translational regulatory sequences operably linked to a structural gene sequence.

The term "structural gene" shall be taken to refer to a nucleotide sequence which is capable of being transmitted to produce mRNA and optionally, encodes a peptide, oligopeptide, polypeptide or biologically active protein molecule. Those skilled in the art will be aware that not all mRNA is capable of being translated into a peptide, oligopeptide, polypeptide or protein, for example if the mRNA lacks a functional translation start signal or alternatively, if the mRNA is antisense mRNA. The present invention clearly encompasses synthetic genes comprising nucleotide sequences which are not capable of encoding peptides, oligopeptides, polypeptides or biologically-active proteins. In particular, the present inventors have found that such synthetic genes may be advantageous in modifying target gene expression in cells, tissues or organs of a prokaryotic or eukaryotic organism.

The term "structural gene region" refers to that part of a synthetic gene which comprises a dispersed nucleic acid molecule or foreign nucleic acid molecule as described herein which is expressed in a cell, tissue or organ under the control of a promoter sequence to which it is operably connected. A structural gene region may comprise one or more dispersed nucleic acid molecules and/or foreign nucleic acid molecules operably under the control of a single promoter sequence or multiple promoter sequences. Accordingly, the structural gene region of a synthetic gene may comprise a nucleotide sequence which is capable of encoding an amino acid sequence or is complementary thereto. In this regard, a structural gene region which is used in the performance of the instant invention may also comprise a nucleotide sequence which encodes an animo acid sequence yet lacks a functional translation initiation codon and/or a functional translation stop codon and, as a consequence, does not comprise a complete open reading frame. In the present context, the term "structural gene region" also extends to a non-coding nucleotide sequences, such as 5'-upstream or 3'-downstream sequences of a gene which would not normally be translated in a eukaryotic cell which expresses said gene.

Accordingly, in the context of the present invention, a structural gene region may also comprise a fusion between two or more open reading frames of the same or different genes. In such embodiments, the invention may be used to modulate the expression of one gene, by targeting different non-contiguous regions thereof or alternatively, to simultaneously modulate the expression of several different genes, including different genes of a multigene family. In the case of a fusion nucleic acid molecule which is non-endogenous to the animal cell and in particular comprises two or more nucleotide sequences derived from a viral pathogen, the fusion may provide the added advantage of conferring simultaneous immunity or protection against several pathogens, by targeting the expression of genes in said several pathogens. Alternatively or in addition, the fusion may provide more effective immunity against any pathogen by targeting the expression of more than one gene of that pathogen.

Particularly preferred structural gene regions according to this aspect of the invention are those which include at least one translatable open reading frame, more preferably further including a translational start codon located at the 5'-end of said open reading frame, albeit not necessarily at the 5'-terminus of said structural gene region. In this regard, notwithstanding that the structural gene region may comprise at least one translatable open reading frame and/or AUG or ATG translational start codon, the inclusion of such sequences in no way suggests that the present invention requires translation of the introduced nucleic acid molecule to occur in order to modulate the expression of the target gene. Whilst not being bound by any theory or mode of action, the inclusion of at least one translatable open reading frame and/or translational start codon in the subject nucleic acid molecule may serve to increase stability of the mRNA transcription product thereof, thereby improving the efficiency of the invention.

The optimum number of structural gene sequences which may be involved in the synthetic gene of the present invention will vary considerably, depending upon the length of each of said structural gene sequences, their orientation and degree of identity to each other. For example, those skilled in the art will be aware of the inherent instability of palindromic nucleotide sequences in vivo and the difficulties associated with constructing long synthetic genes comprising inverted repeated nucleotide sequences, because of the tendency for such sequences to recombine in vivo. Notwithstanding such difficulties, the optimum number of structural gene sequences to be included in the synthetic genes of the present invention may be determined empirically by those skilled in the art, without any undue experimentation and by following standard procedures such as the construction of the synthetic gene of the invention using recombinase-deficient cell lines, reducing the number of repeated sequences to a level which eliminates or minimises recombination events and by keeping the total length of the multiple structural gene sequence to an acceptable limit, preferably no more than 5-10 kb, more preferably no more than 2-5 kb and even more preferably no more than 0.5-2.0 kb in length.

Wherein the structural gene region comprises more than one dispersed nucleic acid molecule or foreign nucleic acid molecule it shall be referred to herein as a "multiple structural gene region" or similar term. The present invention clearly extends to the use of multiple structural gene regions which preferably comprise a direct repeat sequence, inverted repeat sequence or interrupted palindrome sequence of a particular structural gene, dispersed nucleic acid molecule or foreign nucleic acid molecule, or a fragment thereof.

Each dispersed or foreign nucleic acid molecule contained within the multiple structural gene unit of the subject synthetic gene may comprise a nucleotide sequence which is substantially identical to a different target gene in the same organism. Such an arrangement may be of particular utility when the synthetic gene is intended to provide protection against a pathogen in a cell, tissue or organ, in particular a viral pathogen, by modifying the expression of viral target genes. For example, the multiple structural gene may comprise nucleotide sequences (i.e. two or more dispersed or foreign nucleic acid molecules) which are substantially identical to two or more target genes selected from the list comprising DNA polymerase, RNA polymerase, Nia protease, and coat protein or other target gene which is essential for viral infectivity, replication or reproduction. However, it is preferred with this arrangement that the structural gene units are selected such that the target genes to which they are substantially identical are normally expressed at approximately the same time (or later) in an infected cell, tissue or organ as (than) the multiple structural gene of the subject synthetic gene is expressed under control of the promoter sequence. This means that the promoter controlling expression of the multiple structural gene will usually be selected to confer expression in the cell, tissue or organ over the entire life cycle of the virus when the viral target genes are expressed at different stages of infection.

As with the individual sequence units of a dispersed or foreign nucleic acid molecule, the individual units of the multiple structural gene may be spatially connected in any orientation relative to each other, for example head-to-head, head-to-tail or tail-to-tail and all such configurations are within the scope of the invention.

For expression in eukaryotic cells, the synthetic gene generally comprises, in addition to the nucleic acid molecule of the invention, a promoter and optionally other regulatory sequences designed to facilitate expression of the dispersed nucleic acid molecule or foreign nucleic acid molecule.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', of a structural gene region, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a nucleic acid molecule in a cell.

Preferred promoters may contain additional copies of one or more specific regulatory elements, to further enhance expression of the sense molecule and/or to alter the spatial expression and/or temporal expression of said sense molecule. For example, regulatory elements which confer copper inducibility may be placed adjacent to a heterologous promoter sequence driving expression of a sense molecule, thereby conferring copper inducibility on the expression of said molecule.

Placing a dispersed or foreign nucleic acid molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in the synthetic genes of the present invention include viral, fungal, bacterial, animal and plant derived promoters capable of functioning in plant, animal, insect, fungal, yeast or bacterial cells. The promoter may regulate the expression of the structural gene component constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and more preferably also immediately preceding the commencement of detectable expression of the target gene in said cell, tissue or organ.

Accordingly, strong constitutive promoters are particularly preferred for the purposes of the present invention or promoters which may be induced by virus infection or the commencement of target gene expression.

Plant-operable and animal-operable promoters are particularly preferred for use in the synthetic genes of the present invention. Examples of preferred promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter, SCSV promoter, SCBV promoter and the like.

In consideration of the preferred requirement for high-level expression which coincides with expression of the target gene or precedes expression of the target gene, it is highly desirable that the promoter sequence is a constitutive strong promoter such as the CMV-IE promoter or the SV40 early promoter sequence, the SV40 late promoter sequence, the CaMV 35S promoter, or the SCBV promoter, amongst others. Those skilled in the art will readily be aware of additional promoter sequences other than those specifically described.

In the present context, the terms "in operable connection with" or "operably under the control" or similar shall be taken to indicate that expression of the structural gene region or multiple structural gene region is under the control of the promoter sequence with which it is spatially connected; in a cell, tissue, organ or whole organism.

In a preferred embodiment of the invention, a structural gene region (i.e. dispersed nucleic acid molecule or foreign nucleic acid molecule) or multiple structural gene region is placed operably in connection with a promoter orientation relative to the promoter sequence, such that when it is transcribed an mRNA product is synthesized which, if translated, is capable of encoding a polypeptide product of the target gene or a fragment thereof.

However, the present invention is not to be limited to the use of such an arrangement and the invention clearly extends to the use of synthetic genes and genetic constructs wherein the a structural gene region or multiple structural gene region is placed in the "antisense" orientation relative to the promoter sequence, such that at least a part of the mRNA transcription product thereof is complementary to the mRNA encoded by the target gene or a fragment thereof.

Clearly, as the dispersed nucleic acid molecule, foreign nucleic acid molecule or multiple structural gene region comprises tandem direct and/or inverted repeat sequences of the target gene, all combinations of the above-mentioned configurations are encompassed by the invention.

In an alternative embodiment of the invention, the structural gene region or multiple structural gene region is operably connected to both a first promoter sequence and a second promoter sequence, wherein said promoters are located at the distal and proximal ends thereof such that at least one unit of said a structural gene region or multiple structural gene region is placed in the "sense" orientation relative to the first promoter sequence and in the "antisense" orientation relative to the second promoter sequence. According to this embodiment, it is also preferred that the first and second promoters be different, to prevent competition there between for cellular transcription factors which bind thereto. The advantage of this arrangement is that the effects of transcription from the first and second promoters in reducing target gene expression in the cell may be compared to determine the optimum orientation for each nucleotide sequence tested.

The synthetic gene preferably contains additional regulatory elements for efficient transcription, for example a transcription termination sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo.

As with promoter sequences, the terminator may be any terminator sequence which is operable in the cells, tissues or organs in which it is intended to be used.

Examples of terminators particularly suitable for use in the synthetic genes of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSVTK polyadenylation signal which are operable in animal cells, tissues and organs, octopine synthase (OCS) or nopaline synthase (NOS) terminator active in plant cells, tissues or organs, or the lacZ alpha terminator which is active in prokaryotic cells.

Those skilled in the art will be aware of additional terminator sequences which may be suitable for use in performing the invention. Such sequences may readily be used without any undue experimentation.

Means for introducing (i.e. transfecting or transforming) cells with the synthetic genes described herein or a genetic construct comprising same are well-known to those skilled in the art.

In a further alternative embodiment, a genetic construct is used which comprises two or more structural gene regions or multiple structural gene regions wherein each of said structural gene regions is placed operably under the control of its own promoter sequence. As with other embodiments described herein, the orientation of each structural gene region may be varied to maximise its modulatory effect on target gene expression.

According to this embodiment, the promoters controlling expression of the structural gene unit are preferably different promoter sequences, to reduce competition there between for cellular transcription factors and RNA polymerases. Preferred promoters are selected from those referred to supra.

Those skilled in the art will know how to modify the arrangement or configuration of the individual structural genes as described supra to regulate their expression from separate promoter sequences.

The synthetic genes described supra are capable of being modified further, for example by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and expressed, for example as a fusion polypeptide with the translation product(s) of any one or more of the structural genes or alternatively as a non-fusion polypeptide.

Those skilled in the art will be aware of how to produce the synthetic genes described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell.

The synthetic genes of the present invention may be introduced to a suitable cell, tissue or organ without modification as linear DNA in the form of a genetic construct, optionally contained within a suitable carrier, such as a cell, virus particle or liposome, amongst others. To produce a genetic construct, the synthetic gene of the invention is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly a further aspect of the invention provides a genetic construct which at least comprises the synthetic gene according to any one or more of the embodiments described herein and one or more origins of replication and/or selectable marker gene sequences.

Genetic constructs are particularly suitable for the transformation of a eukaryotic cell to introduce novel genetic traits thereto, in addition to the provision of resistance characteristics to viral pathogens. Such additional novel traits may be introduced in a separate genetic construct or, alternatively on the same genetic construct which comprises the synthetic genes described herein. Those skilled in the art will recognise the significant advantages, in particular in terms of reduced genetic manipulations and tissue culture requirements and increased cost-effectiveness, of including genetic sequences which encode such additional traits and the synthetic genes described herein in a single genetic construct.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

In a particularly preferred embodiment, the origin of replication is functional in a bacterial cell and comprises the pUC or the ColE1 origin or alternatively the origin of replication is operable in a eukaryotic cell, tissue and more preferably comprises the 2 micron (2 µm) origin of replication or the SV40 origin of replication.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin-resistance gene (Amp$^r$), tetracycline-resistance gene (Tc$^r$), bacterial kanamycin-resistance gene (Kan$^r$), is the zeocin resistance gene (Zeocin is a drug of bleomycin family which is trademark of InVitrogen Corporation), the AURI-C gene which confers resistance to the antibiotic aureobasidin A, phosphinothricin-resistance gene, neomycin phosphotransferase gene (nptII), hygromycin-resistance gene, β-glucuronidase (GUS) gene, chloramphenicol acetyltransferase (CAT) gene, green fluorescent protein-encoding gene or the luciferase gene, amongst others.

Preferably, the selectable marker gene is the nptII gene or Kan$^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as described herein, which include further genetic sequences intended for the maintenance and/or replication of said genetic construct in prokaryotes or eukaryotes and/or the integration of said genetic construct or a part thereof into the genome of a eukaryotic cell or organism.

As with dispersed or foreign nucleic acid molecules, standard methods described supra may be used to introduce synthetic genes and genetic constructs into the cell, tissue or organ for the purposes of modulating the expression of the target gene, for example liposome-mediated transfection or transformation, transformation of cells with attenuated virus particles or bacterial cells, cell mating, transformation or transfection procedures known to those skilled in the art or described by Ausubel et al. (1992).

Additional means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Herrera-Estrella et al. (1983a, 1983b, 1985).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

In a further embodiment of the present invention, the synthetic genes and genetic constructs described herein are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the *Agrobacterium tumefaciens* Ti plasmid will generally be required.

The present invention further extends to an isolated cell, tissue or organ comprising the synthetic gene described herein or a genetic construct comprising same. The present invention extends further to regenerated tissues, organs and whole organisms derived from said cells, tissues and organs and to propagules and progeny thereof.

For example, plants may be regenerated from transformed plant cells or tissues or organs on hormone-containing media and the regenerated plants may take a variety of forms, such as chimeras of transformed cells and non-transformed cells; clonal transformants (e.g., all cells transformed to contain the expression cassette); grafts of transformed and untransformed tissues (e.g., a transformed root stock grafted to an untransformed scion in citrus species). Transformed plants may be propagated by a variety of means, such as by clonal propagation or classical breeding techniques. For example, a first generation (or T1) transformed plants may be selfed to give homozygous second generation (or T2) transformed plants, and the T2 plants further propagated through classical breeding techniques.

The present invention is further described with reference to the following non-limiting Examples.

Example 1

Genetic Constructs Comprising BEV Polymerase Gene Sequences Linked to the CMV Promoter Sequence and/or the SV40L Promoter Sequence 1. Commercial Plasmids Plasmid pBluescript II (SK+)

Plasmid pBluescript II (SK+) is commercially available from Stratagene and comprises the LacZ promoter sequence and lacZ-alpha transcription terminator, with a multiple cloning site for the insertion of structural gene sequences therein. The plasmid further comprises the ColE1 and fl origins of replication and ampicillin-resistance gene.

Plasmid pSVL

Plasmid pSVL is commercially-obtainable from Pharmacia and serves as a source of is the SV40 late promoter sequence. The nucleotide sequence of pSVL is also publicly available as GenBank Accession Number U13868.

Plasmid pCR2.1

Plasmid pCR2.1 is commercially available from Invitrogen and comprises the LacZ promoter sequence and lacZ-α transcription terminator, with a cloning site for the insertion of structural gene sequences there between. Plasmid pCR2.1 is designed to clone nucleic acid fragments by virtue of the A-overhang frequently synthesized by Taq polymerase during the polymerase chain reaction. PCR fragments cloned in this fashion are flanked by two EcoRI sites. The plasmid further comprises the ColE1 and f1 origins of replication and kanamycin-resistance and ampicillin-resistance genes.

Plasmid pEGFP-N1 MCS

Plasmid pEGFP-N1 MCS (FIG. 1; Clontech) contains the CMV IE promoter operably connected to an open reading frame encoding a red-shifted variant of wild-type green fluorescent protein (GFP; Prasher et al., 1992; Chalfie et al., 1994; Inouye and Tsuji, 1994), which has been optimised for brighter fluorescence. The specific GFP variant encoded by pEGFP-N1 MCS has been disclosed by Cormack et al. (1996). Plasmid pEGFP-N1 MCS contains a multiple cloning site comprising BglII and BamHI sites and many other restriction endonuclease cleavage sites, located between the CMV IE promoter and the GFP open reading frame. Structural genes cloned into the multiple cloning site will be expressed at the transcriptional level if they lack a functional translation start site, however such structural gene sequences will not be expressed at the protein level (i.e. translated). Structural gene sequences inserted into the multiple cloning site which comprise a functional translation start site will be expressed as GFP fusion polypeptides if they are cloned in-frame with the GFP-encoding sequence. The plasmid further comprises an SV40 polyadenylation signal downstream of the GFP open reading frame to direct proper processing of the 3'-end of mRNA transcribed from the CMV-IE promoter sequence. The plasmid further comprises the SV40 origin of replication functional in animal cells; the neomycin-resistance gene comprising SV40 early promoter (SV40 EP in FIG. 1) operably connected to the neomycin/kanamycin-resistance gene derived from Tn5 (Kan/neo in FIG. 1) and the HSV thymidine kinase polyadenylation signal (HSV TK poly (A) in FIG. 1), for selection of transformed cells on kamanycin, neomycin or G418; the pUC19 origin of replication which is functional in bacterial cells (pUC Ori in FIG. 1); and the f1 origin of replication for single-stranded DNA production (f1 Ori in FIG. 1).

2. Expression Cassettes

Plasmid pCMV.cass

Plasmid pCMV.cass (FIG. 2) is an expression cassette for driving expression of a structural gene sequence under control of the CMV-IE promoter sequence. Plasmid pCMV.cass was derived from pEGFP-N1 MCS by deletion of the GFP open reading frame as follows: Plasmid pEGFP-N1 MCS was digested with PinAI and Not I, blunt-ended using PfuI polymerase and then re-ligated. Structural gene sequences are cloned into pCMV.cass using the multiple cloning site, which is identical to the multiple cloning site of pEGFP-N1 MCS, except it lacks the PinAI site.

Plasmid pCMV.SV40L.cass

Plasmid pCMV.SV40L.cass (FIG. 3) comprises the synthetic poly A site and the SV40 late promoter sequence from plasmid pCR.SV40L (FIG. 4), sub-cloned as a Sal I fragment, into the Sal I site of plasmid pCMV.cass (FIG. 2), such that the CMV-IE promoter and SV40 late promoter sequences are capable of directing transcription in the same direction. Accordingly, the synthetic poly(A) site at the 5' end of the SV40 promoter sequence is used as a transcription terminator for structural genes expressed from the CMV IE promoter in this plasmid, which also provides for the insertion of said structural gene via the multiple cloning site present between the SV40 late promoter and the synthetic poly(A) site (FIG. 5). The multiple cloning sites are located behind the CMV-IE and SV40 late promoters, including BamHI and BglII sites.

Plasmid pCMV.SV40LR.cass

Plasmid pCMV.SV40LR.cass (FIG. 4) comprises the SV40 late promoter sequence derived from plasmid pCR.SV40L, sub-cloned as a SalI fragment into the SalI site of the plasmid pCMV.cass (FIG. 2), such that the CMV-IE or the SV40 late promoter may drive transcription of a structural gene or a multiple structural gene unit, in the sense or antisense orientation, as desired. A multiple cloning site is positioned between the opposing CMV-IE and SV40 late promoter sequences in this plasmid to facilitate the introduction of a structural gene sequence. In order for expression of a structural gene sequence to occur from this plasmid, it must be introduced with its own transcription termination sequence located at the 3' end, because there are no transcription termination sequences located between the opposing CMV-IE and SV40 late promoter sequences in this plasmid. Preferably, the structural gene sequence or multiple structural gene unit which is to be introduced into pCMV.SV40LR.cass will comprise both a 5' and a 3' polyadenylation signal as follows:

(i) where the structural gene sequence or multiple structural gene unit is to be expressed in the sense orientation from the CMV IE promoter sequence and/or in the antisense orientation from the SV40 late promoter, the 5' polyadenylation signal will be in the antisense orientation and the 3' polyadenylation signal will be in the sense orientation; and (ii) where the structural gene sequence or multiple structural gene unit is to be expressed in the antisense orientation from the CMV IE promoter sequence and/or in the sense orientation from the SV40 late promoter, the 5' polyadenylation signal will be in the sense orientation and the 3' polyadenylation signal will be in the antisense orientation.

Figure 4:
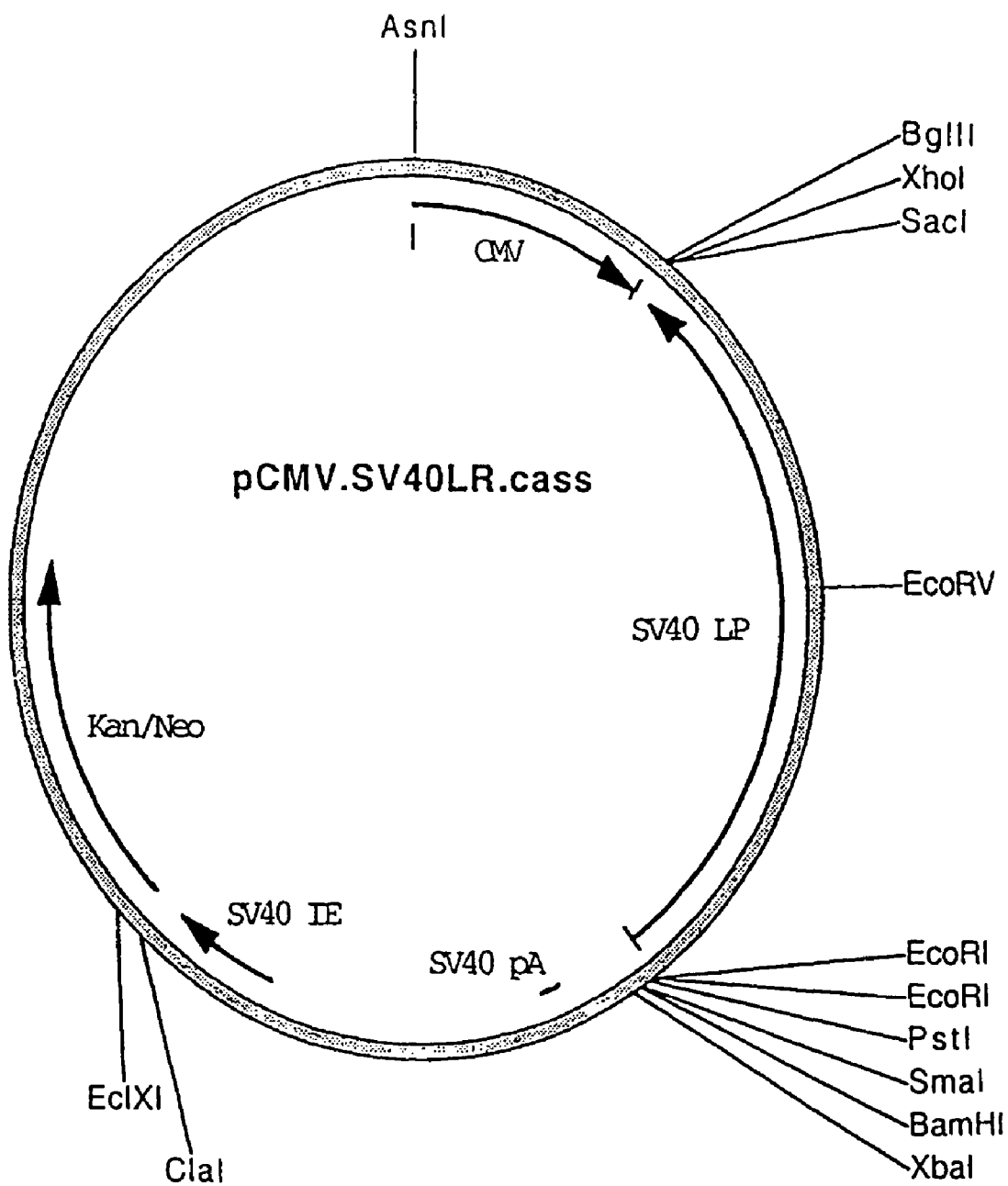
FIG. 4 is a diagrammatic representation of the plasmid pCMV.SV40LR.cass.
Figure 5:
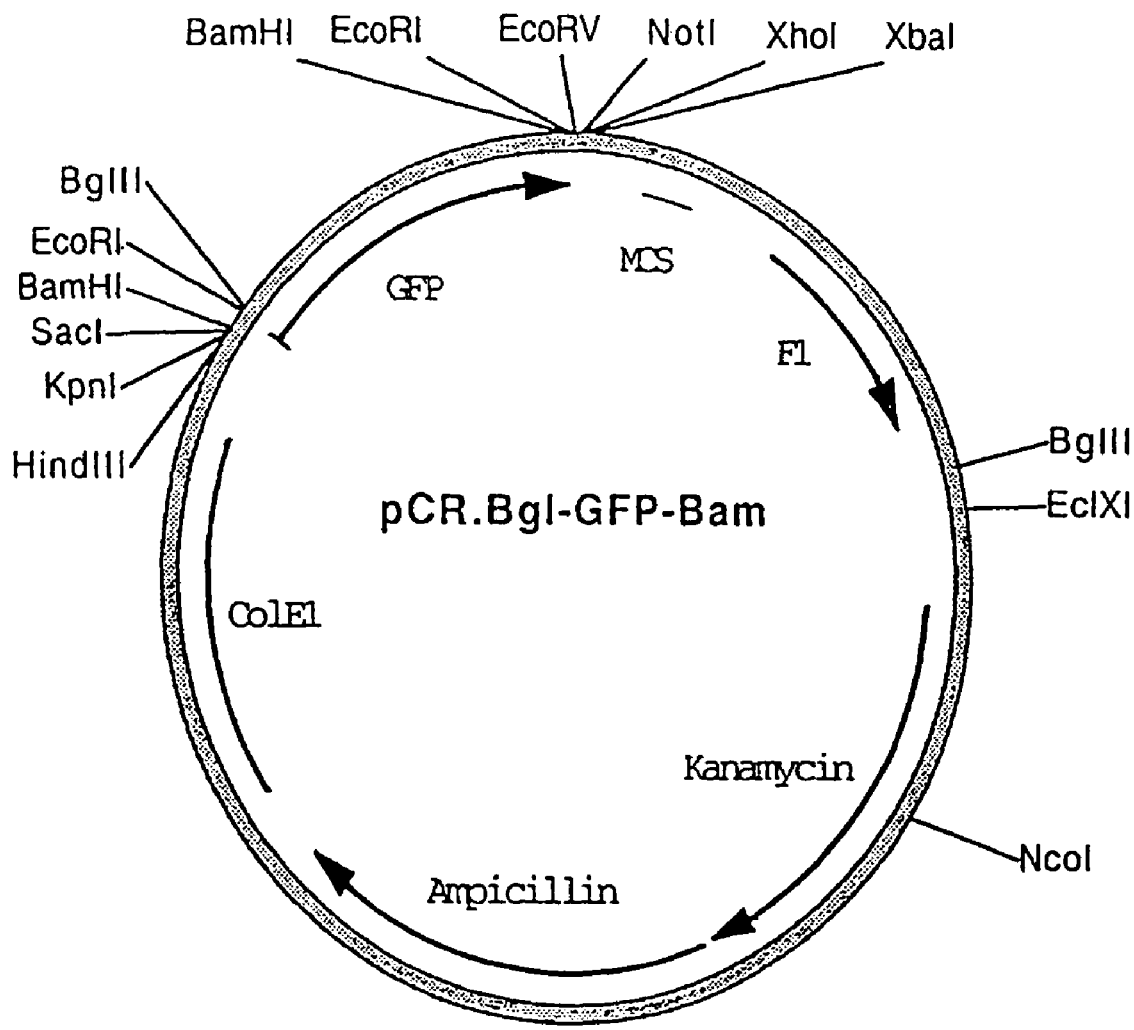
FIG. 5 is a diagrammatic representation of the plasmid pCR.Bgl-GFP-Bam.

Alternatively or in addition, suitably-oriented terminator sequences may be placed at the 5'-end of the CMV and SV40L promoters, as shown in FIG. 4.

Alternatively, plasmid pCMV.SV40LR.cass is further modified to produce a derivative plasmid which comprises two polyadenylation signals located between the CMV IE and SV40 late promoter sequences, in approriate orientations to facilitate expression of any structural gene located therebetween in the sense or antisense orientation from either the CMV IE promoter or the SV40 promoter sequence. The present invention clearly encompasses such derivatives.

Alternatively appropriately oriented terminators could be placed upstream of the CMV and SV40L promoters such that transcriptional termination could occur after readthrough of each of the two promoters in the antisense orientation.

3. Intermediate Constructs

Plasmid pCR.Bgl-GFP-Bam

Plasmid pCR.Bgl-GFP-Bam (FIG. 5) comprises an internal region of the GFP open reading frame derived from plasmid pEGFP-N1 MCS (FIG. 1) placed operably under the control of the lacZ promoter. To produce this plasmid, a region of the GFP open reading frame was amplified from pEGFP-N1 MCS using the amplification primers Bgl-GFP and GFP-Bam and cloned into plasmid pCR2.1. The internal GFP-encoding region in plasmid pCR.Bgl-GFP-Bam lacks functional translational start and stop codons.

Plasmid pBSII(SK+).EGFP

Figure 6:
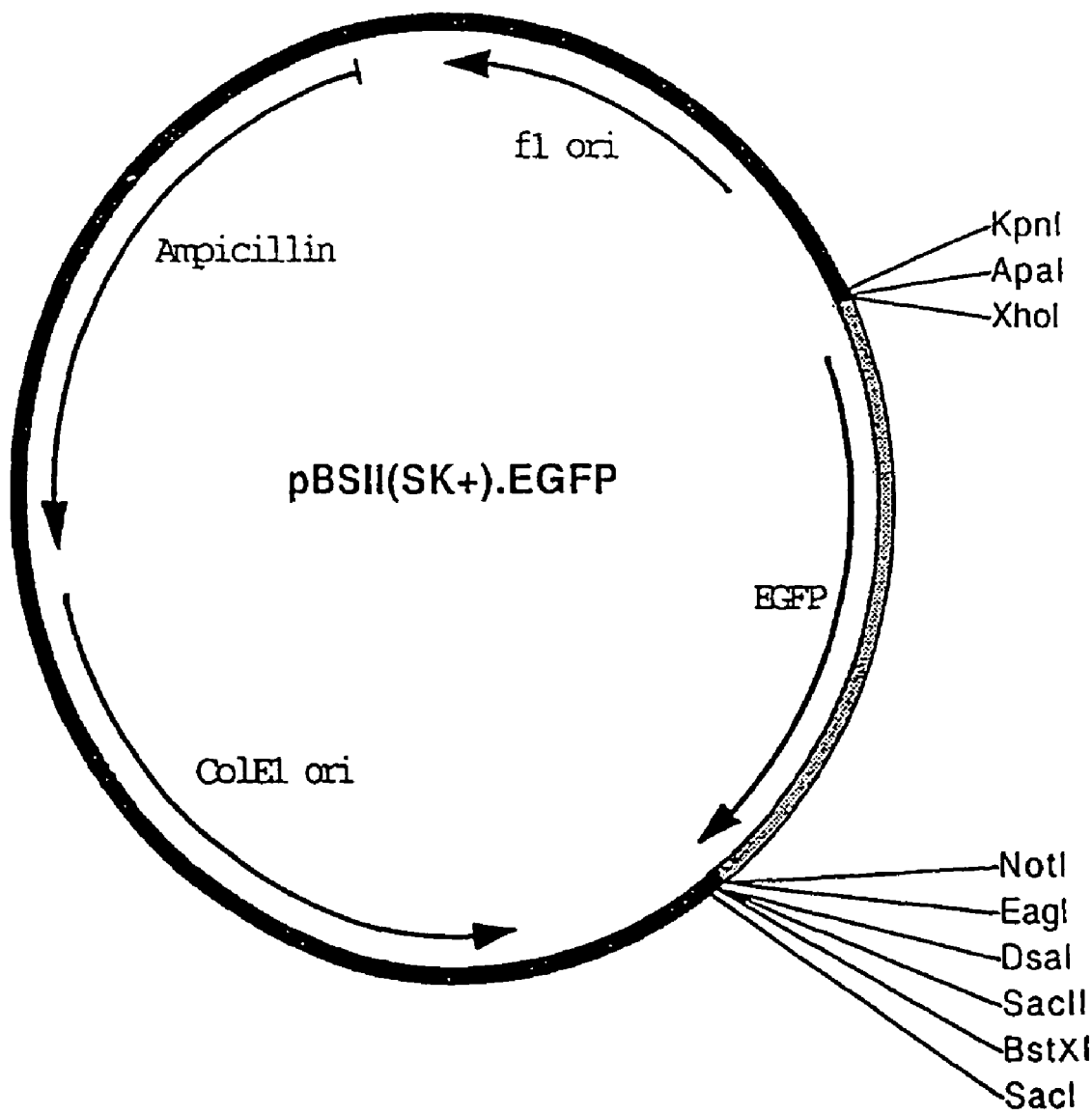
FIG. 6 is a diagrammatic representation of the plasmid pBSII(SK+).EGFP.

Plasmid pBSII(SK+).EGFP (FIG. 6) comprises the EGFP open reading frame derived from plasmid pEGFP-N1 MCS (FIG. 1) placed operably under the control of the lacZ promoter. To produce this plasmid, the EGFP encoding region of pEGFP-N1 MCS was excised as a Not1/Xho1 fragment and cloned into the Not1/Xho1 cloning sites of plasmid pBluescript II (SK+).

Plasmid pCMV.EGFP

Figure 2:
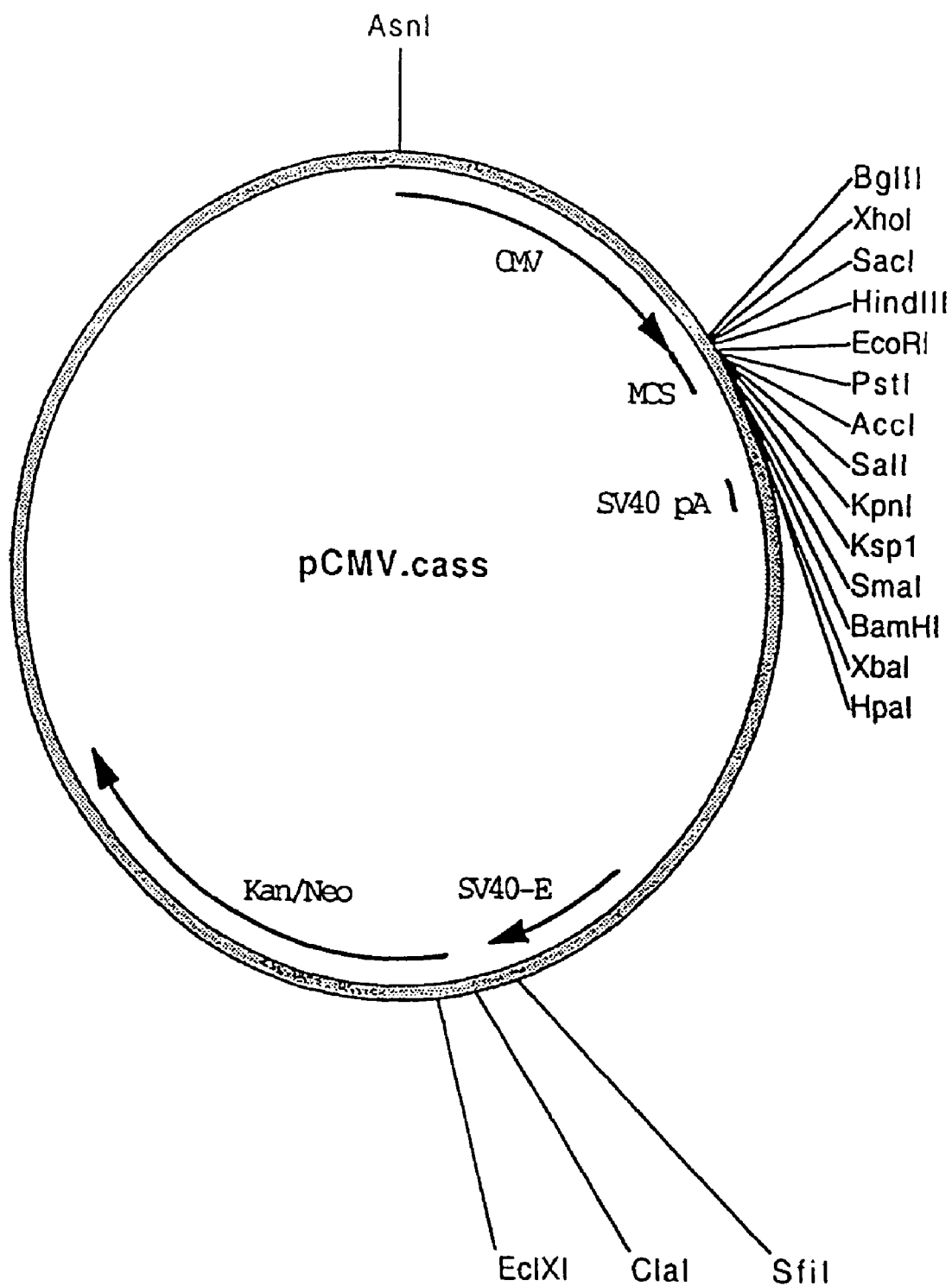
FIG. 2 is a diagrammatic representation of the plasmid pCMV.cass.
Figure 3:
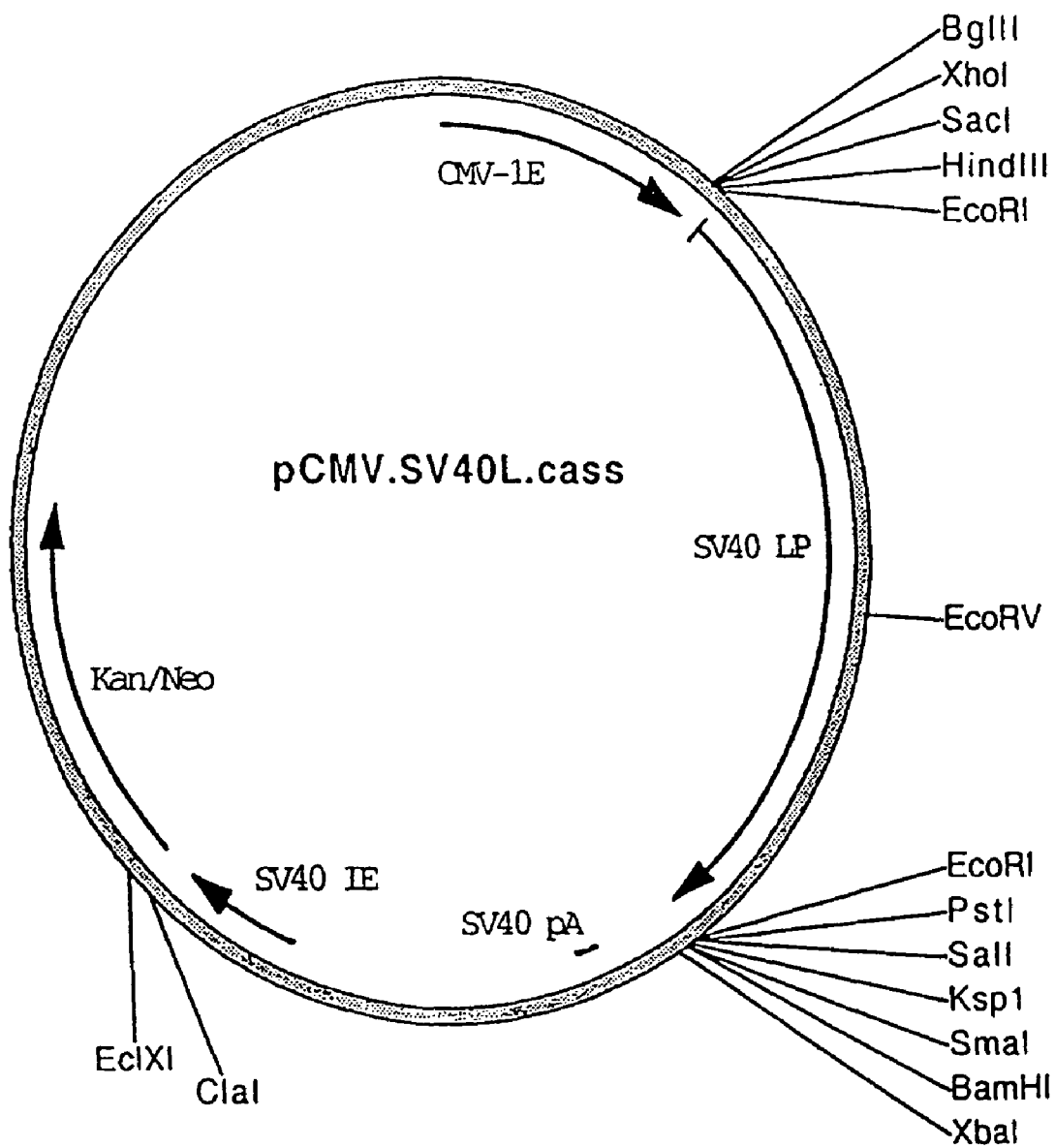
FIG. 3 is a diagrammatic representation of the plasmid pCMV.SV40L.cass.
Figure 7:
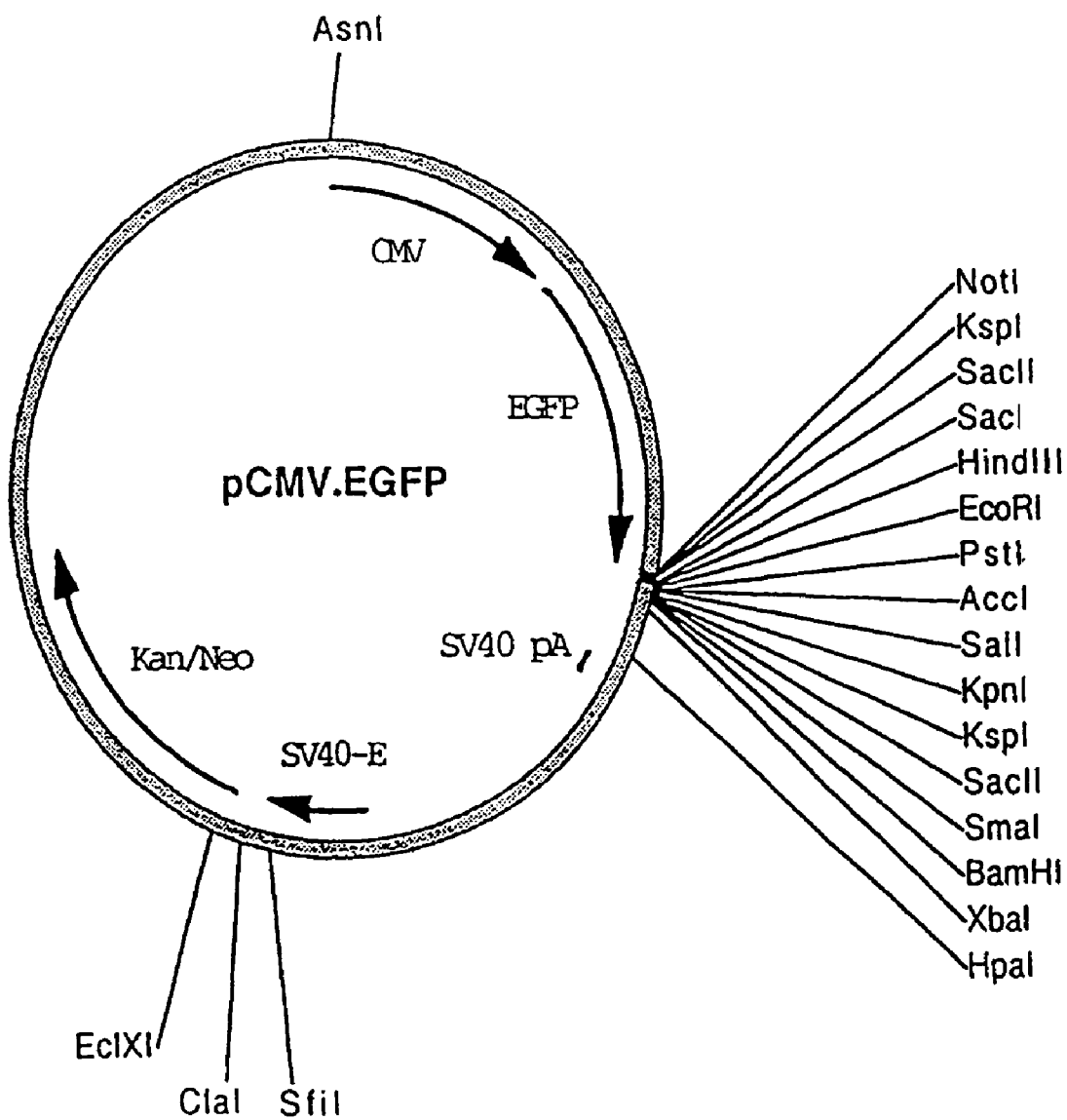
FIG. 7 is a diagrammatic representation of the plasmid pCMV.EGFP.

Plasmid pCMV.EGFP (FIG. 7) is capable of expressing the EGFP structural gene under the control of the CMV-IE promoter sequence. To produce this plasmid the EGFP sequence from plasmid pBSII(SK+).EGFP was excised as BamHI/SacI fragment and cloned into the BglII/SacI sites of plasmid pCMV.cass (FIG. 2).

Plasmid pCR.SV40L

Figure 8:
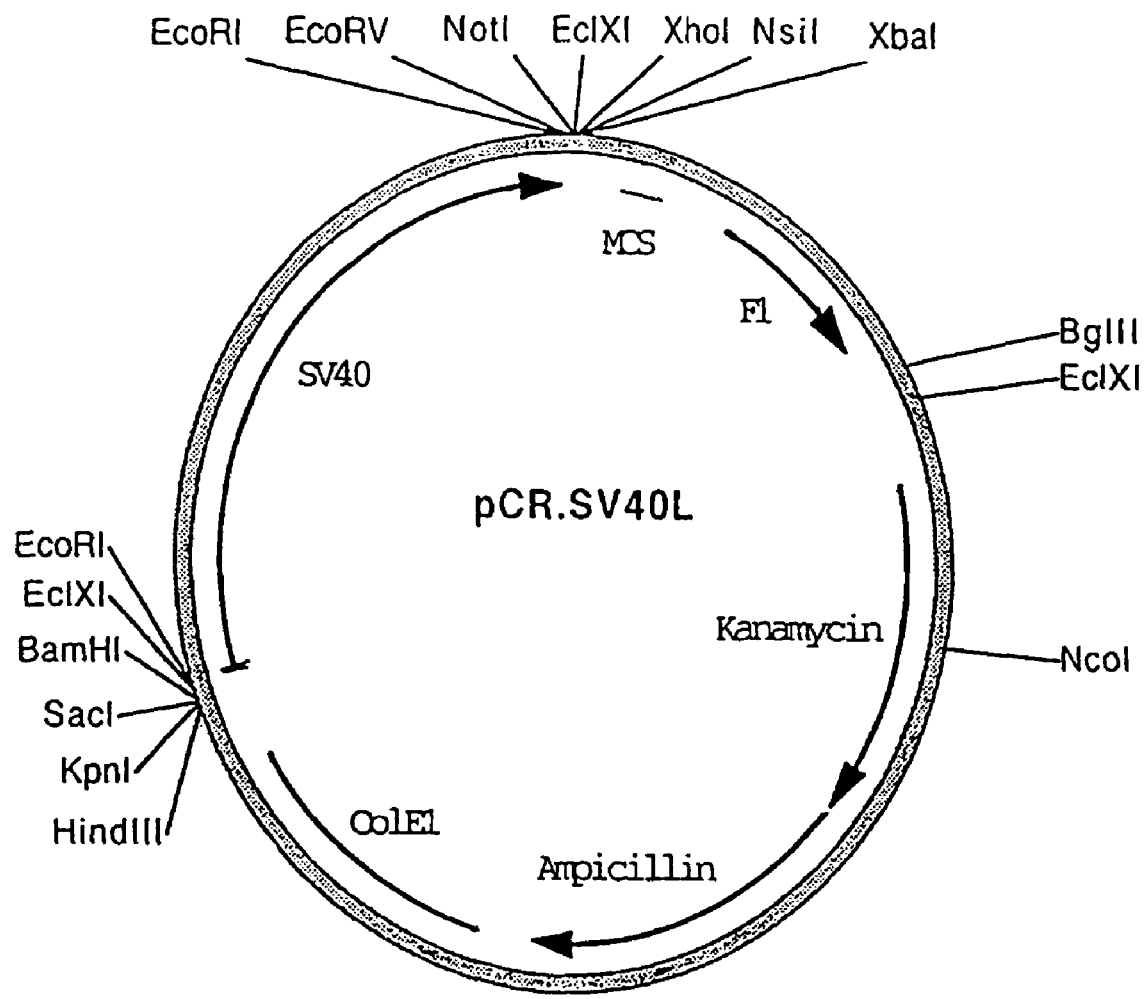
FIG. 8 is a diagrammatic representation of the plasmid pCR.SV40L.

Plasmid pCR.SV40L (FIG. 8) comprises the SV40 late promoter derived from plasmid pSVL (GenBank Accession No. U13868; Pharmacia), cloned into pCR2.1 (Stratagene). To produce this plasmid, the SV40 late promoter was amplified using the primers SV40-1 and SV40-2 which comprise Sal I cloning sites to facilitate sub-cloning of the amplified DNA fragment into pCMV.cass. The primer also contains a synthetic poly (A) site at the 5' end, such that the amplicification product comprises the synthetic poly(A) site at the 5' end of the SV40 promoter sequence.

Plasmid pCR.BEV.1

Figure 9:
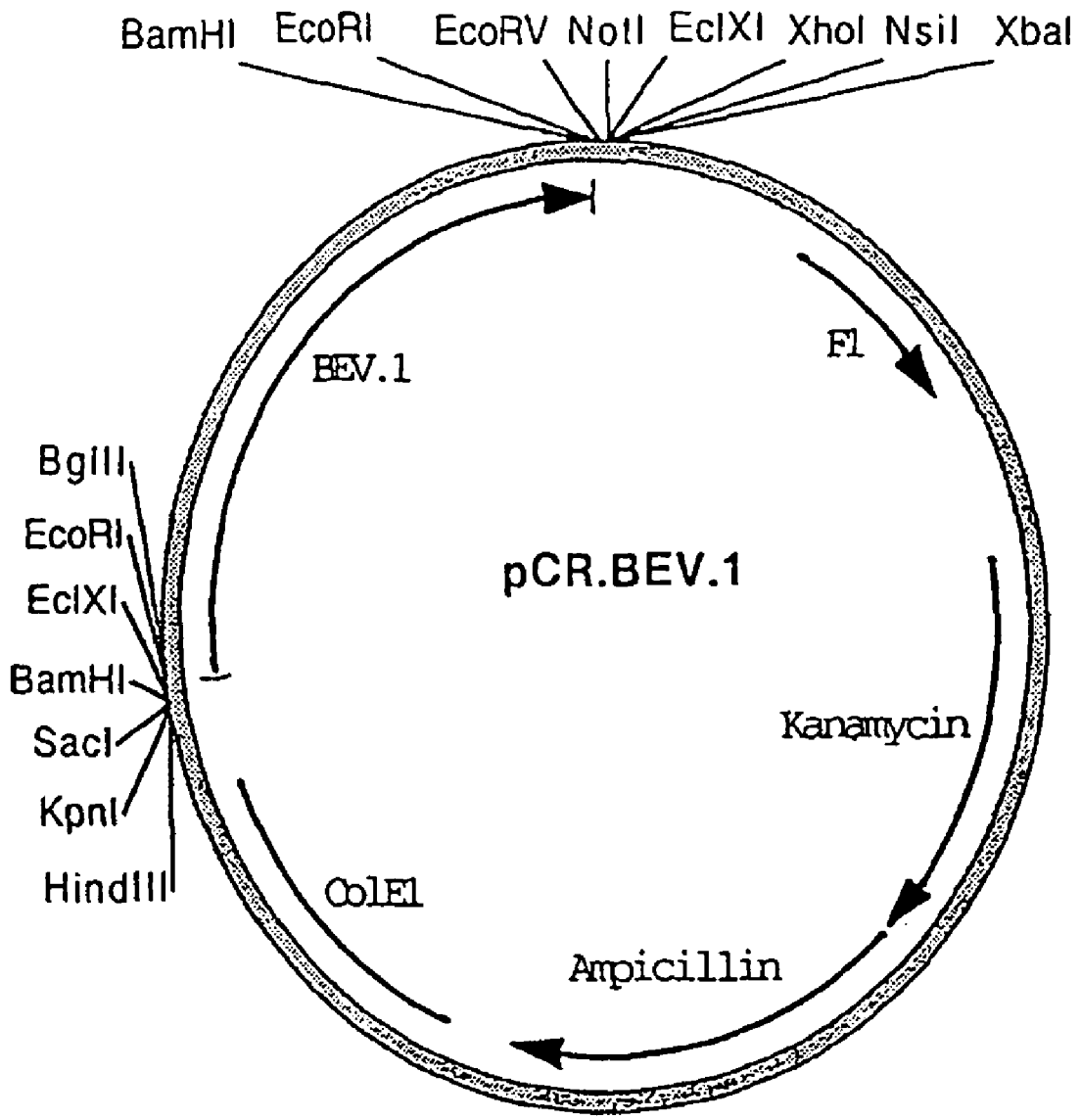
FIG. 9 is a diagrammatic representation of the plasmid pCR.BEV.1.

The BEV RNA-dependent RNA polymerase coding region was amplified as a 1,385 bp DNA fragment from a full-length cDNA clone encoding same, using primers designated BEV-1 and BEV-2, under standard amplification conditions. The amplified DNA contained a 5'-Bgl II restriction enzyme site, derived from the BEV-1 primer sequence and a 3'BamHI restriction enzyme site, derived from the BEV-2 primer sequence. Additionally, as the BEV-1 primer sequence contains a translation start signal 5'-ATG-3' engineered at positions 15-17, the amplified BEV polymerase structural gene comprises the start site in-frame with BEV polymerase-encoding nucleotide sequences. Thus, the amplified BEV polymerase structural gene comprises the ATG start codon immediately upstream (ie. juxtaposed) to the BEV polymerase-encoding sequence. There is no translation stop codon in the amplified DNA. This plasmid is present as FIG. 9.

Plasmid pCR.BEV.2

Figure 10:
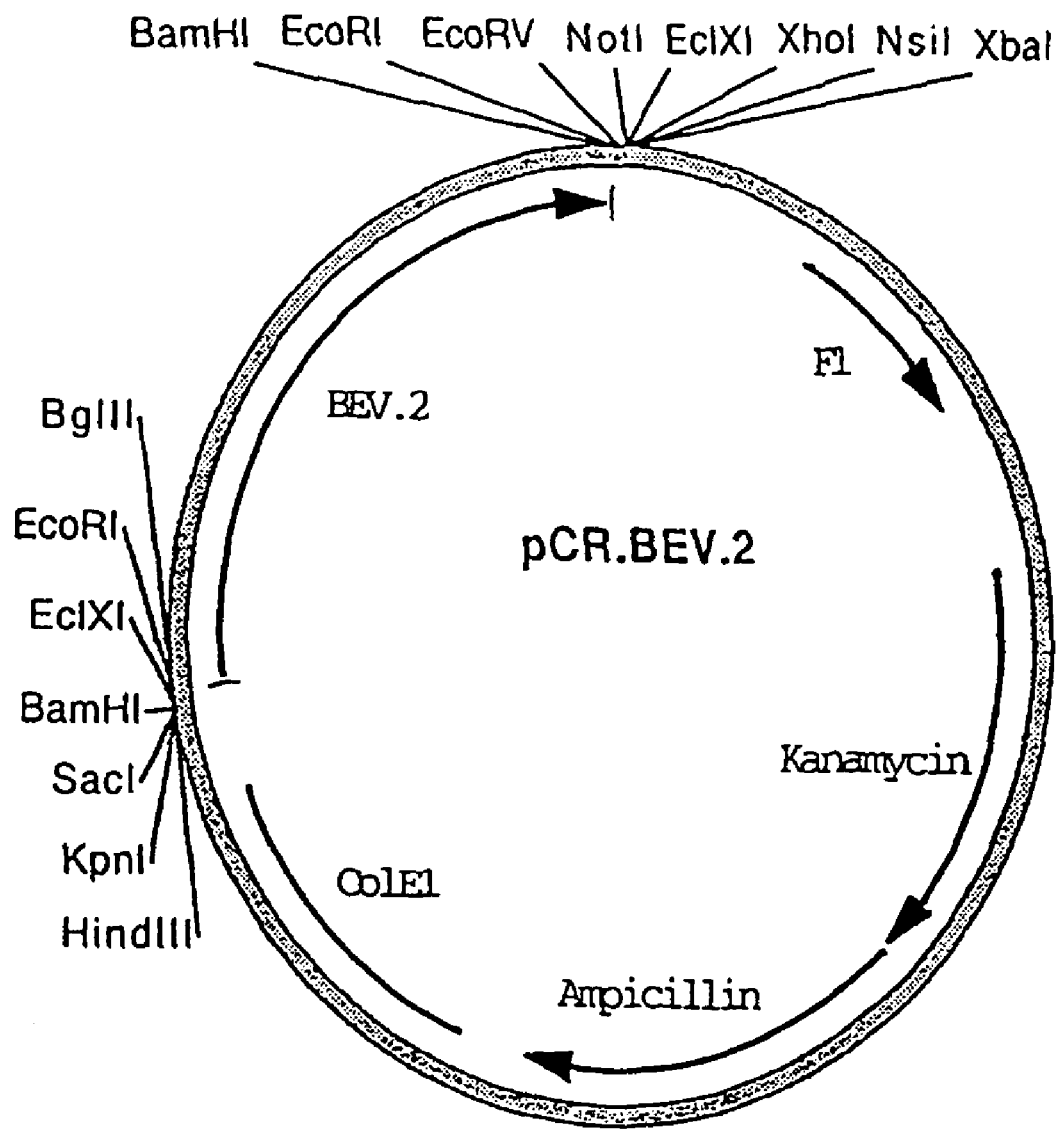
FIG. 10 is a diagrammatic representation of the plasmid pCR.BEV.2.
Figure 11:
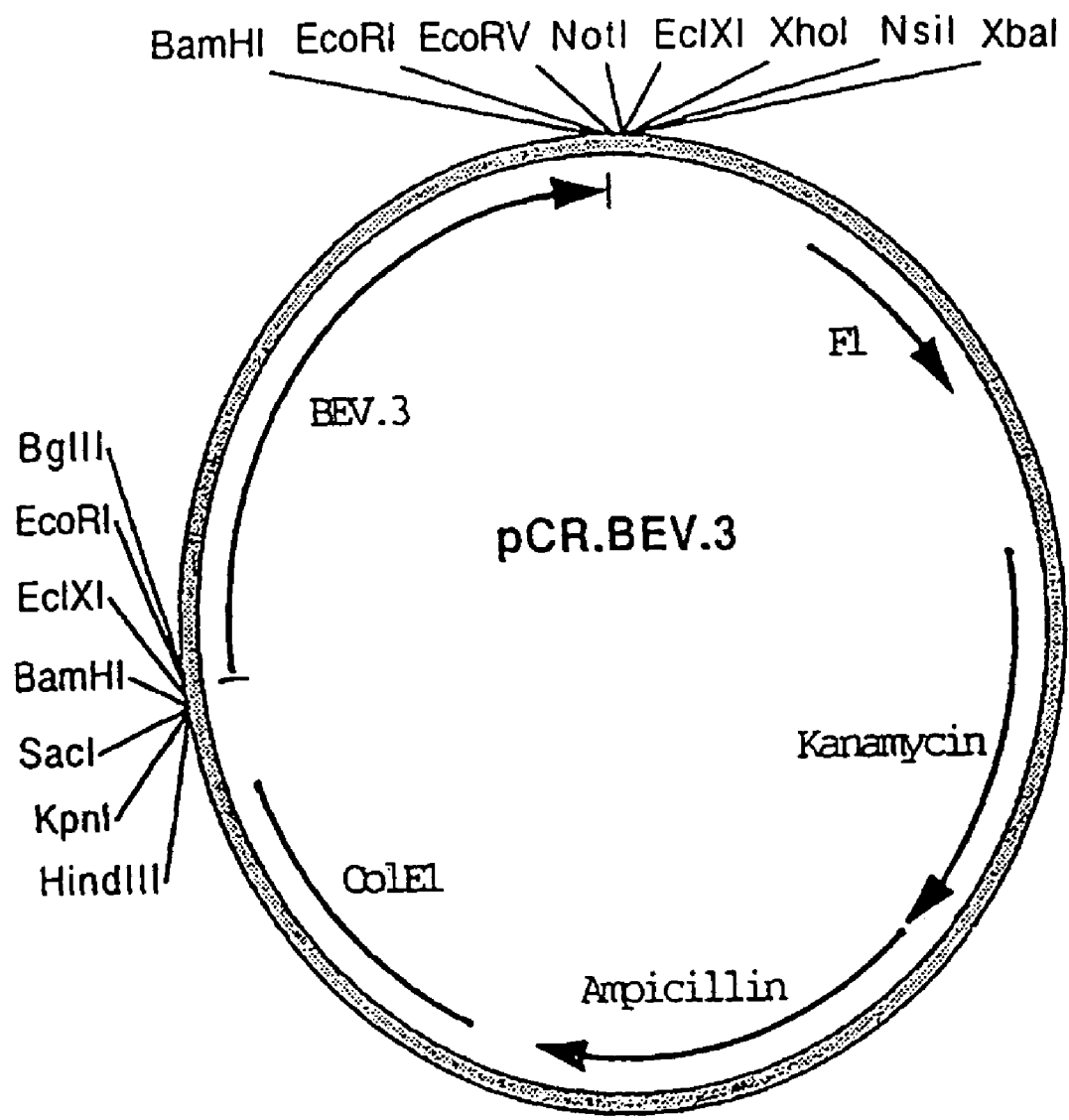
FIG. 11 is a diagrammatic representation of the plasmid pCR.BEV.3.
Figure 12:
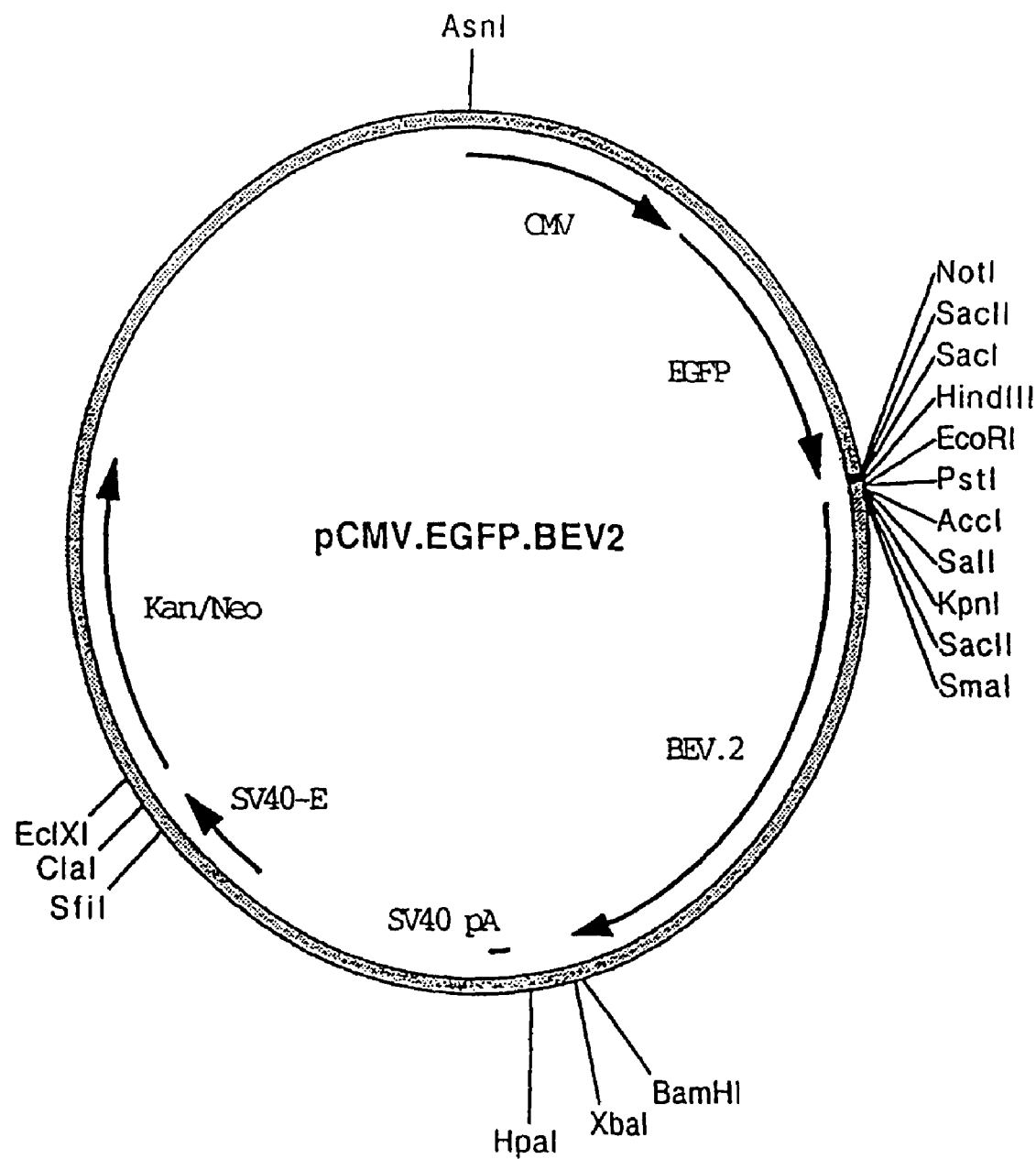
FIG. 12 is a diagrammatic representation of the plasmid pCMV.EGFP.BEV2.
Figure 13:
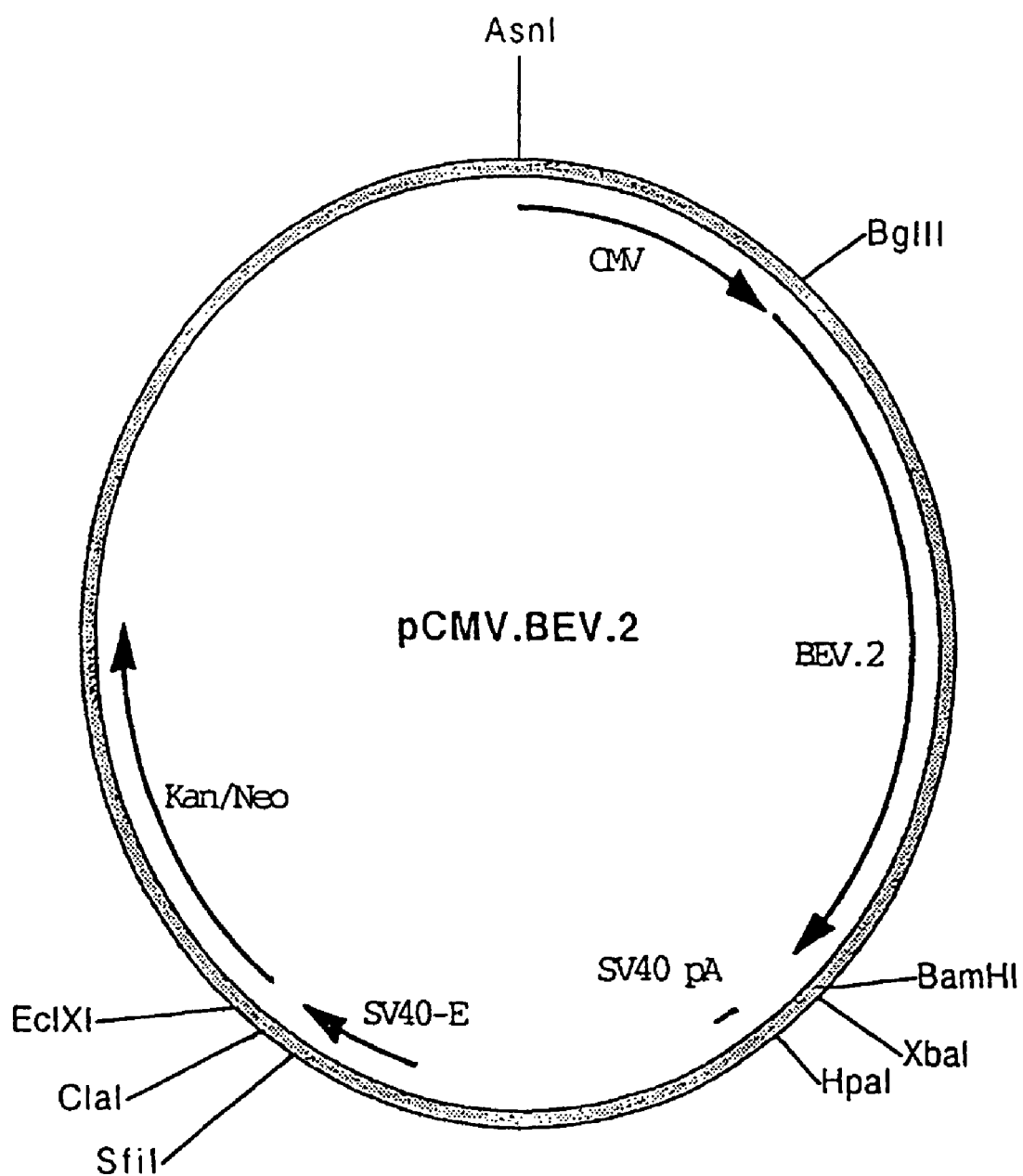
FIG. 13 is a diagrammatic representation of the plasmid pCMV.BEV.2.
Figure 14:
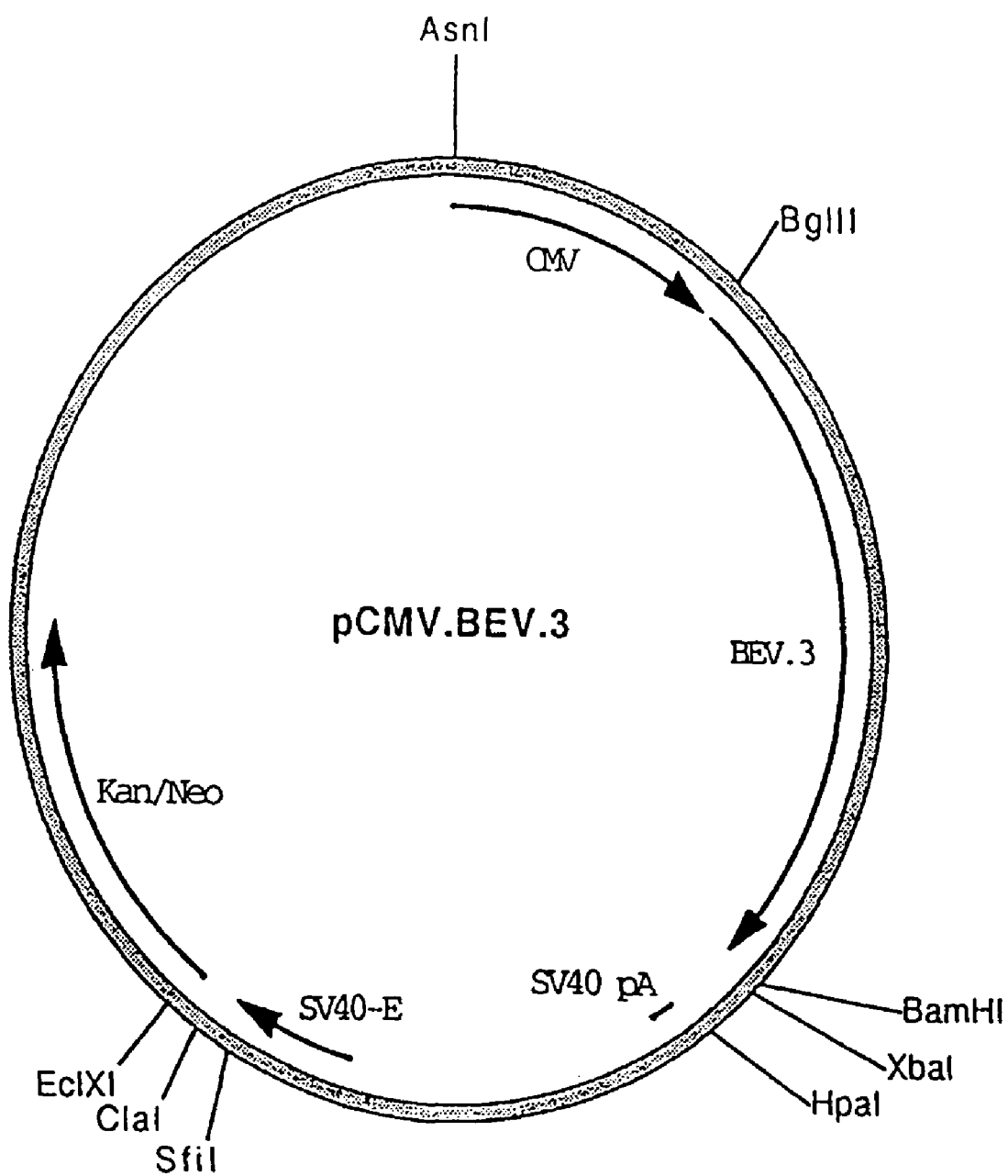
FIG. 14 is a diagrammatic representation of the plasmid pCMV.BEV.3.
Figure 15:
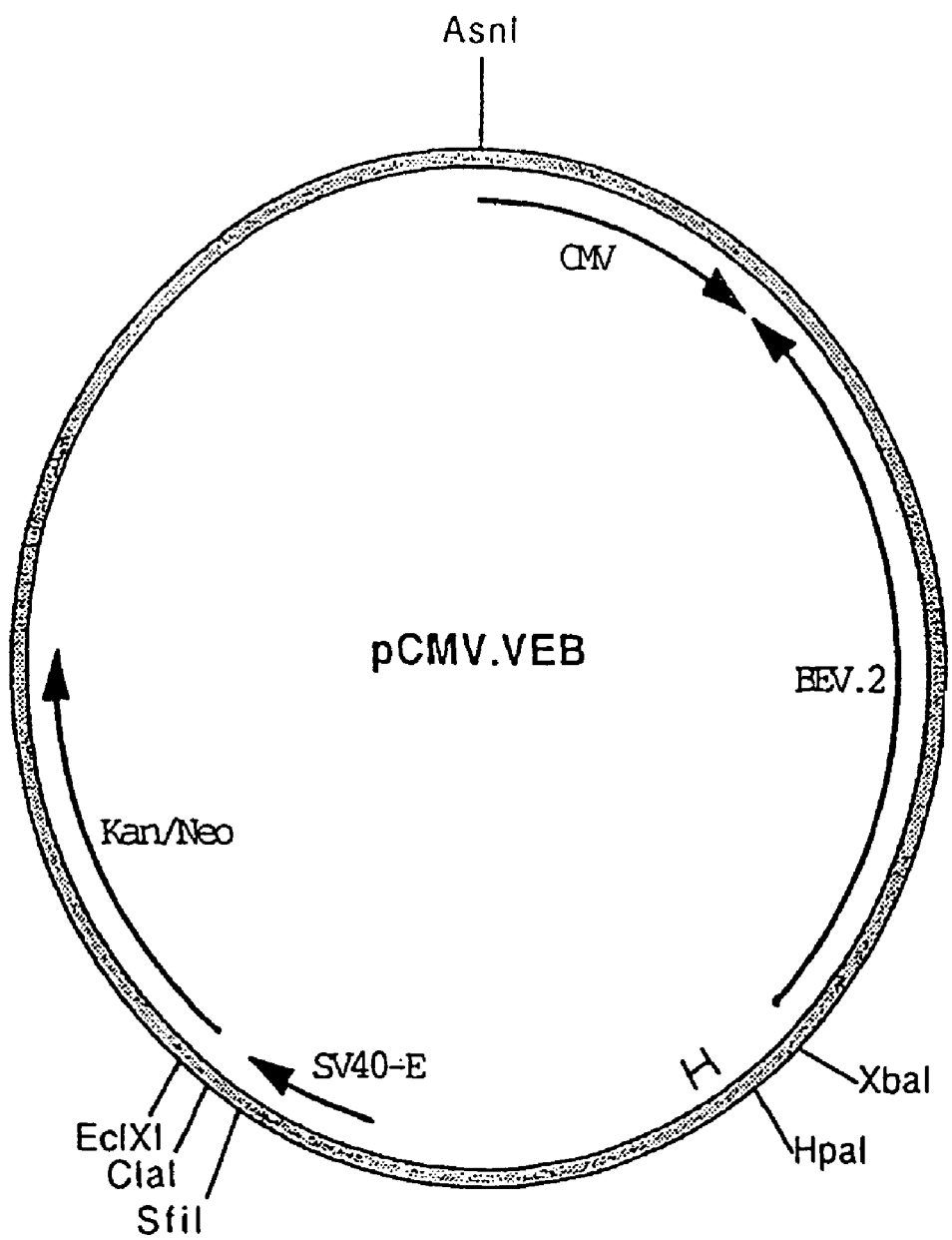
FIG. 15 is a diagrammatic representation of the plasmid pCMV.VEB.
Figure 16:
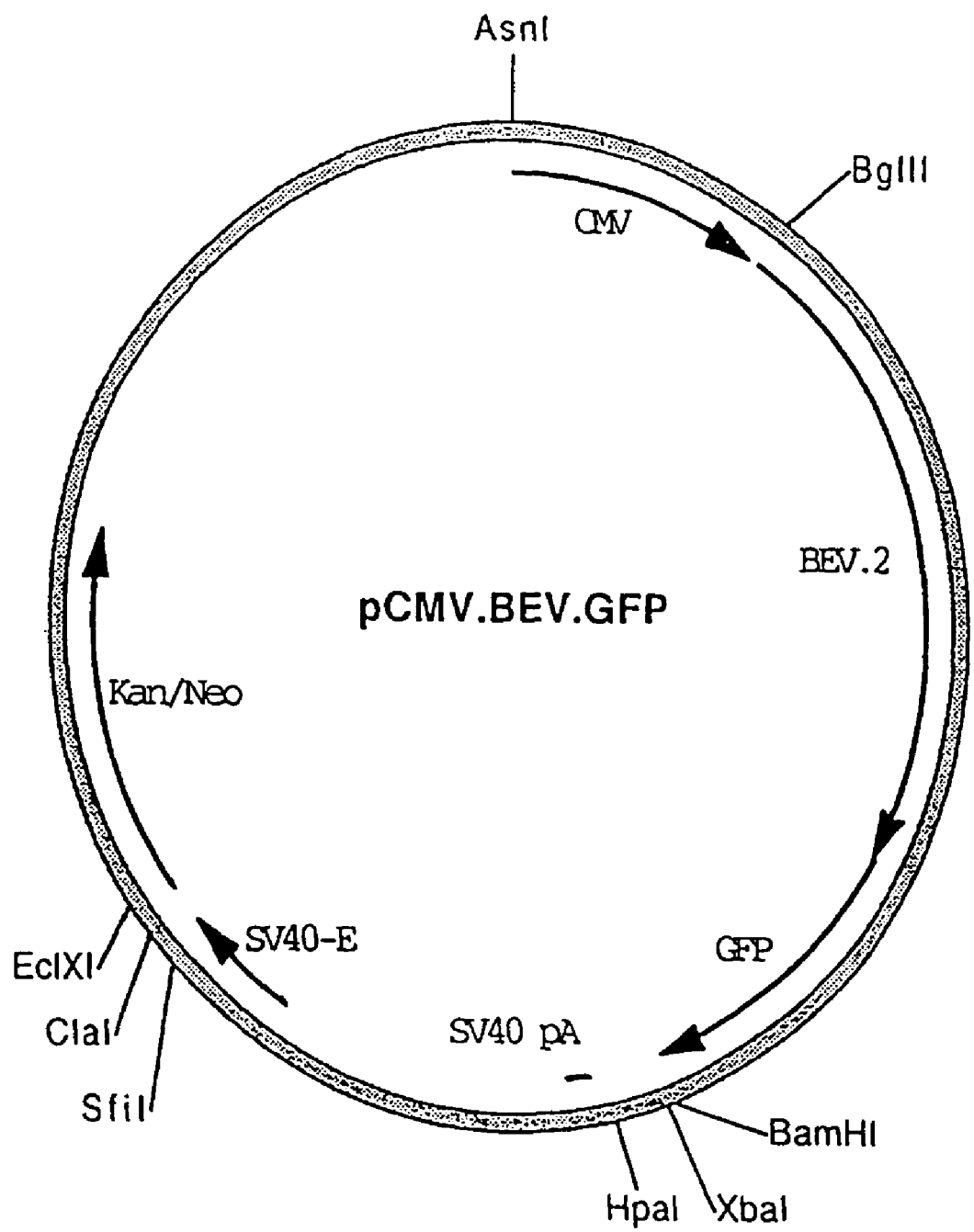
FIG. 16 is a diagrammatic representation of the plasmid pCMV.BEV.GFP.
Figure 17:
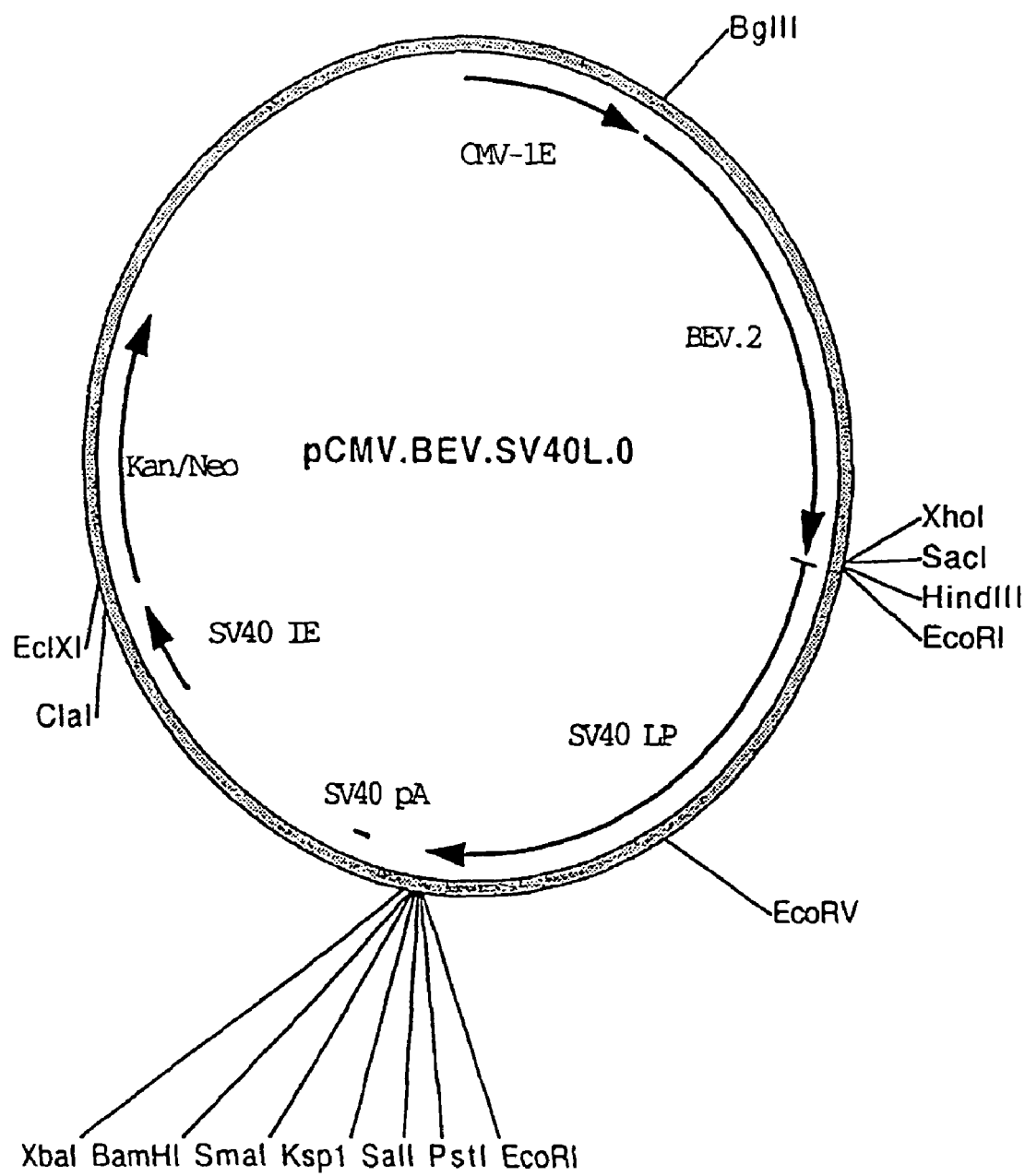
FIG. 17 is a diagrammatic representation of the plasmid pCMV.BEV.SV40L-0.
Figure 18:
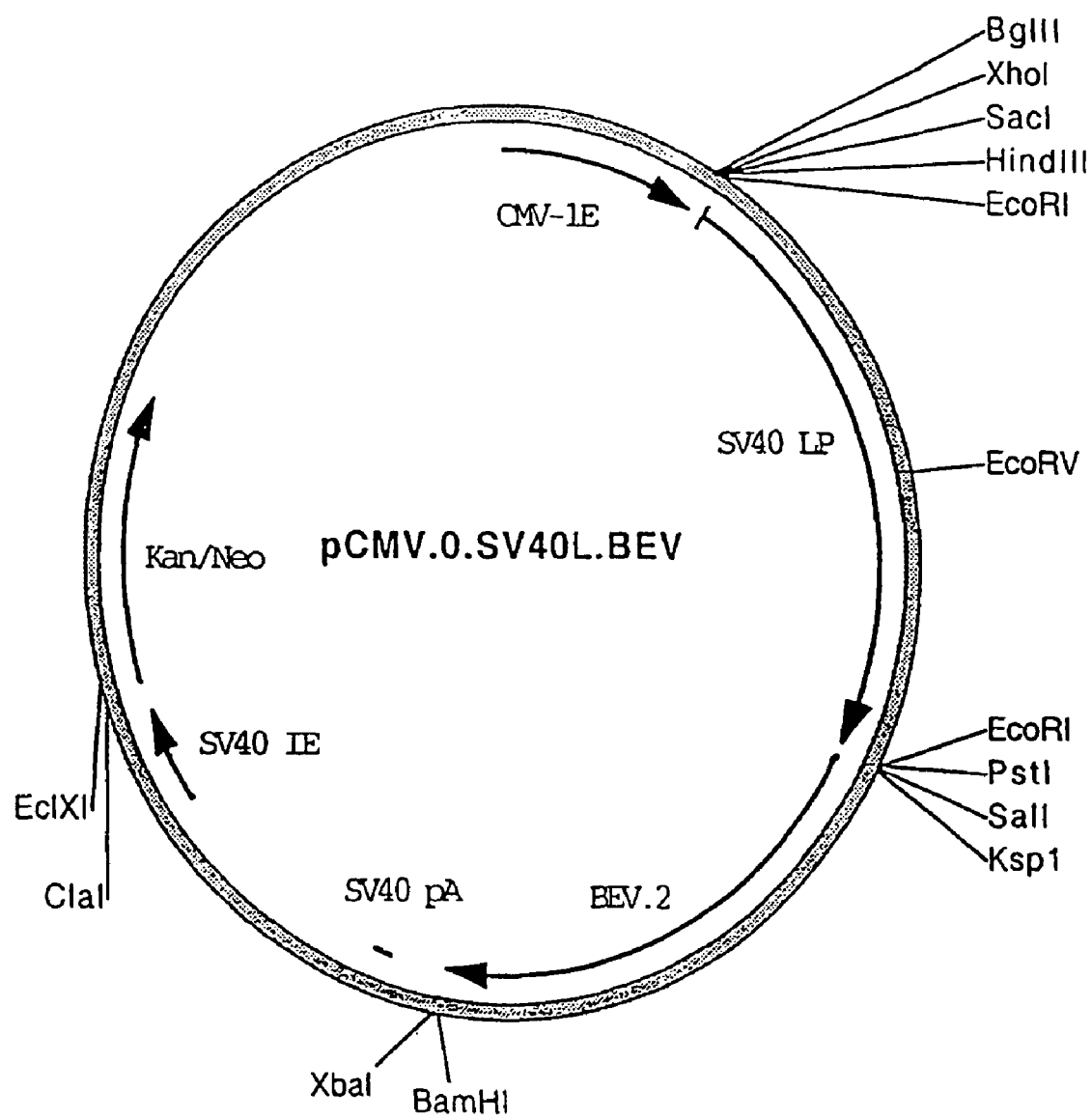
FIG. 18 is a diagrammatic representation of the plasmid pCMV.0.SV40L.BEV.
Figure 19:
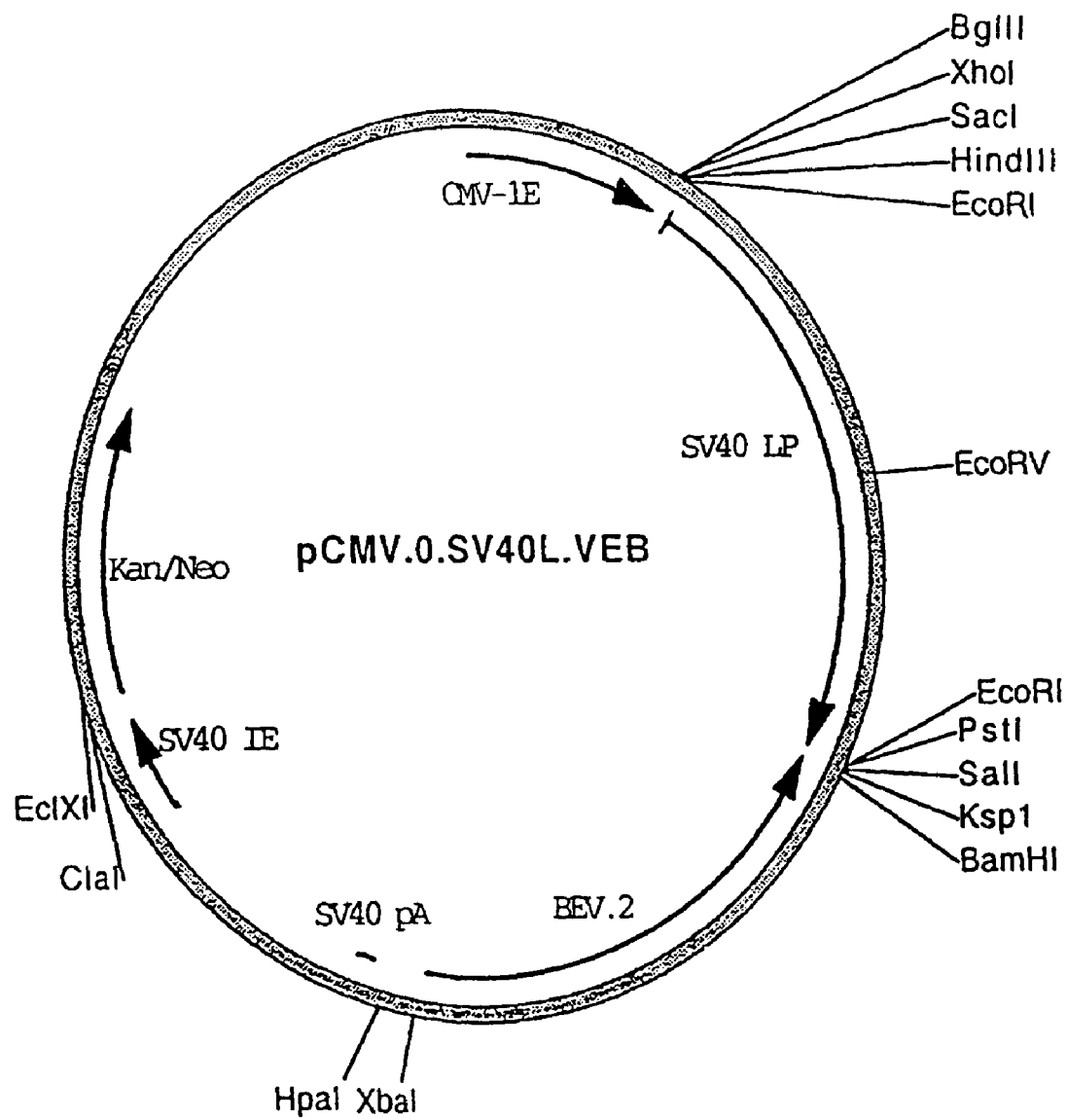
FIG. 19 is a diagrammatic representation of the plasmid pCMV.0.SV40L.VEB.
Figure 20:
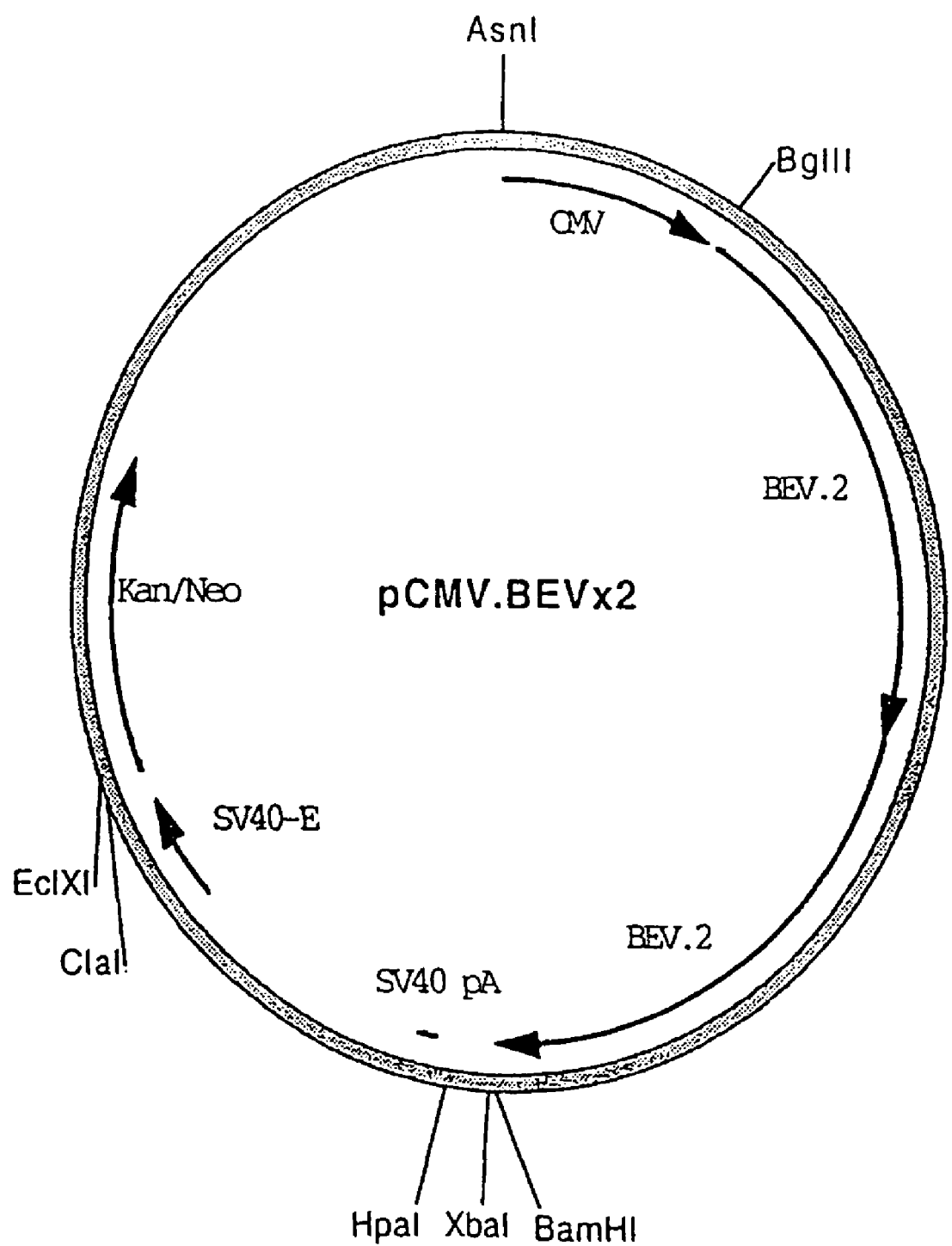
FIG. 20 is a diagrammatic representation of the plasmid pCMV.BEVx2.
Figure 21:
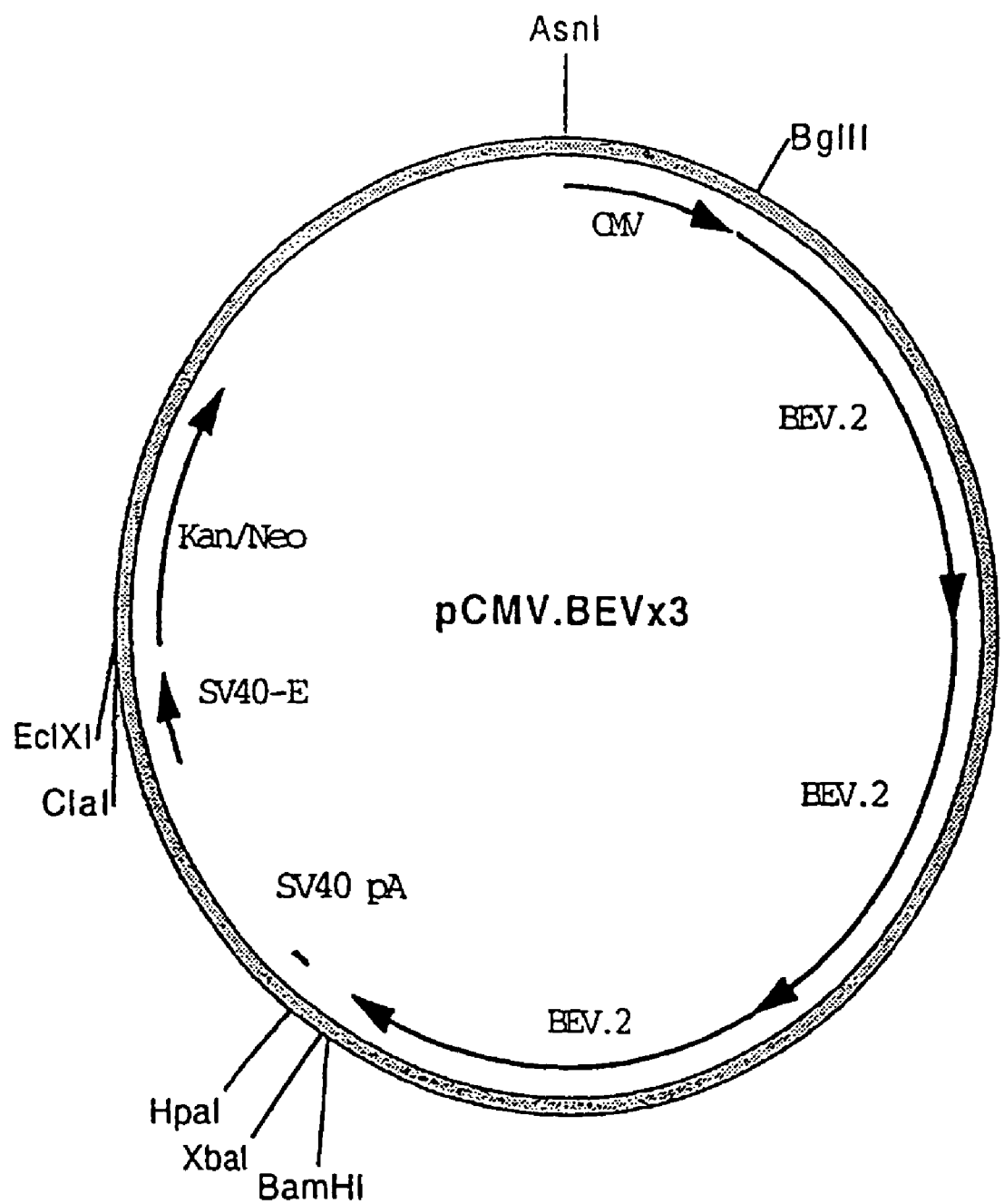
FIG. 21 is a diagrammatic representation of the plasmid pCMV.BEVx3.
Figure 22:
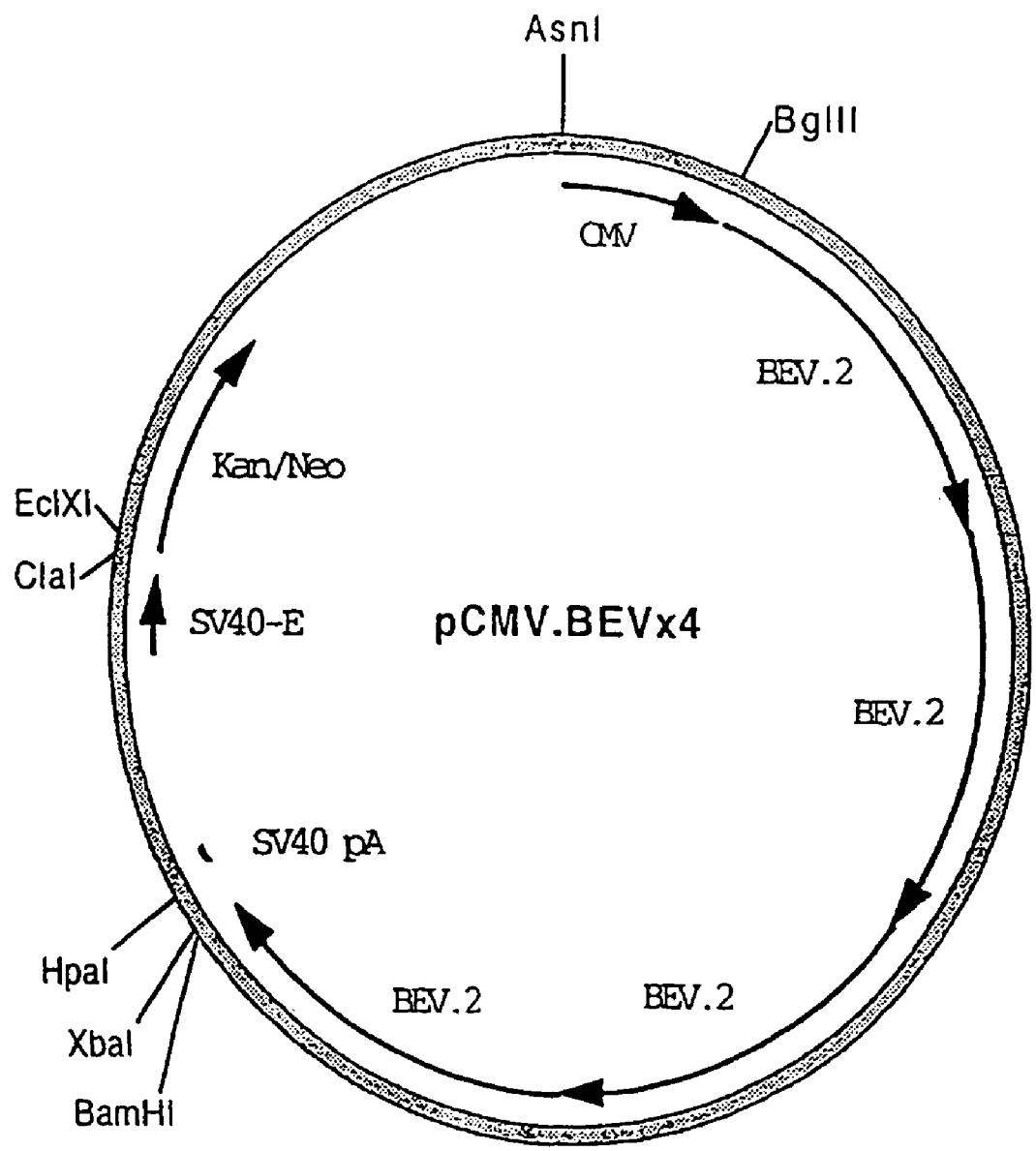
FIG. 22 is a diagrammatic representation of the plasmid pCMV.BEVx4.
Figure 23:
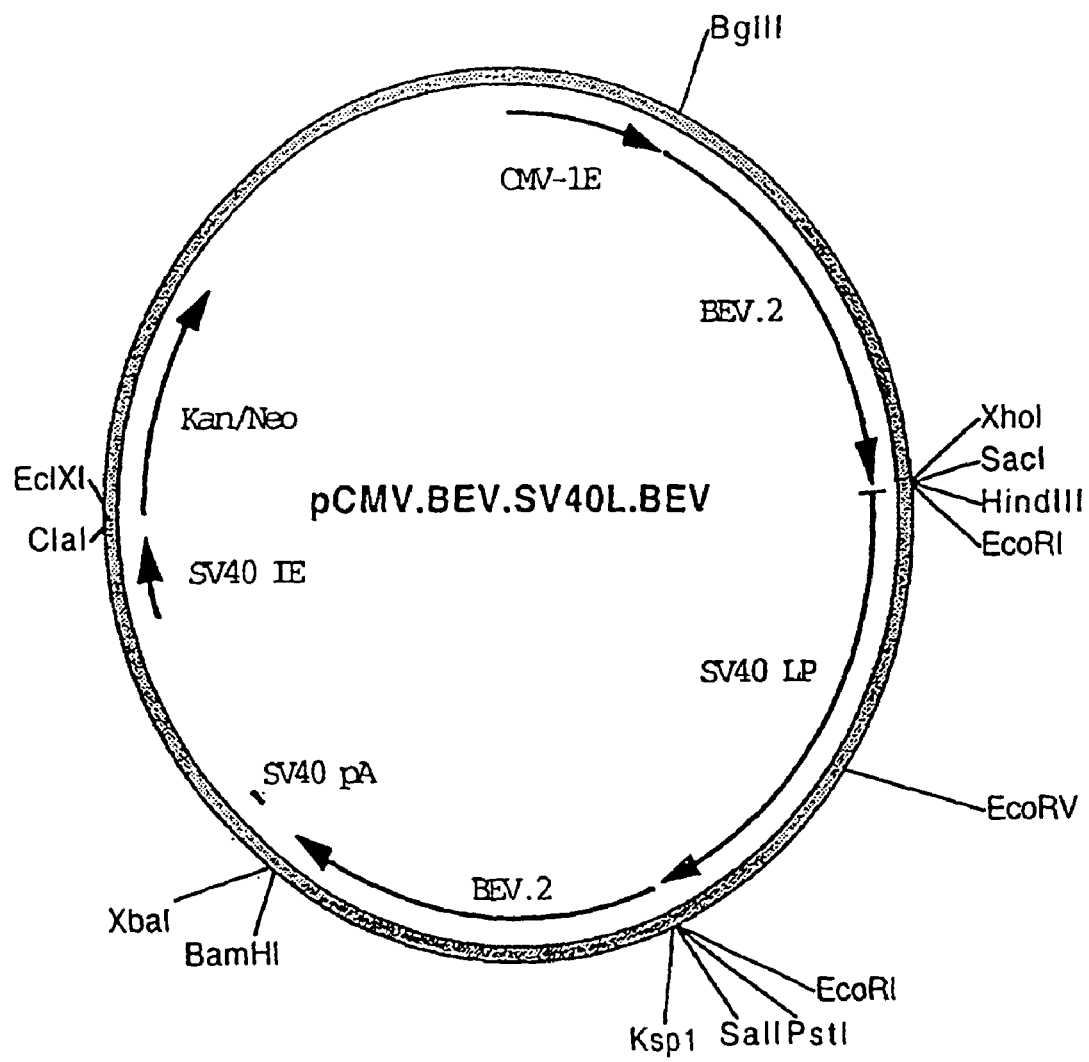
FIG. 23 is a diagrammatic representation of the plasmid pCMV.BEV.SV40L.BEV.
Figure 24:
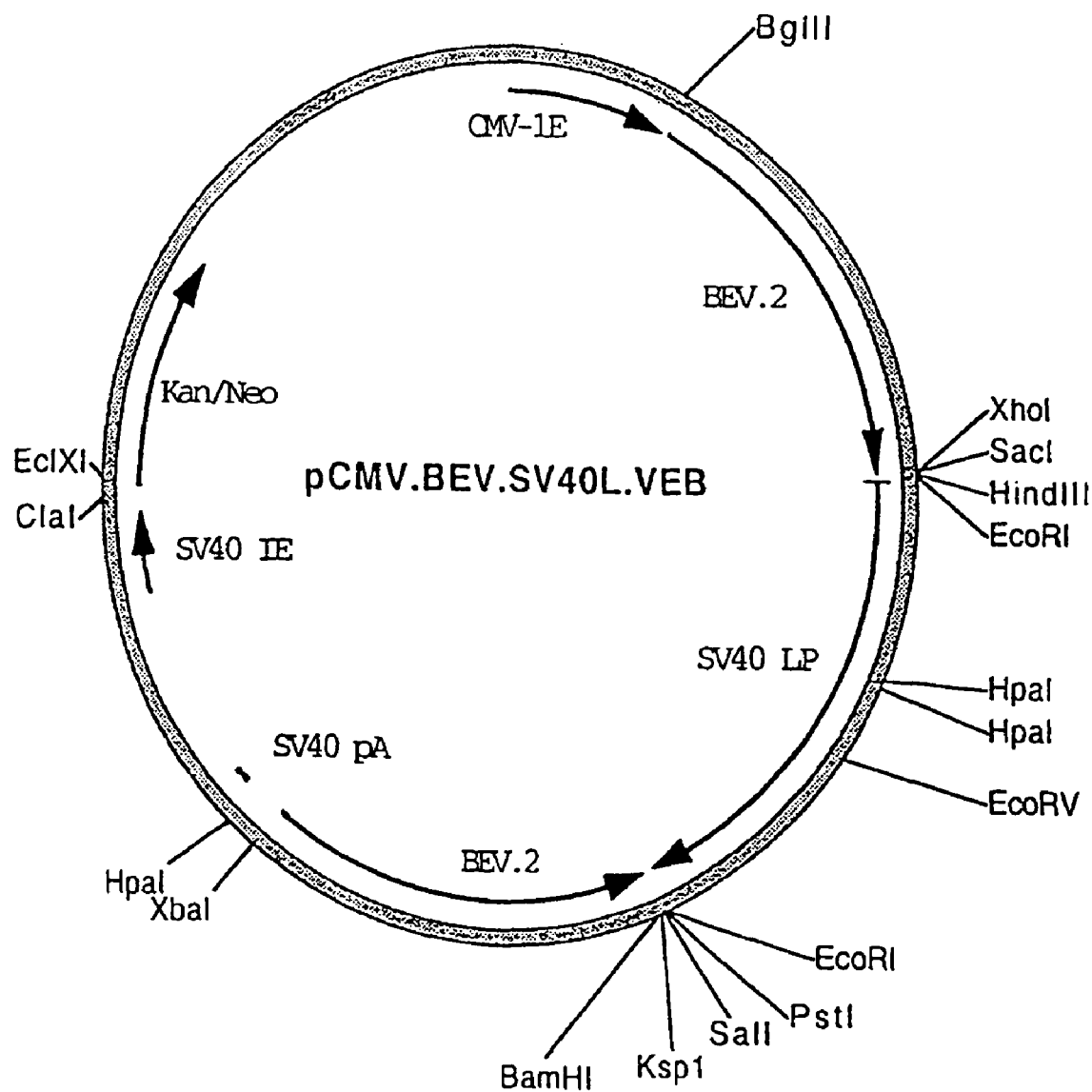
FIG. 24 is a diagrammatic representation of the plasmid pCMV.BEV.SV40L.VEB.
Figure 26:
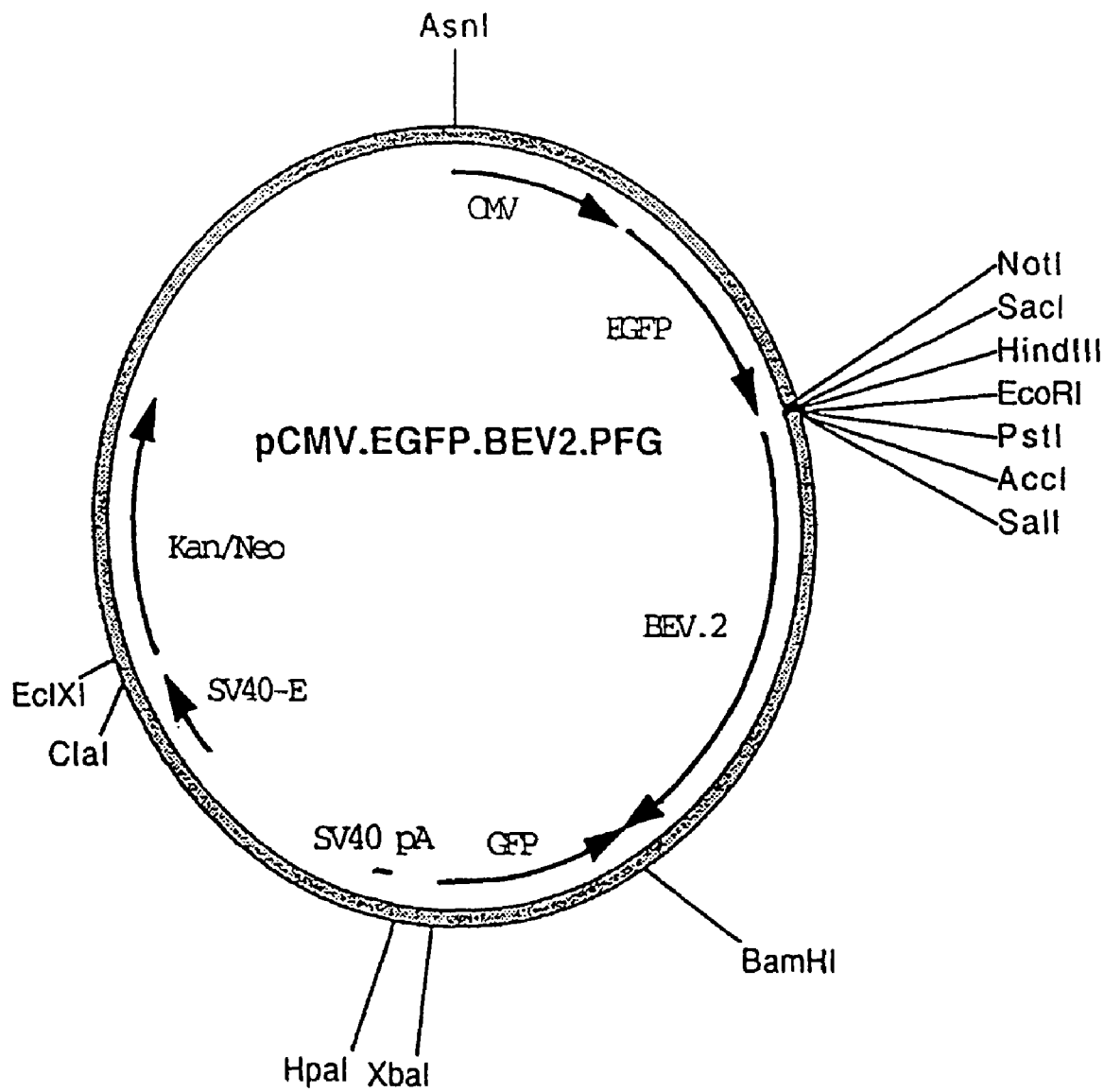
FIG. 26 is a diagrammatic representation of the plasmid pCMV.EGFP.BEV2.PFG.
Figure 27:
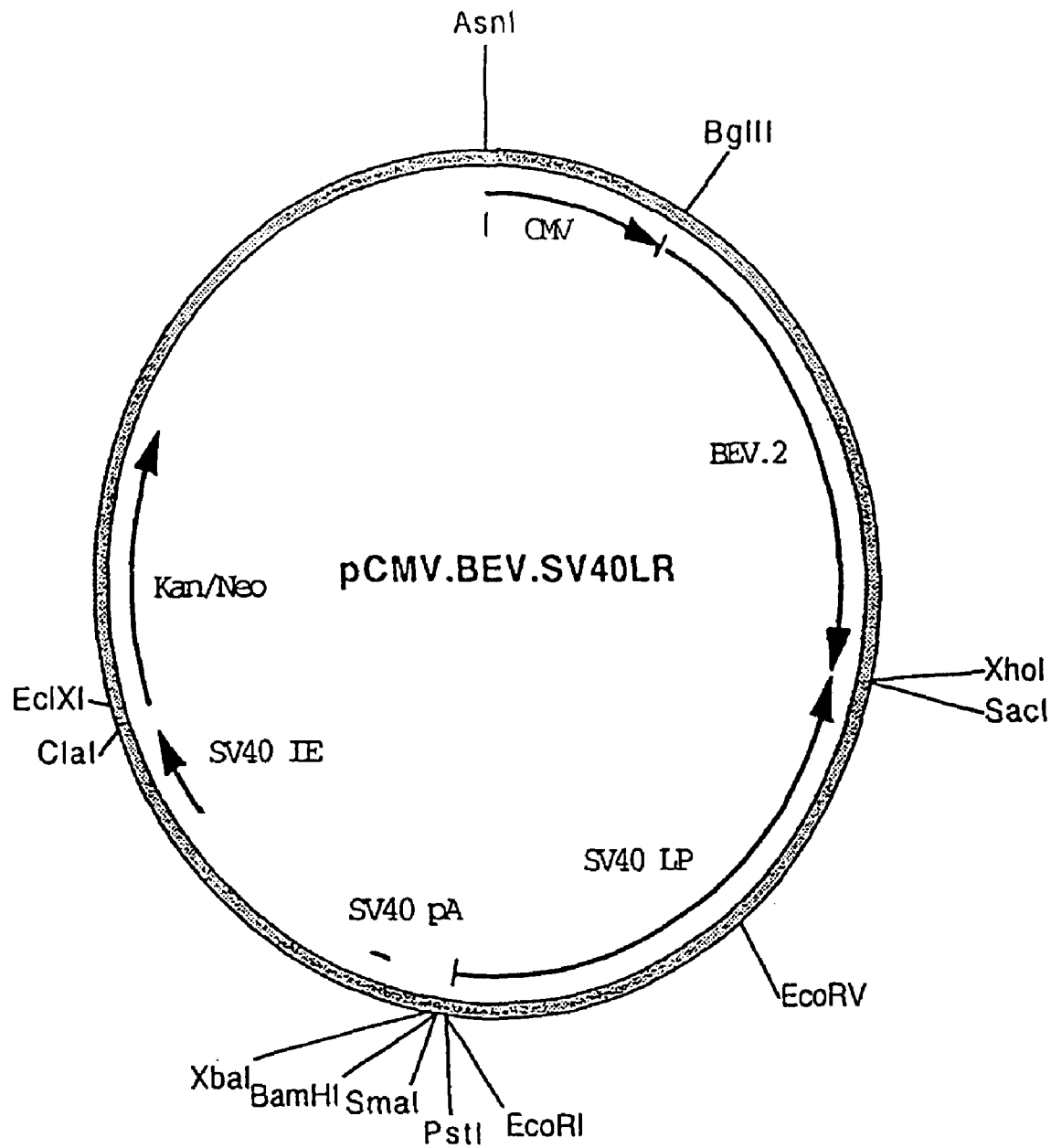
FIG. 27 is a diagrammatic representation of the plasmid pCMV.BEV.SV40LR.
Figure 28:
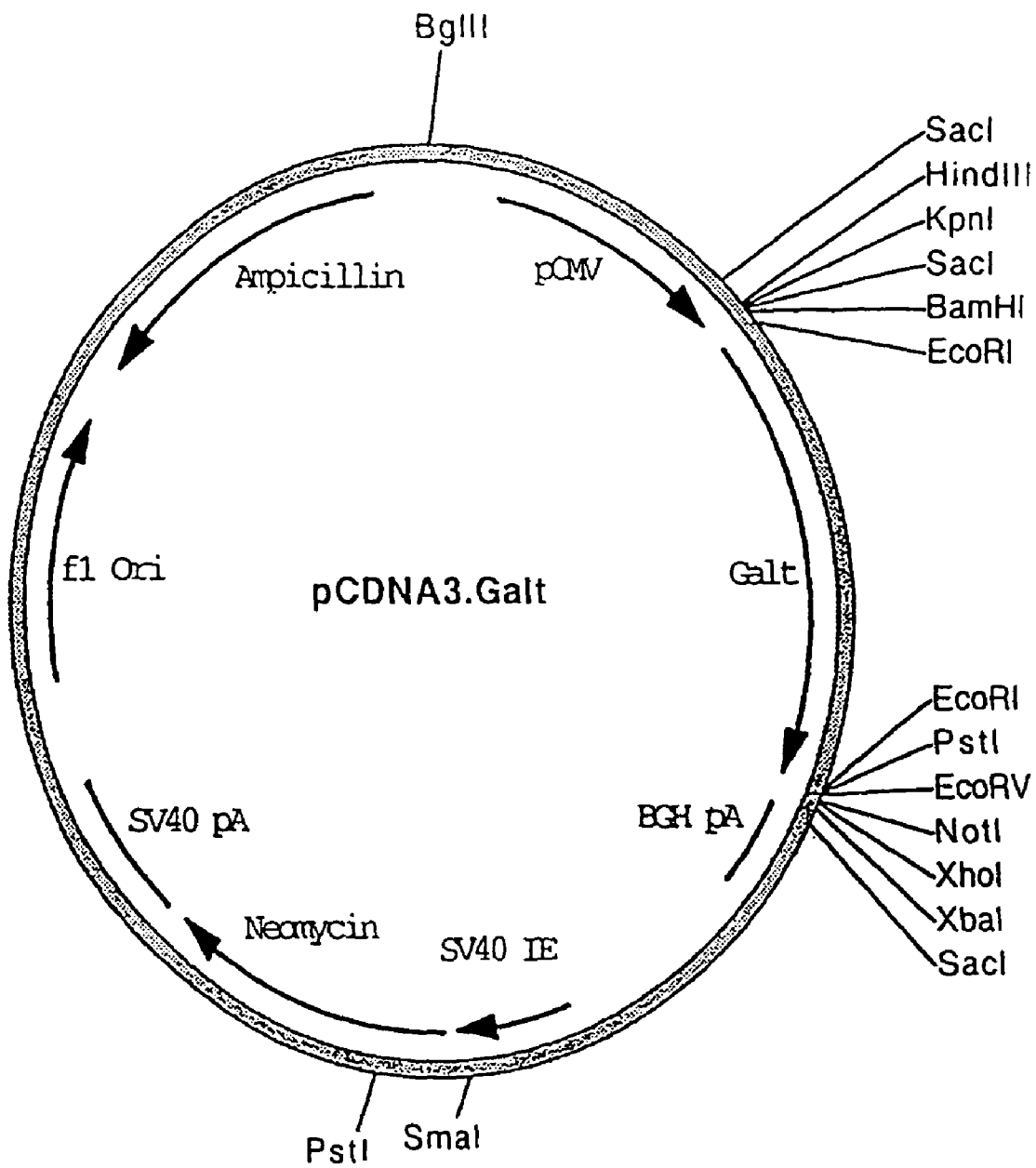
FIG. 28 is a diagrammatic representation of the plasmid pCDNA3.Galt.
Figure 29:
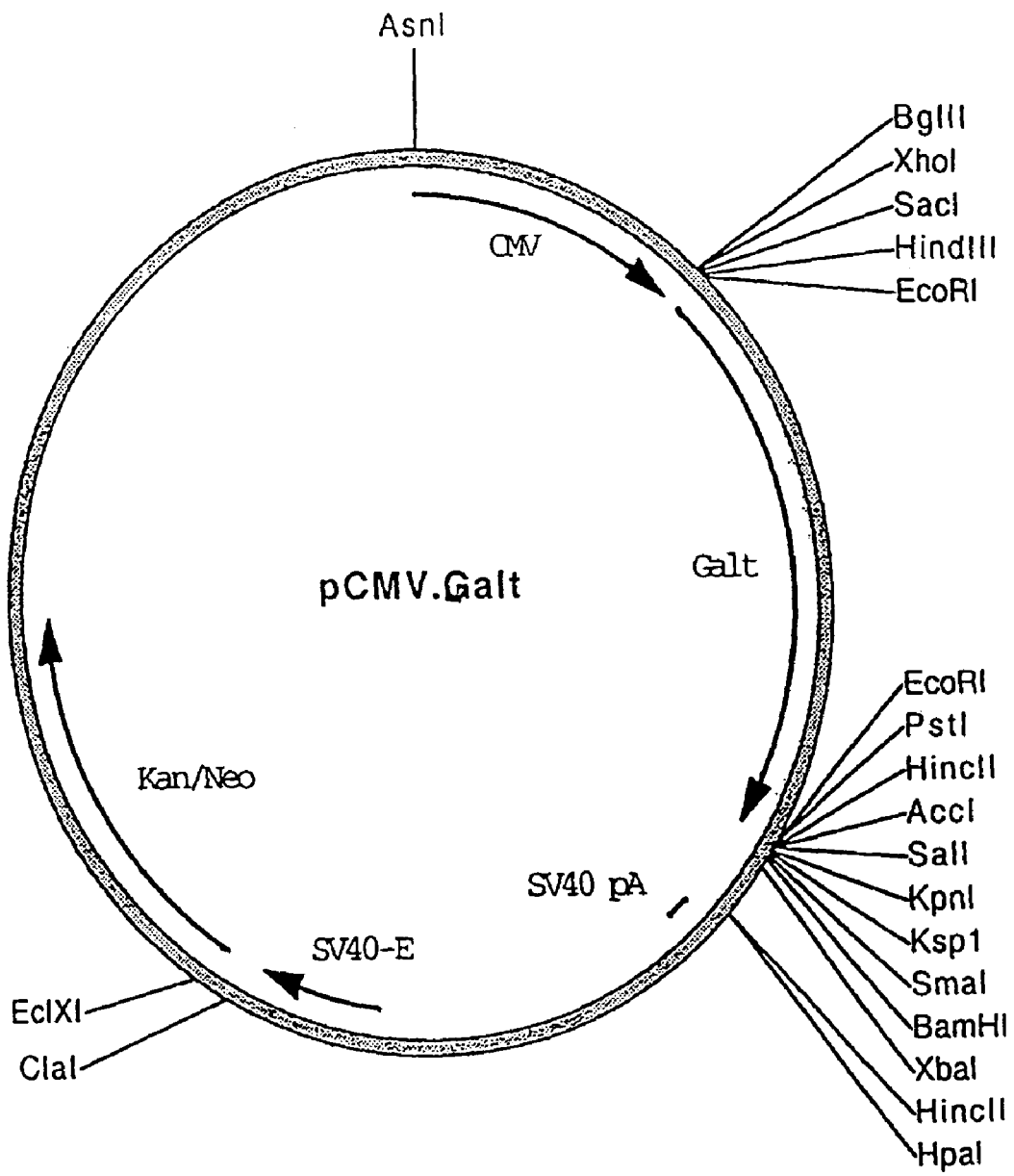
FIG. 29 is a diagrammatic representation of the plasmid pCMV.Galt.
Figure 30:
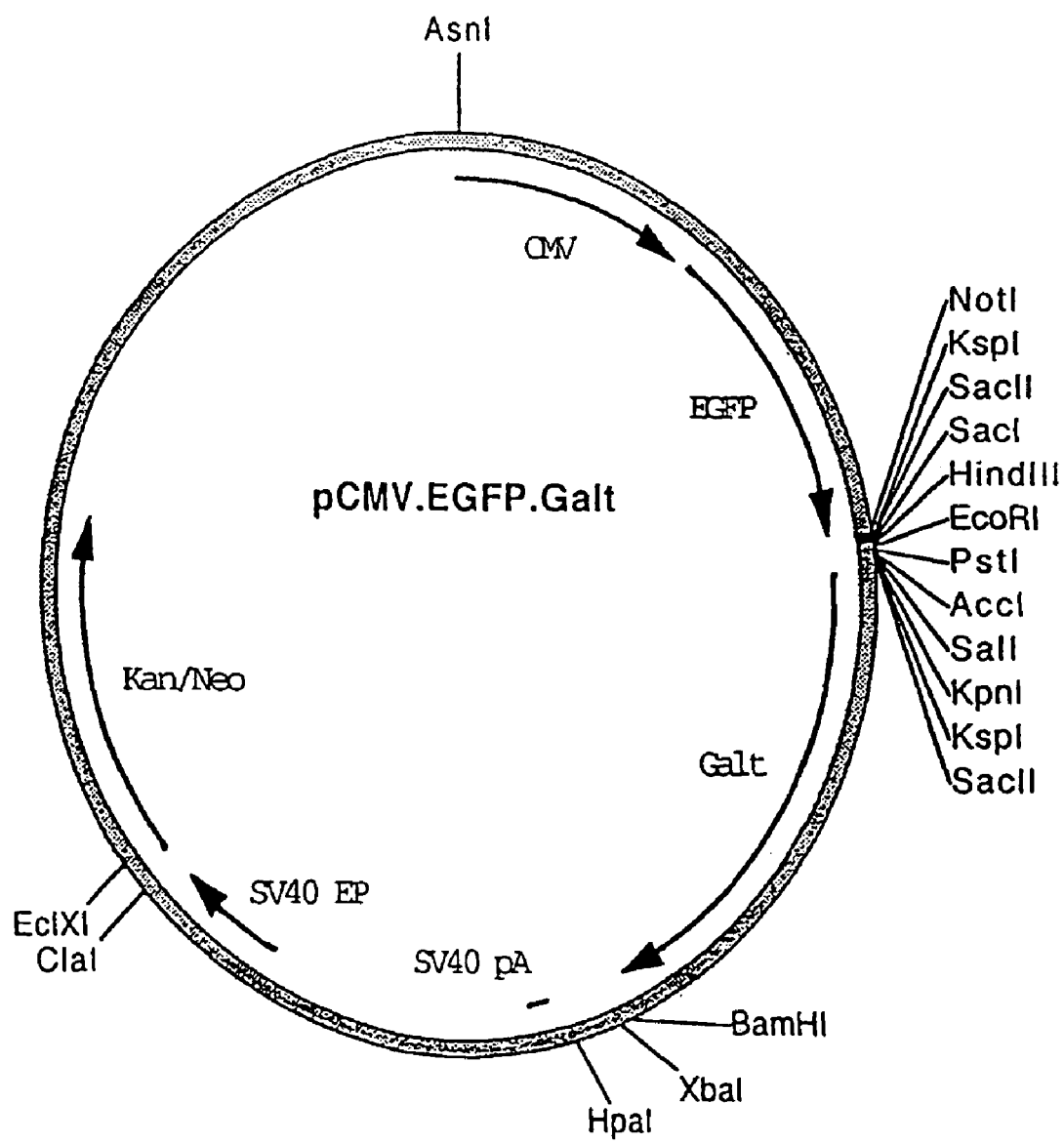
FIG. 30 is a diagrammatic representation of the plasmid pCMV.EGFP.Galt.
Figure 31:
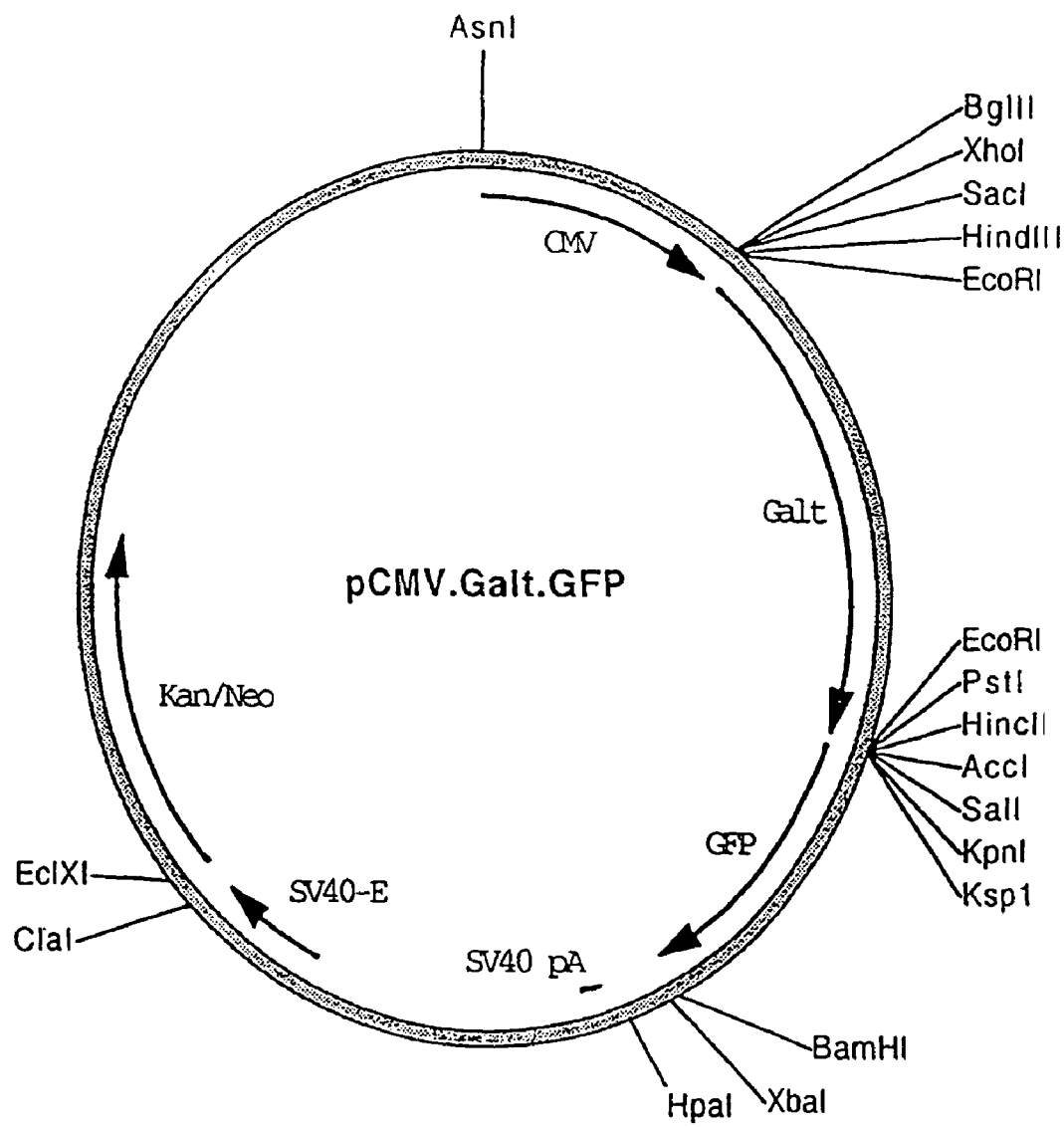
FIG. 31 is a diagrammatic representation of the plasmid pCMV.Galt.GFP.
Figure 32:
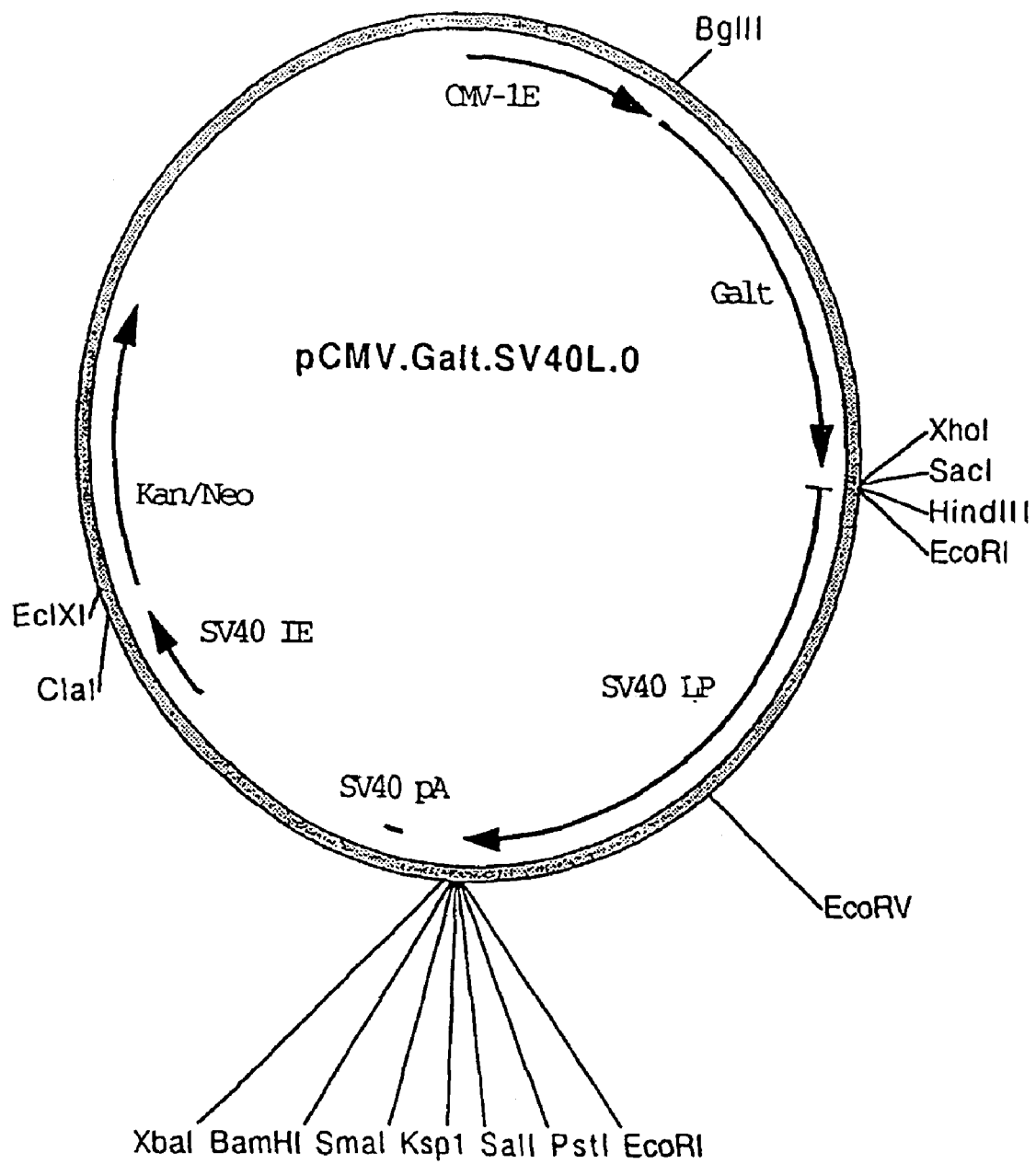
FIG. 32 is a diagrammatic representation of the plasmid pCMV.Galt.SV40L.0.
Figure 33:
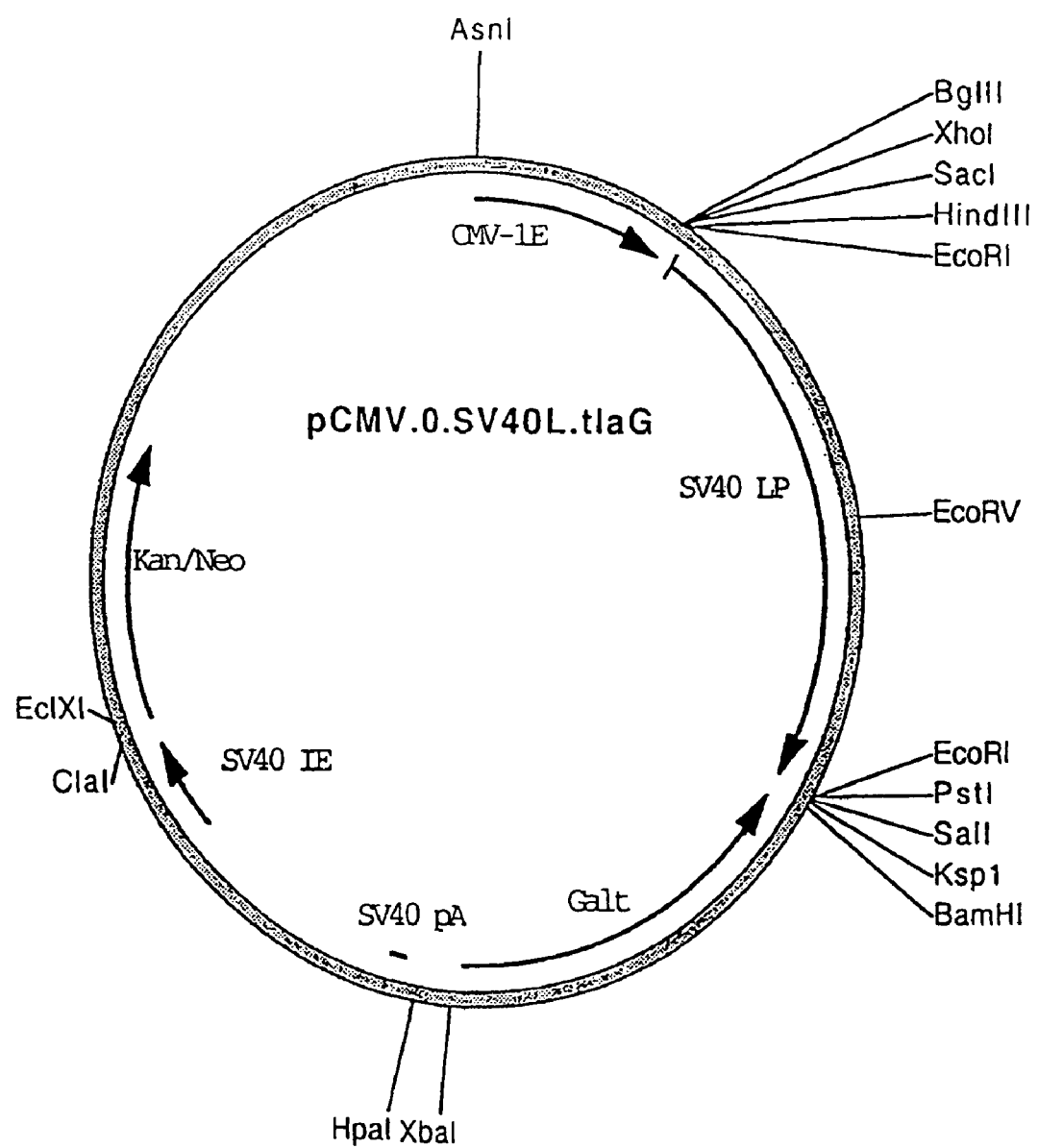
FIG. 33 is a diagrammatic representation of the plasmid pCMV.Galt.SV40LtlaG.
Figure 34:
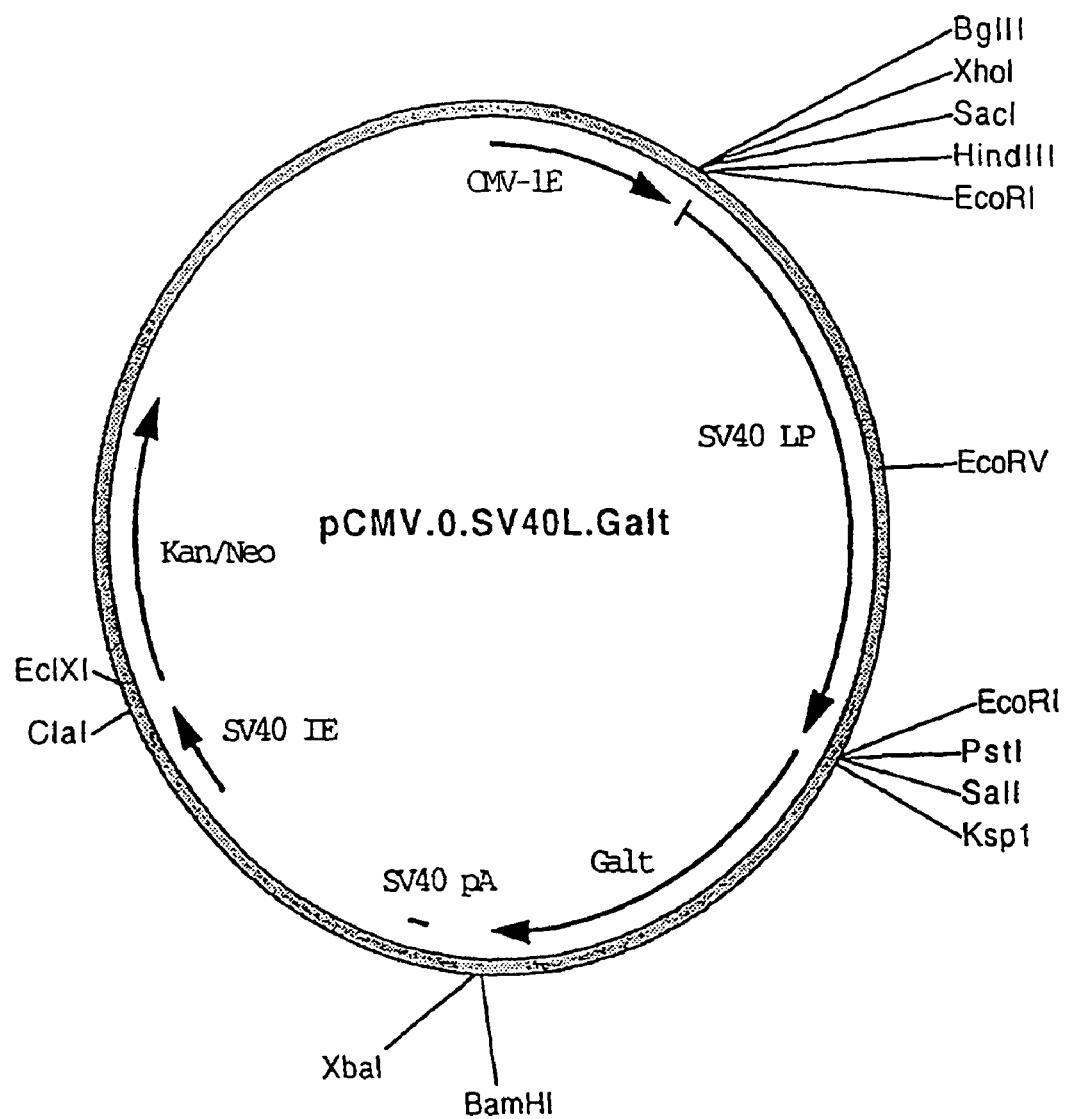
FIG. 34 is a diagrammatic representation of the plasmid pCMV.0.SV40L.Galt.
Figure 35:
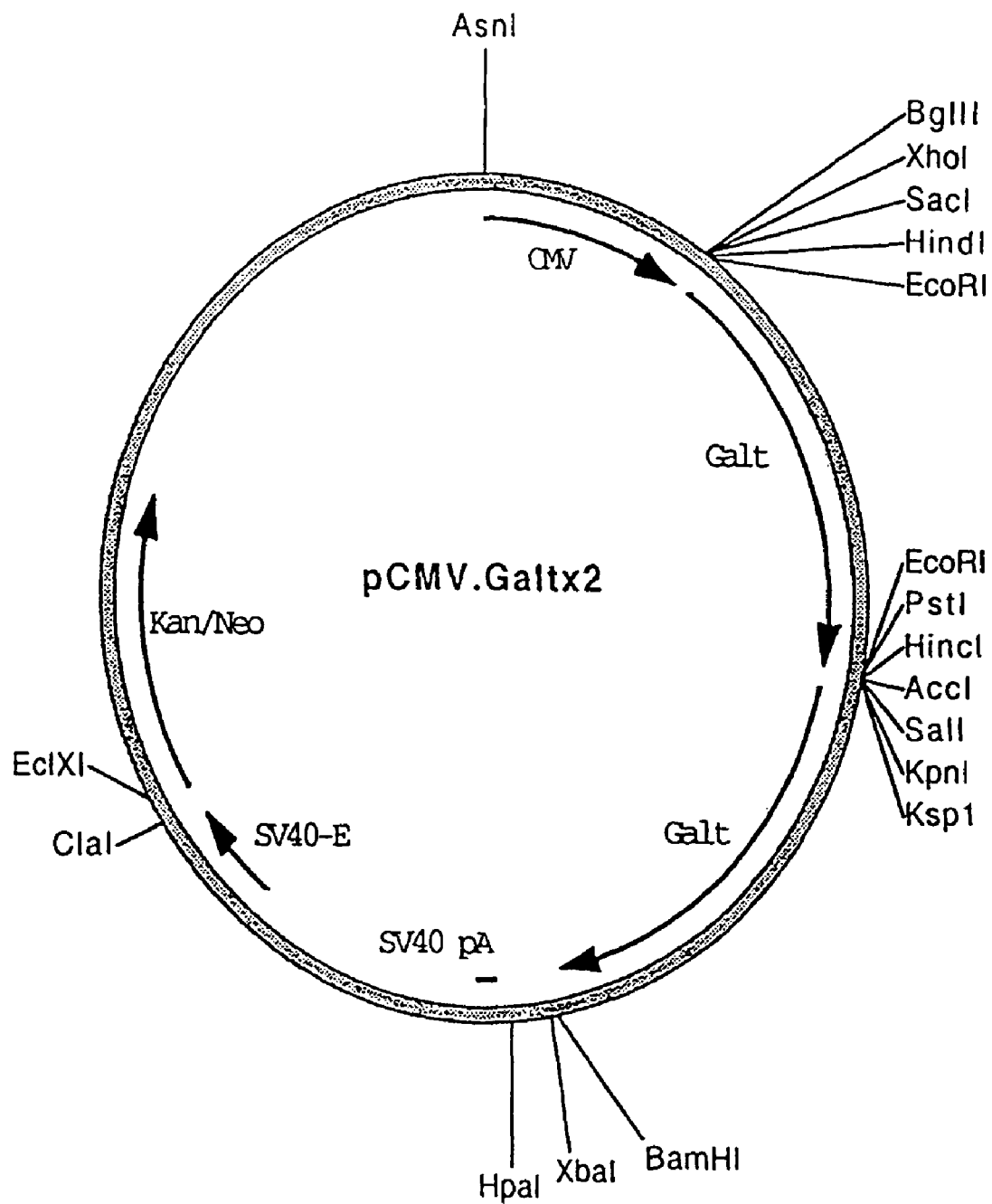
FIG. 35 is a diagrammatic representation of the plasmid pCMV.Galtx2.

The complete BEV polymerase coding region was amplified from a full-length cDNA clone encoding same, using primers BEV-1 and BEV-3. Primer BEV-3 comprises a BamHI restriction enzyme site at positions 5 to 10 inclusive and the complement of a translation stop signal at positions 11 to 13. As a consequence, an open reading frame comprising a translation start signal and translation stop signal, contained between the Bgl II and BamHI restriction sites. The amplified fragment was cloned into pCR2.1 (Stratagene) to produce plasmid pCR2.BEV.2 (FIG. 10).

Plasmid pCR.BEV.3

A non-translatable BEV polymerase structural gene was amplified from a full-length BEV polymerase cDNA clone using the amplification primers BEV-3 and BEV4. Primer BEV-4 comprises a BglII cloning site at positions 5-10 and sequences downstream of this BglII site are homologous to nucleotide sequences of the BEV polymerase gene. There is no functional ATG start codon in the amplified DNA product of primers BEV-3 and BEV-4. The BEV polymerase is expressed as part of a polyprotein and, as a consequence, there is no ATG translation start site in this gene. The amplified DNA was cloned into plasmid pCR2.1 (Stratagene) to yield plasmid pCR.BEV.3 (FIG. 11).

Plasmid pCMV.EGFP.BEV2

Plasmid pCMV.EGFP.BEV2 (FIG. 12) was produced by cloning the BEV polymerase sequence from pCR.BEV.2 as a BglII/BamHI fragment into the BamHI site of pCMV.EGFP.

4. Control Plasmids

Plasmid pCMV.BEV.2

Plasmid pCMV.BEV.2 (FIG. 13) is capable of expressing the entire BEV polymerase open reading frame under the control of CMV-IE promoter sequence. To produce pCMV.BEV.2, the BEV polymerase sequence from pCR.BEV.2 was sub-cloned in the sense orientation as a BglII-to-BamHI fragment into BglII/BamHI-digested pCMV.cass (FIG. 2).

Plasmid pCMV.BEV.3

Plasmid pCMV.BEV.3 (FIG. 14) expresses a non-translatable BEV polymerase structural gene in the sense orientation under the control of the CMV-IE promoter sequence. To produce pCMV.BEVnt, the BEV polymerase sequence from pCR.BEV.3 was sub cloned in the sense orientation as a BglII-to-BamHI fragment into BglII/BamHI-digested pCMV.cass (FIG. 2).

Plasmid pCMV.VEB

Plasmid pCMV.VEB (FIG. 15) expresses an antisense BEV polymerase mRNA under the control of the CMV-IE promoter sequence. To produce plasmid pCMV.VEB, the BEV polymerase sequence from pCR.BEV.2 was sub-cloned in the antisense orientation as a BglII-to-BamHI fragment into BglII/BamHI-digested pCMV.cass (FIG. 2).

Plasmid pCMV.BEV.GFP

Plasmid pCMV.BEV.GFP (FIG. 16) was constructed by cloning the GFP fragment from pCR.Bgl-GFP-Bam as a BglII/BamHI fragment into BamHI-digested pCMV.BEV.2. This plasmid serves as a control in some experiments and also as an intermediate construct.

Plasmid pCMV.BEV.SV40-L

Plasmid pCMV.BEV.SV40-L (FIG. 17) comprises a translatable BEV polymerase structural gene derived from plasmid pCR.BEV.2 inserted in the sense orientation between the CMV-IE promoter and the SV40 late promoter sequences of plasmid pCMV.SV40L.cass. To produce plasmid pCMV.BEV.SV40L-O, the BEV polymerase structural gene was sub-cloned as a BglII-to-BamHI fragment into BglII-digested pCMV.SV40L.cass DNA.

Plasmid pCMV.O.SV40L.BEV

Plasmid pCMV.O.SV40L.BEV (FIG. 18) comprises a translatable BEV polymerase structural gene derived from plasmid pCR.BEV.2 cloned downstream of tandem CMV-IE promoter and SV40 late promoter sequences present in plasmid pCMV.SV40L.cass. To produce plasmid pCMV.O.SV40L.BEV, the BEV polymerase structural gene was sub-cloned in the sense orientation as a BglII-to-BamHI fragment into BamHI-digested pCMV.SV40L.cass DNA.

Plasmid pCMV.O.SV40L.VEB

Plasmid pCMV.O.SV40L.VEB (FIG. 19) comprises an antisense BEV polymerase structural gene derived from plasmid pCR.BEV.2 cloned downstream of tandem CMV-IE promoter and SV40 late promoter sequences present in plasmid pCMV.SV40L.cass. To produce plasmid pCMV.O.SV40L.VEB, the BEV polymerase structural gene was sub-cloned in the antisense orientation as a BglII-to-BamHI fragment into BamHI-digested pCMV.SV40L.cass DNA.

5. Test Plasmids

Plasmid pCMV.BEVx2

Plasmid pCMV.BEVx2 (FIG. 20) comprises a direct repeat of a complete BEV polymerase open reading frame under the control of the CMV-IE promoter sequence. In eukaryotic cells at least, the open reading frame located nearer the CMV-IE promoter is translatable. To produce pCMV.BEVx2, the BEV polymerase structural gene from plasmid pCR.BEV.2 was sub-cloned in the sense orientation as a BglII-to-BamHI fragment into BamHI-digested pCMV.BEV.2, immediately downstream of the BEV polymerase structural gene already present therein.

Plasmid pCMV.BEVx3

Plasmid pCMV.BEVx3 (FIG. 21) comprises a direct repeat of three complete BEV polymerase open reading frames under the control of the CMV-1E promoter. To produce pCMV.BEVx3, the BEV polymerase fragment from pCR.BEV.2 was cloned in the sense orientation as a BglII/BamHI fragment into the BamHI site of pCMV.BEVx2, immediately downstream of the BEV polymerase sequences already present therein.

Plasmid pCMV.BEVx4

Plasmid pCMV.BEVx4 (FIG. 22) comprises a direct repeat of four complete BEV polymerase open reading frames under the control of the CMV-1E promoter. To produce pCMV.BEVx4, the BEV polymerase fragment from pCR.BEV.2 was cloned in the sense orientation as a BglII/BamHI fragment into the BamHI site of pCMV.BEVx3, immediately downstream of the BEV polymerase sequences already present therein.

Plasmid pCMV.BEV.SV40L.BEV

Plasmid pCMV.BEV.SV40L.BEV (FIG. 23) comprises a multiple structural gene unit comprising two BEV polymerase structural genes placed operably and separately under control of the CMV-IE promoter and SV40 late promoter sequences. To produce plasmid pCMV.BEV.SV40L.BEV, the translatable BEV polymerase structural gene present in pCR-.BEV.2 was sub-cloned in the sense orientation as a BglII-to-BamHI fragment behind the SV40 late promoter sequence present in BamHI-digested pCMV.BEV.SV40L-O.

Plasmid pCMV.BEV.SV40L.VEB

Plasmid pCMV.BEV.SV40L.VEB (FIG. 24) comprises a multiple structural gene unit comprising two BEV polymerase structural genes placed operably and separately under control of the CMV-IE promoter and SV40 late promoter sequences. To produce plasmid pCMV.BEV.SV40L.VEB, the translatable BEV polymerase structural gene present in pCR.BEV.2 was sub-cloned in the antisense orientation as a BglII-to-BamHI fragment behind the SV40 late promoter sequence present in BamHI-digested pCMV.BEV.SV40L-O. In this plasmid, the BEV polymerase structural gene is expressed in the sense orientation under control of the CMV-IE promoter to produce a translatable mRNA, whilst the BEV polymerase structural gene is also expressed under control of the SV40 promoter to produce an antisense mRNA species.

Plasmid pCMV.BEV.GFP.VEB

Plasmid pCMV.BEV.GFP.VEB (FIG. 25) comprises a BEV structural gene inverted repeat or palindrome, interrupted by the insertion of a GFP open reading frame (stuffer fragment) between each BEV structural gene sequence in the inverted repeat. To produce plasmid pCMV.BEV.GFP.VEB, the GFP stuffer fragment from pCR.Bgl-GFP-Bam was first sub-cloned in the sense orientation as a BglII-to-BamHI fragment into BamHI-digested pCMV.BEV.2 to produce an intermediate plasmid pCMV.BEV.GFP wherein the BEV polymerase-encoding and GFP-encoding sequences are contained within the same 5'-BglII-to-BamHI-3' fragment. The BEV polymerase structural gene from pCMV.BEV.2 was then cloned in the antisense orientation as a BglII-to-BamHI fragment into BamHI-digested pCMV.BEV.GFP. The BEV polymerase structural gene nearer the CMV-IE promoter sequence in plasmid pCMV.BEV.GFP.VEB is capable of being translated, at least in eukaryotic cells.

Plasmid pCMV.EGFP.BEV2.PFG

Plasmid pCMV.EGFP.BEV2.PFG (FIG. 26) comprise a GFP palindrome, interrupted by the insertion of a BEV polymerase sequence between each GFP structural gene in the inverted repeat. To produce this plasmid the GFP fragment from pCR.Bgl-GFP-Bam was cloned as a BglII/BamHI fragment into the BamHI site of pCMV.EGFP.BEV2 in the antisense orientation relative to the CMV promoter.

Plasmid pCMV.BEV.SV40LR

Plasmid pCMV.BEV.SV40LR (FIG. 27) comprises a structural gene comprising the entire BEV polymerase open reading frame placed operably and separately under control of opposing CMV-IE promoter and SV40 late promoter sequences, thereby potentially producing BEV polymerase transcripts at least from both strands of the full-length BEV polymerase structural gene. To produce plasmid pCMV.BEV.SV40LR, the translatable BEV polymerase structural gene present in pCR.BEV.2 was sub-cloned, as a BglII-to-BamHI fragment, into the unique BglII site of plasmid pCMV.SV40LR.cass, such that the BEV open reading frame is present in the sense orientation relative to the CMV-IE promoter sequence.

Those skilled in the art will recognise that it is possible to generate a plasmid wherein the BEV polymerase fragment from pCR.BEV.2 is inserted in the antisense orientation, relative to the CMV IE promoter sequence, using this cloning strategy. The present invention further encompasses such a genetic construct.

Example 2

Genetic Constructs Comprising the Porcine α-1,3-Galactosyltransferase (Galt) Structural Gene Sequence or Sequences Operably Connected to the CMV Promoter Sequence and/or the SV40L Promoter Sequence 1. Commercial Plasmids Plasmid pcDNA3

Plasmid pcDNA3 is commercially available from Invitrogen and comprises the CMV-IE promoter and BGHpA transcription terminator, with multiple cloning sites for the insertion of structural gene sequences there between. The plasmid further comprises the ColE1 and fl origins of replication and neomycin-resistance and ampicillin-resistance genes.

2. Intermediate Plasmids

Plasmid pcDNA3.Galt

Plasmid pcDNA3.Galt (BresaGen Limited, South Australia, Australia; FIG. 28) is plasmid pcDNA3 (Invitrogen) and comprises the cDNA sequence encoding porcine gene alpha-1,3-galactosyltransferase (Galt) operably under the control of the CMV-IE promoter sequence such that it is capable of being expressed therefrom. To produce plasmid pcDNA3.Galt, the porcine gene alpha-1,3-galactosyltransferase cDNA was cloned as an EcoRI fragment into the EcoRI cloning site of pcDNA3. The plasmid further comprises the ColE1 and fl origins of replication and the neomycin and ampicillin-resistance genes.

3. Control Plasmids

Plasmid pCMV.Galt

Plasmid pCMV.Galt (FIG. 29) is capable of expressing the Galt structural gene under the control of the CMV-IE promoter sequence. To produce plasmid pCMV.Galt, the Gait sequence from plasmid pcDNA3.Galt was excised as an EcoRI fragment and cloned in the sense orientation into the EcoRI site of plasmid pCMV.cass (FIG. 2).

Plasmid pCMV.EGFP.Galt

Plasmid pCMV.EGFP.Galt (FIG. 30) is capable of expressing the Galt structural gene as a Gait fusion polypeptide under the control of the CMV-IE promoter sequence. To produce plasmid pCMV.EGFP.Galt, the Galt sequence from pCMV.Galt (FIG. 29) was excised as a BglII/BamHI fragment and cloned into the BamHI site of pCMV.EGFP.

Plasmid pCMV.Galt.GFP

Plasmid pCMV.Galt.GFP (FIG. 31) was produced by cloning the Gait cDNA as an EcORI fragment from pCDNA3 into EcoRI-digested pCMV.EGFP in the sense orientation. This plasmid serves as both a control and construct intermediate.

Plasmid pCMV.Galt.SV40L.0

The plasmid pCMV.Galt.SV40L.0 (FIG. 32) comprises a Galt structural gene cloned downstream of the CMV promoter present in pCMV.SV40L.cass. To produce the plasmid the Galt cDNA fragment from pCMV.Galt was cloned as a BglII/BamHI into BglII-digested pCMV.SV40L.cass in the sense orientation.

Plasmid pCMV.O.SV40L.tlaG

The plasmid pCMV.O.SV40L.tlaG (FIG. 33) comprises a Galt structural gene clones in an antisense orientation downstream of the SV40L promoter present in pCMV.SV40L.cass. To produce this plasmid the Galt cDNA fragment from pCMV.Galt was cloned as a BglII/BamHI into BamHI-digested pCMV.SV40L.cass in the antisense orientation.

Plasmid pCMV.O.SV40L.Galt

The plasmid pCMV.O.SV40L.Galt (FIG. 34) comprises a Galt structural gene cloned downstream of the SV40L promoter present in pCMV.SV40L.cass. To produce the plasmid the Galt cDNA fragment from pCMV.Galt was cloned as a BglII/BamHI into BamHI-digested pCMV.SV40L.cass in the sense orientation.

4. Test Plasmids

Plasmid pCMV.Galtx2

Plasmid pCMV.Galtx2 (FIG. 35) comprises a direct repeat of a Galt open reading frame under the control of the CMV-IE promoter sequence. In eukaryotes cells at least, the open reading frame located nearer the CMV-IE promoter is translatable. To produce pCMV.Galtx2, the Galt structural gene from pCMV.Galt was excised as a BglII/BamHI fragment and cloned in the sense orientation into the BamHI cloning site of pCMV.Galt.

Plasmid pCMV.Galtx4

Figure 36:
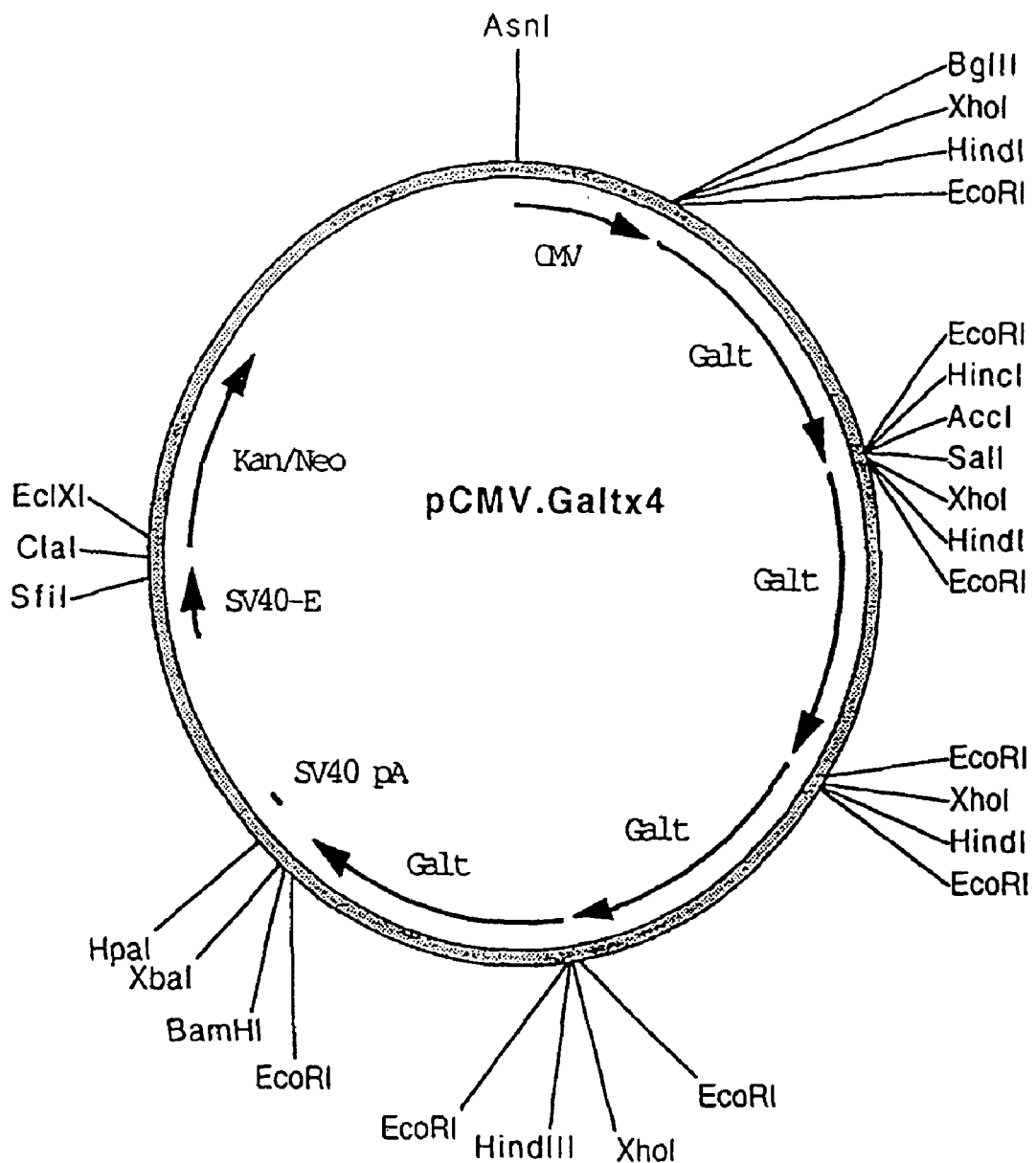
FIG. 36 is a diagrammatic representation of the plasmid pCMV.Galtx4.

Plasmid pCMV.Galtx4 (FIG. 36) comprises a quadruple direct repeat of a Galt open reading frame under the control of the CMV-IE promoter sequence. In eukaryotes cells at least, the open reading frame located nearer the CMV-IE promoter is translatable. To produce pCMV.Galtx4, the Galtx2 sequence from pCMV.Galtx2 was excised as a BglII/BamHI fragment and cloned in the sense orientation into the BamHI cloning site of pCMV.Galtx2.

Plasmid pCMV.Galt.SV40L.Galt

Figure 37:
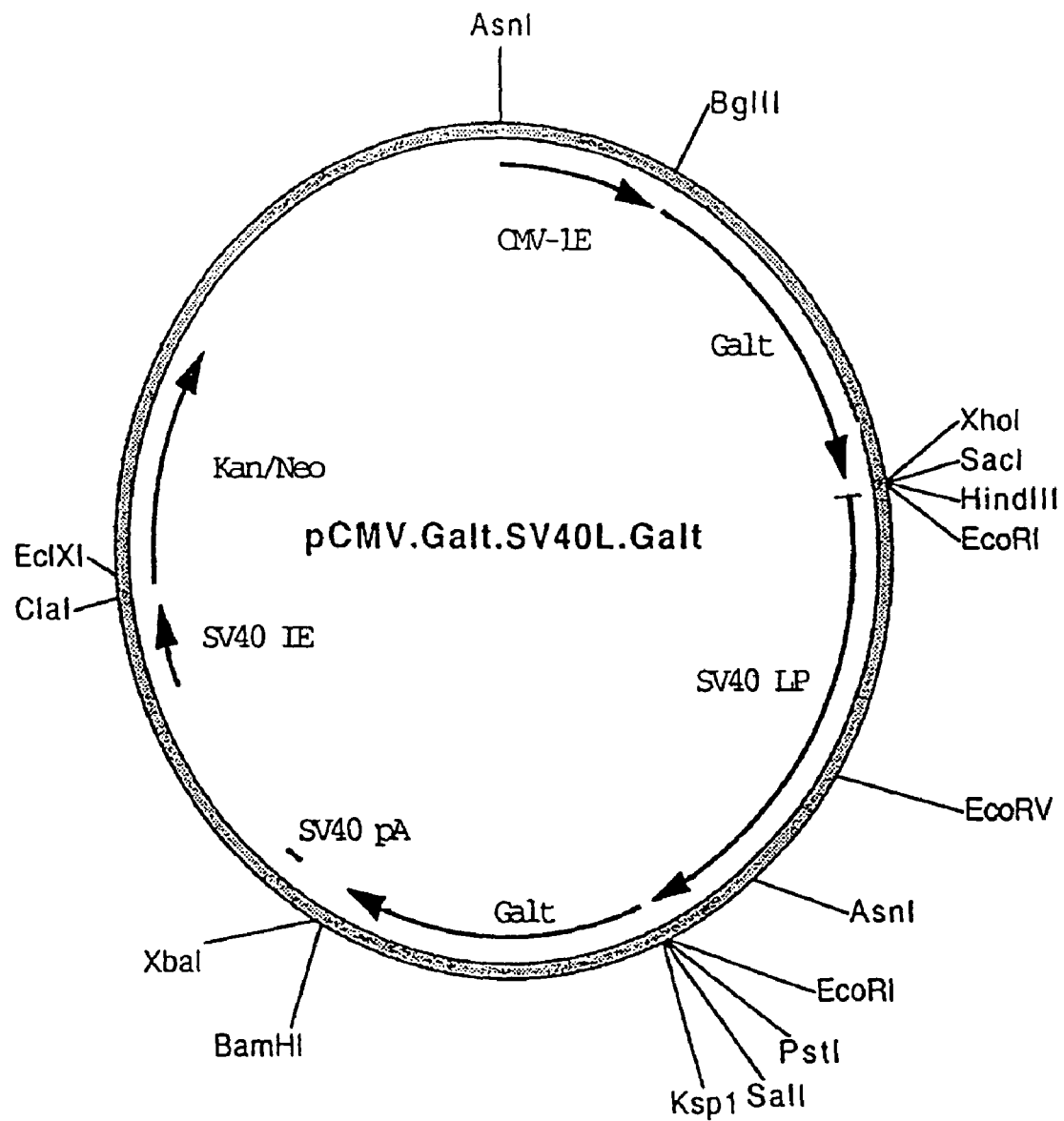
FIG. 37 is a diagrammatic representation of the plasmid pCMV.Galt.SV40L.Galt.

The plasmid pCMV.Galt.SV40L.Galt (FIG. 37) is designed to express two sense transcripts of Galt, one driven by the CMV promoter, the other by the SV40L promoter. To produce the plasmid a Galt cDNA fragment from pCMV.Galt was cloned as a BglII/BamHI fragment into BglII-digested pCMV.O.SV40.Galt in the sense orientation.

Plasmid pCMV.Galt.SV40L.tlaG

Figure 38:
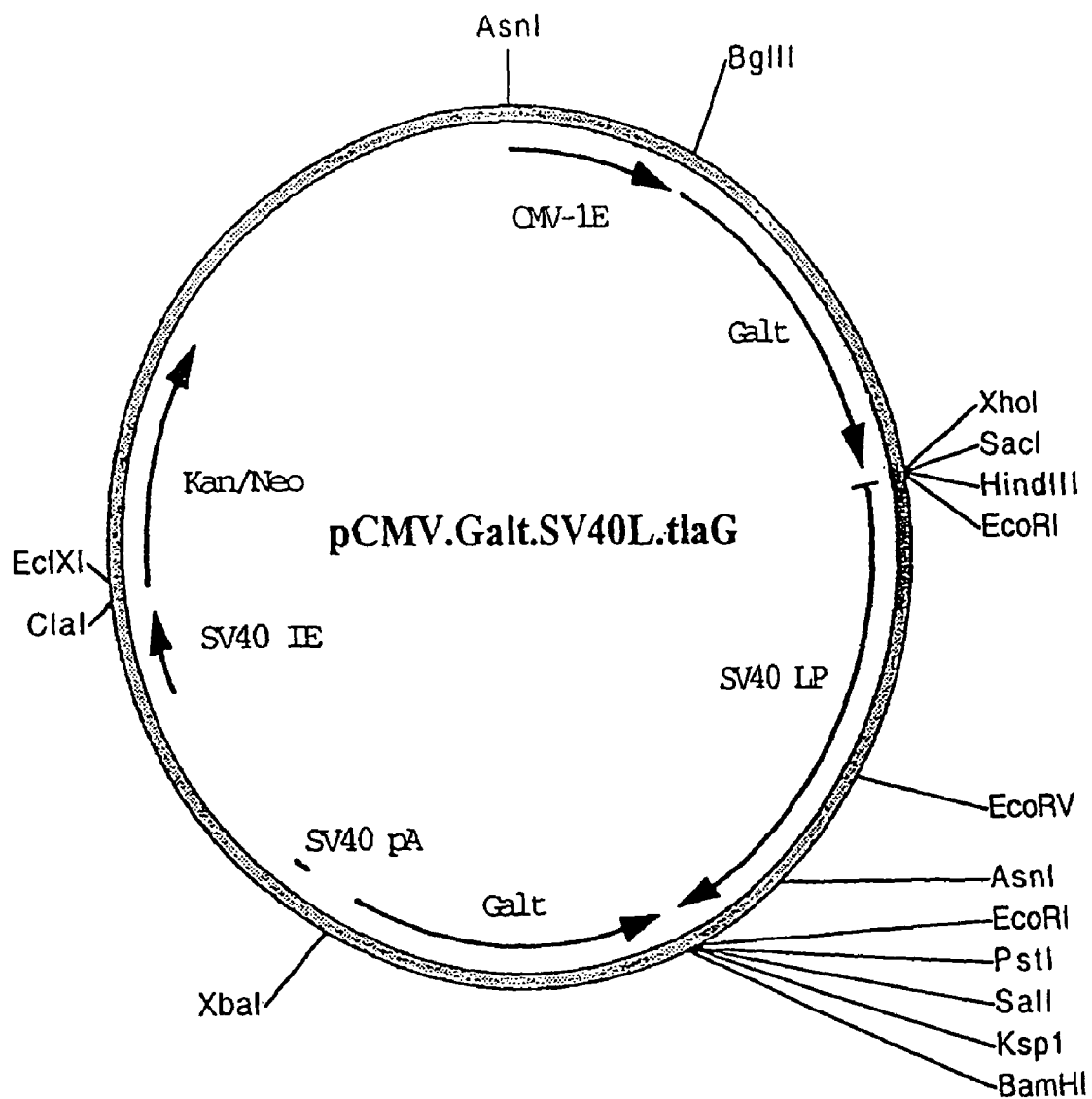
FIG. 38 is a diagrammatic representation of the plasmid pCMV.Galt.SV40L.tlaG.

The plasmid pCMV.Galt.SV40.tlaG (FIG. 38) is designed to express a sense transcript of Galt driven by the CMV promoter and an antisense transcript driven by the SV40L promoter. To produce the plasmid a Galt cDNA fragment from pCMV.Galt was cloned as a BglII/BamHI fragment into BglII-digested pCMV.O.SV40.talG in the sense orientation.

Plasmid pCMV.Galt.GFP.tlaG

Figure 39:
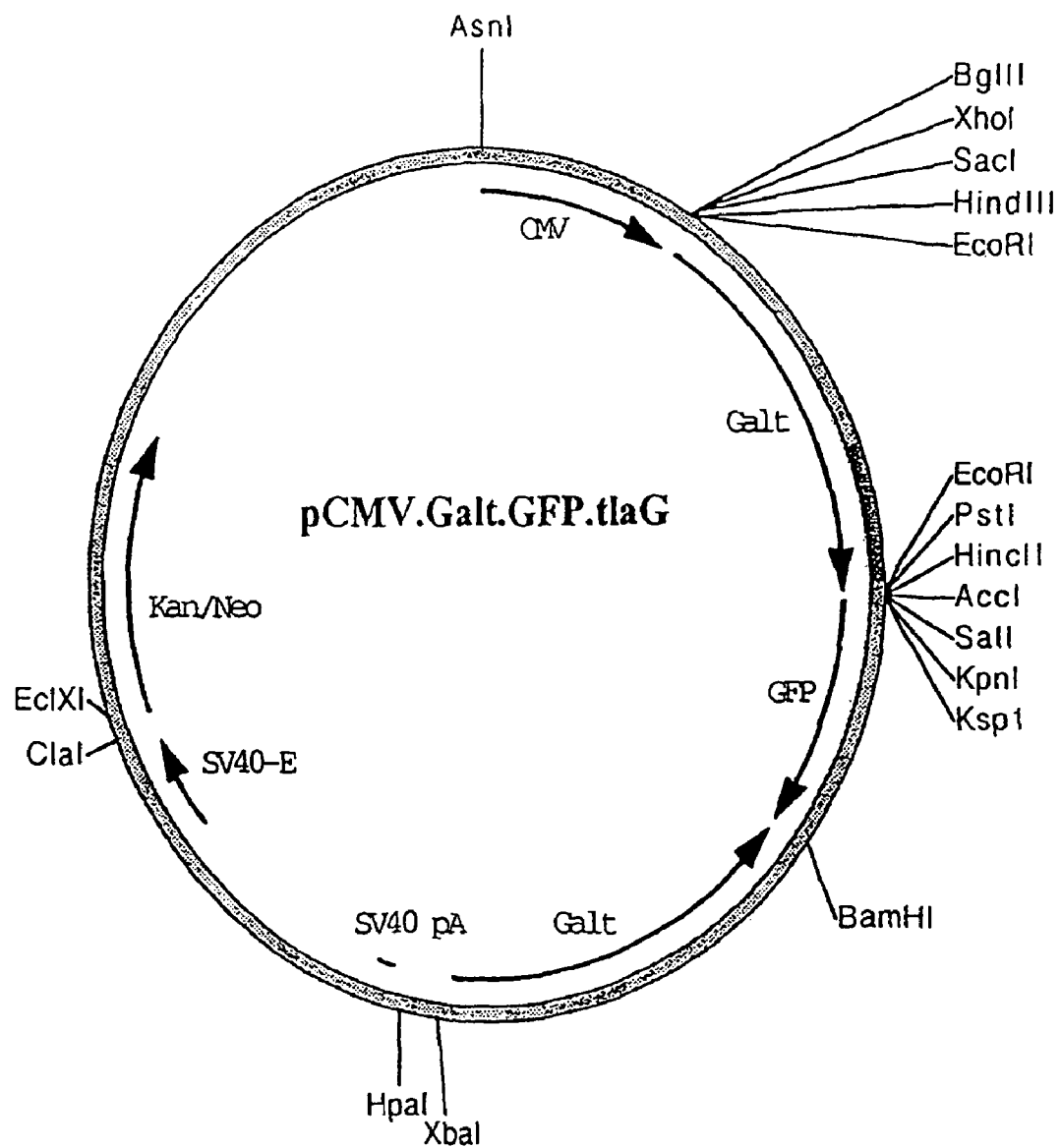
FIG. 39 is a diagrammatic representation of the plasmid pCMV.Galt.GFP.tlaG.

Plasmid pCMV.Galt.GFP.tlaG (FIG. 39) comprise a Galt palindrome, interrupted by the insertion of a GFP sequence between each Galt structural gene in the inverted repeat. To produce this plasmid the BglII/BamHI Galt cDNA fragment from pCMV.Galt was cloned into the BamHI site of pCMV-.Galt.GFP in the antisense relative to the CMV promoter.

Plasmid pCMV.EGFP.Galt.PFG

Figure 40:
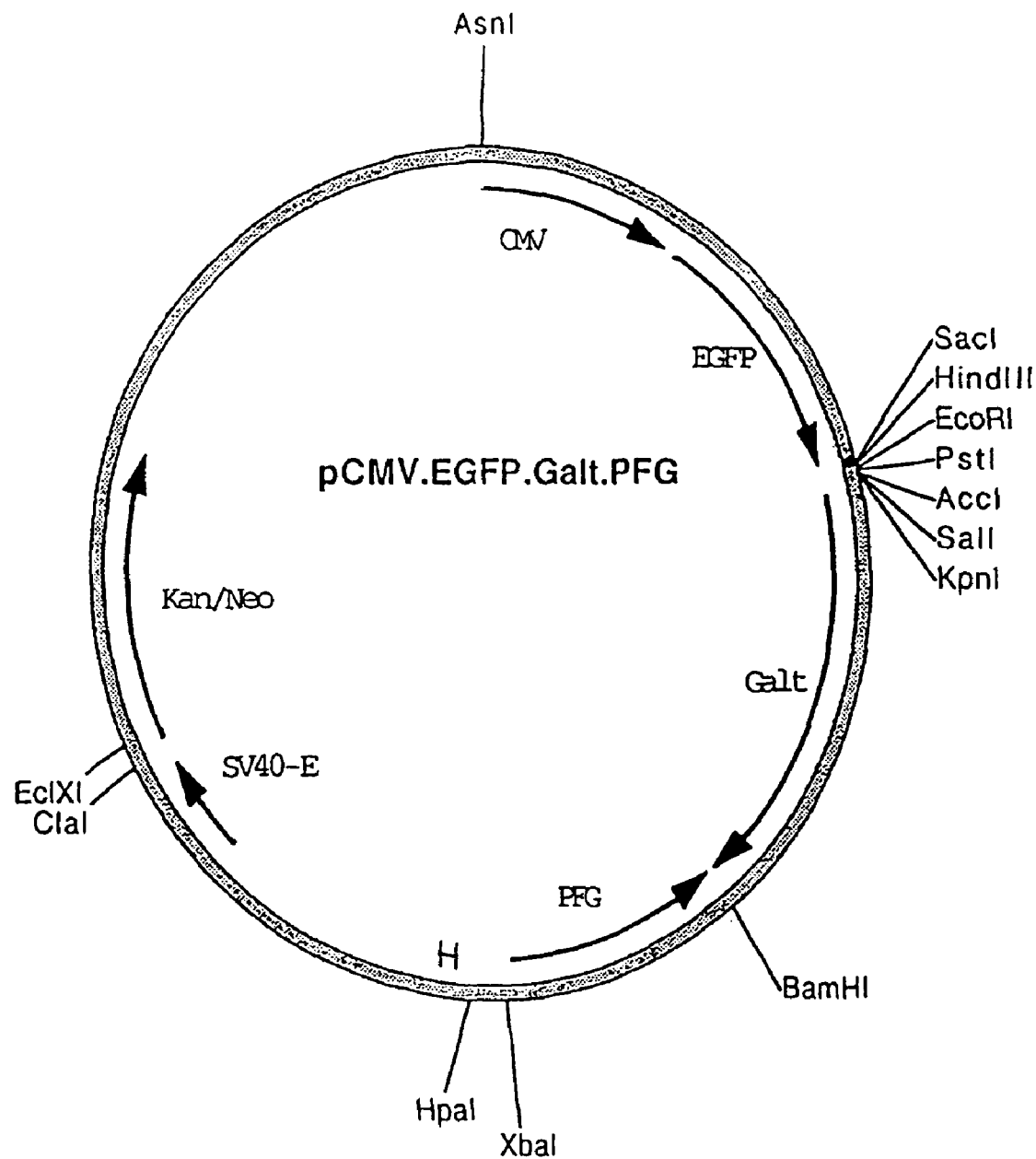
FIG. 40 is a diagrammatic representation of the plasmid pCMV.EGFP.Galt.PFG.

The plasmid pCMV.EGFP.Galt.PFG (FIG. 40) comprises a GFP palindrome, interrupted by the insertion of a Galt sequence between each GFP structural gene of the inverted repeat, expression of which is driven by the CMV promoter. To produce this plasmid the Gait sequences from pCMV.Galt were cloned as a BglII/BamHI fragment into BamHI-digested pCMV.EGFP in the sense orientation to produce the intermediate pCMV.EGFP.Galt (not shown); following this further GFP sequences from pCR.Bgl-pCMV.EGFP.Galt in the antisense orientation.

Plasmid pCMV.Galt.SV40LR

Figure 41:
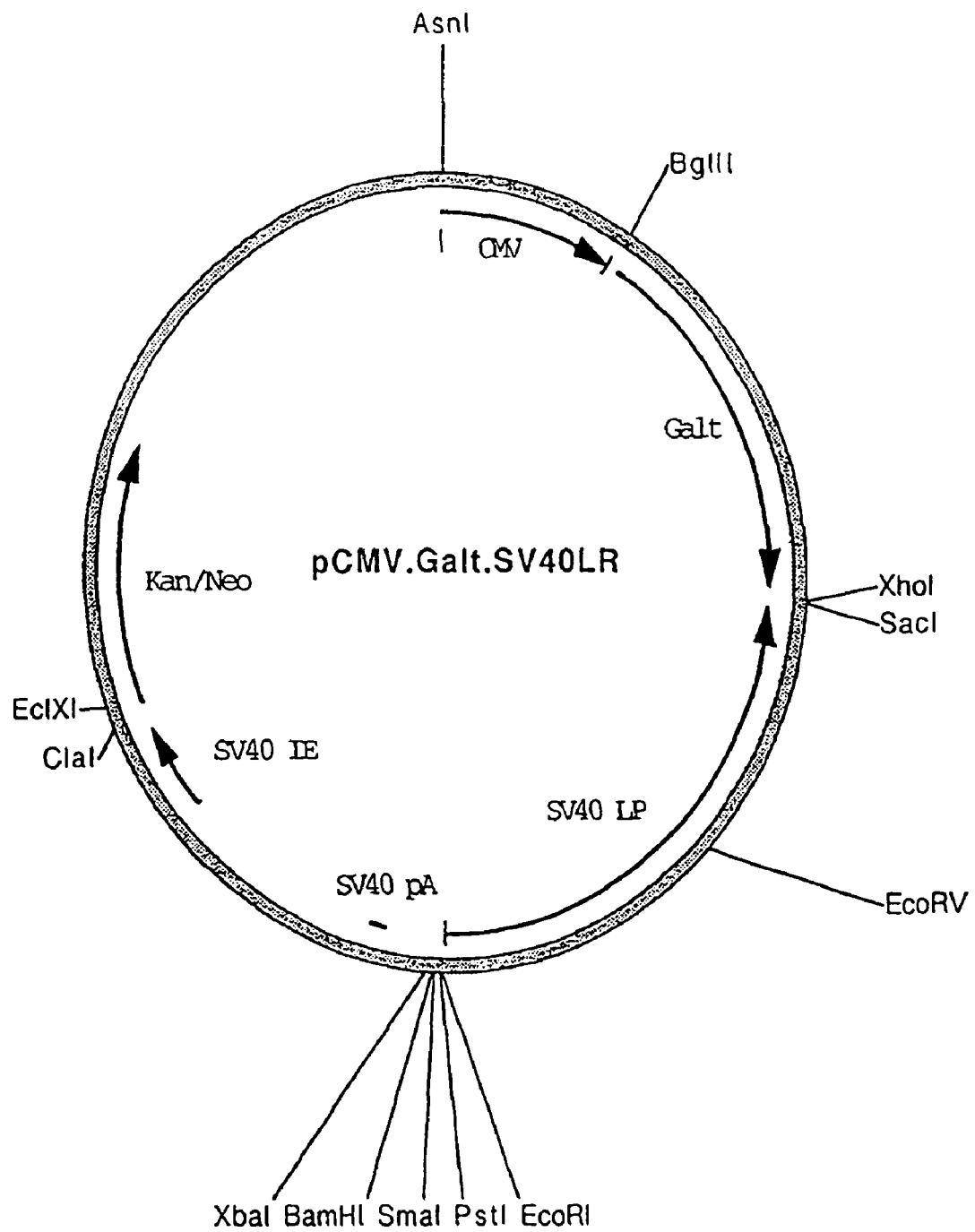
FIG. 41 is a diagrammatic representation of the plasmid pCMV.Galt.SV40LR.
Figure 42:
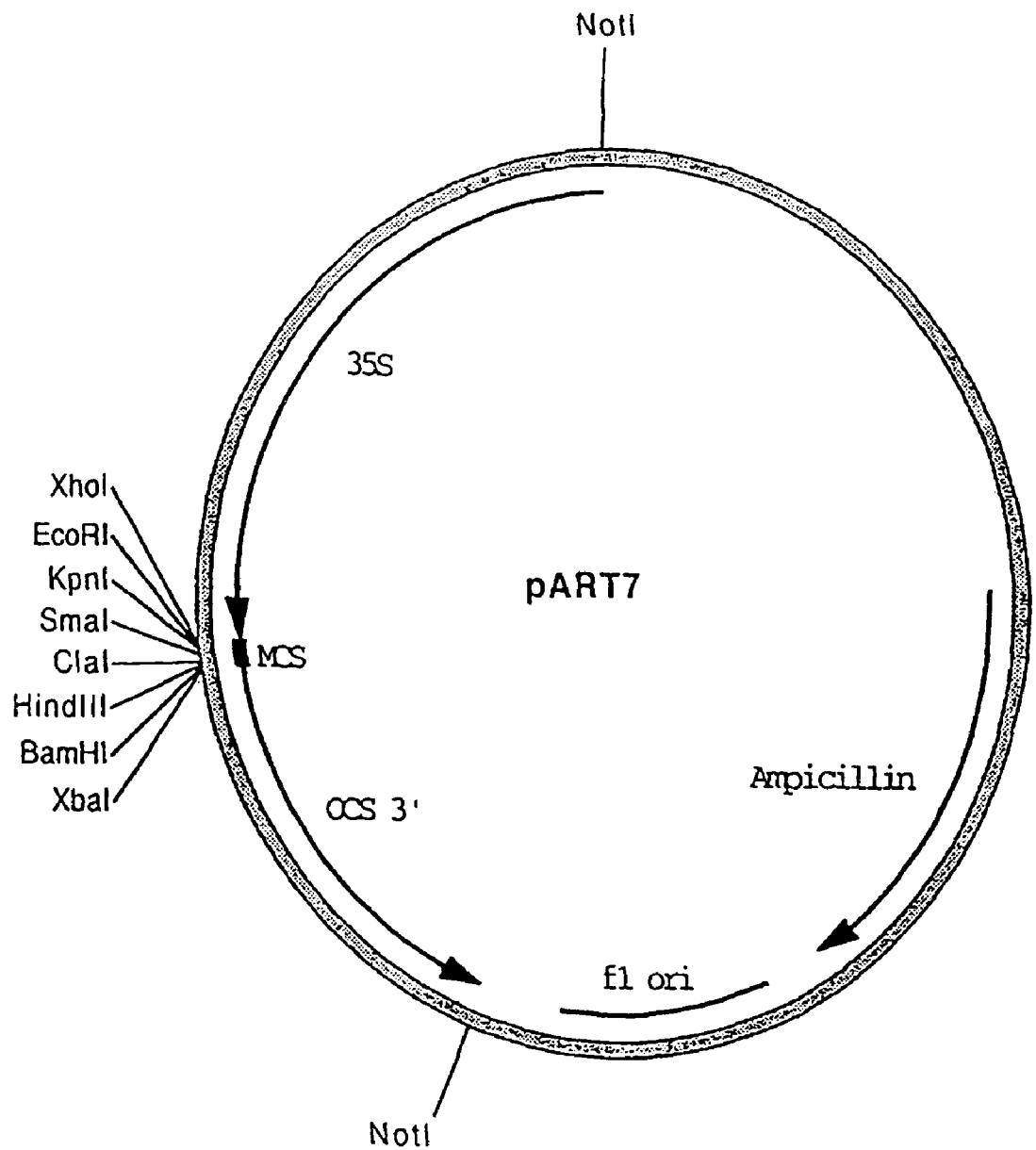
FIG. 42 is a diagrammatic representation of the plasmid pART7.

The plasmid pCMV.Galt.SV40LR (FIG. 41) is designed to express GalT cDNA sequences cloned between the opposing CMV and SV40L promoters in the expression cassette pCMV.SV40LR.cass. To produce this plasmid Galt sequences from pCMV.Galt were cloned as a BglII/BamHI fragment in BglII-digested pCMV.SV40LR.cass in the sense orientation relative to the 35S promoter.

Example 3

Genetic Constructs Comprising PVY Nia Sequences Operably Linked to the 35S Promoter Sequence and/or the SCBV Promoter Sequence 1: Binary Vector Plasmid pART27

Plasmid pART27 is a binary vector, specifically designed to be compatible with the pART7 expression cassette. It contains bacterial origins of replication for both *E. coli* and *Agrobacterium tumefaciens*, a spectinomycin resistance gene for bacterial selection, left and right T-DNA borders for transfer of DNA from *Agrobacterium* to plant cells and a kanamycin resistance cassette to permit selection of transformed plant cells. The kanamycin resistance cassette is located between the T-DNA borders, pART27 also contains a unique NotI restriction site which permits cloning of constructs prepared in vectors such as pART7 to be cloned between the T-DNA borders Construction of pART27 is described in Gleave, AP (1992).

When cloning NotI inserts into this vector, two insert orientations can be obtained. In all the following examples the same insert orientation, relative to the direction of the 35S promoter in the described pART7 constructs was chosen; this was done to minimise any experimental artefacts that may arise from comparing different constructs with different insert orientations.

2. Commercial Plasmids

Plasmid pBC (KS−)

Plasmid pBC (KS−) is commercially available from Stratagene and comprises the LacZ promoter sequence and lacZ-alpha transcription terminator, with a multiple cloning site for the insertion of structural gene sequences therein. The plasmid further comprises the ColE1 and fl origins of replication and a chloroamphenicol-resistance gene.

Plasmid pSP72

Plasmid pSP72 is commercially available from Promega and contains a multiple cloning site for the insertion of structural gene sequences therein. The plasmid further comprises the ColE1 origin of replication and an ampicillin-resistance gene.

3. Expression Cassettes

Plasmid pART7

Plasmid pART7 is an expression cassette designed to drive expression of sequences cloned behind the 35S promoter. It contains a polylinker to assist cloning and a region of the octipine synthase terminator. The 35S expression cassette is flanked by two Not I restriction sites which permits cloning into binary expression vectors, such as pART27 which contains a unique NotI site. Its construction as described in Gleave, AP (1992), a map is shown in FIG. 43.

Plasmid pAR17.35S.SCBV.cass

Plasmid p35S.CMV.cass was designed to express two separate gene sequences cloned into a single plasmid. To create this plasmid, sequences corresponding to the nos terminator and the SCBV promoter were amplified by PCR then cloned in the polylinker of pART7 between the $^{35}$S promoter and OCS.

The resulting plasmid has the following arrangement of elements:

35S promoter-polylinker 1-NOS terminator-SCBV promoter-polylinker 2-OCS terminator.

Expression of sequences cloned into polylinker 1 is controlled by the 35S promoter, expression of sequences cloned into polylinker 2 is controlled by the SCBV promoter.

The NOS terminator sequences were amplified from the plasmid pAHC27 (Christensen and Quail, 1996) using the two oligonucleotides;

```
NOS 5' (forward primer; SEQ ID ??)
5'-GGATTCCCGGGACGTCGCGAATTTCCCCCGATCGTTC-3';
and NOS 3' (reverse primer; SEQ ID ??)
5'-CCATGGCCATATAGGCCCGATCTAGTAACATAG-3'
```

Nucleotide residues 1 to 17 for NOS 5' and 1 to 15 for NOS 3' represent additional nucleotides designed to assist in construct preparation by adding additional restriction sites. For NOS 5' these are BamHI, SmaI, AatII and the first 4 bases of an NruI site, for NOS 3' these are NcoI and SfiI sites. The remaining sequences for each oligonucleotide are homologous to the 5' and 3' ends respectively of NOS sequences in pAHC 27.

The SCBV promoter sequences were amplified from the plasmid pScBV-20 (Tzafir et al, 1998) using the two oligonucleotides:

```
SCBV 5': 5'-CCATGGCCTATATGGCCATTCCCCACATTCAAG-3';
and

SCBV 3': 5'-AACGTTAACTTCTACCCAGTTCCAGAG-3'
```

Nucleotide residues 1 to 17 of SCBV 5' encode NcoI and SfiI restriction sites designed to assist in construct preparation, the remaining sequences are homologous to upstream sequences of the SCMV promoter region. Nucleotide residues 1 to 9 of SCBV 3' encode Psp10461 and Hpa1 restriction sites designed to assist in construct preparation, the remaining sequences are homologous to the reverse and complement of sequences near the transcription initiation site of SCBV.

Figure 43:
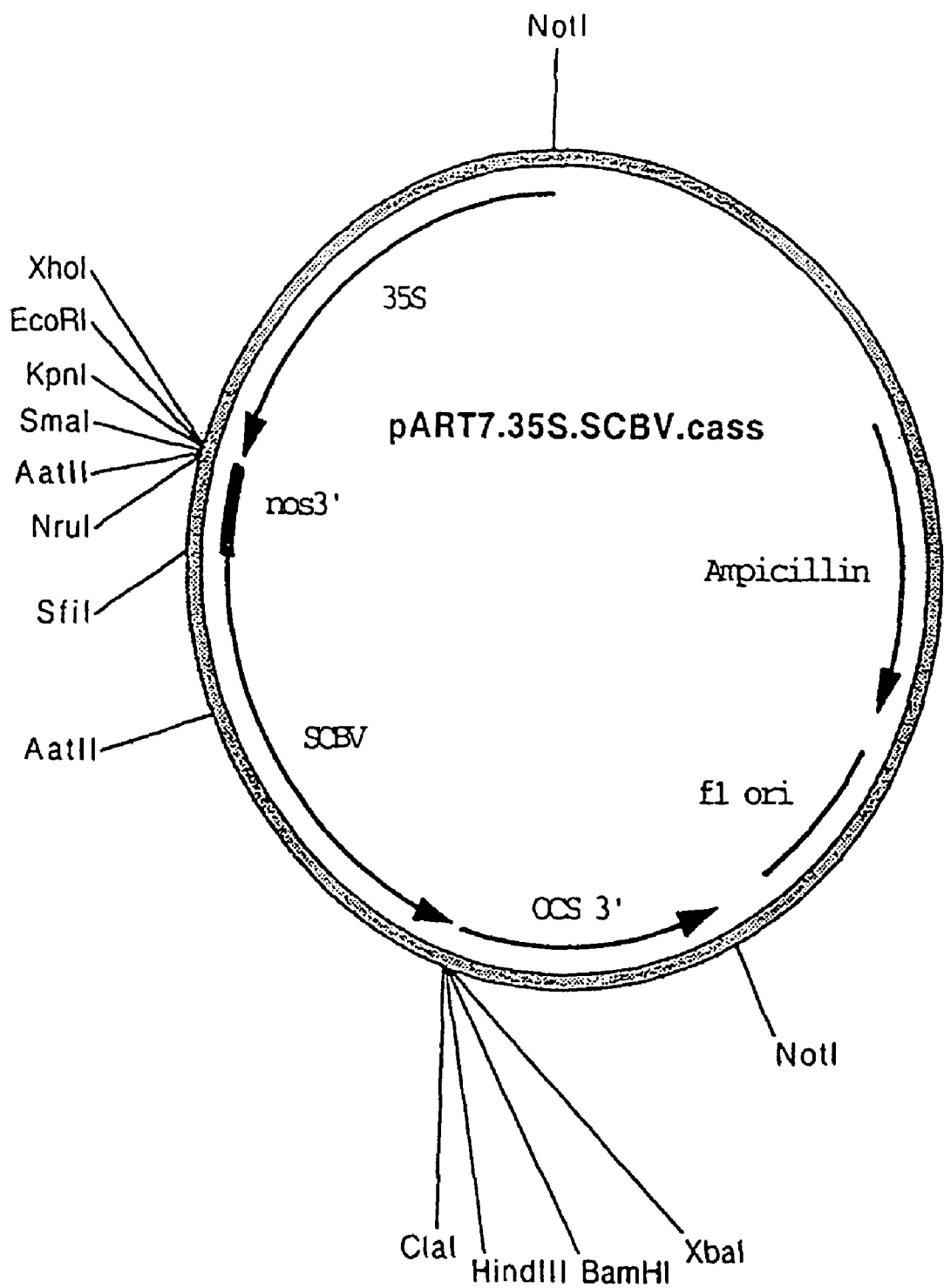
FIG. 43 is a diagrammatic representation of the plasmid pART7.35S.SCBV.cass.

Sequences amplified from pScBV-20 using PCR and cloned into pCR2.1 (Invitrogen) to produce pCR.NOS and pCR.SCBV respectively. Smal I/SfiI cut pCR.NOS and SfiI/HpaI cut pCR.SCBV were ligated into Sma I cut pART7 and a plasmid with a suitable orientation was chosen and designated pART7.35S.SCBV.cass, a map of this construct is shown in FIG. 43.

4. Intermediate Constructs

Plasmid pBC.PVY

Figure 44:
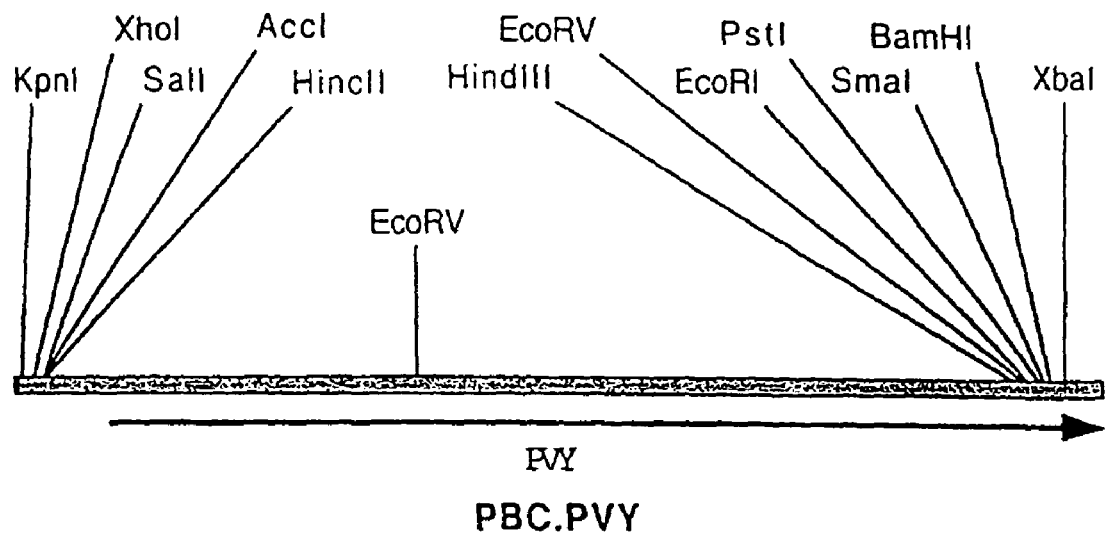
FIG. 44 is a diagrammatic representation of the plasmid pBC.PVY.

A region of the PVY genome was amplified by PCR using reverse-transcribed RNA isolated from PVY-infected tobacco as a template using standard protocols and cloned into a plasmid pGEM 3 (Stratagene), to create pGEM.PVY. A SalI/HindIII fragment from pGEM.PVY, corresponding to a SalI/HindIII fragment positions 1536-2270 of the PVY strain O sequence (Acc. No D12539, Genbank), was then subcloned into the plasmid pBC (Stratagene Inc.) to create pBC.PVY (FIG. 44).

Plasmid pSP72.PVY

Figure 45:
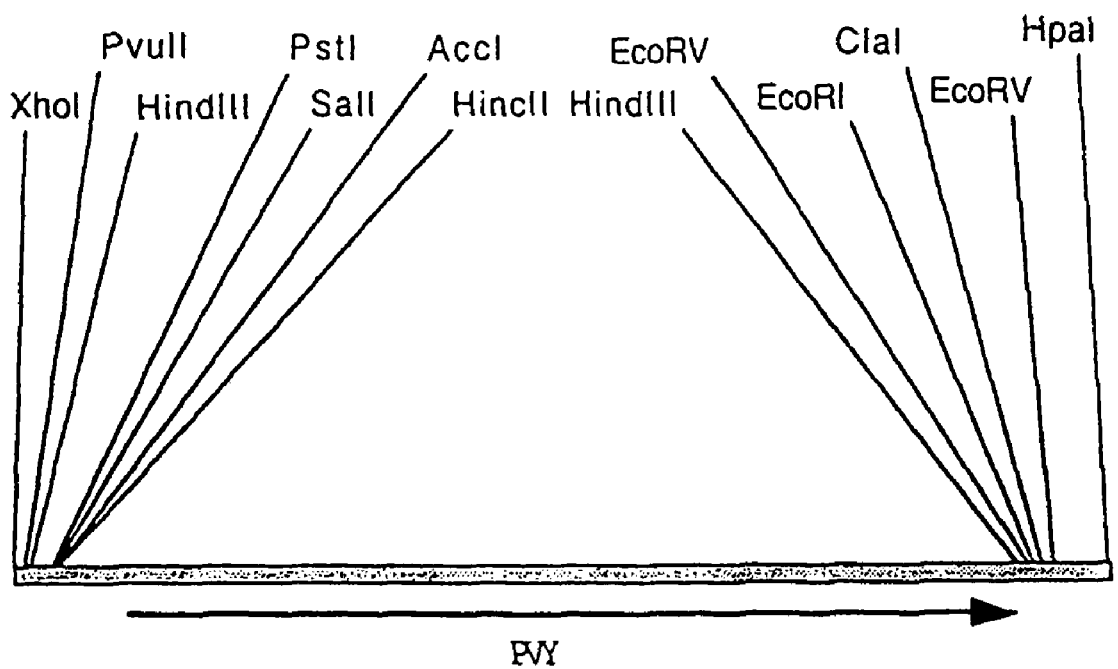
FIG. 45 is a diagrammatic representation of the plasmid pSP72.PVY.

Plasmid pSP72.PVY was prepared by inserting an EcoRI/SalI fragment from pBC.PVY into EcoRI/SalI cut pSP72 (Promega). This construct contains additional restriction sites flanking the PVY insert which were used to assist subsequent manipulations. A map of this construct is shown in FIG. 45.

Plasmid ClapBC.PVY

Figure 46:
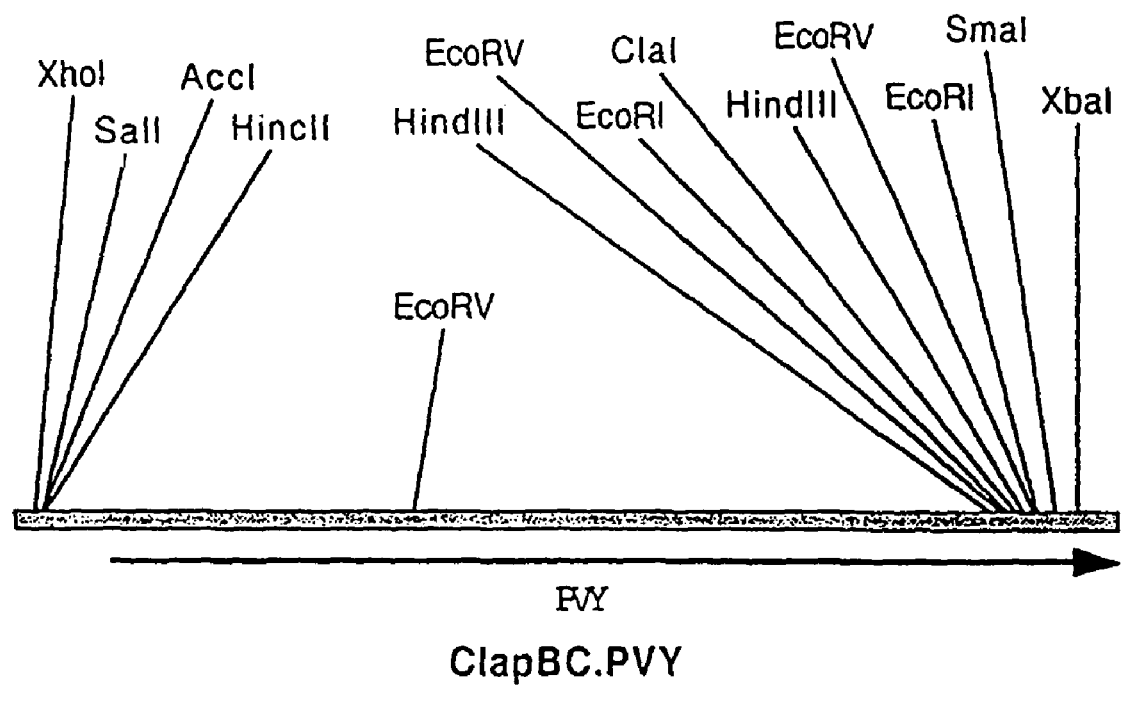

Plasmid Cla pBC.PVY was prepared by inserting a ClaI/SalI fragment from pSP72.PVY into ClaI/Sal I cutpBC (Stratagene). This construct contains additional restriction sites flanking the PVY insert which were used to assist subsequent manipulations. A map of this construct is shown in FIG. 46.

Plasmid pBC.PVYx2

Figure 47:
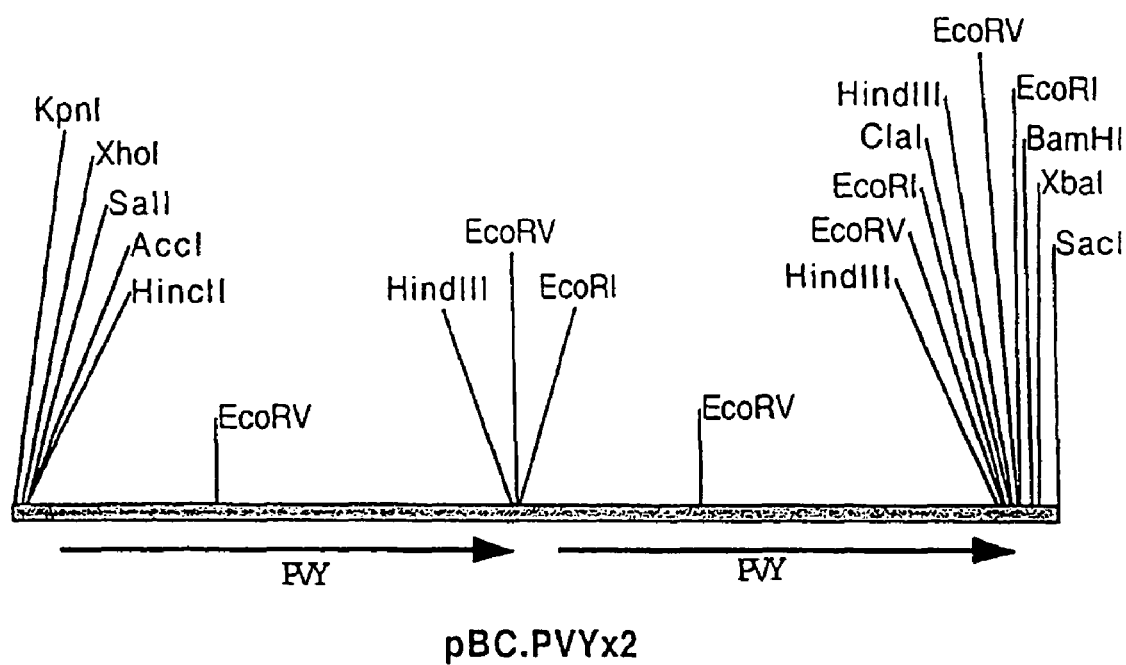
FIG. 47 is a diagrammatic representation of the plasmid pBC.PVYx2.

Plasmid pBC.PVYx2 contains two direct head-to-tail repeats of the PVY sequences derived from pBC.PVY. The plasmid was generated by cloning an AccI/ClaI PVY fragment from pSP72.PVY into AccI cut pBC.PVY and is shown in FIG. 47.

Plasmid pSP72.PVYx2

Figure 48:
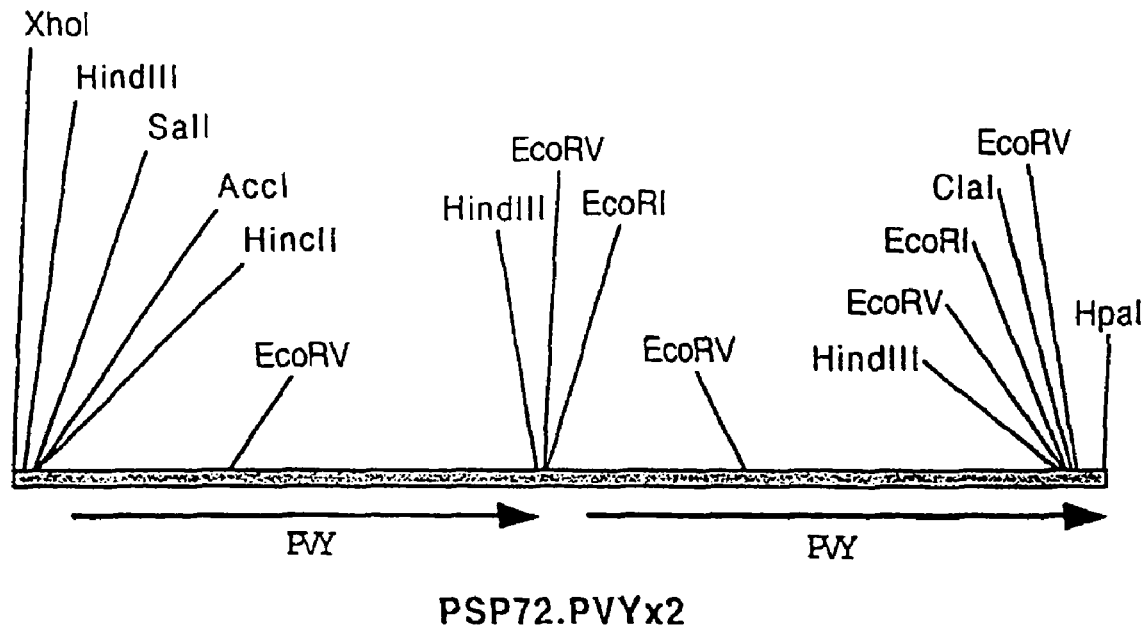
FIG. 48 is a diagrammatic representation of the plasmid pSP72.PVYx2.

Plasmid pSP72.PVYx2 contains two direct head-to-tail repeats of the PVY sequences derived from pBC.PVY. The plasmid was generated by cloning an AccI/ClaI PVY fragment from pBc.PVY into AccI cut pSP72.PVY and is shown in FIG. 48.

Plasmid pBC.PVYx3

Figure 49:
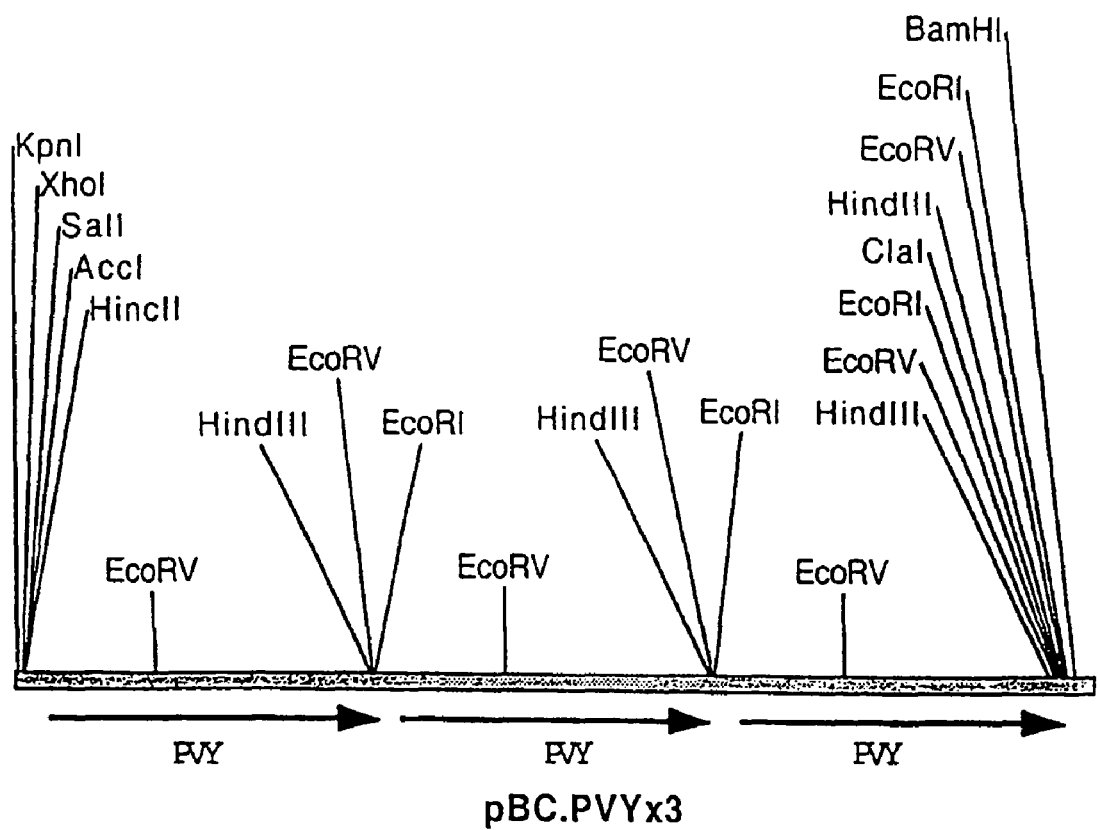
FIG. 49 is a diagrammatic representation of the plasmid pBC.PVYx3.

Plasmid pBC.PVYx3 contains three direct head-to-tail repeats of the PVY sequences derived from pBC.PVY. The plasmid was prepared by cloning an AccI/ClaI PVY fragment from pSP72.PVY into AccI cut pBC.PVYx2 and is shown in FIG. 49.

Plasmid pBC.PVYx4

Figure 50:
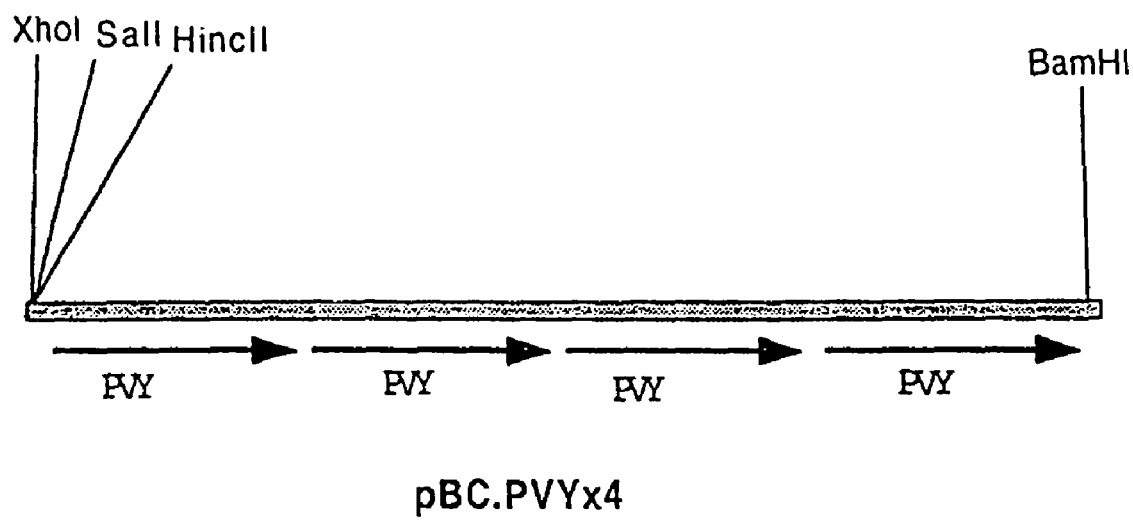
FIG. 50 is a diagrammatic representation of the plasmid pBC.PVYx4.

Plasmid pBC.PVYx4 contains four direct head-to-tail repeats of the PVY sequences derived from pBC.PVY. The plasmid was prepared by cloning the direct repeat of PVY sequences from pSP72.PVYx2 as an AccI/ClaI fragment into AccI cut pBC.PVYx2 and is shown in FIG. 50.

Plasmid pBC.PVY.LNYV

All attempts to create direct palindromes of PVY sequences failed, presumably such sequence arrangements are unstable in commonly used E. coli cloning hosts. Interrupted palindromes however proved stable.

To create interrupted palindromes of PVY sequences a "stuffer" fragment of approximately 360 bp was inserted into Cla pBV.PVY downstream of the PVY sequences. The stuffer fragment was made as follows:

A clone obtained initially from a cDNA library prepared from lettuce necrotic yellows virus (LNYV) genomic RNA (Deitzgen et al, 1989), known to contain the 4b gene of the virus, was amplified by PCR using the primers:

```
LNYV 1:5'-ATGGGATCCGTTATGCCAAGAAGAAGGA-3';
and

LNYV 2:5'-TGTGGATCCCTAACGGACCCGATG-3'
```

The first 9 nucleotide of these primers encode a BamHI site, the remaining nucleotides are homologous to sequences of the LNYV 4b gene.

Figure 51:
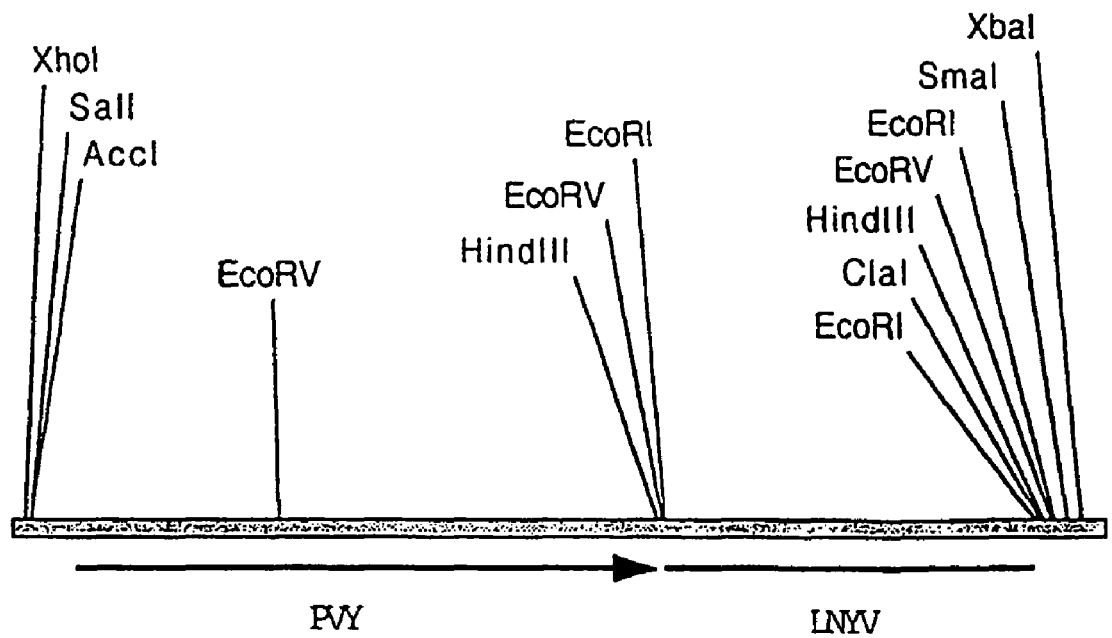
FIG. 51 is a diagrammatic representation of the plasmid pBC.PVY.LNYV.

Following amplification, the fragment was cloned into the EcoRI site of pCR2.1 (Stratagene). This EcoRI fragment was cloned into the EcoRI site of Cla pBC.PVY to create the intermediate plasmid pBC.PVY.LNYV which is shown in FIG. 51.

Plasmid pBC.PVY.LNYV.PVY

Figure 52:
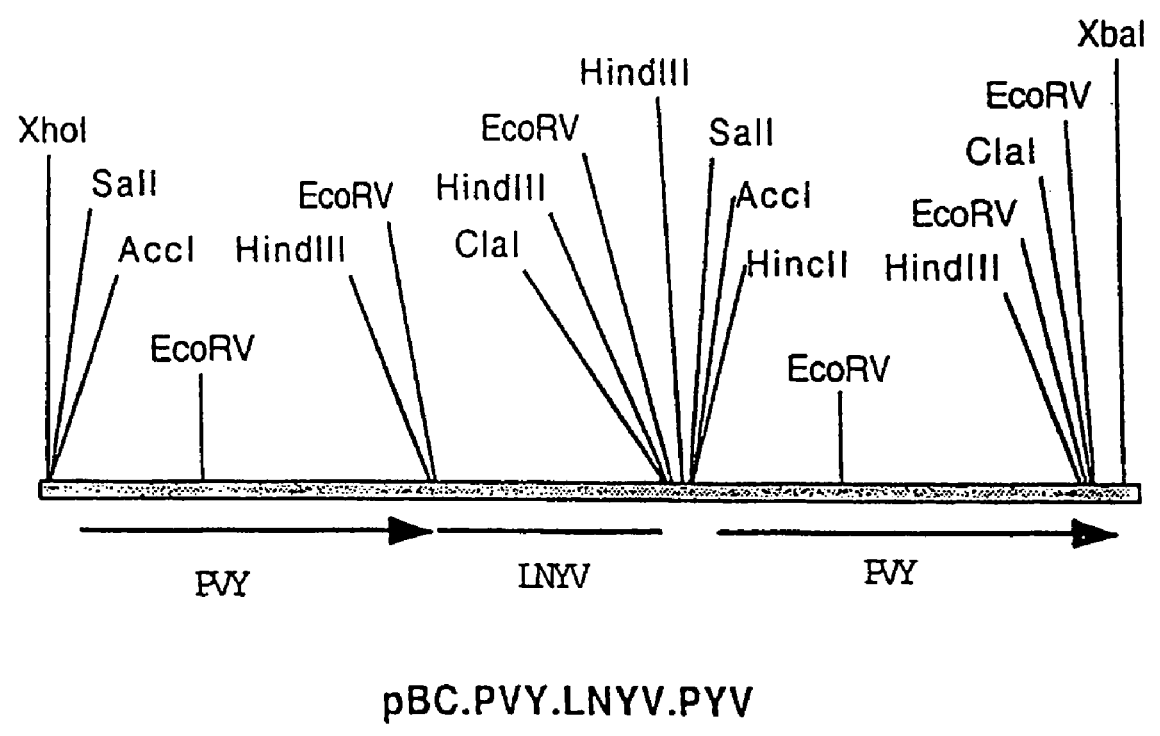

The plasmid pBC.PVY.LNYV.YVP contains an interrupted direct repeat of PVY sequences. to create this plasmid a HpaI/HincII fragment from pSP72 was cloned into SmaI-digested pBC.PVY.LNYV and a plasmid containing the sense orientation isolated, a map of this construct is shown in FIG. 52.

Plasmid pBC.PVY.LNYV.YVPΔ

The plasmid pBV.PVY.LNYV.YVPΔ contains a partial interrupted palindrome of PVY sequences. One arm of the palindrome contains all the PVY sequences from pBC.PVY, the other arm contains part of the sequences from PVY, corresponding to sequences between the EcoRV and HincII sites of pSP72.PVY. To create this plasmid an EcoRV/HincII fragment from pSP72.PVY was cloned into SmaI-digested pBC.PVY.LNYV and a plasmid containing the desired orientation isolated, a map of this construct is shown in FIG. 53.

Plasmid pBC.PVY.LNYV.YVP

Figure 54:
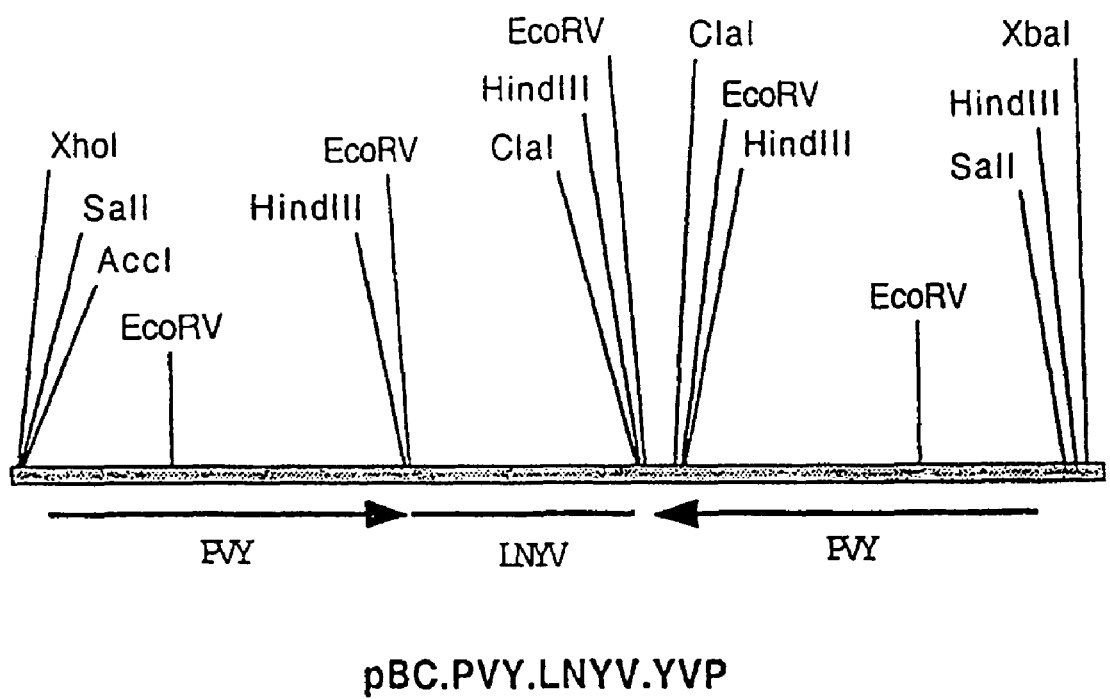
FIG. 54 is a diagrammatic representation of the plasmid pBC.PVY.LNYV.YVP.

The plasmid pBC.PVY.LNYV.YVP contains an interrupted palindrome of PVY sequences. To create this plasmid a HpaI/HincII fragment from pSP72. was cloned into SmaI-digested pBC.PVY.LNYV and a plasmid containing the antisense orientation isolated, a map of this construct is shown in FIG. 54.

5. Control Plasmids

Plasmids pART7.PVY & pART7.PVY

Figure 55:
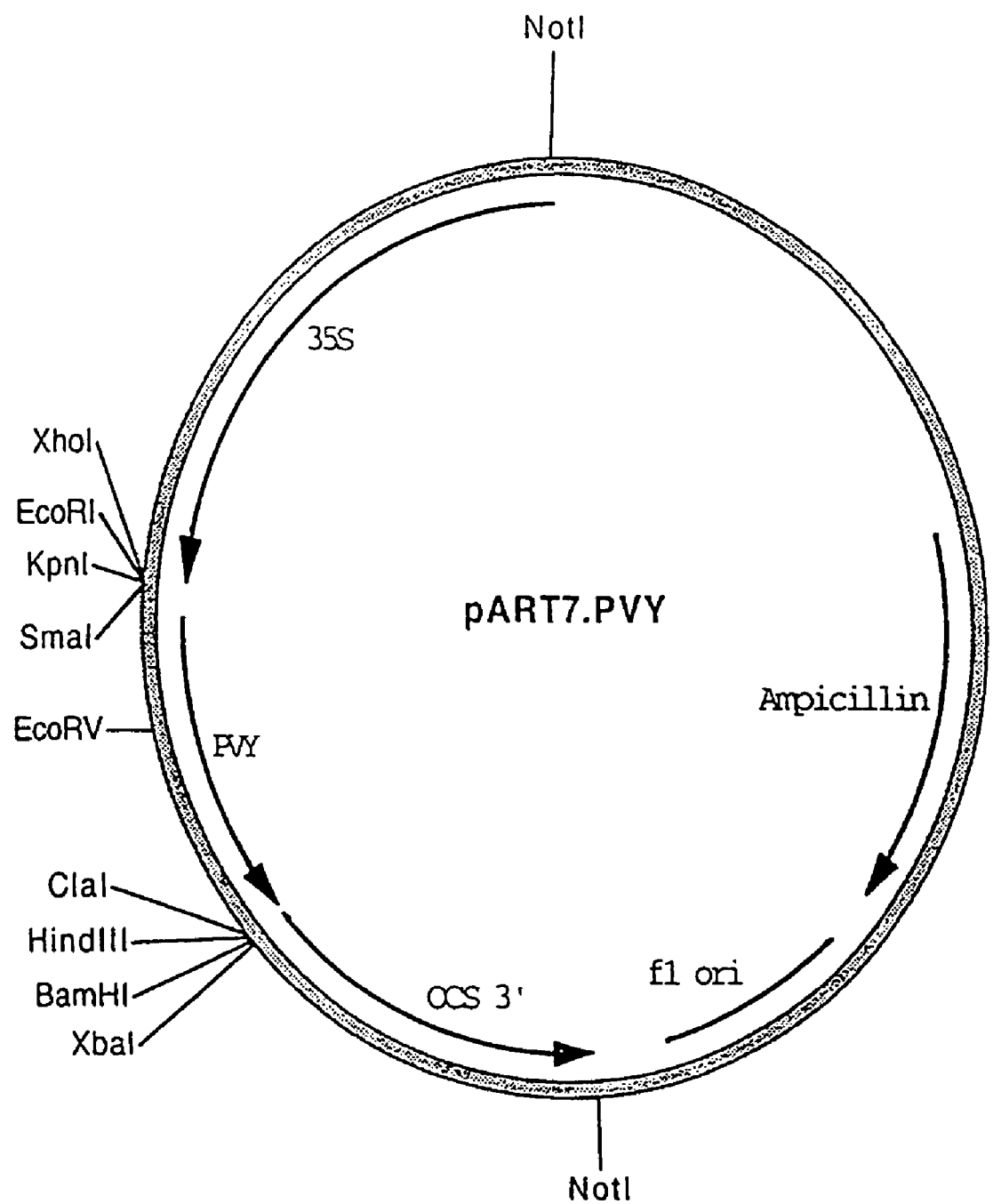
FIG. 55 is a diagrammatic representation of the plasmid pART27.PVY
Figure 56:
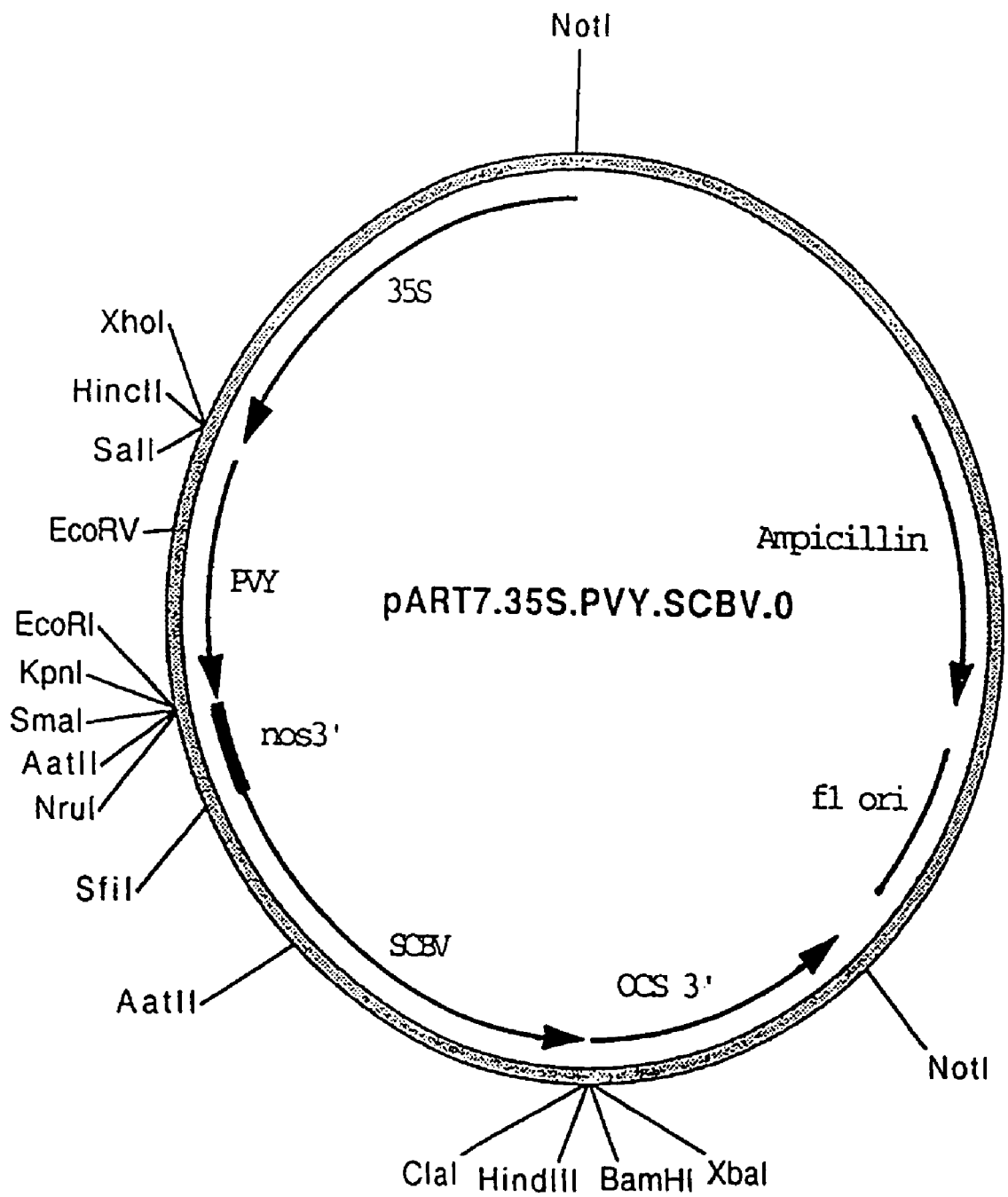
FIG. 56 is a diagrammatic representation of the plasmid pART27.35S.PVY.SCBV.O.
Figure 57:
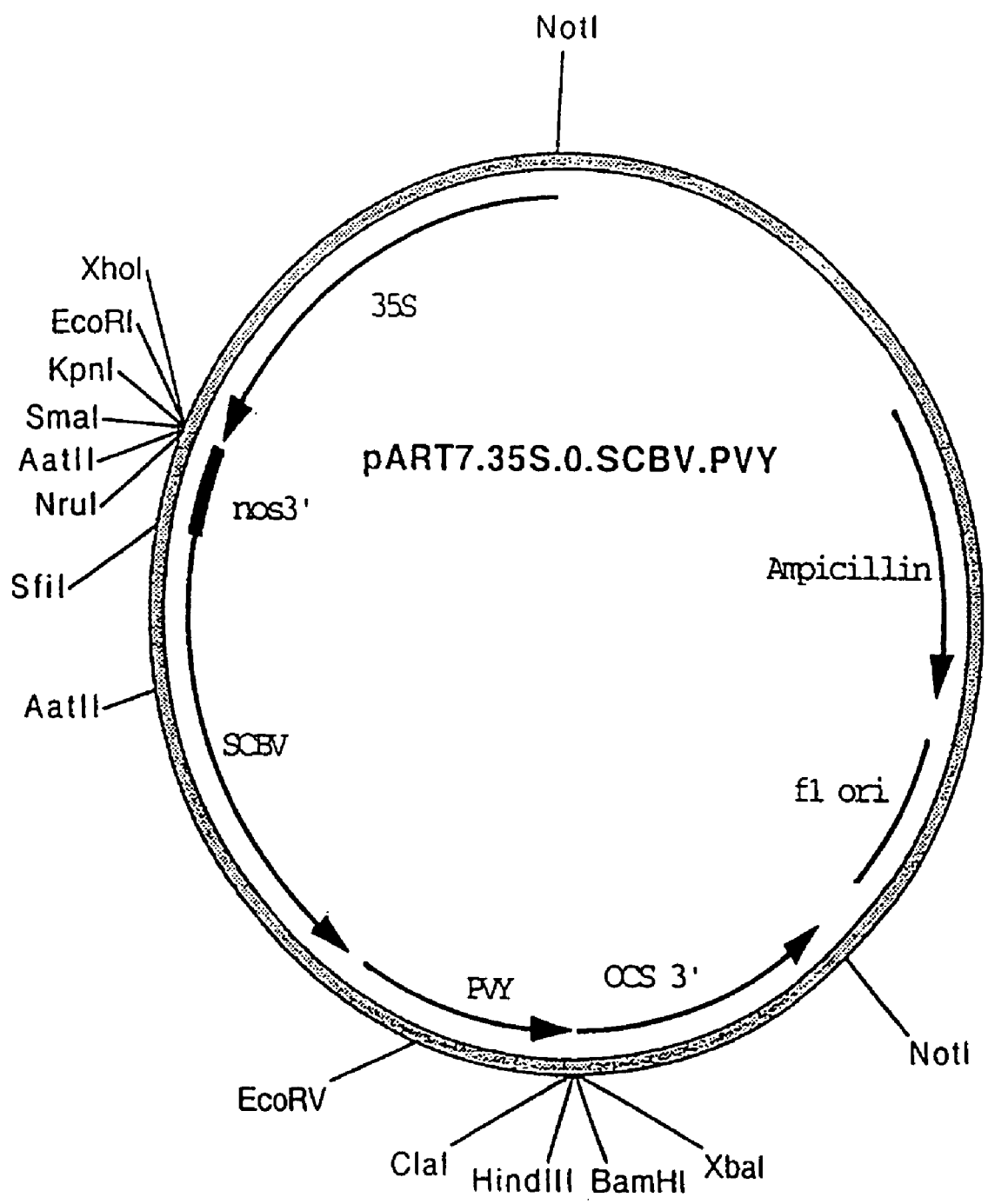
FIG. 57 is a diagrammatic representation of the plasmid pART27.35S.O.SCBV.PVY.
Figure 58:
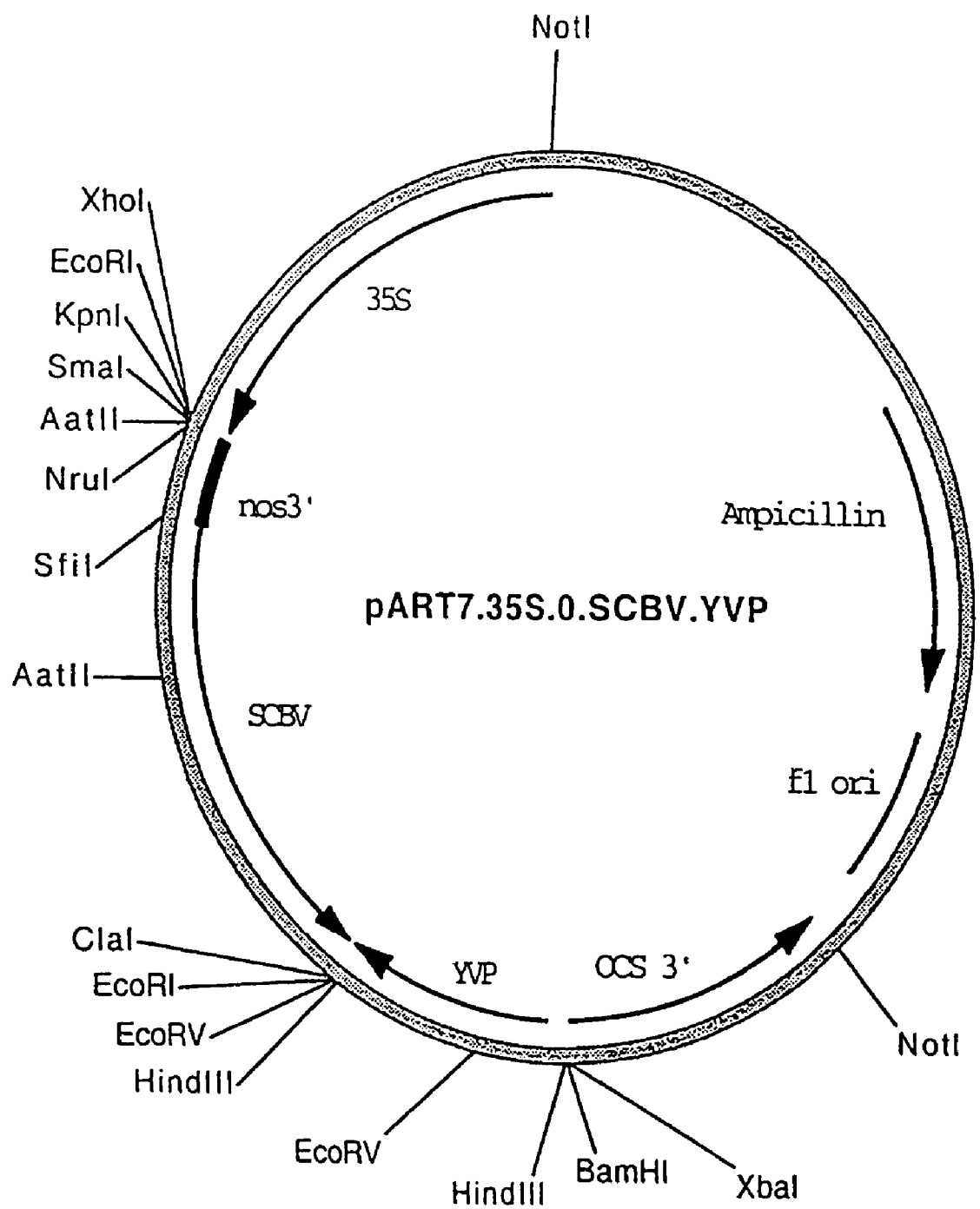
FIG. 58 is a diagrammatic representation of the plasmid pART27.35S.O.SCBV.YVP.
Figure 59:
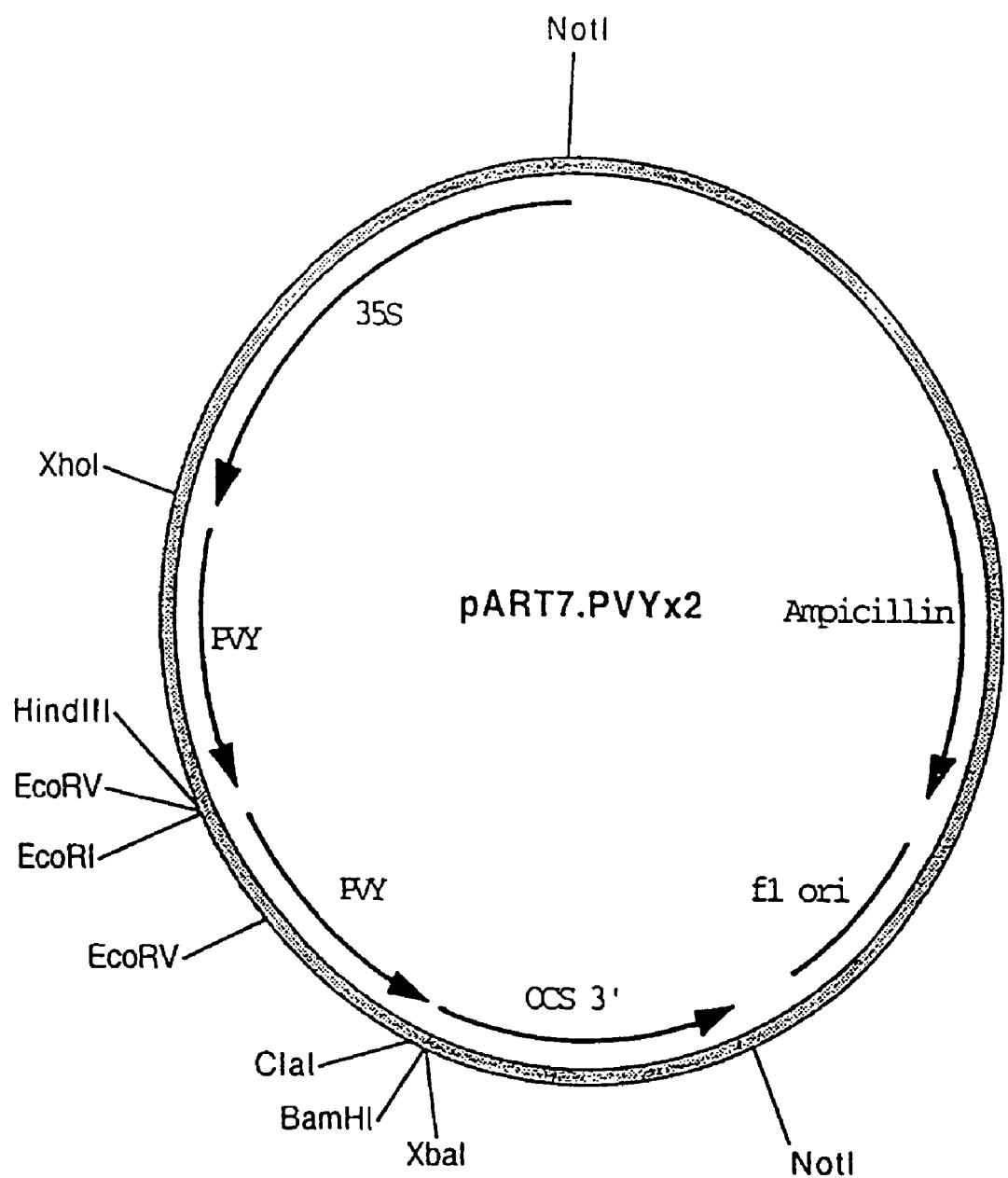
FIG. 59 is a diagrammatic representation of the plasmid pART7.PVYx2.
Figure 60:
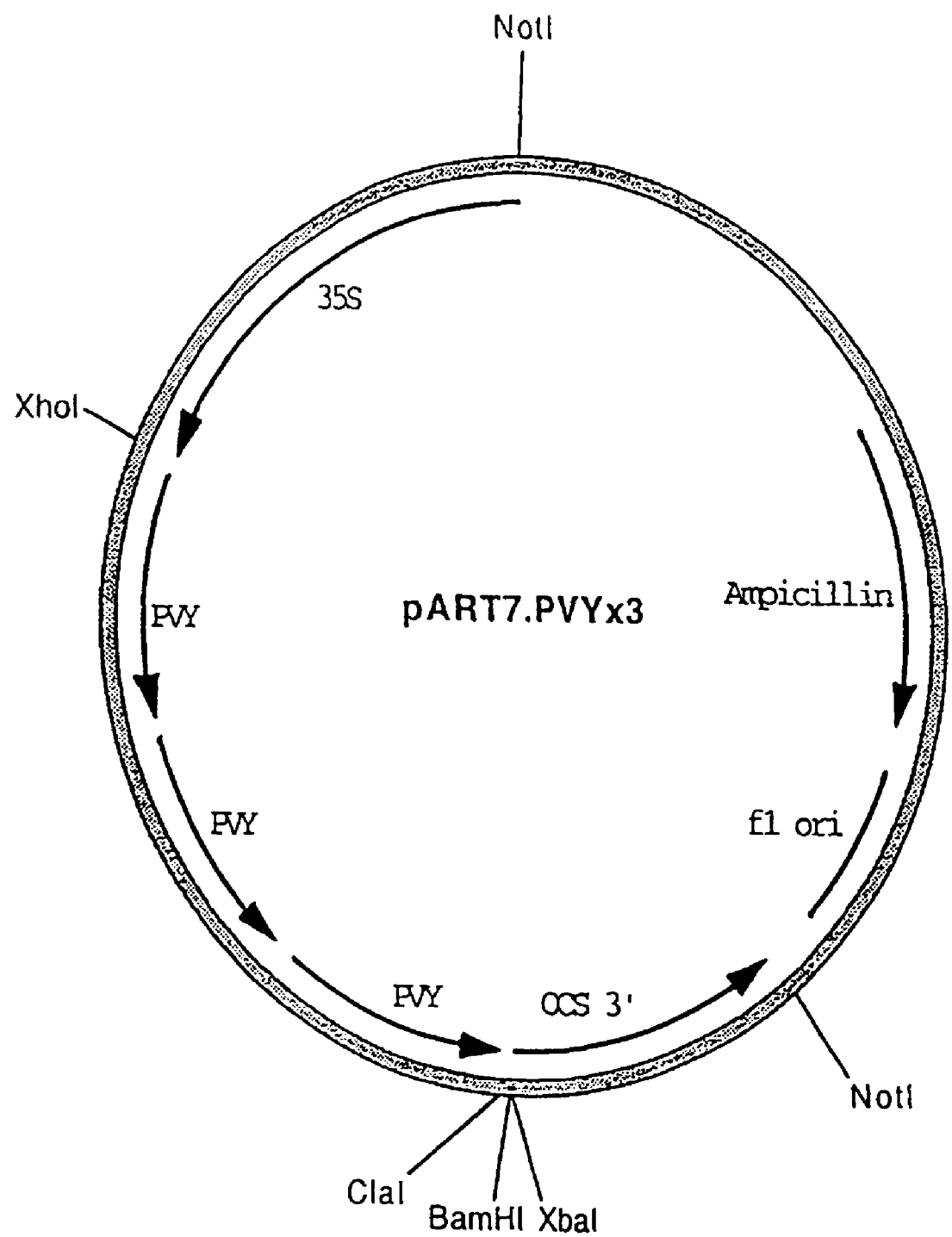
FIG. 60 is a diagrammatic representation of the plasmid pART7.PVYx3.
Figure 61:
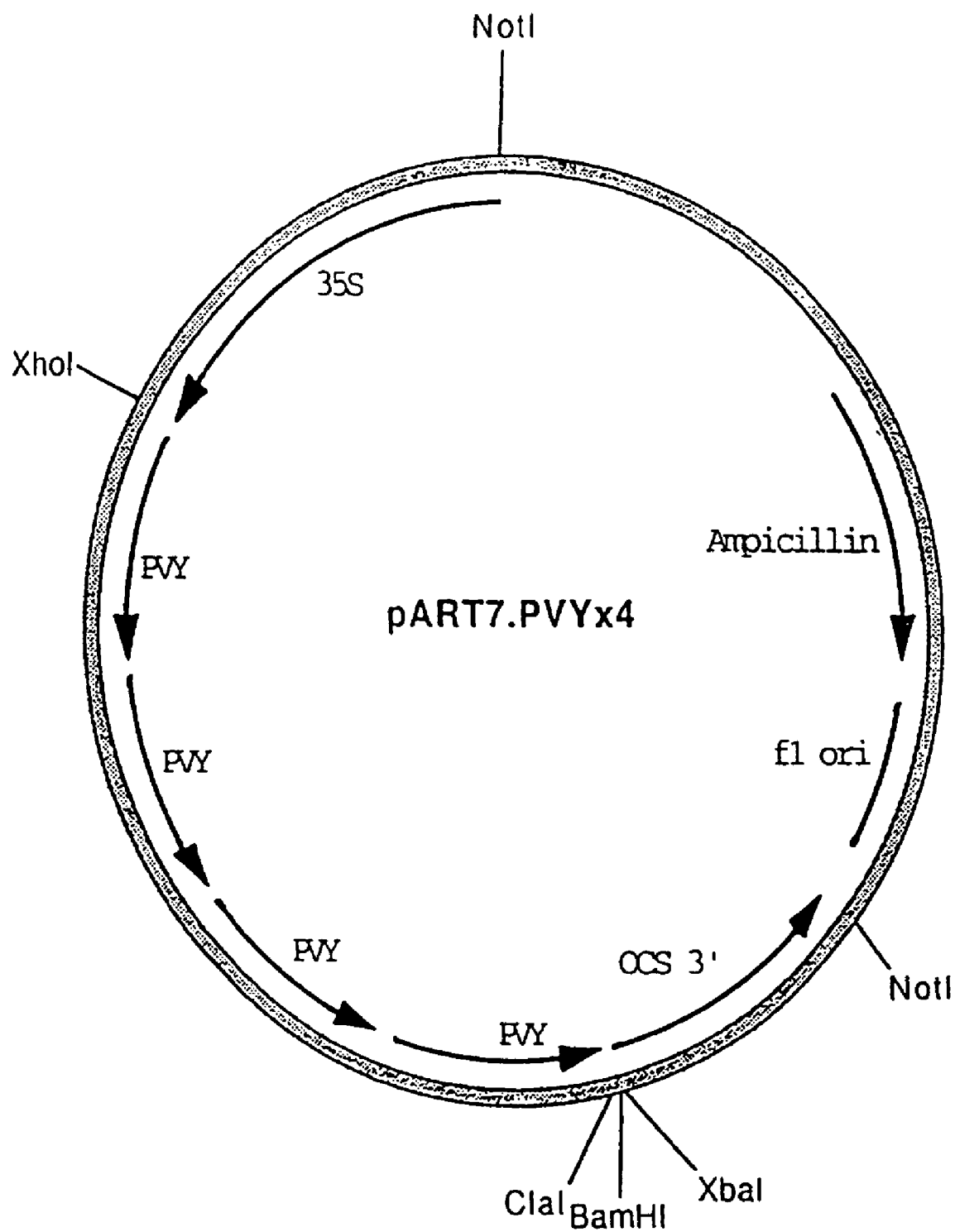
FIG. 61 is a diagrammatic representation of the plasmid pART7.PVYx4.
Figure 62:
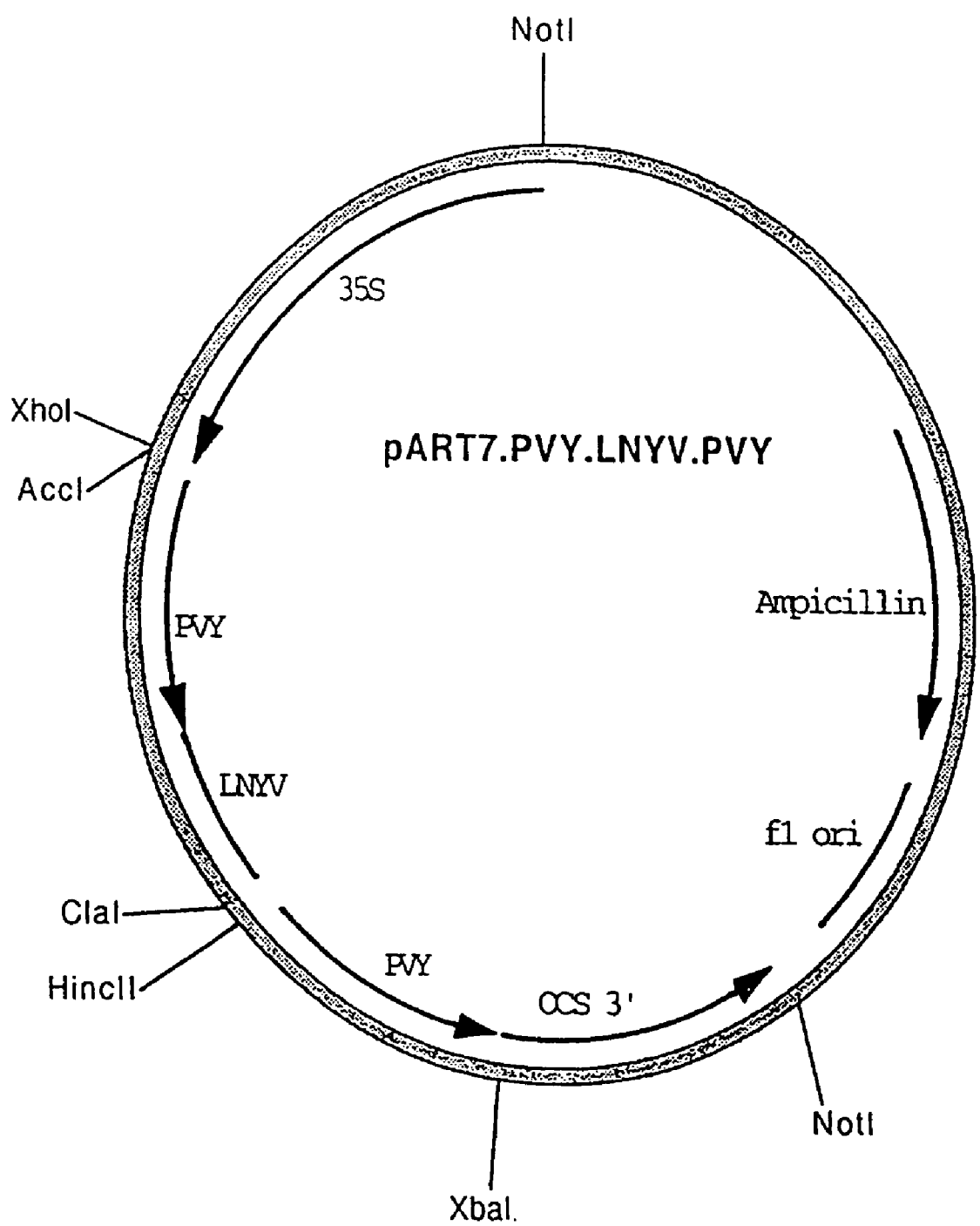
FIG. 62 is a diagrammatic representation of the plasmid pART7.PVY.LNYV.PVY.

Plasmid pART7.PVY (FIG. 55) was designed to express PVY sequences driven by the 35S promoter. This plasmid serves as a control construct in these experiments, against which all other constructs was compared. To generate this plasmid a ClaI/AccI fragment from ClapBC.PVY was cloned into ClaI-digested pART7 and a plasmid with expected to express a sense PVY sequence with respect to the PVY genome, was selected. Sequences consisting of the 35S promoter, PVY sequences and the OCS terminator were excised as a NotI fragment and cloned into NotI-digested pART27, a plasmid with the desired insert orientation was selected and designated pART27.

Plasmids pART7.35S.PVY.SCBV.O & pART27.35S.PVY.SCBV.O

Plasmid pART7.35S.PVY.SCBV.0 (FIG. 56) was designed to act as a control for co expression of multiple constructs from a single plasmid in transgenic plants. The 35S promoter was designed to express PVY sense sequences, whilst the SCBV promoter was empty. To generate this plasmid, the PVY fragment from Cla pBC.PVY was cloned as a XhoI/EcoRI fragment into XhoI/EcoRI-digested pAR17.35S.SCBV.cass to create p35S.PVY.SCBV>O. Sequences consisting of the 35S promoter driving sense PVY sequences and the NOS terminator and the SCBV promoter and OCS terminator were excised as a NotI fragment and cloned into pART27, a plasmid with the desired insert orientation was isolated and designated pART27.35S.PVY.SCBV.O.

Plasmids pART7.35S.O.SCBV.PVY & pART27.35S.O.SCBV.PVY

Plasmid pART27.35S.O.SCBV.PVY (FIG. 57) was designed to act as an additional control for co-expression of multiple constructs from a single plasmid in transgenic plants. No expressible sequences were cloned behind the 35S promoter, whilst the SCBV promoter drove expression of a PVY sense fragment. To generate this plasmid, the PVY fragment from Cla pBC.PVY was cloned as a ClaI fragment into ClaI-digested pART7.35S.SCBV.cass, a plasmid containing PVY sequences in a sense orientation was isolated and designated p35S.O.SCBV.PVY. Sequences, consisting of the 35S promoter and NOS terminator, the SCBV promoter driving sense PVY sequences and the OCS terminator were excised as a NotI fragment and cloned into pART27, a plasmid with the desired insert orientation was isolated and designated pART27.35S.O.SCBV.PVY.

Plasmids pART7.35S.O.SCBV.YVP & pART7.35S.O.SCBV.YVP

Plasmid pART7.35S.O.SCBV.YVP (FIG. 58) was designed to act as an additional control for co-expression of multiple constructs from a single plasmid in transgenic plants. No expressible sequences were cloned behind the 35S promoter, whilst the SCBV promoter drove expression of a PVY antisense fragment. To generate this plasmid, the PVY fragment from Cla pBC.PVY was cloned as a ClaI fragment into ClaI-digested p35S.SCBV.cass, a plasmid containing PCY sequences in an antisense orientation was isolated and designated p35S.O.SCBV.YVP. Sequences, consisting of the 35S promoter and NOS terminator, the SCBV promoter driving sense PVY sequences and the OCS terminator were excised as a NotI fragment and cloned into pART27, a plasmid with the desired insert orientation was isolated and designated pART27.35S.O.SCBV.YVP.

6. Test Plasmids

Plasmids pART7.PVYx2 & pART27.PVYx2

Plasmid pART7.PVYx2 (FIG. 59) was designed to express a direct repeat of PVY sequences driven by the 35S promoter in transgenic plants. To generate this plasmid, direct repeats from pBC.PVYx2 were cloned as a XhoI/BamHI fragment into XhoI/BamHI cut pART7. Sequences consisting of the 35 S promoter, direct repeats of PVY and the OCS terminator were excised as a NotI fragment from pART7.PVYx2 and cloned into NotI-digested pART27, a plasmid with the desired insert orientation was selected and designated pART27.PVYx2.

Plasmids pART7.PVYx3 & pART27.PVYx3

Plasmid pART7.PVYx3 (FIG. 60) was designed to express a direct repeat of three PVY sequences driven by the 35S promoter in transgenic plants. To generate this plasmid, direct repeats from pBC.PVYx3 were cloned as a XhoI/BamHI fragment into XhoI/BamHI cut pART7. Sequences consisting of the 35S promoter, direct repeats of PVY and OCS terminator were excised as a NotI fragment from pART.PVYx3 and cloned into NotI-digested pART27, a plasmid with the desired insert orientation was selected and designated pART27.PVYx3.

Plasmids pART7.PVYx4 & pART27.PVYx4

Plasmid pART7.PVYx4 (FIG. 61) was designed to express a direct repeat of four PVY sequences driven by the 35S promoter in transgenic plants. To generate this plasmid, direct repeats from pBC.PVYx4 were cloned as a XhoI/BamHI fragment into xhoI/BamHI cut pART7. Sequences consisting of the 35S promoter, direct repeats of PVY and the OCS terminator were excised as a NotI fragment from pART7.PVYx3 and cloned into NotI-digested pART27, a plasmid with the desired insert orientation was selected and designated pART27.PVYx3.

Plasmids pART7.PVY.LNYV.PVY & pART27.PVY.LNYV.PVY

Plasmid pART7.PVY.LNYV.PVY (FIG. 62) was designed to express the interrupted direct repeat of PVY sequences driven by the 35S promoter in transgenic plants. This construct was prepared by cloning the interrupted direct repeat of PVY from pBC.PVY.LNYV.PVY as a XhoI/XbaI fragment into pART7 digested with XhoI/XbaI. Sequences consisting of the 35S promoter, the interrupted direct repeat of PVY sequences and the OCS terminator were excised from pART7.PVY.LNYV.PVY as a NotI fragment and cloned into NotI-digested pART27, a plasmid with the desired insert orientation was selected and designated pART27.PVY.LNYV.PVY.

Plasmids pART7.PVY.LNYV.YVP▵ & pART27.PVY.LNYV.YVP▵

Plasmid pART7.PVY.LNYV.YVP▵ (FIG. 63) was designed to express the partial interrupted palindrome of PVY sequences driven by the 35S promoter in transgenic plants. This construct was prepared by cloning the partial interrupted palindrome of PVY sequences from pBC.PVY.LNYV.YVP▵ as a XhoI/XbaI fragment into pART7 digested with XhoI/XbaI. Sequences consisting of the 35S promoter, the partial interrupted palindrome of PVY sequences and the OCS terminator were excised from pART7.PVY.LNYV.YVP▵ as a NotI fragment and cloned into NotI-digested pART27, a plasmid with the desired insert orientation was selected and designated pART27.PVY.LNYV.YVP.

Plasmids pART7.PVY.LNYV.YVP & pART27.PVY.LNYV.YVP

Plasmid pART7.PVY.LNYV.YVP (FIG. 64) was designed to express the interrupted palindrome of PVY sequences driven by the 35S promoter in transgenic plants. This construct was prepared by cloning the interrupted palindrome of PVY sequences from pBC.PVY.LNYV.YVP▵ as a XhoI/XbaI fragment into pART7 digested with XhoI/XbaI. Sequences consisting of the 35S promoter, the interrupted palindrome of PVY sequences and the OCS terminator were excised from pART7.PVY.LNYV.YVP as a NotI fragment and cloned into pART27, a plasmid with the desired insert orientation was selected and designated pART27.PVY.LNYV.YVP.

Plasmids pART7.35S.PVY.SCBV.YVP & pART27.35S.PVY.SCBV.YVP

Figure 65:
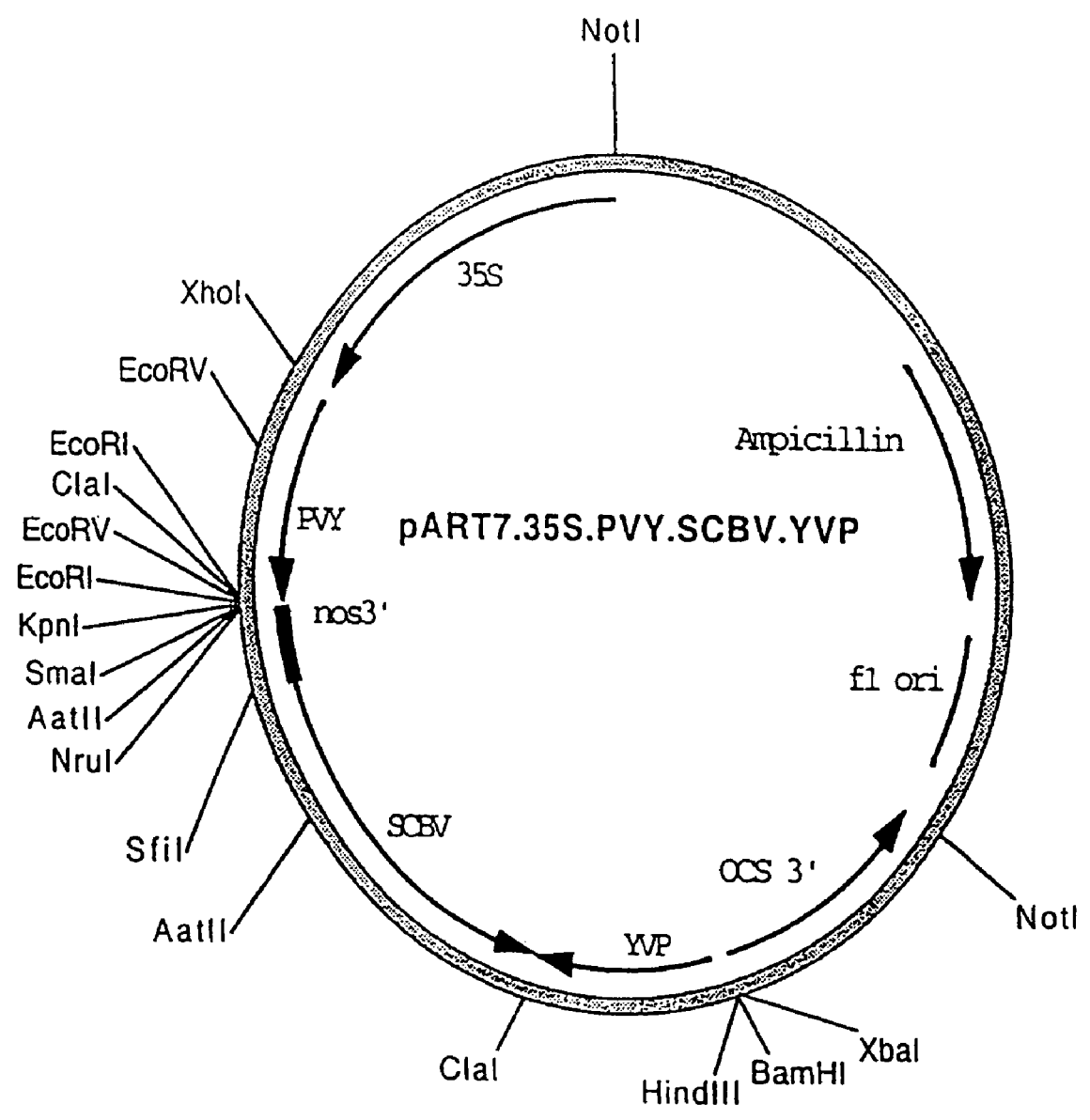

Plasmid pART7.35S.PVY.SCBV.YVP (FIG. 65) was designed to co-express sense and antisense constructs in transgenic plants. To generate this plasmid the PVY fragment from Cla pBC.PVY was cloned as a XhoI/EcoRI fragment into xhoI/EcoRI-digested p35S.SCBV.O.SCBV.YVP. Sequences, consisting of the 35S promoter driving sense PVY sequences and the NOS terminator and the SCBV promoter driving antisense PVY and the OCS terminator were excised as a NotI fragment and cloned into pART27, a plasmid with the desired insert orientation was isolated and designated pART27.35S.PVY.SCBV.YVP.

Plasmids pART7.35S.PVYx3.5CBV.YVPx3 & pART27.35S.PVYx3.5CBV.YVPx3

Figure 66:
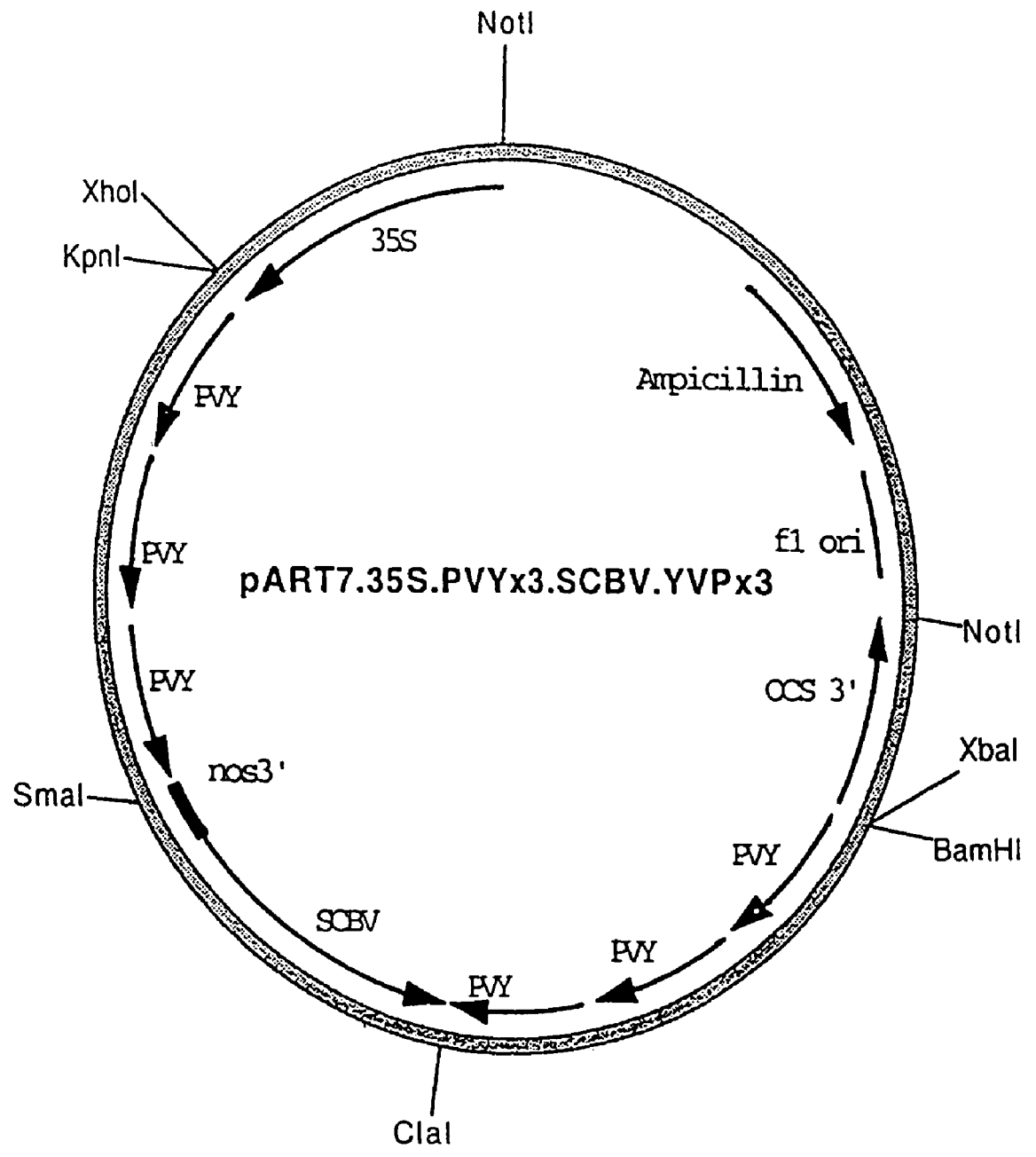

Plasmid pART7.35S.PVYx3.5CBV.YVPx3 (FIG. 66) was designed to co-express sense and antisense repeats of PVY in transgenic plants. to generate this plasmid, the intermediate pART7.35S.O.SCBV.YVPx3 was constructed by cloning the triple direct PVY repeat from ClapBC.PVYx3 as a ClaI/AccI fragment into Cla-digested p35S.SCBV.cass and isolating a plasmid with an antisense orientation. for p35S.PVYx3.5CBV.YVPx3 the triple direct PVY repeat from Cla pBC.PVYx3 was cloned as a KpnI/SmaI fragment into KpnI/SmaI-digested p35S.O.SCBV.YVPx3 to create p35S.PVYx3.5CBV.YVPx3. Sequences including both promoters, terminators and direct PVY repeats were isolated as a NotI fragment and cloned into pART27. A plasmid with an appropriate orientation was chosen and designated pART27.35S.PVYx3.5CBV.

Plasmids pART7.PVYx3.LNYV.YVPx3 & pART27.PVYx3.LNYV.YVPx3

Figure 67:
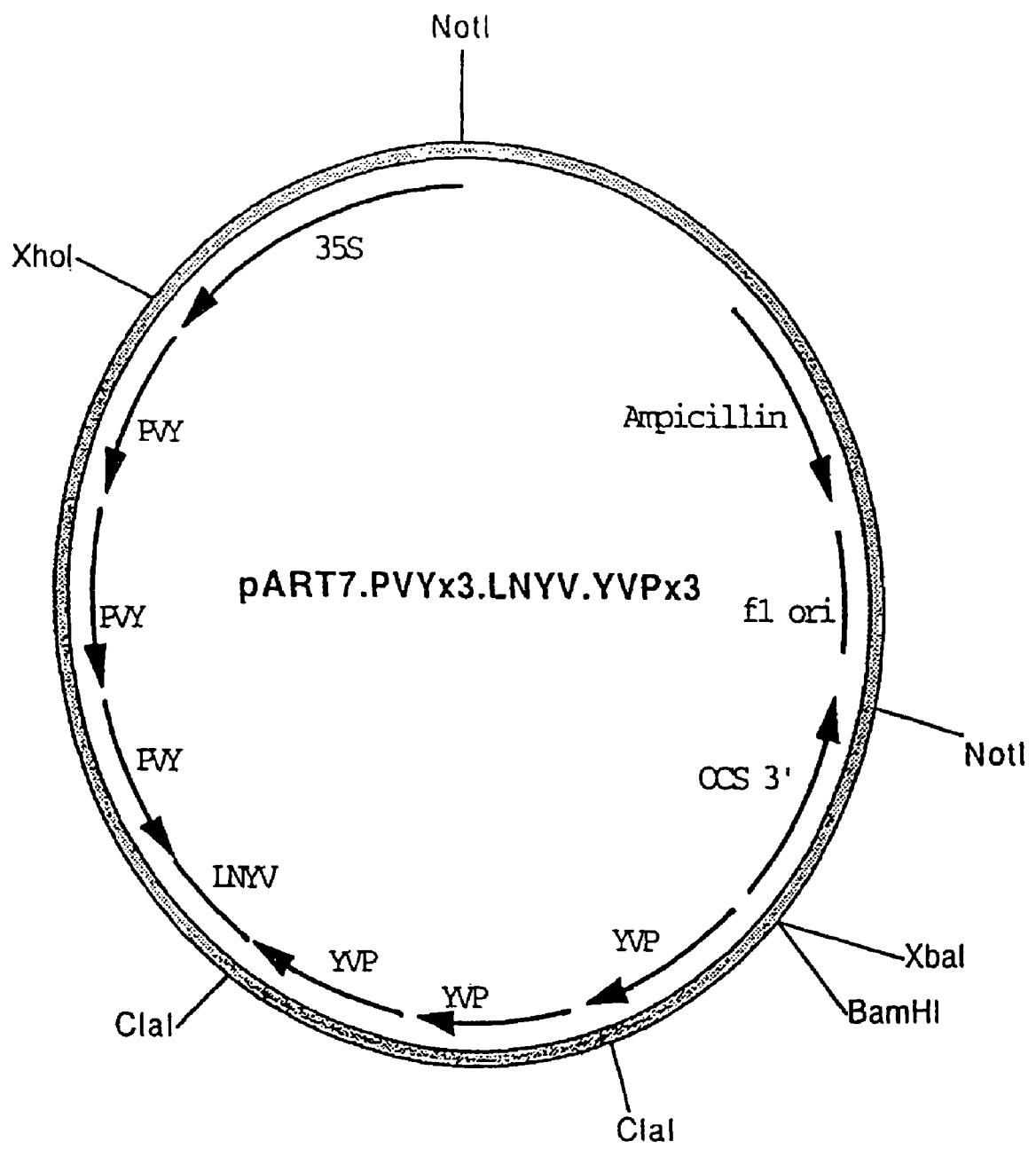

Plasmid pART7.PVYx3.LNYV.YVPx3 (FIG. 67) was designed to express triple repeats of PVY sequences as an interrupted palindrome. To generate this plasmid an intermediate, pART7x3.PVY.LNYV.YV was constructed by cloning a PVY.LNYV.YVP fragment from pBC.PVY.LNYV.YVP as an AccI/ClaI fragment into the plasmid pART7.PVYx2. pART7.35S.PVYx3.LNYV.YVPx3, was made by cloning an additional PVY direct repeat from pBC.PVYx2 as an AccI/ClaI fragment into ClaI digested pART7x3.PVY.LNYV.YVP. Sequences from pART7.35S.PVYx3.LNYV.YVPx3, including the 35S promoter, all PVY sequences and the OCS terminator were excised as a NotI fragment and cloned into NotI-digested pART27, a plasmid with an appropriate orientation was chosen and designated pART27.35S.PVYx3.LNYV.

Plasmids pART7.PVY Multi & pART27.PVY Multi

Figure 68:
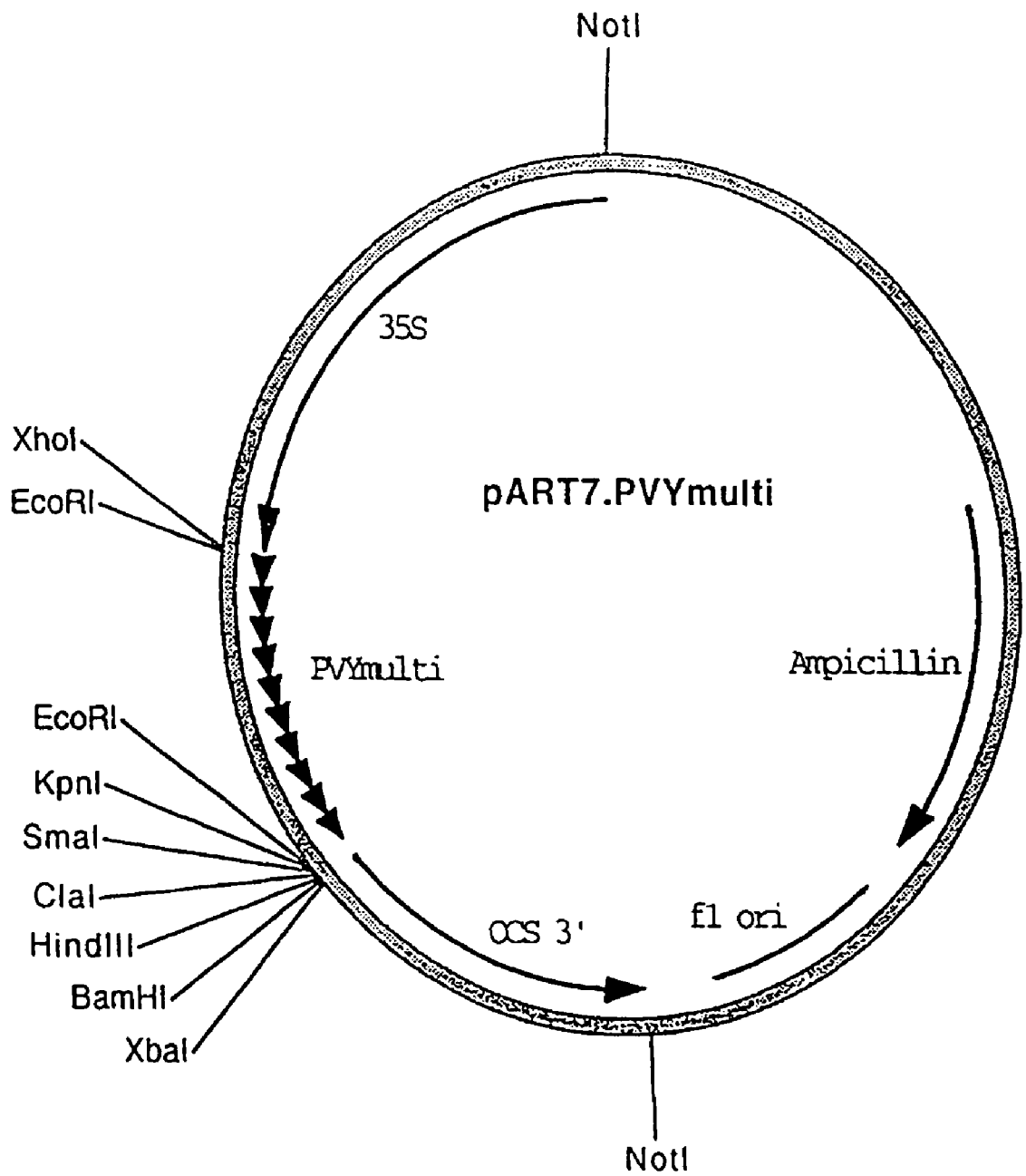
FIG. 68 is a diagrammatic representation of the plasmid pART7.PVYMULTI.

Plasmid pART7.35S.PVY multi (FIG. 68) was designed to express higher order direct repeats of regions of PVY sequences in transgenic plants. Higher order direct repeats of a 72 bp of the PVY Nia region from PVY were prepared by annealing two partially complementary oligonucleotides as follows:

```
PVY1:
5'-TAATGAGGATGATGTCCCTACCTTTAATTGGCAGAAATTTCTGTGGA
AAGACAGGGAAATCTTTCGGCATTT-3';
and PVY2:
5'-TTCTGCCAATTAAAGGTAGGGACATCATCCTCATTAAAATGCCGAAA
GATTTCCCTGTCTTTCCACAGAAAT-3'
```

The oligonucleotides were phosphorylated with T4 polynucleotide kinase, heated and cooled slowly to permit self-annealing, ligated with T4 DNA ligase, end-filled with Klenow polymerase and cloned into pCR2.1 (Invitrogen). Plasmids containing multiple repeats were isolated and sequences were cloned as EcoRI fragments in a sense orientation into EcoRI-digested pART7, to create the intermediate pART7.PVY multi. to create pART27.PVY multi, the 35S promoter, PVY sequences and the OCS terminator were excised as a NotI fragment and cloned into NotI-digested pART27. A plasmid with an appropriate insert orientation was isolated and designated pART27.PVY multi.

Example 6

Inactivation of Virus Gene Expression in Mammals

Viral immune lines are created by expressing viral sequences in stably transformed cell lines.

In particular, lytic viruses are used for this approach since cell lysis provides very simple screens and also offer the ability to directly select for potentially rare transformation events which might create viral immunity. Sub-genomic fragments derived from a simple single stranded RNA virus (Bovine enterovirus—BEV) or a complex double stranded DNA virus, Herpes Simplex Virus I (HSV I) are cloned into a suitable vector and expressed in transformed cells. Mammalian cell lines are transformed with genetic constructs designed to express viral sequences driven by the strong cytomegalovirus (CMV-IE) promoter. Sequences utilised include specific viral replicase genes. Random "shotgun" libraries comprising representative viral gene sequences, may also be used and the introduced dispersed nucleic acid molecule, to target the expression of virus sequences.

Exemplary genetic constructs for use in this procedure, comprising nucleotide sequences derived from the BEV RNA-dependent RNA polymerase gene, are presented herein.

For viral polymerase constructs, large numbers (approximately 100) of transformed cell lines are generated and infected with the respective virus. For cells transformed with shotgun libraries very large numbers (hundreds) of transformed lines are generated and screened in bulk for viral immunity. Following virus challenge, resistant cell lines are selected and analysed further to determine the sequences conferring immunity thereon.

Resistant cell lines are supportive of the ability of the introduced nucleotide sequences to inactivate viral gene expression in a mammalian system.

Additionally, resistant lines obtained from such experiments are used to more precisely define molecular and biochemical characteristics of the modulation which is observed Example 8

Induction of Virus Resistance in Transgenic Plants

*Agrobacterium tumefaciens*, strain LBA4404, was transformed independently with the constructs pART27.PVY, pART27.PVYx2, pART27.PVYx3, pART27.PVYx4, pART27.PVY.LNYV.PVY, pART27.PVY.LNYV.YVP△, pART27.PVY.LNYV.YVP, pART27.35S.PVY.SCBV.O, pART27.35S.O.SCBV.PVY, pART27.35S.O.SCBV.YVP, pART27.35S.PVY.SCBV.YVP, pART27.35S.PVYx3.SCBV.YPVx3, pART27.PVYx3.LNYV.YVPx3 and pART27.PVYx10, using tri-parental matings. DNA mini-preps from these strains were prepared and examined by restriction with NotI to ensure they contained the appropriate binary vectors.

*Nicotiana tabaccum* (cultivar W38) were transformed with these *Agrobacterium* strains using standard procedures. Putative transformed shoots were excised and rooted on media containing kanamycin. Under these conditions we have consistently observed that only transgenic shoots will root on kanamycin plates. Rooted shoots were transferred to soil and allowed to establish. After two to three weeks, vigorous plants with at least three sets of leaves were chosen and infected with PVY.

Viral inoculum was prepared from W38 tobacco previously infected with the virus, approximately 2 g of leaf material, showing obvious viral symptoms were ground with carbarundum in 10 ml of 100 mM Na phosphate buffer (pH 7.5). the inoculum was diluted to 200 ml with additional Na phosphate buffer. Two leaves from each transgenic plant were sprinkled with carbarundum, then 0.4 ml of inoculum was applied to each leaf and leaves rubbed fairly vigorously with fingers. Using this procedure 100% of non-transgenic control plants were infected with PVY.

To assay for viral resistance and immunity transgenic plants are monitored for symptom development. The PVY strain (PVY-D, an Australian PVY isolate) gives obvious symptoms on W38 tobacco, a vein clearing symptom is readily observed on the two leaves above the inoculated leaves, subsequent leaves show uniform chlorotic lesions. Symptom development was monitored over a six week period.

Transgenic lines were described as resistant if they showed reduced viral symptoms, which manifests as a reduction in the leaf are showing chlorotic lesions. Resistance ranges from very strong resistance where only a few viral lesions are observed on a plant to weak resistance which manifests as reduced symptoms on leaves that develop late in plant growth.

Transgenic plants which showed absolutely no evidence of viral symptoms were classified as immune. To ensure these plants were immune they were re-inoculated with virus, most plants remained immune, the few that showed symptoms were re-classified as resistant.

For plant lines generated Southern blots are performed, resistance in subsequent generations is monitored to determine that resistance/immunity is transmissable. Additionally, the breadth of viral resistance is monitored by challenging lines with other PVY strains, to determine whether host range susceptibility is modified.

Results from these experiments are described in Table 2. These data indicate that constructs comprising tandem repeats of target gene sequence, either in the configuration of palindromes, interrupted palindromes as direct repeat sequences, are capable of conferring viral resistance and/or immunity in transgenic plants.

Accordingly, such inverted and/or direct repeat sequences modulate expression of the virus target gene in the transgenic plant.

Constructs combining the use of direct and inverted repeat sequences, namely pART27.35S.PVYx3.5CBV.YVPx3 and pART27.PVYx3.LNYV.YVPx3, are also useful in modulating gene expression.

Example 9

Inactivation of Gait in Animal Cells

To assay for Galt inactivation, porcine PK2 cells were transformed with the relevant constructs. PK2 cells constitutively express Galt enzyme, the activity of which results in the addition of a variety of α-1,3-galactosyl groups to a range of proteins expressed on the cell surface of these cells. Cells were transformed using lipofectin and stably transformed lines were selected using genetecin.

As an initial assay cell lines were probed for the presence of the Galt-encoded epitope, i.e. α-1,3-galactosyl moieties decorating cell surface proteins, using the lectin IB4. IB4 binding was assayed either in situ or by FACS sorting.

For in situ binding, cells were fixed to solid supports with cold methanol for 5 mins, cells were rinsed in PBS (phosphate buffered saline) and non-specific IB4 binding was blocked with 1% BSA in PBS for 10 mins. Fixed cells were probed using 20 ug/ml IB4-biotin (Sigma) in 1% BSA, PBS for 30 mins at room temperature, cells were washed in PBS then probed with a 1:200 dilution of ExtrAvidin-FITC (Sigma) in PBS for 30 mins followed by further rinses in PBS. Cells were then examined using fluorescence microscopy, under these conditions the outer surface of PK2 control cells uniformly stained green.

For FACS analysis, cells were suspended after treatment with trypsin, washed in HBSS/Hepes (Hank's buffered saline solution with 20 mM Hepes, pH7.4) and probed with 10 ug/ml IB4-biotin (Sigma) in HBSS/Hepes for 45 mins at 4° C. Cells were washed in HBSS/Hepes, probed with a 1:200 dilution of ExtrAvidin-FITC (Sigma) in HBSS/Hepes for 45 mins at 4° C. at and rinsed in cold HBSS/Hepes prior to FACS sorting.

Using this approach transformed cell lines are assayed for Galt inactivation and quantitative assessment of construct effectiveness is determined. Moreover cell lines showing Galt inactivation are isolated and subject to further molecular analyses to determine the mechanism of gene inactivation.

| PLASMID CONSTRUCT | No. OF PLANTS TESTED | PERCENTAGE OF PLANTS SHOWING SPECIFIED PHENOTYPE | | |
|---|---|---|---|---|
| | | SUSCEPTIBLE | IMMUNE | RESISTANT |
| pART27.PVY | 19 | 16 | 1 | 2 |
| pART27.PVYx2 | 13 | 5 | 4 | 4 |
| pART27.PVYX3 | 21 | 2 | 5 | 14 |
| pART27.PVYx4 | 21 | 5 | 7 | 9 |
| pART27.35S.PVY.SCBC.0 | 25 | 8 | 0 | 17 |
| pART27.35S.O.SCBV.PVY | 22 | 8 | 0 | 14 |
| pART27.35S.O.SCBV.YVP | 18 | 14 | 0 | 4 |
| pART27.35S.PVY.SCBV.YVP | 17 | 3 | 8 | 6 |
| pART27.PVY.LNYV.PVY | 26 | 18 | 2 | 6 |
| pART27.PVY.LNYV.YVP | 20 | 6 | 10 | 4 |
| pART27.PVY.LNYV.YVPΔ | 18 | 7 | 11 | 0 |

REFERENCES

1. An et al. (1985) *EMBO J* 4:277-284.
2. Armstrong, et al. *Plant Cell Reports* 9: 335-339, 1990.
3. Ausubel, F. M. et al. (1987) In: Current Protocols in Molecular Biology, Wiley Interscience (ISBN 047140338).
4. Chalfie, M. et al (1994) *Science* 263: 802-805.
5. Christensen, A. H. and Quail, P. H. (1996) *Transgenic Research* 5: 213-218.
6. Christou, P., et al. *Plant Physiol* 87: 671-674, 1988.
7. Cormack, B. et al (1996) *Gene* 173: 33-38.
8. Crossway et al., *Mol. Gen. Genet.* 202:179-185, 1986.
9. Dorer, D. R., and Henikoff, S. (1994) *Cell* 7: 993-1002.
10. Fromm et al. *Proc. Natl. Acad. Sci. (USA)* 82:5824-5828, 1985.
11. Gleave, A. P. (1992) *Plant Molecular Biology* 20:1203-1207.
12. Hanahan, D. (1983) *J. Mol. Biol.* 166: 557-560.
13. Herrera-Estella et al., *Nature* 303: 209-213, 1983a.
14. Herrera-Estella et al., *EMBO J.* 2: 987-995, 1983b.
15. Herrera-Estella et al. In: Plant Genetic Engineering, Cambridge University Press, N.Y., pp 63-93, 1985.
16. Inouye, S. and Tsuji, F. I. (1994) *FEBS Letts.* 341: 277-280.
17. Jackson, I. J. (1995) *Ann. Rev. Genet.* 28: 189-217.
18. Krens, F. A., et al., *Nature* 296: 72-74, 1982.
19. Kwon, B. S. et al. (1988) *Biochem. Biophys. Res. Comm.* 153:1301-1309.
20. Pal-Bhadra, M. et al. (1997) *Cell* 90: 479-490.
21. Paszkowski et al., *EMBO J.* 3:2717-2722, 1984
22. Prasher, D. C. et al. (1992) *Gene* 111: 229-233.
23. Sanford, J. C., et al., *Particulate Science and Technology* 5: 27-37, 1987.

The invention claimed is:

1. A double-stranded DNA construct comprising two copies of a structural gene region whose nucleotide sequence is identical to the nucleotide sequence of a region of a target gene in an animal cell,
wherein one of the two copies is in the sense orientation and the other of the two copies is in the antisense orientation operably under the control of a single promoter sequence which is operable in the cell, and wherein
the copy of the structural gene region in the sense orientation and the copy of the structural gene region in the antisense orientation are arranged as an interrupted palindrome sequence such that the copy of the structural gene region in the sense orientation and the copy of the structural gene region in the antisense orientation are separated and linked by nucleotides other than the nucleotides of the copy of the structural gene region in the sense orientation and the copy of the structural gene region in the antisense orientation.

2. The double-stranded DNA construct of claim 1, wherein the target gene is endogenous to the animal cell.

3. The double-stranded DNA construct of claim 1, wherein the region of the target gene is in an exon.

4. The double-stranded DNA construct of claim 1, wherein the target gene is a foreign gene to the animal cell.

5. The double-stranded DNA construct of claim 1, wherein the target gene is a viral gene.

6. The double-stranded DNA construct of claim 5, wherein the viral gene encodes a DNA polymerase, a RNA polymerase, or a viral coat protein.

7. The double-stranded DNA construct of claim 5, wherein the viral gene is from a lentivirus.

8. The double-stranded DNA construct of claim 5, wherein the viral gene is from an immunodeficiency virus.

9. The double-stranded DNA construct of claim 5, wherein the viral gene is from a single stranded (+) RNA virus.

10. The double-stranded DNA construct of claim 5, wherein the viral gene is from a double-stranded DNA virus.

11. The double-stranded DNA construct of claim 1, wherein the structural gene region is greater than 20 nucleotides long.

12. The double-stranded DNA construct of claim 11, wherein the target gene is endogenous to the animal cell.

13. The double-stranded DNA construct of claim 11, wherein the region of the target gene is in an axon.

14. The double-stranded DNA construct of claim 11, wherein the target gene is a foreign gene to the animal cell.

15. The double-stranded DNA construct of claim 11, wherein the target gene is a viral gene.

16. The double-stranded DNA construct of claim 15, wherein the viral gene encodes a DNA polymerase, a RNA polymerase, or a viral coat protein.

17. The double-stranded DNA construct of claim 15, wherein the viral gene is from a lentivirus.

18. The double-stranded DNA construct of claim 15, wherein the viral gene is from an immunodeficiency virus.

19. The double-stranded DNA construct of claim 15, wherein the viral gene is from a single stranded (+) RNA virus.

20. The double-stranded DNA construct of claim 15, wherein the viral gene is from a double-stranded DNA virus.

21. The double-stranded DNA construct of claim 1, wherein the structural gene region is greater than 20-100 nucleotides long.

22. The double-stranded DNA construct of claim 1, wherein the structural gene region is greater than 20 nucleotides long and has a length up to the full length of the target gene.

23. The double-stranded DNA construct of claim 1, wherein the structural gene region placed in the sense orientation and the structural gene region placed in the antisense orientation are separated by a sequence of nucleotides that is 10-50 nucleotides in length.

24. The double-stranded DNA construct of claim 1, wherein the structural gene region placed in the sense orientation and the structural gene region placed in the antisense orientation are separated by a sequence of nucleotides that is 50-100 nucleotides in length.

25. The double-stranded DNA construct of claim 1, wherein the structural gene region placed in the sense orientation and the structural gene region placed in the antisense orientation are separated by a sequence of nucleotides that is 100-500 nucleotides in length.

26. An animal cell having a DNA comprising
two copies of a structural gene region whose nucleotide sequence is identical to the nucleotide sequence of a region of a target gene in an animal cell,
wherein one of the two copies is in the sense orientation and the other of the two copies is in the antisense orientation operably under the control of a single promoter sequence which is operable in the cell, and wherein
the copy of the structural gene region in the sense orientation and the copy of the structural gene region in the antisense orientation are arranged as an interrupted palindrome sequence such that the copy of the structural gene region in the sense orientation and the copy of the structural gene region in the antisense orientation are separated and linked by nucleotides other than the nucleotides of the copy of the structural gene region in the sense orientation and the copy of the structural gene region in the antisense orientation.

27. The animal cell of claim 26, wherein the target gene is endogenous to the animal cell.

28. The animal cell of claim 26, wherein the region of the target gene is in an exon.

29. The animal cell of claim 26, wherein the target gene is a foreign gene to the animal cell.

30. The animal cell of claim 26, wherein the target gene is a viral gene.

31. The animal cell of claim 30, wherein the viral gene encodes a DNA polymerase, a RNA polymerase, or a viral coat protein.

32. The animal cell of claim 30, wherein the viral gene is from a lentivirus.

33. The animal cell of claim 30, wherein the viral gene is from an immunodeficiency virus.

34. The animal cell of claim 30, wherein the viral gene is from a single stranded (+) RNA virus.

35. The animal cell of claim 30, wherein the viral gene is from a double-stranded DNA virus.

36. The animal cell, of claim 26, wherein the structural gene region is greater than 20 nucleotides long.

37. The animal cell of claim 36, wherein the target gene is endogenous to the animal cell.

38. The animal cell of claim 36, wherein the region of the target gene is in an exon.

39. The animal cell of claim 36, wherein the target gene is a foreign gene to the animal cell.

40. The animal cell of claim 36, wherein the target gene is a viral gene.

41. The animal cell of claim 40, wherein the viral gene encodes a DNA polymerase, a RNA polymerase, or a viral coat protein.

42. The animal cell of claim 40, wherein the viral gene is from a lentivirus.

43. The animal cell of claim 40, wherein the viral gene is from an immunodeficiency virus.

44. The animal cell of claim 40, wherein the viral gene is from a single stranded (+) RNA virus.

45. The animal cell of claim 40, wherein the viral gene is from a double-stranded DNA virus.

46. The animal cell of claim 26, wherein the structural gene region is greater than 20-100 nucleotides long.

47. The animal cell of claim 26, wherein the structural gene region is greater than 20 nucleotides long and has a length up to the full length of the target gene.

48. The animal cell of claim 26, wherein the structural gene region placed in the sense orientation and the structural gene region placed in the antisense orientation are separated by a sequence of nucleotides that is 10-50 nucleotides in length.

49. The animal cell of claim 26, wherein the structural gene region placed in the sense orientation and the structural gene region placed in the antisense orientation are separated by a sequence of nucleotides that is 50-100 nucleotides in length.

50. The animal cell of claim 26, wherein the structural gene region placed in the sense orientation and the structural gene region placed in the antisense orientation are separated by a sequence of nucleotides that is 100-500 nucleotides in length.

51. A method of modulating the expression of a target gene in an animal cell comprising introducing into a cell a double-stranded DNA comprising two copies of a structural gene region whose nucleotide sequence is identical to the nucleotide sequence of a region of a target gene in an animal cell,
    wherein one of the two copies is in the sense orientation and the other of the two copies is in the antisense orientation operably under the control of a single promoter sequence which is operable in the cell, and wherein
    the copy of the structural gene region in the sense orientation and the copy of the structural gene region in the antisense orientation are arranged as an interrupted palindrome sequence such that the copy of the structural gene region in the sense orientation and the copy of the structural gene region in the antisense orientation are separated and linked by nucleotides other than the nucleotides of the copy of the structural gene region in the sense orientation and the copy of the structural gene region in the antisense orientation,
    such that the double-stranded DNA is transcribed to produce a RNA molecule in the cell.

52. The method of claim 51, wherein the target gene is endogenous to the animal cell.

53. The method of claim 51, wherein the region of the target gene is in an exon.

54. The method of claim 51, wherein the target gene is a foreign gene to the animal cell.

55. The method of claim 51, wherein the target gene is a viral gene.

56. The method of claim 55, wherein the viral gene encodes a DNA polymerase, a RNA polymerase, or a viral coat protein.

57. The method of claim 55, wherein the viral gene is from a lentivirus.

58. The method of claim 55, wherein the viral gene is from an immunodeficiency virus.

59. The method of claim 55, wherein the viral gene is from a single stranded (+) RNA virus.

60. The method of claim 55, wherein the viral gene is from a double-stranded DNA virus.

61. The method of claim 51, wherein the structural gene region is greater than 20 nucleotides long.

62. The method of claim 61, wherein the target gene is endogenous to the animal cell.

63. The method of claim 61, wherein the region of the target gene is in an exon.

64. The method of claim 61, wherein the target gene is a foreign gene to the animal cell.

65. The method of claim 61, wherein the target gene is a viral gene.

66. The method of claim 65, wherein the viral gene encodes a DNA polymerase, a RNA polymerase, or a viral coat protein.

67. The method of claim 65, wherein the viral gene is from a lentivirus.

68. The method of claim 65, wherein the viral gene is from an immunodeficiency virus.

69. The method of claim 65, wherein the viral gene is from a single stranded (+) RNA virus.

70. The method of claim 65, wherein the viral gene is from a double-stranded DNA virus.

71. The method of claim 51, wherein the structural gene region is greater than 20-100 nucleotides long.

72. The method of claim 51, wherein the structural gene region is greater than 20 nucleotides long and has a length up to the full length of the target gene.

73. The method of claim 51, wherein the structural gene region placed in the sense orientation and the structural gene region placed in the antisense orientation are separated by a sequence of nucleotides that is 10-50 nucleotides in length.

74. The method of claim 51, wherein the structural gene region placed in the sense orientation and the structural gene region placed in the antisense orientation are separated by a sequence of nucleotides that is 50-100 nucleotides in length.

75. The method of claim 51, wherein the structural gene region placed in the sense orientation and the structural gene region placed in the antisense orientation are separated by a sequence of nucleotides that is 100-500 nucleotides in length.

76. The method of claim 51, wherein the RNA molecule modulates the expression of the target gene by reducing or delaying translation of a mRNA transcript of the target gene as a consequence of sequence-specific degradation of the mRNA transcript of the target gene by an endogenous host cell system.

* * * * *